(12) United States Patent
Frank et al.

(10) Patent No.: US 8,084,484 B2
(45) Date of Patent: Dec. 27, 2011

(54) VANILLOID RECEPTOR LIGANDS, PHARMACEUTICAL COMPOSITIONS CONTAINING THEM, PROCESS FOR MAKING THEM, AND USE THEREOF FOR TREATING PAIN AND OTHER CONDITIONS

(75) Inventors: Robert Frank, Aachen (DE); Gregor Bahrenberg, Aachen (DE); Thomas Christoph, Aachen (DE); Klaus Schiene, Juechen (DE); Jean De Vry, Stolberg (DE); Derek Saunders, Aachen (DE); Bernd Sundermann, Friedrichsdorf (DE); Jeewoo Lee, Gyenggi-Do (KR)

(73) Assignee: Gruenenthal GmbH, Aachen (DE)

( * ) Notice: Subject to any disclaimer, the term of this patent is extended or adjusted under 35 U.S.C. 154(b) by 482 days.

(21) Appl. No.: 12/103,667

(22) Filed: Apr. 15, 2008

(65) Prior Publication Data
US 2009/0156590 A1 Jun. 18, 2009

(30) Foreign Application Priority Data
Apr. 16, 2007 (DE) .......................... 10 2007 018 149

(51) Int. Cl.
*C07D 263/54* (2006.01)
*C07D 265/36* (2006.01)
*C07D 235/24* (2006.01)
*A61K 31/538* (2006.01)
*A61K 31/422* (2006.01)
*A61K 31/4184* (2006.01)

(52) U.S. Cl. ..................................... 514/394; 548/309.7
(58) Field of Classification Search ............... 548/309.7; 514/394
See application file for complete search history.

(56) References Cited

U.S. PATENT DOCUMENTS
2005/0113576 A1   5/2005   Lee et al.

FOREIGN PATENT DOCUMENTS
WO   WO 03/070247 A   8/2003
WO   WO 2005/016890 A   2/2005

OTHER PUBLICATIONS

Chalmers (TiPS vol. 17, pp. 166-172 Apr. 1996).*
International Search Report mailed Oct. 30, 2008 with English translation, sixteen (16) pages.
International Preliminary Report on Patentability mailed Nov. 19, 2009, with English translation, thirteen (13) pages.
S. Marinelli et al., The Journal of Neuroscience, vol. 23, Issue 8, pp. 3136-3144 (2003).
Donnerer J., Liebmann I., Schicho R., Pharmacology. Feb. 2005; vol. 73, Issue 2, pp. 97-101 (2005) E pub Oct. 18, 2004.
V. Micale et al., Neurobiology of Disease, Issue 36, pp. 70-80 (2009).
M. Fu et al., Medical Hypotheses vol. 73, pp. 100-102 (2009).
C. Maggi, Life Sciences, vol. 51, No. 23, pp. 1777-1781 (1992).
H. Rami et al., Therapeutic Strategies, vol. 1, Issue 1, pp. 97-104 (2004).
L.A. Birder et al., Nature Neuroscience, vol. 5, No. 9, pp. 856-860 (2002).
P. Holzer, European Journal of Pharmacology vol. 500, pp. 231-241 (2004).
Y. Yiangou et al., The Lancet, vol. 357, p. 1338-1339, Apr. 28, 2001.
P. Geppetti et al., British Journal of Pharmacology, vol. 141, No. 8, pp. 1313-1320 (2004).
W. Huang et al., Journal of Hypertension vol. 27 (2009).
E. Bodo et al., American Journal of Pathology, vol, 166, No. 4, pp. 985-998 (2005).
Won-Sik Shim et al., The Journal of Neuroscience, vol. 27, No. 9, pp. 2331-2337 (2007).
F. Leung, Life Sciences, Issue 83, pp. 1-5 (2008).
A. Suri et al., TRENDS in Pharmacological Sciences, vol. 29, No. 1, pp. 29-36 (2007).
G. Ahern, The Journal of Biological Chemistry, vol. 278, No. 33, pp. 30429-30434 (2003).
I.-J. You et al., Soc. Neurosci. Abstr. vol. 912.22 (2007).
J. Li et al., Pharmacological Research vol. 57, Issue 3, pp. 239-246 (2008).
H. Schultz, Journal of Physiology, 551.2, p. 400 (2003).
M. Zahner et al., Journal of Physiology 551.2, pp. 515-523 (2003).
H. Pan et al., Circulation Journal of the American Heart Association, Circulation vol. 110, Issue 13, pp. 1826-1831 (2004).
M. Ghasemi et al., European Journal of Pharmacology vol. 544, Issues 1-3, pp. 138-145 (2006).
S. Mandadi et al., Neuroscience vol. 162 pp. 1377-1397 (2009).
D. Dawbarn et al., Neuropharmacology, vol. 20, pp. 341-346 (1981).
R. Marsch et al., The Journal of Neuroscience, vol. 27, No. 4, pp. 832-839 (2007).
H. Eilers, Molecular Interventions, vol. 8, Issue 5, pp. 226-229 (2008).

* cited by examiner

*Primary Examiner* — Kahsay T Habte
(74) *Attorney, Agent, or Firm* — Crowell & Moring LLP

(57) ABSTRACT

Vanilloid receptor ligand compounds corresponding to formula I:

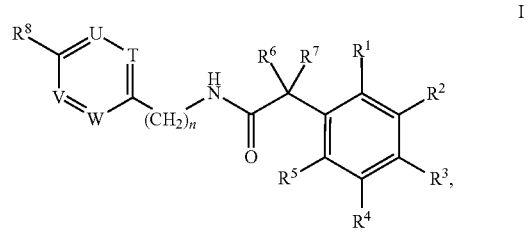

pharmaceutical compositions containing such compounds, a process for producing such compounds, and methods of using such compounds for treating or inhibiting pain and various other disorders or conditions.

33 Claims, No Drawings

VANILLOID RECEPTOR LIGANDS, PHARMACEUTICAL COMPOSITIONS CONTAINING THEM, PROCESS FOR MAKING THEM, AND USE THEREOF FOR TREATING PAIN AND OTHER CONDITIONS

The present invention relates to novel vanilloid receptor ligands, to methods for producing them, to medicaments containing these compounds and to the use of these compounds for the production of medicaments.

The treatment of pain, in particular neuropathic pain, is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

One suitable approach to the treatment of pain, in particular of pain selected from the group consisting of acute pain, chronic pain, neuropathic pain and visceral pain, particularly preferably of neuropathic pain, is the vanilloid receptor subtype 1 (VR1/TRPV1), which is often also known as the capsaicin receptor. This receptor is stimulated inter alia by vanilloids such as for example capsaicin, heat and protons and plays a central role in the genesis of pain. It is furthermore of significance to numerous other physiological and pathophysiological processes, such as for example migraine; depression; neurodegenerative diseases; cognitive disorders; anxiety states; epilepsy; coughing; diarrhoea; pruritus; inflammation; disorders of the cardiovascular system; disorders of food intake; dependency on medicines; abuse of medicines and in particular urinary incontinence.

One object of the present invention was accordingly to provide novel compounds which are suitable in particular as pharmacological active ingredients in medicaments, preferably in medicaments for the treatment of disorders or diseases which are mediated at least in part by vanilloid receptors 1 (VR1/TRPV1 receptors).

It has surprisingly now been found that the substituted compounds of the general formula I stated below display excellent affinity for the vanilloid receptor of the subtype 1 (VR1/TRPV1 receptor) and are therefore suitable in particular for the prevention and/or treatment of disorders or diseases which are mediated at least in part by vanilloid receptors 1 (VR1/TRPV1). Likewise the substituted compounds of the general formula I stated below exhibit antiinflammatory activity.

The present invention accordingly provides substituted compounds of the general formula I

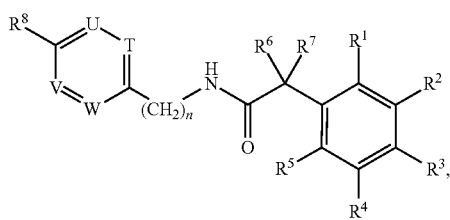

in which
n denotes 0, 1, 2, 3 or 4;
$R^1$ and $R^2$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}$—C(=O)—$NR^{65}$—; —$NR^{66}$—C(=S)—$NR^{65}$—; —O—$CH_2$—C(=O)—NH—; —O—$CH_2$—O—; —O—$CH_2$—$CH_2$—O—; —O—$CH_2$—$CH_2$—$CH_2$—O—; —O—$CH_2$—$CH_2$—NH—, and —CH=CH—N=CH—, which is attached in any desired direction to the parent structure,
or $R^2$ and $R^3$ together denote a residue selected from the group consisting —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure,
or $R^3$ and $R^4$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure, or $R^4$ and $R^5$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}$—C(=O)—$NR^{65}$—; —$NR^{66}$—C(=S)—$NR^{65}$—; —O—$CH_2$—C(=O)—NH—; —O—$CH_2$—O—; —O—$CH_2$—$CH_2$—O—, —O—$CH_2$—$CH_2$—$CH_2$—O—; —O—$CH_2$—$CH_2$—NH—, and —CH=CH—N=CH—, which is attached in any desired direction to the parent structure, and the remaining residues of $R^1$, $R^2$, $R^3$, $R^4$ and $R^5$, mutually independently, in each case denote H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; —S(=O)$_2$—$R^{27}$ or denote a linear or branched, saturated or unsaturated, unsubstituted or at least monosubstituted aliphatic $C_{1-10}$ residue;

$R^6$ in each case denotes H or a linear or branched, saturated or unsaturated, unsubstituted or at least monosubstituted aliphatic $C_{1-10}$ residue;

$R^7$ denotes hydrogen or —OH;

or $R^6$ and $R^7$ in each case together with the carbon atom joining them together as a ring member form a saturated or unsaturated, unsubstituted or at least monosubstituted 3-, 4-, 5-, 6- or 7-membered cycloaliphatic residue;

$R^8$ denotes —$SF_5$; —O—$CF_3$; —$CF_3$; —O—$CFH_2$; —O—$CF_2H$; —$CFH_2$; —$CF_2H$; or denotes an unsubstituted or at least monosubstituted tert.-butyl residue;

T denotes C—$R^{35}$ and U denotes C—$R^{36}$ V denotes N and W denotes C—$R^{38}$ or T denotes C—$R^{35}$ and U denotes N and V denotes C—$R^{37}$ and W denotes C—$R^{38}$ or T denotes N and U denotes C—$R^{36}$ and V denotes C—$R^{37}$ and W denotes C—$R^{38}$ or T denotes N and U denotes N and V denotes C—$R^{37}$ and W denotes C—$R^{38}$ or T denotes N and U denotes C—$R^{36}$ and V denotes N and W denotes C—$R^{38}$ or T denotes C—$R^{35}$ and U denotes N and V denotes N and W denotes C—$R^{38}$ or T denotes C—$R^{35}$ and U denotes C—$R^{36}$ and V denotes C—$R^{37}$ and W denotes C—$R^{38}$;

$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, mutually independently, in each case denote a linear or branched, saturated or unsaturated, unsubstituted or at least monosubstituted aliphatic $C_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

$R^{28}$ denotes F; Cl; Br; I; —$SF_5$; —$NO_2$; —$CF_3$; —CN; —$NH_2$ or denotes a linear or branched, saturated or unsaturated, unsubstituted or at least monosubstituted aliphatic $C_{1-10}$ residue;

$R^{29}$ and $R^{30}$, mutually independently, in each case denote —NH—C(=O)—$R^{31}$; —$NH_2$; —NH—S(=O)$_2$—$R^{32}$; —NH—C(=O)—O—$R^{33}$; —S—$R^{34}$ or denote a linear or branched, saturated or unsaturated, unsubstituted or at least monosubstituted aliphatic $C_{1-10}$ residue;

$R^{31}$, $R^{32}$, $R^{33}$ and $R^{34}$, mutually independently, in each case denote a linear or branched, saturated or unsaturated, unsubstituted or at least monosubstituted aliphatic $C_{1-10}$ residue;

$R^{35}$, $R^{36}$ and $R^{37}$, mutually independently, in each case denote H; F; Cl; Br; I; —$SF_5$; —$NO_2$; —$CF_3$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; —S(=O)$_2$—$R^{27}$;

denote a linear or branched, saturated or unsaturated, unsubstituted or at least monosubstituted aliphatic $C_{1-10}$ residue;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

$R^{38}$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{39}$; —$NR^{40}R^{41}$; —$OR^{42}$; —$SR^{43}$; —C(=O)—$NHR^{44}$; —C(=O)—$NR^{45}R^{46}$; —S(=O)$_2$—$NHR^{47}$; —S(=O)$_2$—$NR^{48}R^{49}$; —C(=O)—$OR^{50}$; —C(=O)—$R^{51}$; —S(=O)—$R^{52}$; —S(=O)$_2$—$R^{53}$; —C(=NH)—$NH_2$; —C(=NH)—NH—$R^{54}$; —N=C($NH_2$)$_2$; —N=C($NHR^{55}$)($NHR^{56}$);

denotes a linear or branched, saturated or unsaturated, unsubstituted or at least monosubstituted aliphatic $C_{1-10}$ residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

$R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$ and $R^{56}$, mutually independently, in each case denote a linear or branched, saturated or unsaturated, unsubstituted or at least monosubstituted aliphatic $C_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or 2- to 6-membered heteroalkylene group;

or $R^{40}$ and $R^{41}$ in each case together with the nitrogen atom joining them together as a ring member form a saturated or unsaturated or unsubstituted heterocycloaliphatic residue or a 4-, 5-, 6-, 7-, 8- or 9-membered heterocycloaliphatic residue substituted with 1, 2, 3, 4 or 5 residues $R^{57}$ and optionally comprising at least one further heteroatom as a ring member, which heterocycloaliphatic residue may be fused with a saturated or unsaturated, unsubstituted or at least monosubstituted mono- or polycyclic ring system;

$R^{57}$ denotes —$NHR^{58}$, —$NR^{59}R^{60}$ denotes a linear or branched, saturated or unsaturated, unsubstituted or at least monosubstituted aliphatic $C_{1-10}$ residue;

$R^{58}$, $R^{59}$ and $R^{60}$, mutually independently, in each case denote —C(=O)—$R^{61}$; denote a linear or branched, saturated or unsaturated, unsubstituted or at least monosubstituted aliphatic $C_{1-10}$ residue or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

$R^{61}$ denotes a linear or branched, saturated or unsaturated, unsubstituted or at least monosubstituted aliphatic $C_{1-10}$ residue;

$R^{62}$, $R^{63}$, $R^{64}$, $R^{65}$, $R^{66}$ and $R^{67}$, mutually independently, in each case denote a linear or branched, saturated or unsaturated, unsubstituted or at least monosubstituted aliphatic $C_{1-10}$ residue;

$R^{68}$, $R^{69}$ and $R^{70}$, mutually independently, in each case denote F, Cl, Br, I, or denote a linear or branched, saturated or unsaturated, unsubstituted or at least monosubstituted aliphatic $C_{1-10}$ residue; and $R^{71}$ denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates;

wherein the above-stated aliphatic $C_{1-10}$ residues and tert.-butyl residues may optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —C(=O)—O—$C_{1-5}$-alkyl, —O—C(=O)—$C_{1-5}$-alkyl, —O-phenyl, phenyl, —$OCF_3$ and —$SCF_3$;

the above-stated 2- to 6-membered heteroalkylene groups, $C_{1-6}$ alkylene groups and $C_{2-6}$ alkenylene groups and $C_{2-6}$ alkynylene groups may optionally in each case be substituted with 1, 2, 3, 4, 5, 6, 7, 8 or 9 substituents mutually independently selected from the group consisting of F, Cl, Br, I, —CN, —$NO_2$, —OH, —$NH_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —$OCF_3$ and —$SCF_3$;

the above-stated heteroalkylene groups may in each case optionally comprise 1, 2 or 3 heteroatom(s) mutually independently selected from the group consisting of oxygen, sulfur and nitrogen (NH) as chain link(s);

the above-stated (hetero)cycloaliphatic residues may optionally be substituted in each case with 1, 2, 3, 4 or 5 substituents mutually independently selected from the group consisting of —$C_{1-6}$-alkylene-OH, =$CH_2$, —O—$C_{1-5}$-alkylene-oxetanyl, —$C_{1-5}$-alkylene-O—$C_{1-5}$-alkylene-oxetanyl, —$CH_2$—NH—$C_{1-5}$-alkyl, —$CH_2$—N($C_{1-5}$-alkyl)$_2$, —N[—C(=O)—$C_{1-5}$-alkyl]-phenyl, —$CH_2$—O—$C_{1-5}$-alkyl, oxo (=O), thioxo (=S), F, Cl, Br, I, —CN, —$CF_3$, —$SF_5$, —OH, —O—$C_{1-5}$-alkyl, —O—C(=O)—$C_{1-5}$-alkyl, —$NH_2$, —$NO_2$, —O—$CF_3$, —S—$CF_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH-phenyl, —N(—$C_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[—C(=O)—$C_{1-5}$-alkyl]-phenyl, —NH-phenyl, —N(—$C_{1-5}$-alkyl)-phenyl, —($CH_2$)-pyridinyl, pyridinyl, —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl, and unless otherwise stated the above-stated (hetero)cycloaliphatic residues may in each case optionally comprise 1, 2 or 3 (further) heteroatom(s) mutually independently selected from the group consisting of oxygen, nitrogen and sulfur;

the rings of the above-stated mono- or polycyclic ring systems may in each case optionally be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the rings of the above-stated mono- or polycyclic ring systems are in each case 5-, 6- or 7-membered and may in each case optionally comprise 1, 2, 3, 4 or 5 heteroatom(s) as ring member(s), which are mutually independently selected from the group consisting of oxygen, nitrogen and sulfur;

and the above-stated aryl or heteroaryl residues may optionally be substituted in each case with 1, 2, 3, 4 or 5 substituents mutually independently selected from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—C$_{1-5}$-alkyl, —NH—C$_{1-5}$alkyl, —N(C$_{1-5}$-alkyl)$_2$, —NH—S(=O)$_2$—C$_{1-5}$-alkyl, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, —C(=O)—N—(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the above-stated heteroaryl residues may in each case optionally comprise 1, 2, 3, 4 or 5 heteroatom(s) mutually independently selected from the group consisting of oxygen, nitrogen and sulfur as ring member(s).

The term "heteroalkylene" denotes an alkylene chain in which one or more C atoms have in each case been replaced by a heteroatom mutually independently selected from the group consisting of oxygen, sulfur and nitrogen (NH). Heteroalkylene groups may preferably comprise 1, 2 or 3 heteroatom(s), particularly preferably one heteroatom, mutually independently selected from the group consisting of oxygen, sulfur and nitrogen (NH) as chain link(s). Heteroalkylene groups may preferably be 2- to 6-membered, particularly preferably 2- or 3-membered.

Mention may be made by way of example of heteroalkylene groups such as —CH$_2$—CH$_2$—O—CH$_2$—, —CH$_2$—CH(CH$_3$)—O—CH$_2$—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—CH$_2$.

If one or more of the above-stated substituents comprise a linear or branched C$_{1-6}$ alkylene group, this may preferably be selected from the group consisting of —(CH$_2$)—, —(CH$_2$)$_2$—, —C(H)(CH$_3$)—, —(CH$_2$)$_3$—, —(CH$_2$)$_4$—, —(CH$_2$)$_5$—, —C(H)(C(H)(CH$_3$)$_2$)— and —C(C$_2$H$_5$)(H)—.

Saturated or unsaturated C$_{1-10}$ aliphatic residues may denote a —C$_{1-10}$ alkyl, C$_{2-10}$ alkenyl or C$_{2-10}$ alkynyl residue. C$_{2-10}$ alkenyl residues comprise at least one, preferably 1, 2, 3 or 4 C—C double bonds and C$_{2-10}$ alkynyl residues comprise at least one, preferably 1, 2 3 or 4 C—C triple bonds.

Preference is given to —C$_{1-10}$ alkyl residues selected from the group consisting of methyl, ethyl, n-propyl, isopropyl, n-butyl, sec.-butyl, isobutyl, tert-butyl, n-pentyl, 3-methyl-but-1-yl, 2-pentyl, 3-pentyl, sec.-pentyl, neopentyl, 4-methyl-penta-1-yl, (3,3)-dimethyl-but-1-yl, n-hexyl, n-heptyl, 2-heptyl, 3-heptyl, 4-heptyl, n-octyl, n-nonyl, 2-nonyl, 3-nonyl, 4-nonyl, 5-nonyl and (2,6)-dimethyl-hept-4-yl, which may optionally be substituted with 1, 2, 3, 4, 5, 6, 7, 8 or 9 substituents mutually independently selected from the group consisting of —O-Phenyl, —O—C(=O)—CH$_3$, —O—C(=O)—C$_2$H$_5$, —O—C(=O)—CH(CH$_3$)$_2$, —O—C(=O)—C(CH$_3$)$_3$, —C(=O)—O—CH$_3$, —C(=O)—O—C$_2$H$_5$, —C(=O)—O—CH(CH$_3$)$_2$, —C(=O)—O—C(CH$_3$)$_3$, F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Likewise preferred are C$_{2-10}$ alkenyl residues selected from the group consisting of vinyl, 1-propenyl, 2-propenyl, 1-butenyl, 2-butenyl, 3-butenyl, 2-methyl-propen-1-yl, 3-methyl-but-2-en-1-yl, (3,3)-dimethyl-but-1-enyl, 2-methyl-buten-2-yl, 1-pentenyl, 2-pentenyl, 3-pentenyl, 4-pentenyl, 1-hexenyl, 1-heptenyl and 1-octenyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Preference is further given to C$_{2-10}$ alkynyl residues selected from the group consisting of (3,3)-dimethyl-but-1-ynyl, 4-methyl-pent-1-ynyl, 1-hexynyl, ethynyl, 1-propynyl, 2-propynyl, 1-butynyl, 2-butynyl, 3-butynyl, 1-pentynyl, 2-pentynyl, 3-pentynyl and 4-pentynyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Particularly preferred optionally substituted C$_{1-10}$ aliphatic residues are selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), Ethyl, —CF$_2$—CH$_3$, —CHF—CF$_2$Cl, —CF$_2$—CFCl$_2$, —CFCl—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-Propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH $(CH_3)(O-CH_3)$, $-CH(CH_3)(S-CH_3)$, n-Butyl, $-CF_2-CF_2-CF_2-CF_3$, $-CH_2-CH_2-CH_2-CH_2-CN$, $-CH_2-CH_2-CH_2-CF_3$, $-CH_2-CH_2-CH_2-CH_2-CF_3$, $-CH_2-O-C(=O)-CH_3$, $-CH_2-O-C(=O)-C_2H_5$, $-CH_2-O-C(=O)-CH(CH_3)_2$, $-CH_2-O-C(=O)-C(CH_3)_3$, $-CH_2-C(=O)-O-CH_3$, $-CH_2-C(=O)-O-C_2H_5$, $-CH_2-C(=O)-O-C(CH_3)_3$, $-CH_2-CH_2-O-CH_3$, $-CH_2-CH_2-O-C_2H_5$, $-CH_2-CH_2-O-Phenyl$, $-CH_2-CH_2-CH_2-O-CH_3$, sec.-butyl, isobutyl, tert.-butyl, n-pentyl, sec.-pentyl, neopentyl, n-hexyl, vinyl, 1-propenyl, 2-propenyl, 1-butenyl, 2-butenyl, 3-butenyl, 2-methyl-buten-2-yl, (1,1,2)-trifluoro-1-butenyl, 1-pentenyl, 2-pentenyl, 3-pentenyl, 4-pentenyl, $-CF=CF_2$, $-CCl=CCl_2$, $-CH_2-CF=CF_2$, $-CH_2-CCl=CCl_2$, $-C\equiv C-I$, $-C\equiv C-F$ and $-C\equiv C-Cl$.

If one or more of the above-stated substituents denote a (hetero)cycloaliphatic residue, which may optionally be fused with a saturated or unsaturated, unsubstituted or at least monosubstituted mono- or polycyclic ring system, the latter may preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, (1,2,3,6)-tetrahydropyridinyl, azepanyl, azocanyl, diazepanyl, dithiolanyl, (1,3,4,5)-tetrahydropyrido[4,3-b]indolyl, (3,4)-dihydro-1H-isoquinolinyl, (1,3,4,9)-tetrahydro-[b]-carbolinyl and (1,3)-thiazolidinyl.

Examples which may be mentioned of suitable (hetero) cycloaliphatic residues which may be unsubstituted or mono- or polysubstituted and are fused with a mono- or bicyclic ring system are (4,5,6,7)-tetrahydroisoxazolo[5,4-c]pyridinyl, (2,3)-dihydro-1H-indenyl, 3-aza-bicyclo[3.1.1]heptyl, 3-aza-bicyclo[3.2.1]octyl, 6-aza-bicyclo[3.3.1]heptyl, 8-aza-bicyclo[3.2.1]octyl, isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, benzo[1.3]dioxolyl, (1,4)-benzodioxanyl, (2,3)-dihydrothieno[3,4-b][1.4]dioxinyl, (3,4)-Dihydro-2H-benzo[1,4]oxazinyl, octahydro-1H-isoindolyl and octahydro-pyrrolo[3,4c]pyrrolyl.

For the purposes of the present invention, (hetero)cycloaliphatic residues may, together with a further (hetero) cycloaliphatic residue, form a spirocyclic residue by way of a common carbon atom in the two rings.

Suitable spirocyclic residues which may be mentioned are, for example, a 6-aza-spiro[2.5]octyl residue, 8-azaspiro[4.5]decyl residue and a 1-oxa-2,8-diaza-spiro[4.5]dec-2-enyl residue.

Particularly preferably, the (hetero)cycloaliphatic residues may in each case optionally be substituted with 1, 2, 3, 4 or 5 substituents selected mutually independently from the group consisting of oxo ($=O$), thioxo ($=S$), F, Cl, Br, I, $-CN$, $-CF_3$, $-SF_5$, $-OH$, $-O-CH_3$, $-O-C_2H_5$, $-O-CH(CH_3)_2$, $-O-C(CH_3)_3$, $-NH_2$, $-NO_2$, $-O-CF_3$, $-S-CF_3$, $-SH$, $-S-CH_3$, $-S-C_2H_5$, $-S-CH(CH_3)_2$, $-S-C(CH_3)_3$, methyl, ethyl, n-propyl, isopropyl, n-butyl, sec.-butyl, isobutyl, tert.-butyl, n-pentyl, $-C(=O)-CH_3$, $-C(=O)-C_2H_5$, $-C(=O)-CH(CH_3)_2$, $-C(=O)-C(CH_3)_3$, $-C(=O)-OH$, $-C(=O)-O-CH_3$, $-C(=O)-O-C_2H_5$, $-C(=O)-O-CH(CH_3)_2$, $-C(=O)-O-C(CH_3)_3$, $-NH-CH_3$, $-NH-C_2H_5$, $-NH-C(CH_3)_3$, $-N(CH_3)_2$, $-N(C_2H_5)_2$, $-N(CH_3)(C_2H_5)$, $-CH_2-OH$, $-CH_2-CH_2-OH$, $=CH_2$, $-CH_2-O-CH_2$-oxetanyl, $-O-CH_2$-oxetanyl, $-CH_2-N(CH_3)_2$, $-CH_2-N(C_2H_5)_2$, $-CH_2-NH-CH_3$, $-CH_2-NH-C_2H_5$, $-N-[C(=O)-C_2H_5]$-phenyl, $-N-[C(=O)-CH_3]$-phenyl, $-CH_2-O-CH_3$, $-CH_2-O-CH_2-CH_3$, $-NH$-phenyl, $-N(CH_3)$-phenyl, $-N(C_2H_5)$-phenyl, $-N(C_2H_5)$-phenyl, $-O-CH_2-CH_2-CH_2-CH_3$, (4,5)-dihydroisoxazolyl, thiazolyl, (1,2,5)-thiadiazolyl, thiophenyl, phenethyl, cyclohexyl, cyclopentyl, piperidinyl, pyrrolidinyl, $-O-C(=O)-CH_3$, $-O-C(=O)-C_2H_5$, $-O-C(=O)-C(CH_3)_3$, $-(CH_2)$-pyridinyl, pyridinyl, $-O$-phenyl, $-O$-benzyl, phenyl and benzyl, wherein in each the cyclic moiety of the residues oxetanyl, (4,5)-dihydroisoxazolyl, thiazolyl, (1,2,5)-thiadiazolyl, thiophenyl, phenethyl, $-N-[C(=O)-C_2H_5]$-phenyl, $-N-[C(=O)-CH_3]$-phenyl, $-NH$-phenyl, $-N(CH_3)$-phenyl, $-N(C_2H_5)-$ phenyl, $-(CH_2)$-pyridinyl, pyridinyl, $-O$-phenyl, $-O$-benzyl, phenyl and benzyl may be substituted with 1, 2, 3, 4 or 5 substituents mutually independently selected from the group comprising F, Cl, Br, $-OH$, $-CF_3$, $-SF_5$, $-CN$, $-NO_2$, methyl, ethyl, n-propyl, isopropyl, n-butyl, sec.-butyl, isobutyl, tert.-butyl, $-O-CH_3$, $-O-C_2H_5$, $-O-CH(CH_3)_2$, $-O-C(CH_3)_3$, $-O-CF_3$, $-S-CF_3$, phenyl and $-O$-benzyl.

If one or more of the above-stated substituents denote an aryl residue, the latter may preferably be selected from the group consisting of phenyl and naphthyl (1-naphthyl and 2-naphthyl).

If one or more of the above-stated substituents denote a heteroaryl residue, the latter may preferably be selected from the group consisting of tetrazolyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl.

Examples of suitable aryl- and heteroaryl residues which may be unsubstituted or mono- or polysubstituted and are fused with a mono- or bicyclic ring system include isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, (2,3)-dihydrothieno[3,4-b][1.4]dioxinyl, benzo[1.3]dioxolanyl and (1,4)-benzodioxanyl.

The aryl or heteroaryl residues may particularly preferably in each case optionally be substituted with 1, 2, 3, 4 or 5 substituents mutually independently selected from the group consisting of F, Cl, Br, I, $-CN$, $-CF_3$, $-SF_5$, $-OH$, $-O-CH_3$, $-O-C_2H_5$, $-O-CH(CH_3)_2$, $-O-C(CH_3)_3$, $-NH_2$, $-NO_2$, $-O-CF_3$, $-S-CF_3$, $-SH$, $-S-CH_3$, $-S-C_2H_5$, $-S-CH(CH_3)_2$, $-S-C(CH_3)_3$, methyl, ethyl, n-propyl, isopropyl, n-butyl, sec.-butyl, isobutyl, tert.-butyl, n-pentyl, $-C(=O)-OH$, $-C(=O)-O-CH_3$, $-C(=O)-O-C_2H_5$, $-C(=O)-O-CH(CH_3)_2$, $-C(=O)-O-C(CH_3)_3$, $-NH-CH_3$, $-NH-C_2H_5$, $-NH-C(CH_3)_3$, $-N(CH_3)_2$, $-N(C_2H_5)_2$, $-N(CH_3)(C_2H_5)$, $-NH-S(=O)_2-CH_3$, $-NH-S(=O_2)-C_2H_5$, $-NH-S(=O)_2-CH(CH_3)_2$, $-NH-C(=O)-O-CH_3$, $-NH-C(=O)-O-C_2H_5$, $-NH-C(=O)-O-C(CH_3)_3$, $-C(=O)-H$, $-C(=O)-CH_3$, $-C(=O)-C_2H_5$, $-C(=O)-CH(CH_3)_2$, $-C(=O)-C(CH_3)_3$, $-C(=O)-NH_2$, $-C(=O)-NH-CH_3$, $-C(=O)-NH-C_2H_5$, $-C(=O)-N(CH_3)_2$, $-C(=O)-N(C_2H_5)_2$, $-O$-phenyl, $-O$-benzyl, phenyl and benzyl, wherein in each case the cyclic moiety of the residues $-O$-phenyl, $-O$-benzyl, phenyl and benzyl may be substituted with 1, 2, 3, 4 or 5 substituents mutually independently selected from the group consisting of F, Cl, Br, $-OH$, $-CF_3$, $-SF_5$, $-CN$, $-NO_2$, methyl, ethyl, n-propyl, isopropyl, n-butyl, sec.-butyl, isobutyl, tert.-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl.

If a polycyclic ring system, such as for example a bicyclic ring system, is present, the various rings may in each case mutually independently be of a different degree of saturation, i.e. be saturated or unsaturated. A polycyclic ring system is preferably a bicyclic ring system.

Examples of aryl residues which are fused with a mono- or polycyclic ring system and may be mentioned are (1,3)-benzodioxolyl and (1,4)-benzodioxanyl.

If one or more of the above-stated substituents comprise a mono- or polycyclic ring system, the latter may preferably be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, methyl, ethyl, n-propyl, isopropyl, n-butyl, sec.-butyl, isobutyl, tert.-butyl, —O—CH$_3$, —O—C$_2$H$_5$, —O—CH(CH$_3$)$_2$, —O—C(CH$_3$)$_3$, —O—CF$_3$, —S—CF$_3$, phenyl and —O-benzyl.

If R$^{41}$ and R$^{42}$ together with the nitrogen atom joining them together as ring member form a heterocycloaliphatic radical, which is substituted by 1, 2, 3, 4, or 5 radicals R$^{57}$, said radicals R$^{57}$ may each be independently from one another selected from the meanings given herein.

Preferred compounds are those of the general formula Ia,

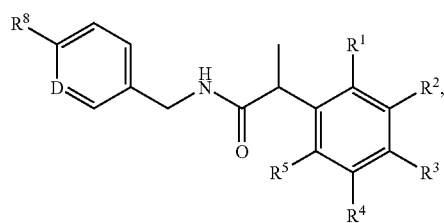

Ia in which
D denotes N or CH;
R$^1$ and R$^2$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—; —O—CH$_2$—CH$_2$—CH$_2$—O—; —O—CH$_2$—CH$_2$—NH—, and —CH=CH—N=CH—, which is attached in any desired direction to the parent structure, or R$^2$ and R$^3$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure, or R$^3$ and R$^4$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure, or R$^4$ and R$^5$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH=CH—N=CH—, which is attached in any desired direction to the parent structure, and the remaining residues of $R^1$, $R^2$, $R^3$, $R^4$ and $R^5$, mutually independently, in each case denote H; F; Cl; Br; I; —$CF_3$; —CN; —$OR^{16}$; —$SR^{17}$; or denote a residue selected from the group consisting of methyl, —$CF_3$, —$CHF_2$, —$CH_2F$, ethyl, n-propyl, isopropyl, n-butyl, sec.-butyl, isobutyl and tert.-butyl;

$R^8$ denotes —$SF_5$; —O—$CF_3$; —$CF_3$; tert.-butyl, or —$C(CH_3)_2(CH_2OH)$;

$R^{16}$ and $R^{17}$, mutually independently, in each case denote a residue selected from the group consisting of methyl, —$CF_3$, —$CHF_2$, —$CH_2F$, ethyl, —$CF_2$—$CH_3$, —$CH_2$—$CF_3$, —$C_2F_5$, n-propyl, isopropyl, n-butyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl and (3,3)-dimethylbutyl;

$R^{28}$ denotes F; Cl; Br; I; —$CF_3$; —CN; —$NH_2$ or denotes an alkyl residue selected from the group consisting of methyl, ethyl, n-propyl, isopropyl, n-butyl, sec.-butyl, isobutyl, tert.-butyl and n-pentyl;

$R^{29}$ and $R^{30}$, mutually independently, in each case denote —NH—C(=O)—$R^{31}$; —$NH_2$; —NH—S(=O)$_2$—$R^{32}$; —NH—C(=O)—O—$R^{33}$; —S—$R^{34}$ or denote an alkyl residue selected from the group consisting of methyl, ethyl, n-propyl, isopropyl, n-butyl, sec.-butyl, isobutyl, tert.-butyl, and n-pentyl;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{62}$, $R^{63}$, $R^{64}$, $R^{65}$, $R^{66}$ and $R^{67}$, mutually independently, in each case denote an alkyl residue selected from the group consisting of methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —$(CH_2)$, —$(CH_2)_2$ or —$(CH_2)_3$ group and/or in each case unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec.-butyl, isobutyl, tert.-butyl, —O-phenyl, —O-benzyl, phenyl and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Ia,

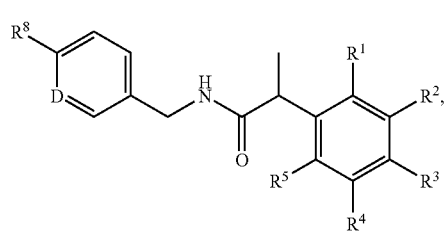

Ia in which

D denotes N or CH;

$R^1$ and $R^2$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}C$(=O)—$NR^{65}$—; —$NR^{66}$—C(=S)—$NR^{65}$—; —O—$CH_2$—C(=O)—NH—; —O—$CH_2$—O—; —O—$CH_2$—$CH_2$—O—; —O—$CH_2$—$CH_2$—$CH_2$—O—; —O—$CH_2$—$CH_2$—NH—, and —CH=CH—N=CH—, which is attached in any desired direction to the parent structure, or $R^2$ and $R^3$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure, or $R^3$ and $R^4$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure, or $R^4$ and $R^5$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—;

—O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH=CH—N=CH—, which is attached in any desired direction to the parent structure, and the remaining residues of $R^1$, $R^2$, $R^3$, $R^4$ and $R^5$, mutually independently, in each case denote H; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ and $R^{30}$, mutually independently, in each case denote —NH—C(=O)—R$^{31}$; —NH$_2$; —NH—S(=O)$_2$—R$^{32}$; —NH—C(=O)—O—R$^{33}$ or —S—R$^{34}$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{62}$, $R^{63}$, $R^{64}$, $R^{65}$, $R^{66}$ and $R^{67}$, mutually independently, in each case denote an alkyl residue selected from the group consisting of methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —(CH$_2$), —(CH$_2$)$_2$ or —(CH$_2$)$_3$ group and/or in each case unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, —O-phenyl, —O-benzyl, phenyl and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Ia,

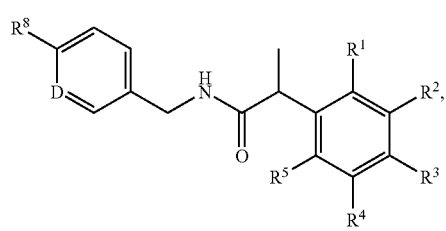

in which
D denotes N or CH;
$R^1$ and $R^2$ together denote a residue selected from the group consisting of —CH=N—NH—; —CH=N—NR$^{71}$—; S—CH=N—; —S—CR$^{29}$=N—; —N=CH—O—, —N=CR$^{30}$—O—, —O—CH$_2$—O—; and —CH=CH—N=CH—, which is attached in any desired direction to the parent structure, or $R^2$ and $R^3$ together denote a residue selected from the group consisting of —CH=N—NH—; —CR$^{28}$=N—NH—; —S—C(=S)—NH—; —O—C(=S)—NH—; —S—C(=O)—NH—; —O—C(=O)—NH—; —S—CH=N—; —S—CR$^{29}$=N—; —N=CH—O—; —N=CR$^{30}$—O—; —N=CH—NH—; —NH—C(=O)—NH—; —NH—C(=S)—NH—; —N=N—NH—; —O—CH$_2$—C(=O)—NH—; —O—CH$_2$—O—; —CH$_2$—CH$_2$—NH—; —CH$_2$—CH$_2$—CH$_2$—NH—; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=CH—CH=N—; —CH=CH—CH=N—; —CH=CH—N=CH—; —CH=N—N=CH— and —O—CH$_2$—CH$_2$—NH—, which is attached in any desired direction to the parent structure, or $R^3$ and $R^4$ together denote a residue selected from the group consisting of —CH=N—NH—; —CR$^{28}$=N—NH—; —S—C(=S)—NH—; —O—C(=S)—NH—; —S—C(=O)—NH—; —O—C(=O)—NH—; —S—CH=N—; —S—CR$^{29}$=N—; —N=CH—O—; —N=CR$^{30}$—O—; —N=CH—NH—; —NH—C(=O)—NH—; —NH—C(=S)—NH—; —N=N—NH—; —O—CH$_2$—C(=O)—NH—; —O—CH$_2$—O—; —CH$_2$—CH$_2$—NH—; —CH$_2$—CH$_2$—CH$_2$—NH—; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=CH—CH=N—; —CH=CH—CH=N—; —CH=CH—N=CH—; —CH=N—N=CH— and —O—CH$_2$—CH$_2$—NH—, which is attached in any desired direction to the parent structure, or $R^4$ and $R^5$ together denote a residue selected from the group consisting of —CH=N—NH—; —CH=N—NR$^{71}$—; —S—CH=N—; —S—CR$^{29}$=N—; —N=CH—O—; —N=CR$^{30}$—O—, —O—CH$_2$—O—; and —CH=CH—N=CH—, which is attached in any desired direction to the parent structure, and the remaining residues of $R^1$, $R^2$, $R^3$, $R^4$ and $R^5$, mutually independently, in each case denote H; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

$R^8$ denotes —SF$_5$; —O—CF$_3$; —CF$_3$; tert.-butyl, or —C(CH$_3$)$_2$(CH$_2$OH);

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ denotes —NH—C(=O)—R$^{31}$; —NH$_2$; —NH—S(=O)$_2$—R$^{32}$; —NH—C(=O)—O—R$^{33}$ or —S—R$^{34}$;

$R^{30}$ denotes —NH$_2$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl; and $R^{71}$ denotes a phenyl radical, which is capable of being attached via a —(CH$_2$), —(CH$_2$)$_2$ or —(CH$_2$)$_3$ group and/or which may be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, methyl, ethyl, n-propyl, isopropyl, n-butyl, sec.-butyl, isobutyl and tert.-butyl;

in each case optionally in the form of one of the stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred compounds are those of the general formula Ib,

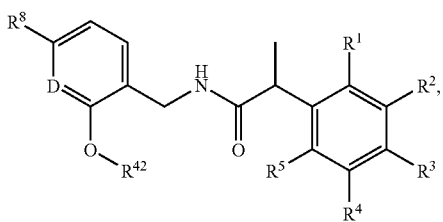

Ib in which
D denotes N or CH;
$R^1$ and $R^2$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—; —O—CH$_2$—CH$_2$—CH$_2$—O—; —O—CH$_2$—CH$_2$—NH—, and —CH=CH—N=CH—, which is attached in any desired direction to the parent structure, or $R^2$ and $R^3$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure, or $R^3$ and $R^4$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure, or $R^4$ and $R^5$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH=CH—N=CH—, which is attached in any desired direction to the parent structure, and the remaining residues of $R^1$, $R^2$, $R^3$, $R^4$ and $R^5$, mutually independently, in each case denote H; F; Cl; Br; I; —CF$_3$; —CN; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

$R^8$ denotes —SF$_5$; —O—CF$_3$; —CF$_3$; tert.-butyl, or —C(CH$_3$)$_2$(CH$_2$OH);

$R^{16}$ and $R^{17}$, mutually independently, in each case denote a residue selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl and (3,3)-dimethylbutyl;

$R^{28}$ denotes F; Cl; Br; I; —CF$_3$; —CN; —NH$_2$ or denotes an alkyl residue selected from the group consisting of methyl, ethyl, n-propyl, isopropyl, n-butyl, sec.-butyl, isobutyl, tert.-butyl and n-pentyl;

$R^{29}$ and $R^{30}$, mutually independently, in each case denote —NH—C(=O)—R$^{31}$; —NH$_2$; —NH—S(=O)$_2$—R$^{32}$; —NH—C(=O)—O—R$^{33}$; —S—R$^{34}$ or denote an alkyl residue selected from the group consisting of methyl, ethyl, n-propyl, isopropyl, n-butyl, sec.-butyl, isobutyl, tert.-butyl, and n-pentyl;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{42}$ denotes a residue selected from the group consisting of methyl, —CH$_2$—O—CH$_3$, ethyl, n-propyl, n-butyl, sec.-butyl, isobutyl, tert.-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$ and —CH$_2$—CH$_2$—CH$_2$—O—CH$_3$;

or denotes a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl; $R^{62}$, $R^{63}$, $R^{64}$, $R^{65}$, $R^{66}$ and $R^{67}$, mutually independently, in each case denote an alkyl residue selected from the group consisting of —$CF_3$, —$CH_2$—$CF_3$, methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —($CH_2$), —($CH_2$)$_2$ or —($CH_2$)$_3$ group and/or in each case unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec.-butyl, isobutyl, tert.-butyl, —O-phenyl, —O-benzyl, phenyl and benzyl; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Ib,

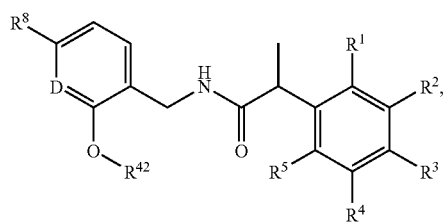

in which
D denotes N or CH;
$R^1$ and $R^2$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—$CH_2$—C(=O)—NH—; —O—$CH_2$—O—; —O—$CH_2$—$CH_2$—O—; —O—$CH_2$—$CH_2$—$CH_2$—O—; —O—$CH_2$—$CH_2$—NH—, and —CH=CH—N=CH—, which is attached in any desired direction to the parent structure, or $R^2$ and $R^3$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—$CH_2$—$CH_2$—NH—, which is attached in any desired direction to the parent structure, or $R^3$ and $R^4$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{65}$=N—N=CR$^{69}$— and —O—$CH_2$—$CH_2$—NH—, which is attached in any desired direction to the parent structure, or $R^4$ and $R^5$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—$CH_2$—C(=O)—NH—; —O—$CH_2$—O—; —O—$CH_2$—$CH_2$—O—, —O—$CH_2$—$CH_2$—$CH_2$—O—; —O—$CH_2$—$CH_2$—NH—, and —CH=CH—N=CH—, which is attached in any desired direction to the parent structure, and the remaining residues of $R^1$, $R^2$, $R^3$, $R^4$ and $R^5$, mutually independently, in each case denote H; —OR$^{16}$; —SR$^{17}$; or denote a residue selected from the group consisting of methyl, —$CF_3$, —$CHF_2$, —$CH_2F$, ethyl, n-propyl, isopropyl, n-butyl, sec.-butyl, isobutyl and tert.-butyl;

$R^8$ denotes —$SF_5$; —O—$CF_3$; —$CF_3$; tert.-butyl, or —C($CH_3$)$_2$($CH_2OH$);

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ and $R^{30}$, mutually independently, in each case denote —NH—C(=O)—$R^{31}$; —$NH_2$; —NH—S(=O)$_2$—$R^{32}$; —NH—C(=O)—O—$R^{33}$ or —S—$R^{34}$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{42}$ denotes a residue selected from the group consisting of methyl, ethyl, n-propyl, n-butyl, sec.-butyl, isobutyl, tert.-butyl, n-pentyl, 3-pentyl, n-hexyl and (3,3)-dimethylbutyl;

or denotes a residue selected from the group consisting of cyclopropyl, cyclobutyl, cyclopentyl, cyclohexyl and cycloheptyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl;

$R^{62}$, $R^{63}$, $R^{64}$, $R^{65}$, $R^{66}$ and $R^{67}$, mutually independently, in each case denote an alkyl residue selected from the group consisting of methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —($CH_2$), —($CH_2$)$_2$ or —($CH_2$)$_3$ group and/or in each case unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec.-butyl, isobutyl, tert.-butyl, —O-phenyl, —O-benzyl, phenyl and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula,

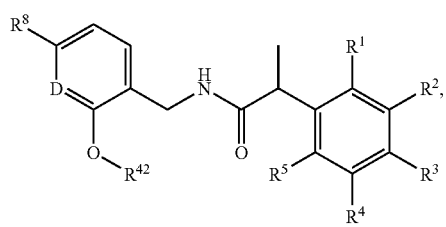

Ib in which
D denotes N or CH;

$R^1$ and $R^2$ together denote a residue selected from the group consisting of —CH=N—NH—; —CH=N—$NR^{71}$—; S—CH=N—; —S—$CR^{29}$=N—; —N=CH—O—, —N=$CR^{30}$—O—, —O—$CH_2$—O—; and —CH=CH—N=CH—, which is attached in any desired direction to the parent structure, or $R^2$ and $R^3$ together denote a residue selected from the group consisting of —CH=N—NH—; —$CR^{28}$=N—NH—; —S—C(=S)—NH—; —O—C(=S)—NH—; —S—C(=O)—NH—; —O—C(=O)—NH—; —S—CH=N—; —S—$CR^{29}$=N—; —N=CH—O—; —N=$CR^{30}$—O—; —N=CH—NH—; —NH—C(=O)—NH—; —NH—C(=S)—NH—; —N=N—NH—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH; —$CH_2$—$CH_2$—C(=O)—NH—; —O—$CH_2$—$CH_2$—O—; —O—$CH_2$—$CH_2$—$CH_2$—O—; —N=CH—CH=N—; —CH=CH—CH=N—; —CH=CH—N=CH—; —CH=N—N=CH— and —O—$CH_2$—$CH_2$—NH—, which is attached in any desired direction to the parent structure, or $R^3$ and $R^4$ together denote a residue selected from the group consisting of —CH=N—NH—; —$CR^{28}$=N—NH—; —S—C(=S)—NH—; —O—C(=S)—NH—; —S—C(=O)—NH—; —O—C(=O)—NH—; —S—CH=N—; —S—$CR^{29}$=N—; —N=CH—O—; —N=$CR^{30}$—O—; —N=CH—NH—; —NH—C(=O)—NH—; —NH—C(=S)—NH—; —N=N—NH—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH—; —$CH_2$—$CH_2$—C(=O)—NH—; —O—$CH_2$—$CH_2$—O—; —O—$CH_2$—$CH_2$—$CH_2$—O—; —N=CH—CH=N—; —CH=CH—CH=N—; —CH=CH—N=CH—; —CH=N—N=CH— and —O—$CH_2$—$CH_2$—NH—, which is attached in any desired direction to the parent structure, or $R^4$ and $R^5$ together denote a residue selected from the group consisting of —CH=N—NH—; —CH=N—$NR^{71}$—; —S—CH=N—; —S—$CR^{29}$=N—; —N=CH—O—; —N=$CR^{30}$—O—, —O—$CH_2$—O—; and —CH=CH—N=CH—, which is attached in any desired direction to the parent structure, and the remaining residues $R^1$, $R^2$, $R^3$, $R^4$ and $R^5$, mutually independently, in each case denote H; —$OR^{16}$; —$SR^{17}$; or denote a residue selected from the group consisting of methyl, —$CF_3$, —$CHF_2$, —$CH_2F$, ethyl, n-propyl, isopropyl, n-butyl, sec.-butyl, isobutyl and tert.-butyl;

$R^8$ denotes —$SF_5$; —O—$CF_3$; —$CF_3$; tert.-butyl, or —C($CH_3$)$_2$($CH_2OH$);

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ denotes —NH—C(=O)—$R^{31}$; —$NH_2$; —NH—S(=O)$_2$—$R^{32}$; —NH—C(=O)—O—$R^{33}$ or —S—$R^{34}$;

$R^{30}$ denotes —$NH_2$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{42}$ denotes a residue selected from the group consisting of methyl, ethyl, n-propyl, n-butyl, sec.-butyl, isobutyl, tert.-butyl, n-pentyl, 3-pentyl, n-hexyl and (3,3)-dimethylbutyl;

or denotes a residue selected from the group consisting of cyclopropyl, cyclobutyl, cyclopentyl, cyclohexyl and cycloheptyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl; and $R^{71}$ denotes a phenyl radical, which optionally may be attached via a —($CH_2$), —($CH_2$)$_2$ or —($CH_2$)$_3$ group and/or which may be unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, methyl, ethyl, n-propyl, isopropyl, n-butyl, sec.-butyl, isobutyl and tert.-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Preferred compounds are those of the general formula Ic,

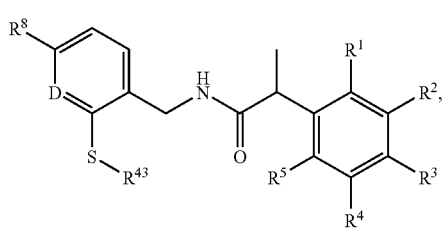

Ic in which
D denotes N or CH;
$R^1$ and $R^2$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—; —O—CH$_2$—CH$_2$—CH$_2$—O—; —O—CH$_2$—CH$_2$—NH—, and —CH=CH—N=CH—, which is attached in any desired direction to the parent structure,
or $R^2$ and $R^3$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure,
or $R^3$ and $R^4$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=C R$^{30}$—O—; —N=CH—NH—; —N=C H—NR$^{64}$—; —NH—C(=O)—NH—; —NH—C(=S)—NH—; —NR$^{66}$—C(=O)—NR$^{65}$—; —NR$^{66}$—C (=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure,
or $R^4$ and $R^5$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=C H—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH=CH—N=CH—, which is attached in any desired direction to the parent structure,
and the remaining of residues $R^1$, $R^2$, $R^3$, $R^4$ and $R^5$, mutually independently, in each case denote H; F; Cl; Br; I; —CF$_3$; —CN; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;
$R^8$ denotes —SF$_5$; —O—CF$_3$; —CF$_3$; tert.-butyl, or —C(CH$_3$)$_2$(CH$_2$OH);
$R^{16}$ and $R^{17}$, mutually independently, in each case denote a residue selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl and (3,3)-dimethylbutyl;
$R^{28}$ denotes F; Cl; Br; I; —CF$_3$; —CN; —NH$_2$ or denotes an alkyl residue selected from the group consisting of methyl, ethyl, n-propyl, isopropyl, n-butyl, sec.-butyl, isobutyl, tert.-butyl and n-pentyl;
$R^{29}$ and $R^{30}$, mutually independently, in each case denote —NH—C(=O)—R$^{31}$; —NH$_2$; —NH—S(=O)$_2$—R$^{32}$; —NH—C(=O)—O—R$^{33}$; —S—R$^{34}$ or denote an alkyl residue selected from the group consisting of methyl, ethyl, n-propyl, isopropyl, n-butyl, sec.-butyl, isobutyl, tert.-butyl, and n-pentyl;
$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;
$R^{43}$ denotes a residue selected from the group consisting of methyl, —CH$_2$—O—CH$_3$, ethyl, n-propyl, n-butyl, sec.-butyl, isobutyl, tert.-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$ and —CH$_2$—CH$_2$—CH$_2$—O—CH$_3$;
or denotes a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl; $R^{62}$, $R^{63}$, $R^{64}$, $R^{65}$, $R^{66}$ and $R^{67}$, mutually independently, in each case denote an alkyl residue selected from the group consisting of —$CF_3$, —$CH_2$—$CF_3$, methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —($CH_2$), —($CH_2$)$_2$ or —($CH_2$)$_3$ group and/or in each case unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec.-butyl, isobutyl, tert.-butyl, —O-phenyl, —O-benzyl, phenyl and benzyl; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Ic,

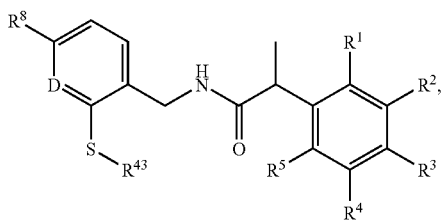

Ic in which
D denotes N or CH;
$R^1$ and $R^2$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}$—C(=O)—$NR^{65}$—; —$NR^{66}$—C(=S)—$NR^{65}$—; —O—$CH_2$—C(=O)—NH—; —O—$CH_2$—O—; —O—$CH_2$—$CH_2$—O—; —O—$CH_2$—$CH_2$—$CH_2$—O—; —O—$CH_2$—$CH_2$—NH—, and —CH=CH—N=CH—, which is attached in any desired direction to the parent structure,
or $R^2$ and $R^3$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH—; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure,
or $R^3$ and $R^4$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—(C=O)—NH—; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure,
or $R^4$ and $R^5$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}$—C(=O)—$NR^{65}$—; —$NR^{66}$—C(=S)—$NR^{65}$—; —O—$CH_2$—C(=O)—NH—; —O—$CH_2$—O—; —$CH_2$—$CH_2$—O—, —O—$CH_2$—$CH_2$—$CH_2$—O—; —O—$CH_2$—$CH_2$—NH—, and —CH=CH—N=CH—, which is attached in any desired direction to the parent structure,
and the remaining residues of $R^1$, $R^2$, $R^3$, $R^4$ and $R^5$, mutually independently, in each case denote H; —$OR^{16}$; —$SR^{17}$; or denote a residue selected from the group consisting of methyl, —$CF_3$, —$CHF_2$, —$CH_2F$, ethyl, n-propyl, isopropyl, n-butyl, sec.-butyl, isobutyl and tert.-butyl;
$R^8$ denotes —$SF_5$; —O—$CF_3$; —$CF_3$; tert.-butyl, or —$C(CH_3)_2(CH_2OH)$;
$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;
$R^{28}$ denotes F; Cl; Br or I;
$R^{29}$ and $R^{30}$, mutually independently, in each case denote —NH—C(=O)—$R^{31}$; —$NH_2$; —NH—S(=O)$_2$—$R^{32}$; —NH—C(=O)—O—$R^{33}$ or —S—$R^{34}$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{43}$ denotes a residue selected from the group consisting of methyl, ethyl, n-propyl, n-butyl, sec.-butyl, isobutyl, tert.-butyl, n-pentyl, 3-pentyl, n-hexyl and (3,3)-dimethylbutyl;

or denotes a residue selected from the group consisting of cyclopropyl, cyclobutyl, cyclopentyl, cyclohexyl and cycloheptyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl;

$R^{62}$, $R^{63}$, $R^{64}$, $R^{65}$, $R^{66}$ and $R^{67}$, mutually independently, in each case denote an alkyl residue selected from the group consisting of methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —(CH$_2$), —(CH$_2$)$_2$ or —(CH$_2$)$_3$ group and/or in each case unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, —O-phenyl, —O-benzyl, phenyl and benzyl; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Ic,

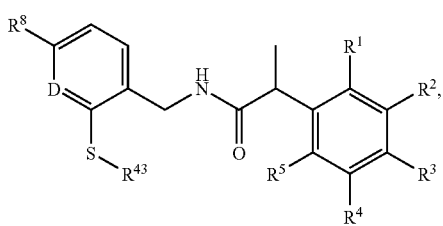

Ic in which
D denotes N or CH;
$R^1$ and $R^2$ together denote a residue selected from the group consisting of —CH=N—NH—; —CH=N—NR$^{71}$—; S—CH=N—; —S—CR$^{29}$=N—; —N=CH—O—, —N=CR$^{30}$—O—, —O—CH$_2$—O—; and —CH=CH—N=CH—, which is attached in any desired direction to the parent structure, or $R^2$ and $R^3$ together denote a residue selected from the group consisting of —CH=N—NH—; —CR$^{28}$=N—NH—; —S—C(=S)—NH—; —O—C(=S)—NH—; —S—C(=O)—NH—; —O—C(=O)—NH—; —S—CH=N—; —S—CR$^{29}$=N—; —N=CH—O—; —N=CR$^{30}$—O—; —N=CH—NH—; —NH—C(=O)—NH—; —NH—C(=S)—NH—; —N=N—NH—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=CH—CH=N—; —CH=CH—CH=N—; —CH=CH—N=CH—; —CH=N—N=CH— and —O—CH$_2$—CH$_2$—NH—, which is attached in any desired direction to the parent structure, or $R^3$ and $R^4$ together denote a residue selected from the group consisting of —CH=N—NH—; —CR$^{28}$=N—NH—; —S—C(=S)—NH—; —O—C(=S)—NH—; —S—C(=O)—NH—; —O—C(=O)—NH—; —S—CH=N—; —S—CR$^{29}$=N—; —N=CH—O—; —N=CR$^{30}$—O—; —N=CH—NH—; —NH—C(=O)—NH—; —NH—C(=S)—NH—; —N=N—NH—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH; —CH$_2$—CH$_2$—C(=O)—NH—; —O—CH$_2$—CH$_2$—O—; —O—CH$_2$—CH$_2$—CH$_2$—O—; —N=CH—CH=N—; —CH=CH—CH=N—; —CH=CH—N=CH—; —CH=N—N=CH— and —O—CH$_2$—CH$_2$—NH—, which is attached in any desired direction to the parent structure, or $R^4$ and $R^5$ together denote a residue selected from the group consisting of —CH=N—NH—; —CH=N—NR$^{71}$—; —S—CH=N—; —S—CR$^{29}$=N—; —N=CH—O—; —N=CR$^{30}$—O—, —O—CH$_2$—O—; and —CH=CH—N=CH—, which is attached in any desired direction to the parent structure, and the remaining residues $R^1$, $R^2$, $R^3$, $R^4$ and $R^5$, mutually independently, in each case denote H; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

$R^8$ denotes —SF$_5$; —O—CF$_3$; —CF$_3$; tert.-butyl, or —C(CH$_3$)$_2$(CH$_2$OH);

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ denotes —NH—C(=O)—R$^{31}$; —NH$_2$; —NH—S(=O)$_2$—R$^{32}$; —NH—C(=O)—O—R$^{33}$ or —S—R$^{34}$;

$R^{30}$ denotes —NH$_2$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{43}$ denotes a residue selected from the group consisting of methyl, ethyl, n-propyl, n-butyl, sec.-butyl, isobutyl, tert.-butyl, n-pentyl, 3-pentyl, n-hexyl and (3,3)-dimethylbutyl;

or denotes a residue selected from the group consisting of cyclopropyl, cyclobutyl, cyclopentyl, cyclohexyl and cycloheptyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl; and $R^{71}$ denotes a phenyl radical, which is capable of being attached via a —(CH$_2$), —(CH$_2$)$_2$ or —(CH$_2$)$_3$ group and/or which may be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, methyl, ethyl, n-propyl, isopropyl, n-butyl, sec.-butyl, isobutyl and tert.-butyl;

in each case optionally in the form of one of the pure stereoisomers thereof, in particular enantiomers or diastereomers, the racemates thereof or in the form of a mixture of stereoisomers, in particular the enantiomers and/or diastereomers, in Preferred compounds are those of the general formula Id,

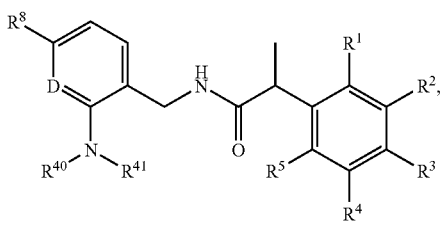

Id in which
D denotes N or CH;
$R^1$ and $R^2$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—; —O—CH$_2$—CH$_2$—CH$_2$—O—; —O—CH$_2$—CH$_2$—NH—, and —CH=CH—N=CH—, which is attached in any desired direction to the parent structure,
or $R^2$ and $R^3$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$—; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure,
or $R^3$ and $R^4$ together denote a residue selected from the group consisting of —CH=N—NH—; —CR$^{28}$=N—NH—; —CH=N—NR$^{62}$—; —CR$^{28}$=N—NR$^{62}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —N=CH—NH—; —N=CH—NR$^{64}$—; —NH—C(=O)—NH—; —NH—C(=S)—NH—; —NR$^{66}$—C(=O)—NR$^{65}$—; —NR$^{66}$—C(=S)—NR$^{65}$—; —N=N—NH—; —N=N—NR$^{67}$—; —O—CH$_2$—C(=O)—NH—; —O—CH$_2$—O—; —CH$_2$—CH$_2$—NH—; —CH$_2$—CH$_2$—CH$_2$—NH; —CH$_2$—(C=O)—NH—; —CH$_2$—CH$_2$—C(=O)—NH—; —O—CH$_2$—CH$_2$—O—; —O—CH$_2$—CH$_2$—CH$_2$—O—; —N=N—CH=CH—; —N=CH—N=CH; —N=CH—CH=N—; —CH=CH—CH=N—; —CH=CH—N=CH—; —CH=N—N=CH—, —N=N—CR$^{68}$=CR$^{69}$—; —N=CR$^{68}$—N=CR$^{69}$—; —N=CR$^{68}$—CR$^{69}$=N—; —CR$^{68}$=CR$^{69}$—CH=N—; —CR$^{68}$=CR$^{69}$—N=CR$^{70}$—; —CR$^{68}$=N—N=CR$^{69}$— and —O—CH$_2$—CH$_2$—NH—, which is attached in any desired direction to the parent structure,
or $R^4$ and $R^5$ together denote a residue selected from the group consisting of —CH=N—NH—; —CH=N—NR$^{71}$—; —S—C(=S)—NH—; —O—C(=S)—NH—; —S—C(=O)—NH—; —O—C(=O)—NH—; —S—C(=S)—NR$^{63}$—; —O—C(=S)—NR$^{63}$—; —S—C(=O)—NR$^{63}$—; —O—C(=O)—NR$^{63}$—; —S—CH=N—; —S—CR$^{29}$=N—; —N=CH—O—; —N=CR$^{30}$—O—; —NH—C(=O)—NH—; —NH—C(=S)—NH—; —NR$^{66}$—C(=O)—NR$^{65}$—; —NR$^{66}$—C(=S)—NR$^{65}$—; —O—CH$_2$—C(=O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH=CH—N=CH—, which is attached in any desired direction to the parent structure,
and the remaining residues of $R^1$, $R^2$, $R^3$, $R^4$ and $R^5$, mutually independently, in each case denote H; F; Cl; Br; I; —CF$_3$; —CN; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;
$R^8$ denotes —SF$_5$; —O—CF$_3$; —CF$_3$; tert.-butyl, or —C(CH$_3$)$_2$(CH$_2$OH);
$R^{16}$ and $R^{17}$, mutually independently, in each case denote a residue selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl and (3,3)-dimethylbutyl;
$R^{28}$ denotes F; Cl; Br; I; —CF$_3$; —CN; —NH$_2$ or denotes an alkyl residue selected from the group consisting of methyl, ethyl, n-propyl, isopropyl, n-butyl, sec.-butyl, isobutyl, tert.-butyl and n-pentyl;
$R^{29}$ and $R^{30}$, mutually independently, in each case denote —NH—C(=O)—R$^{31}$; —NH$_2$; —NH—S(=O)$_2$—R$^{32}$; —NH—C(=O)—O—R$^{33}$; —S—R$^{34}$ or denote an alkyl residue selected from the group consisting of methyl, ethyl, n-propyl, isopropyl, n-butyl, sec.-butyl, isobutyl, tert.-butyl, and n-pentyl;
$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;
$R^{40}$ and $R^{41}$, mutually independently, in each case
denote a residue selected from the group consisting of methyl, —CH$_2$—O—CH$_3$, ethyl, n-propyl, n-butyl, sec.-butyl, isobutyl, tert.-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$ and —CH$_2$—CH$_2$—CH$_2$—O—CH$_3$;
denote a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl; or $R^{40}$ and $R^{41}$ in each case together with the nitrogen atom joining them together as a ring member form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, the heterocycloaliphatic moiety of which may in each case be unsubstituted or substituted with 1, 2, 3, 4 or 5 residues $R^{57}$;

$R^{57}$ denotes —$NHR^{58}$, —$NR^{59}R^{60}$ or denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl;

$R^{58}$, $R^{59}$ and $R^{60}$, mutually independently, in each case denote —C(=O)—$R^{61}$: denote an alkyl residue selected from the group consisting of —$CF_3$, —$CH_2$—$CF_3$, methyl, ethyl, n-propyl, isopropyl, tert.-butyl, n-butyl, sec.-butyl and isobutyl;

or denote a residue selected from the group consisting of phenyl and naphthyl, wherein the residue may in each case be attached via a —($CH_2$)—, —($CH_2$)$_2$— or —($CH_2$)$_3$— group and/or may in each case be unsubstituted or optionally substituted with 1, 2, 3, 4 or 5 substituents mutually independently selected from the group consisting of F, Cl, Br, I, —CN, —$CF_3$, —O—$CH_3$, —O—$C_2H_5$, —O—$CH(CH_3)_2$, —O—$C(CH_3)_3$, methyl, ethyl, n-propyl, isopropyl, n-butyl, sec.-butyl, isobutyl, tert.-butyl and n-pentyl;

$R^{61}$ denotes an alkyl residue selected from the group consisting of —$CF_3$, —$CH_2$—$CF_3$, methyl, ethyl, n-propyl, isopropyl, tert.-butyl, n-butyl, sec.-butyl, and isobutyl;

$R^{62}$, $R^{63}$, $R^{64}$, $R^{65}$, $R^{66}$ and $R^{67}$, mutually independently, in each case denote an alkyl residue selected from the group consisting of —$CF_3$, —$CH_2$—$CF_3$, methyl, ethyl, n-propyl, isopropyl, tert.-butyl, n-butyl, sec.-butyl, and isobutyl; and $R^{71}$ denotes a residue selected from the group consisting of phenyl, naphthyl, thiophenyl, furanyl and pyridinyl, the residue in each case being capable of being attached via a —($CH_2$), —($CH_2$)$_2$ or —($CH_2$)$_3$ group and/or in each case unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—$CH(CH_3)_2$, —O—$C(CH_3)_3$, —$NH_2$, —$NO_2$, —O—$CF_3$, —S—$CF_3$, —SH, —S—$CH_3$, —S—$C_2H_5$, —S—$CH(CH_3)_2$, —S—$C(CH_3)_3$, methyl, ethyl, n-propyl, isopropyl, n-butyl, sec.-butyl, isobutyl, tert.-butyl, —O-phenyl, —O-benzyl, phenyl and benzyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Id,

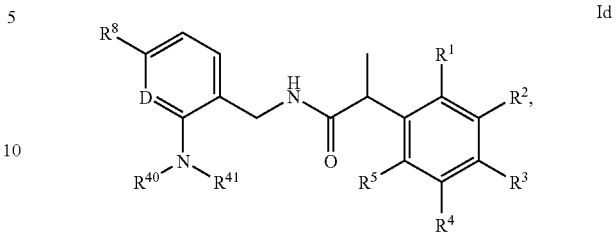

Id in which
D denotes N or CH;
$R^1$ and $R^2$ together denote a residue selected from the group consisting of —CH=N—NH—; —CH=N—$NR^{71}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —NH—C(=O)—NH—; —NH—C(=S)—NH—; —$NR^{66}$—C(=O)—$NR^{65}$—; —$NR^{66}$—C(=S)—$NR^{65}$—; —O—$CH_2$—C(=O)—NH—; —O—$CH_2$—O—; —O—$CH_2$—$CH_2$—O—; —O—$CH_2$—$CH_2$—$CH_2$—O—; —O—$CH_2$—$CH_2$—NH—, and —CH=CH—N=CH—, which is attached in any desired direction to the parent structure, or $R^2$ and $R^3$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH—; —$CH_2$—(C=O)—NH—; —$CH_2$—$CH_2$—C(=O)—NH—; —O—$CH_2$—$CH_2$—O—; —O—$CH_2$—$CH_2$—$CH_2$—O—; —N=N—CH=CH—; —N=CH—N=CH; —N=CH—CH=N—; —CH=CH—CH=N—; —CH=CH—N=CH—; —CH=N—N=CH—, —N=N—$CR^{68}$=$CR^{69}$—; —N=$CR^{68}$—N=$CR^{69}$; —N=$CR^{68}$—$CR^{69}$=N—; —$CR^{68}$=$CR^{69}$—CH=N—; —$CR^{68}$=$CR^{69}$—N=$CR^{70}$—; —$CR^{68}$=N—N=$CR^{69}$— and —O—$CH_2$—$CH_2$—NH—, which is attached in any desired direction to the parent structure, or $R^3$ and $R^4$ together denote a residue selected from the group consisting of —CH=N—NH—; —$CR^{28}$=N—NH—; —CH=N—$NR^{62}$—; —$CR^{28}$=N—$NR^{62}$—; —S—C(=S)—NH—; —O—C(=S)—NH—; —S—C(=O)—NH—; —O—C(=O)—NH—; —S—C(=S)—$NR^{63}$—; —O—C(=S)—$NR^{63}$—; —S—C(=O)—$NR^{63}$—; —O—C(=O)—$NR^{63}$—; —S—CH=N—; —S—$CR^{29}$=N—; —N=CH—O—; —N=$CR^{30}$—O—; —N=CH—NH—; —N=CH—$NR^{64}$—; —NH—C(=O)—NH—; —NH—C(=S)—NH—; —$NR^{66}$—C(=O)—$NR^{65}$—; —$NR^{66}$—C(=S)—$NR^{65}$—; —N=N—NH—; —N=N—$NR^{67}$—; —O—$CH_2$—C(=O)—NH—; —O—$CH_2$—O—; —$CH_2$—$CH_2$—NH—; —$CH_2$—$CH_2$—$CH_2$—NH; —$CH_2$—

(C═O)—NH; —CH$_2$—CH$_2$—C(═O)—NH—; —O—CH$_2$—CH$_2$—O—; —O—CH$_2$—CH$_2$—CH$_2$—O—; —N═N—CH═CH—; —N═CH—N═CH; —N═CH—CH═N—; —CH═CH—CH═N—; —CH═CH—N═CH—; —CH═N—N═CH—, —N═N—CR$^{68}$═CR$^{69}$—; —N═CR$^{68}$—N═CR$^{69}$; —N═CR$^{68}$—CR$^{69}$═N—; —CR$^{68}$═CR$^{69}$—CH═N—; —CR$^{68}$═CR$^{69}$—N═CR$^{70}$—; —CR$^{68}$═N—N═CR$^{69}$— and —O—CH$_2$—CH$_2$—NH—, which is attached in any desired direction to the parent structure, or R$^4$ and R$^5$ together denote a residue selected from the group consisting of —CH═N—NH—; —CH═N—NR$^{71}$—; —S—C(═S)—NH—; —O—C(═S)—NH—; —S—C(═O)—NH—; —O—C(═O)—NH—; —S—C(═S)—NR$^{63}$—; —O—C(═S)—NR$^{63}$—; —S—C(═O)—NR$^{63}$—; —O—C(═O)—NR$^{63}$—; —S—CH═N—; —S—CR$^{29}$═N—; —N═CH—O—; —N═CR$^{30}$—O—; —NH—C(═O)—NH—; —NH—C(═S)—NH—; —NR$^{66}$—C(═O)—NR$^{65}$—; —NR$^{66}$—C(═S)—NR$^{65}$—; —O—CH$_2$—C(═O)—NH—; —O—CH$_2$—O—; —O—CH$_2$—CH$_2$—O—, —O—CH$_2$—CH$_2$—CH$_2$—O—; —O—CH$_2$—CH$_2$—NH—, and —CH═CH—N═CH—, which is attached in any desired direction to the parent structure, and the remaining residues of R$^1$, R$^2$, R$^3$, R$^4$ and R$^5$, mutually independently, in each case denote H; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

R$^8$ denotes —SF$_5$; —O—CF$_3$; —CF$_3$; tert.-butyl, or —C(CH$_3$)$_2$(CH$_2$OH);

R$^{16}$ and R$^{17}$, mutually independently, in each case denote a residue selected from the group consisting of methyl, ethyl, n-propyl, isopropyl, n-butyl, sec.-butyl, isobutyl, tert.-butyl, and n-pentyl;

R$^{28}$ denotes F; Cl; Br or I;

R$^{29}$ and R$^{30}$, mutually independently, in each case denote —NH—C(═O)—R$^{31}$; —NH$_2$; —NH—S(═O)$_2$—R$^{32}$; —NH—C(═O)—O—R$^{33}$ or —S—R$^{34}$;

R$^{31}$, R$^{32}$, R$^{33}$ and R$^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

R$^{40}$ and R$^{41}$ in each case together with the nitrogen atom joining them together as a ring member form a residue selected from the group consisting of pyrrolidinyl, piperidinyl, piperazinyl, morpholinyl and azepanyl, the heterocycloaliphatic moiety of which may in each case be unsubstituted or substituted with 1, 2, 3, 4 or 5 residues R$^{57}$;

R$^{57}$ denotes an alkyl residue selected from the group consisting of methyl, ethyl, n-propyl, isopropyl, tert.-butyl, n-butyl, sec.-butyl, and isobutyl;

R$^{62}$, R$^{63}$, R$^{64}$, R$^{65}$, R$^{66}$ and R$^{67}$, mutually independently, in each case denote an alkyl residue selected from the group consisting of methyl, ethyl, n-propyl, isopropyl, tert.-butyl, n-butyl, sec.-butyl, and isobutyl; and R$^{71}$ denotes a residue selected from the group consisting of phenyl, naphthyl, thiophenyl, furanyl and pyridinyl, the residue in each case being capable of being attached via a —(CH$_2$), —(CH$_2$)$_2$ or —(CH$_2$)$_3$ group and/or in each case unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, —O-phenyl, —O-benzyl, phenyl and benzyl; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Id,

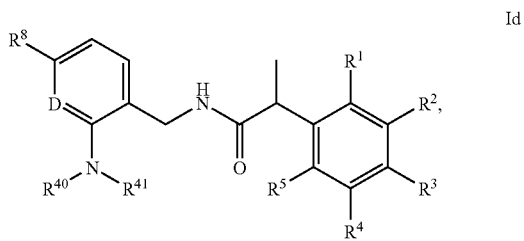

in which
D denotes N or CH;

R$^1$ and R$^2$ together denote a residue selected from the group consisting of —CH═N—NH—; —CH═N—NR$^{71}$—; S—CH═N—; —S—CR$^{29}$═N—; —N═CH—O—, —N═CR$^{30}$—O—, —O—CH$_2$—O—; and —CH═CH—N═CH—, which is attached in any desired direction to the parent structure, or R$^2$ and R$^3$ together denote a residue selected from the group consisting of —CH═N—NH—; —CR$^{28}$═N—NH—; —S—C(═S)—NH—; —O—C(═S)—NH—; —S—C(═O)—NH—; —O—C(═O)—NH—; —S—CH═N—; —S—CR$^{29}$═N—; —N═CH—O—; —N═CR$^{30}$—O—; —N═CH—NH—; —NH—C(═O)—NH—; —NH—C(═S)—NH—; —N═N—NH—; —O—CH$_2$—C(═O)—NH—; —O—CH$_2$—O—; —CH$_2$—CH$_2$—NH—; —CH$_2$—CH$_2$—CH$_2$—NH; —CH$_2$—(C═O)—NH; —CH$_2$—CH$_2$—C(═O)—NH—; —O—CH$_2$—CH$_2$—O—; —O—CH$_2$—CH$_2$—CH$_2$—O—; —N═CH—CH═N—; —CH═CH—CH═N—; —CH═CH—N═CH—; —CH═N—N═CH— and —O—CH$_2$—CH$_2$—NH—, which is attached in any desired direction to the parent structure, or R$^3$ and R$^4$ together denote a residue selected from the group consisting of —CH═N—NH—; —CR$^{28}$═N—NH—; —S—C(═S)—NH—; —O—C(═S)—NH—; —S—C(═O)—NH—; —O—C(═O)—NH—; —S—CH═N—; —S—CR$^{29}$═N—; —N═CH—O—; —N═CR$^{30}$—O—; —N═CH—NH—; —NH—C(═O)—NH—; —NH—C(═S)—NH—; —N═N—NH—; —O—CH$_2$—C(═O)—NH—; —O—CH$_2$—O—; —CH$_2$—CH$_2$—NH—; —CH$_2$—CH$_2$—CH$_2$—NH; —CH$_2$—(C═O)—NH; —CH$_2$—CH$_2$—C(═O)—NH—; —O—CH$_2$—CH$_2$—O—; —O—CH$_2$—CH$_2$—CH$_2$—O—; —N═CH—CH═N—; —CH═CH—CH═N—; —CH═CH—N═CH—; —CH═N—N═CH— and —O—CH$_2$—CH$_2$—NH—, which is attached in any desired direction to the parent structure, or R$^4$ and R$^5$ together denote a residue selected from the group consisting of —CH═N—NH—; —CH═N—NR$^{71}$—; —S—CH═N—; —S—CR$^{29}$═N—; —N═CH—O—; —N═CR$^{30}$—O—, —O—CH$_2$—O—; and —CH═CH—N═CH—, which is attached in any desired direction to the parent structure, and the remaining residues $R^1$, $R^2$, $R^3$, $R^4$ and $R^5$, mutually independently, in each case denote H; —$OR^{16}$; —$SR^{17}$; or denote a residue selected from the group consisting of methyl, —$CF_3$, —$CHF_2$, —$CH_2F$, ethyl, n-propyl, isopropyl, n-butyl, sec.-butyl, isobutyl and tert.-butyl;

$R^8$ denotes —$SF_5$; —O—$CF_3$; —$CF_3$; tert.-butyl, or —$C(CH_3)_2(CH_2OH)$;

$R^{16}$ and $R^{17}$, mutually independently, in each case denote a residue selected from the group consisting of methyl, ethyl, n-propyl, isopropyl, n-butyl, sec.-butyl, isobutyl, tert.-butyl, and n-pentyl;

$R^{28}$ denotes F; Cl; Br or I;

$R^{29}$ denotes —NH—C(=O)—$R^{31}$; —$NH_2$; —NH—S(=O)$_2$—$R^{32}$; —NH—C(=O)—O—$R^{33}$ or —S—$R^{34}$;

$R^{30}$ denotes —$NH_2$;

$R^{31}$, $R^{32}$, $R^{33}$ and $R^{34}$, mutually independently, in each case denote an alkyl residue selected from the group consisting of methyl, ethyl, n-propyl, isopropyl, n-butyl, sec.-butyl, isobutyl, tert.-butyl, and n-pentyl;

$R^{40}$ and $R^{41}$ in each case together with the nitrogen atom joining them together as a ring member form a residue selected from the group consisting of pyrrolidinyl, piperidinyl, piperazinyl, morpholinyl and azepanyl, the heterocycloaliphatic moiety of which may in each case be unsubstituted or substituted with 1, 2, 3, 4 or 5 residues $R^{57}$;

$R^{57}$ denotes an alkyl residue selected from the group consisting of methyl, ethyl, n-propyl, isopropyl, tert.-butyl, n-butyl, sec.-butyl, and isobutyl; and $R^{71}$ denotes a phenyl radical, which is capable of being attached via a —(CH$_2$), —(CH$_2$)$_2$ or —(CH$_2$)$_3$ group and/or which may be unsubstituted or optionally substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, methyl, ethyl, n-propyl, isopropyl, n-butyl, sec.-butyl, isobutyl and tert.-butyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Still more preferred are compounds of the general formulae I, Ia, Ib, Ic, and Id selected from the group consisting of

[1] 2-(benzo[d]oxazol-5-yl)-N-(4-tert.-butylbenzyl)propanamide,
[2] 2-(benzo[d]oxazol-6-yl)-N-(4-tert.-butylbenzyl)propanamide,
[3] 2-(benzo[d]oxazol-7-yl)-N-(4-tert.-butylbenzyl)propanamide,
[4] N-(4-tert.-butylbenzyl)-2-(2-oxo-2,3-dihydro-1H-benzo[d]imidazol-5-yl)-propanamide,
[5] N-(4-tert.-butylbenzyl)-2-(3-oxo-3,4-dihydro-2H-benzo[b][1,4]oxazin-7-yl)-propanamide,
[6] N-(4-tert.-butylbenzyl)-2-(3-oxo-3,4-dihydro-2H-benzo[b][1,4]oxazin-6-yl)-propanamide,
[7] N-(4-tert.-butylbenzyl)-2-(7-methoxybenzo[d]oxazol-5-yl)propanamide,
[8] 2-(benzo[d]oxazol-4-yl)-N-(4-tert.-butylbenzyl)propanamide,
[9] N-(4-tert.-butylbenzyl)-2-(2,3-dihydrobenzo[b][1,4]dioxin-6-yl)propanamide,
[10] N-(4-tert.-butylbenzyl)-2-(2-thioxo-2,3-dihydro-1H-benzo[d]imidazol-5-yl)-propanamide,
[11] N-(4-tert.-butylbenzyl)-2-(quinoxalin-6-yl)propanamide,
[12] 2-(1H-benzo[d][1,2,3]triazol-5-yl)-N-(4-tert.-butylbenzyl)propanamide,
[13] 2-(1H-benzo[d]imidazol-5-yl)-N-((2-(4-methylpiperidin-1-yl)-6-(trifluoromethyl)-pyridin-3-yl)methyl)propanamide,
[14] 2-(1H-benzo[d]imidazol-5-yl)-N-(4-tert.-butylbenzyl)propanamide,
[15] 2-(1H-benzo[d][1,2,3]triazol-5-yl)-N-((2-(4-methylpiperidin-1-yl)-6-(trifluoromethyl)pyridin-3-yl)methyl)propanamide,
[16] N-(4-tert.-butylbenzyl)-2-(2-oxo-2,3-dihydrobenzo[d]oxazol-6-yl)propanamide,
[17] N-(4-tert.-butylbenzyl)-2-(2-thioxo-2,3-dihydrobenzo[d]oxazol-5-yl)propanamide,
[18] 2-(2-aminobenzo[d]oxazol-6-yl)-N-(4-tert.-butylbenzyl)propanamide,
[19] N-(4-tert.-butylbenzyl)-2-(2-thioxo-2,3-dihydrobenzo[d]oxazol-6-yl)-propanamide,
[20] N-(4-tert.-butylbenzyl)-2-(3,4-dihydro-2H-benzo[b][1,4]oxazin-7-yl)-propanamide,
[21] N-(4-tert.-butylbenzyl)-2-(quinolin-6-yl)propanamide,
[22] 2-(1H-benzo[d][1,2,3]triazol-5-yl)-N-((2-butoxy-6-tert.-butylpyridin-3-yl)methyl)-propanamide,
[23] 2-(1H-benzo[d]imidazol-5-yl)-N-((2-butoxy-6-tert.-butylpyridin-3-yl)methyl)-propanamide,
[24] 2-(1H-benzo[d][1,2,3]triazol-5-yl)-N-((6-tert.-butyl-2-(4-methylpiperidin-1-yl)-pyridin-3-yl)methyl)propanamide,
[25] 2-(1H-benzo[d]imidazol-5-yl)-N-((6-tert.-butyl-2-(4-methylpiperidin-1-yl)pyridin-3-yl)methyl)propanamide,
[26] 2-(1H-benzo[d][1,2,3]triazol-5-yl)-N-((6-tert.-butyl-2-(cyclohexylthio)pyridin-3-yl)-methyl)propanamide,
[27] 2-(1H-benzo[d]imidazol-5-yl)-N-((6-tert.-butyl-2-(cyclohexylthio)pyridin-3-yl)-methyl)propanamide,
[28] N-((2-butoxy-6-tert.-butylpyridin-3-yl)methyl)-2-(2-oxo-2,3-dihydrobenzo[d]thiazol-6-yl)propanamide,
[29] N-(2-butoxy-6-tert.-butyl-pyridin-3-ylmethyl)-2-(2-ethylsulfanyl-benzothiazol-6-yl)-propionamide,
[30] N-((2-(4-methylpiperidin-1-yl)-6-(trifluoromethyl)pyridin-3-yl)methyl)-2-(2-(methylthio)benzo[d]thiazol-6-yl)propanamide,
[31] N-((2-butoxy-6-tert.-butylpyridin-3-yl)methyl)-2-hydroxy-2-(2-(methylthio)benzo[d]thiazol-6-yl)propanamide,
[32] N-((2-(4-methylpiperidin-1-yl)-6-(trifluoromethyl)pyridin-3-yl)methyl)-2-(2-thioxo-2,3-dihydrobenzo[d]thiazol-6-yl)propanamide,
[33] N-((6-tert.-butyl-2-(4-methylpiperidin-1-yl)pyridin-3-yl)methyl)-2-(2-thioxo-2,3-dihydrobenzo[d]thiazol-6-yl)propanamide,
[34] N-((6-tert.-butyl-2-(4-methylpiperidin-1-yl)pyridin-3-yl)methyl)-2-(2-(methylthio)benzo[d]thiazol-6-yl)propanamide,
[35] 2-(2-aminobenzo[d]oxazol-5-yl)-N-((2-(4-methylpiperidin-1-yl)-6-(trifluoromethyl)pyridin-3-yl)methyl)propanamide,
[36] 2-(2-acetamidobenzo[d]thiazol-6-yl)-N-(4-tert.-butylbenzyl)propanamide,
[37] 2-(2-acetamidobenzo[d]thiazol-6-yl)-N-((2-(4-methylpiperidin-1-yl)-6-(trifluoromethyl)pyridin-3-yl)methyl)propanamide,
[38] 2-(2-aminobenzo[d]thiazol-6-yl)-N-((2-(4-methylpiperidin-1-yl)-6-(trifluoromethyl)pyridin-3-yl)methyl)propanamide,
[39] N-((2-(4-methylpiperidin-1-yl)-6-(trifluoromethyl)pyridin-3-yl)methyl)-2-(2-(methylsulfonamido)benzo[d]thiazol-6-yl)propanamide,

[40] tert.-butyl 6-(1-((2-(4-methylpiperidin-1-yl)-6-(trifluoromethyl)pyridin-3-yl)methylamino)-1-oxopropan-2-yl)benzo[d]thiazol-2-ylcarbamate,
[41] 2-(2-acetamidobenzo[d]thiazol-6-yl)-N-((2-(4-methylpiperidin-1-yl)-6-(trifluoromethyl)pyridin-3-yl)methyl)propanamide,
[42] 2-(2-acetamidobenzo[d]thiazol-5-yl)-N-((2-(4-methylpiperidin-1-yl)-6-(trifluoromethyl)pyridin-3-yl)methyl)propanamide,
[43] 2-(2-acetamidobenzo[d]thiazol-4-yl)-N-((2-(4-methylpiperidin-1-yl)-6-(trifluoromethyl)pyridin-3-yl)methyl)propanamide,
[44] 2-(1H-indazol-5-yl)-N-((2-(4-methylpiperidin-1-yl)-6-(trifluoromethyl)pyridin-3-yl)-methyl)propanamide,
[45] 2-(3-fluoro-1H-indazol-5-yl)-N-((2-(4-methylpiperidin-1-yl)-6-(trifluoromethyl)-pyridin-3-yl)methyl)propanamide,
[46] N-((2-butoxy-6-tert.-butylpyridin-3-yl)methyl)-2-(1H-indazol-5-yl)propanamide,
[48] N-((6-tert.-butyl-2-(cyclohexylthio)pyridin-3-yl)methyl)-2-(1H-indazol-5-yl)-propanamide
[49] N-(2-butoxy-6-tert.-butyl-pyridin-3-ylmethyl)-2-(2-thioxo-2,3-dihydro-benzothiazol-6-yl)-propionamide;
[50] tert.-butyl 6-(1-(4-tert.-butylbenzylamino)-1-oxopropan-2-yl)benzo[d]thiazol-2-yl-carbamate,
[51] 2-(2-aminobenzo[d]thiazol-6-yl)-N-(4-tert.-butylbenzyl)propanamide,
[52] 2-(2-aminobenzo[d]thiazol-6-yl)-N-((2-(4-methylpiperidin-1-yl)-6-(trifluoromethyl)pyridin-3-yl)methyl)propanamide,
[53] 2-(2-acetamidobenzo[d]thiazol-6-yl)-N-((6-tert.-butyl-2-(4-methylpiperidin-1-yl)pyridin-3-yl)methyl)propanamide and
[54] tert.-butyl 6-(1-((2-(4-methylpiperidin-1-yl)-6-(trifluoromethyl)pyridin-3-yl)methylamino)-1-oxopropan-2-yl)benzo[d]thiazol-2-ylcarbamate;
[55] tert-butyl 6-(1-((6-tert-butyl-2-(4-methylpiperidin-1-yl)pyridin-3-yl)methylamino)-1-oxopropan-2-yl)benzo[d]thiazol-2-ylcarbamate;
[56] 2-(2-aminobenzo[d]thiazol-6-yl)-N-((6-tert-butyl-2-(4-methylpiperidin-1-yl)pyridin-3-yl)methyl)propanamide;
[57] N-(4-tert-butylbenzyl)-2-(2-(methylsulfonamid)benzo[d]thiazol-6-yl)propanamide;
[58] 2-(2,3-dihydrobenzo[b][1,4]dioxin-6-yl)-N-((2-(4-methylpiperidin-1-yl)-6-(trifluoromethyl)pyridin-3-yl)methyl)acetamide;
[59] N-((2-(cyclohexylthio)-6-(trifluoromethyl)pyridin-3-yl)methyl)-2-(2,3-dihydrobenzo[b][1,4]dioxin-6-yl)acetamide;
[60] 2-(benzo[d][1,3]dioxol-5-yl)-N-((2-(4-methylpiperidin-1-yl)-6-(trifluoromethyl)pyridin-3-yl)methyl)propanamide;
[61] 2-(benzo[d][1,3]dioxol-4-yl)-N-((2-(4-methylpiperidin-1-yl)-6-(trifluoromethyl)pyridin-3-yl)methyl)propanamide;
[62] 2-(2,3-dihydrobenzo[b][1,4]dioxin-6-yl)-N-((2-(4-methylpiperidin-1-yl)-6-(trifluoromethyl)pyridin-3-yl)methyl)propanamide;
[63] 2-(2,3-dihydrobenzo[b][1,4]dioxin-5-yl)-N-((2-(4-methylpiperidin-1-yl)-6-(trifluoromethyl)pyridin-3-yl)methyl)propanamide;
[64] 2-(Isochinolin-7-yl)-N-((2-(4-methylpiperidin-1-yl)-6-(trifluormethyl)pyridin-3-yl)methyl)propanamid; [65] 2-(isoquinolin-6-yl)-N-((2-(4-methylpiperidin-1-yl)-6-(trifluoromethyl)pyridin-3-yl)methyl)propanamide;
[66] N-((2-(4-methylpiperidin-1-yl)-6-(trifluoromethyl)pyridin-3-yl)methyl)-2-(quinoline-6-yl)propanamide;
[67] N-((2-(4-methylpiperidin-1-yl)-6-(trifluoromethyl)pyridin-3-yl)methyl)-2-(chinoxalin-6-yl)propanamid;
[68] N-((2-(4-methylpiperidin-1-yl)-6-(trifluoromethyl)pyridin-3-yl)methyl)-2-(chinazolin-6-yl)propanamid;
[69] 2-(1H-indazol-5-yl)-N-(2-(4-methylpiperidin-1-yl)-4-(trifluoromethyl)benzyl)propanamide;
[70] 2-(1H-indazol-4-yl)-N-((2-(4-methylpiperidin-1-yl)-6-(trifluoromethyl)pyridin-3-yl)methyl)propanamide;
[71] 2-(1H-indazol-6-yl)-N-((2-(4-methylpiperidin-1-yl)-6-(trifluoromethyl)pyridin-3-yl)methyl)propanamide;
[72] 2-(1H-indazol-7-yl)-N-((2-(4-methylpiperidin-1-yl)-6-(trifluoromethyl)pyridin-3-yl)methyl)propanamide;
[73] 2-(1-(2-Fluorphenyl)-1H-indazol-4-yl)-N-((2-(4-methylpiperidin-1-yl)-6-(trifluoromethyl)pyridin-3-yl)methyl)propanamide;
[74] 2-(indolin-5-yl)-N-((2-(4-methylpiperidin-1-yl)-6-(trifluoromethyl)pyridin-3-yl)methyl)propanamide;
[75] N-((2-(4-methylpiperidin-1-yl)-6-(trifluoromethyl)pyridin-3-yl)methyl)-2-(1,2,3,4-tetrahydrochinolin-6-yl)propanamide;
[76] N-((2-(4-methylpiperidin-1-yl)-6-(trifluoromethyl)pyridin-3-yl)methyl)-2-(2-oxoindolin-5-yl)propanamide, and
[77] N-((2-(4-methylpiperidin-1-yl)-6-(trifluoromethyl)pyridin-3-yl)methyl)-2-(2-oxo-1,2,3,4-tetrahydrochinolin-6-yl)propanamide, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

In addition, compounds according to the invention of the general formulae I, Ia, Ib, Ic, and Id, may be preferred which in the FLIPR assay with CHO K1 cells, which have been transfected with the human VR1 gene, in a concentration of less than 2000 nM, preferably of less than 1000 nM, particularly preferably of less than 300 nM, very particularly preferably of less than 100 nM, still more preferably of less than 75 nM, further preferably of less than 50 nM and most preferably of less than 10 nM, bring about a 50 percent displacement of capsaicin, which is present in a concentration of 100 nM. In this FLIPR assay, the influx of $Ca^{2+}$ is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA) as described below.

The present invention also provides a method for producing compounds of the above-stated general formula I, in accordance with which at least one compound of the general formula II,

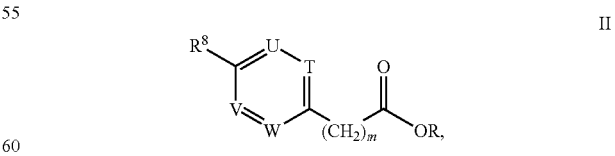

in which $R^8$, U, T, V, and W have the above-stated meanings, m denotes 0, 1, 2 or 3 and R denotes hydrogen or denotes a linear or branched $C_{1-6}$ alkyl residue, is reacted in a reaction medium, in the presence of at least one reducing agent, preferably in the presence of at least one reducing agent selected from the group consisting of sodium hydride, sodium, potassium hydride, lithium aluminium hydride, sodium borohydride and di(isobutyl)aluminium hydride
to yield at least one compound of the general formula III,

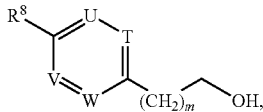

in which $R^8$, U, T, V and W have the above-stated meaning and m denotes 0, 1, 2 or 3 and said compound is optionally purified and/or isolated,
and at least one compound of the general formula III is reacted in a reaction medium in the presence of diphenylphosphoryl azide or in the presence of $HN_3$ to yield at least one compound of the general formula IV,

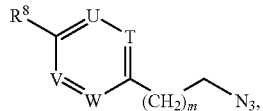

in which $R^8$, U, T, V and W have the above-stated meaning and m denotes 0, 1, 2 or 3 and said compound is optionally purified and/or isolated,
and at least one compound of the general formula IV is reacted in a reaction medium in the presence of at least one reducing agent, preferably in the presence of at least one reducing agent selected from the group consisting of sodium hydride, potassium hydride, lithium aluminium hydride, sodium borohydride and di(isobutyl)aluminium hydride
or in a reaction medium in the presence of a catalyst, preferably in the presence of a catalyst based on platinum or palladium, particularly preferably in the presence of palladium on carbon, and in the presence of hydrogen or in the presence of hydrazine
or in a reaction medium in the presence of triphenylphosphine to yield at least one compound of the general formula V,

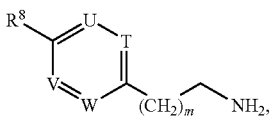

in which $R^8$, U, T, V and W have the above-stated meaning and m denotes 0, 1, 2 or 3 and said compound is optionally purified and/or isolated,
or at least one compound of the general formula VI,

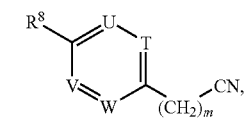

in which $R^8$, U, T, V, and W have the above-stated meanings and m denotes 0, 1, 2 or 3, is reacted in a reaction medium in the presence of at least one catalyst, preferably in the presence of at least one catalyst based on palladium or platinum, particularly preferably in the presence of palladium on carbon, under a hydrogen atmosphere, optionally in the presence of at least one acid, preferably in the presence of hydrochloric acid,
or in the presence of at least one reducing agent selected from the group consisting of $BH_3.S(CH_3)_2$, lithium aluminium hydride and sodium borohydride, optionally in the presence of $NiCl_2$,
to yield at least one compound of the general formula V, optionally in the form of a corresponding salt, preferably in the form of a corresponding hydrochloride, and said compound is optionally purified and/or isolated,
and at least one compound of the general formula V is reacted with at least one compound of the general formula VII,

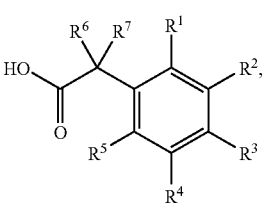

in which $R^1$, $R^2$, $R^3$, $R^4$, $R^5$, $R^6$ and $R^7$ have the above-stated meanings, in a reaction medium, optionally in the presence of at least one suitable coupling agent, optionally in the presence of at least one base,
or with at least one compound of the general formula VIII,

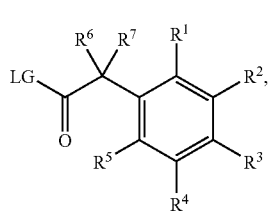

in which $R^1$, $R^2$, $R^3$, $R^4$, $R^5$, $R^6$ and $R^7$ have the above-stated meanings and LG denotes a leaving group, preferably a chlorine or bromine atom, in a reaction medium, optionally in the presence of at least one base, to yield at least one compound of the general formula I,

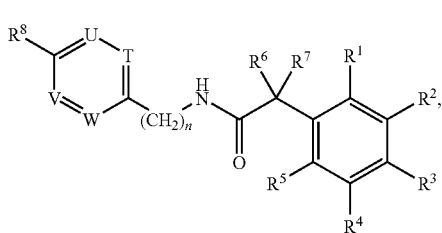

in which T, U, V, W, $R^1$, $R^2$, $R^3$, $R^4$, $R^5$, $R^6$, $R^7$ and $R^8$ have the above-stated meanings and n denotes 1, 2, 3 or 4 and said compound is optionally purified and/or isolated.
The present invention also provides a method for producing compounds of the above-stated general formula I, in accordance with which at least one compound of the general formula X,

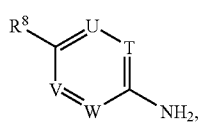

in which $R^8$, U, T, V, and W have the above-stated meanings, is reacted with at least one compound of the general formula VIII,

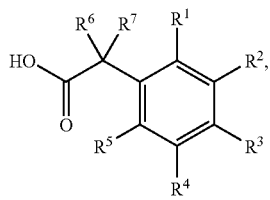

in which $R^1$, $R^2$, $R^3$, $R^4$, $R^5$, $R^6$ and $R^7$ have the above-stated meanings, in a reaction medium, optionally in the presence of at least one suitable coupling agent, optionally in the presence of at least one base,
or with at least one compound of the general formula VIII,

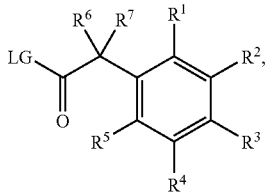

in which $R^1$, $R^2$, $R^3$, $R^4$, $R^5$, $R^6$ and $R^7$ have the above-stated meanings and LG denotes a leaving group, preferably a chlorine or bromine atom, in a reaction medium, optionally in the presence of at least one base, to yield at least one compound of the general formula Im,

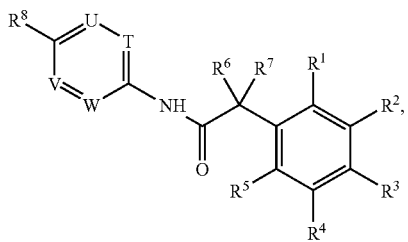

in which T, U, V, W, $R^1$, $R^2$, $R^3$, $R^4$, $R^5$, $R^6$, $R^7$ and $R^8$ have the above-stated meanings, and said compound is optionally purified and/or isolated.

The reaction of compounds of the above-stated general formulae V or X with carboxylic acids of the above-stated general formula VII to yield compounds of the above-stated general formula I or Im preferably proceeds in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N-(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of −70° C. to 100° C.

Alternatively, the reaction of compounds of the above-stated general formulae V or X with carboxylic acid derivatives of the above-stated general formula VIII, in which LG denotes a leaving group, preferably a chlorine or bromine atom, to yield compounds of the above-stated general formulae Ih or Im proceeds in a reaction medium preferably selected from the group consisting of diethyl ether, tetrahydrofuran, acetonitrile, methanol, ethanol, dimethylformamide, dichloromethane and corresponding mixtures, optionally in the presence of an organic base or inorganic base, preferably selected from the group consisting of triethylamine, dimethylaminopyridine, pyridine and diisopropylamine, at temperatures of −70° C. to 100° C.

The compounds of the above-stated formulae II, III, IV, V, X, VI, VII and VIII are in each case commercially obtainable and may also be produced using conventional methods known to a person skilled in the art.

The synthesis method for compounds of the general formula VII may be found in the document "4-(Methylsulfonylamino)phenyl analogues as vanilloid antagonist showing excellent analgesic activity and the pharmaceutical compositions comprising the same" by J. W. Lee et al. [WO 2005/003084-A1]. The corresponding parts of the reference are hereby deemed to be part of the disclosure.

The above-described reactions may in each case be performed under conventional conditions familiar to a person skilled in the art, for example with regard to pressure or the sequence of addition of the components. Optimum control of the process under the respective conditions may optionally be established by the person skilled in the art by simple preliminary testing. The intermediate and final products obtained from the above-described reactions may in each case, if desired and/or necessary, be purified and/or isolated using conventional methods known to a person skilled in the art. Suitable purification methods are, for example, extraction methods and chromatographic methods such as column chromatography or preparative chromatography. All the above-described method steps and in each case also the purification and/or isolation of intermediate or final products may be performed in part or entirely under an inert gas atmosphere, preferably under a nitrogen atmosphere.

The substituted compounds according to the invention of the above-stated general formulae I, Ia, Ib, Ic and Id, hereinafter designated only as compounds of the general formula I, and corresponding stereoisomers may be isolated both in the form of the free bases thereof, the free acids thereof and in the form of corresponding salts, in particular physiologically acceptable salts.

The free bases of the particular substituted compounds according to the invention of the above-stated general formula I and corresponding stereoisomers may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the respective substituted compounds of the above-stated general formula I and corresponding stereoisomers may likewise be converted into the corresponding physiologically acceptable salts with the free acid or a salt of a sugar substitute, such as for example saccharin, cyclamate or acesulfame.

The free acids of the substituted compounds of the above-stated general formula I and corresponding stereoisomers may correspondingly be converted into the corresponding physiologically acceptable salts by reaction with a suitable base. Examples which may be mentioned are alkali metal salts, alkaline earth metal salts or ammonium salts $NH_xR_{4-x}]^+$, in which x=0, 1, 2, 3 or 4 is and R denotes a linear or branched $C_{1-4}$ alkyl residue.

The substituted compounds according to the invention of the above-stated general formula I and corresponding stereoisomers may optionally, like the corresponding acids, the corresponding bases or salts of these compounds, also be obtained in the form of the solvates thereof, preferably in the form of the hydrates thereof, by conventional methods known to a person skilled in the art.

If the substituted compounds according to the invention of the above-stated general formula I are obtained after the production thereof in the form of a mixture of the stereoisomers thereof, preferably in the form of the racemates thereof or other mixtures of their various enantiomers and/or diastereomers, these may be separated and optionally isolated by conventional methods known to a person skilled in the art. Examples are chromatographic separation methods, in particular liquid chromatography methods at standard pressure or at elevated pressure, preferably MPLC and HPLC methods, and fractional crystallisation methods. Individual enantiomers, for example diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted compounds according to the invention of the above-stated general formula I and corresponding stereoisomers as well as in each case the corresponding acids, bases, salts and solvates are toxicologically safe and are therefore suitable as pharmaceutical active ingredients in medicaments.

The present invention accordingly also provides a medicament containing at least one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

These medicaments according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation.

The medicaments according to the invention are likewise preferably suitable for the prevention and/or treatment of disorders and/or diseases, which are mediated at least in part by vanilloid receptors 1.

The medicament according to the invention is preferably suitable for the treatment and/or prevention of one or more diseases selected from the group consisting of pain selected from the group consisting of acute pain, chronic pain, neuropathic pain and visceral pain; joint pain; hyperalgesia; allodynia; causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhoea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia; and/or for inhibiting undesired side-effects, preferably selected from the group consisting of hyperthermia, high blood pressure and constriction of bronchial tubes, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

The medicament according to the invention is particularly preferably suitable for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

The medicament according to the invention is very particularly preferably suitable for the treatment and/or prevention of pain, preferably of pain selected from the group consisting of acute pain, chronic pain, neuropathic pain and visceral pain, and/or urinary incontinence.

The present invention also provides the use of at least one compound according to the invention and optionally one or more pharmaceutically acceptable auxiliary substances for the production of a medicament for vanilloid receptor 1-(VR1/TRPV1) regulation, preferably for vanilloid receptor 1-(VR1/TRPV1) inhibition and/or for vanilloid receptor 1-(VR1/TRPV1) stimulation.

It is preferred to use at least one substituted compound according to the invention and optionally one or more pharmaceutically acceptable auxiliary substances for the production of a medicament for the prevention and/or treatment of disorders or diseases which are mediated at least in part by vanilloid receptors 1.

It is particularly preferred to use at least one compound according to the invention and optionally one or more pharmaceutically acceptable auxiliary substances for the production of a medicament for the treatment and/or prevention of one or more diseases selected from the group consisting of pain, preferably of pain selected from the group consisting of acute pain, chronic pain, neuropathic pain and visceral pain and joint pain.

It is particularly preferred to use at least one compound according to the invention and optionally one or more pharmaceutically compatible auxiliary substances for the production of a medicament for the treatment and/or prevention of one or more diseases selected from the group consisting of hyperalgesia; allodynia causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhoea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia; and/or for inhibiting undesired side-effects, preferably selected from the group consisting of hyperthermia, high blood pressure and constriction of bronchial tubes, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

It is very particularly preferred to use at least one substituted compound according to the invention and optionally one or more pharmaceutically acceptable auxiliary substances for the production of a medicament for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

It is still further preferred to use at least one substituted compound according to the invention and optionally one or more pharmaceutically acceptable auxiliary substances for the production of a medicament for the treatment and/or prevention of pain, preferably selected from the group consisting of acute pain, chronic pain, neuropathic pain and visceral pain, and/or urinary incontinence.

The medicament according to the invention is suitable for administration to adults and children including small children and babies.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted compound of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may for example be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. The substituted compounds according to the invention used in the medicament according to the invention in a depot in dissolved form or in a dressing, optionally with the addition of skin penetration promoters, are suitable percutaneous administration preparations. Orally or percutaneously administrable formulations may also release the particular substituted compound according to the invention in delayed manner.

Production of the medicaments according to the invention proceeds with the assistance of conventional means, devices, methods and processes known from the prior art, as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure. The quantity of the particular substituted compounds according to the invention of the above-stated general formula I to be administered to the patient may vary and is for example dependent on the weight or age of the patient and on the mode of administration, the indication and the severity of the complaint. Conventionally, 0.001 to 100 mg/kg, preferably 0.05 to 75 mg/kg, particularly preferably 0.05 to 50 mg/kg of patient body weight of at least one such compound according to the invention are administered.

Pharmacological Methods

I. Functional Investigation on Vanilloid Receptor 1 (VR1/TRPV1 Receptor)

The agonistic or antagonistic action of the substances to be investigated on the vanilloid receptor 1 (VR1/TRPV1) of the rat species may be determined with the following assay. According to this assay, the influx of $Ca^{2+}$ through the receptor channel is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:

Complete medium: 50 mL HAMS F12 Nutrient Mixture (Gibco Invitrogen GmbH, Karlsruhe, Germany) with 10 vol. % FCS (foetal calf serum, Gibco Invitrogen GmbH, Karlsruhe, Germany, heat-inactivated); 2 mM L-glutamine (Sigma, Munich, Germany); 1 wt. % AA solution (antibiotic/antimycotic solution, PAA, Pasching, Austria) and 25 ng/ml NGF medium (2.5 S, Gibco Invitrogen GmbH, Karlsruhe, Germany)

Cell culture plate: poly-D-lysine-coated, black 96-hole plates with clear base (96 well black/clear plate, BD Biosciences, Heidelberg, Germany) are additionally coated with laminin (Gibco Invitrogen GmbH, Karlsruhe, Germany), by diluting laminin to a concentration of 100 μg/mL with PBS (Ca—Mg-free PBS, Gibco Invitrogen GmbH, Karlsruhe, Germany). Aliquots with a concentration of 100 μg/mL of laminin are taken and stored at −20° C. The aliquots are diluted with PBS in the ratio of 1:10 to 10 μg/mL of laminin and 50 μL of the solution is pipetted into each well of the cell culture plate. The cell culture plates are incubated for at least two hours at 37° C., the supernatant solution is aspirated and the wells are each washed twice with PBS. The coated cell culture plates are stored with supernatant PBS and this is only removed directly prior to introduction of the cells.

Preparation of the Cells:

The spinal column is removed from decapitated rats and this is placed directly in cold HBSS buffer (Hank's buffered saline solution, Gibco Invitrogen GmbH, Karlsruhe, Germany), i.e. located in an ice bath, combined with 1 vol. % (percent by volume) of an AA solution (antibiotic/antimycotic solution, PAA, Pasching, Austria). The spinal column is severed lengthwise and removed from the spinal canal together with fasciae. The dorsal root ganglia (DRGs) are then removed and in turn stored in cold HBSS buffer combined with 1 vol. % of an M solution. The DRGs, from which blood residues and spinal nerves have been completely removed, are in each case transferred into 500 μL cold collagenase type 2 (PAA, Pasching, Austria) and incubated for 35 minutes at 37° C. After the addition of 2.5 vol. % trypsin (PAA, Pasching, Austria) incubation at 37° C. is continued for a further 10 minutes. After complete incubation, the enzyme solution is carefully pipetted off and the remaining DRGs are combined in each case with 500 μL of complete medium. The DRGs are in each case repeatedly suspended, drawn through cannulas no. 1, no. 12 and no. 16 by means of a syringe and transferred into 50 mL Falcon microtubes, these being filled to 15 mL with complete medium. The content of each Falcon microtube is in each case filtered through a 70 μm Falcon filter insert and centrifuged for 10 minutes at 1200 revolutions and RT. The resultant pellet is in each case redissolved in 250 μL of complete medium and the cell count is determined.

The number of cells in the suspension is adjusted to $3 \times 10^5$ per mL and a 150 μL portion of this suspension is in each case placed in a well of the cell culture plates which have been coated as described above. The plates are left to stand in the incubator for two to three days at 37° C., 5 vol. % $CO_2$ and 95% relative atmospheric humidity.

The cells are then loaded with 2 μM Fluo-4 and 0.01 vol. % Pluronic F127 (Molecular Probes Europe BV, Leiden, Netherlands) in HBSS buffer (Hank's buffered saline solution, Gibco Invitrogen GmbH, Karlsruhe, Germany) for 30 mins at 37° C., washed 3× with HBSS buffer and, after a further 15 minutes' incubation at room temperature, used for $Ca^{2+}$ measurement in the FLIPR assay. $Ca^{2+}$-dependent fluorescence is here measured before and after the addition of substances ($\lambda ex=488$ nm, % $\lambda em=540$ nm). Quantification proceeds by measuring the highest fluorescence intensity (FC, fluorescence counts) over time.

FLIPR Assay:

The FLIPR protocol consists of 2 additions of substance. First of all, the compounds to be tested (10 μM) are pipetted onto the cells and $Ca^{2+}$ influx is compared with the control (capsaicin 10 μM). This gives rise to a % activation value relative to the $Ca^{2+}$ signal after addition of 10 μM capsaicin (CP). After 5 minutes' incubation, 100 nM of capsaicin are added and the influx of $Ca^{2+}$ is likewise determined.

Desensitising agonists and antagonists result in suppression of $Ca^{2+}$ influx. The percentage inhibition in comparison with the maximum achievable inhibition with 10 μM capsaicin is calculated.

Three-fold determinations (n=3) are performed and these are repeated in at least 3 independent experiments (N=4).

On the basis of the percentage displacement by different concentrations of the compounds to be tested of the general formula I, $IC_{50}$ inhibition concentrations which bring about 50% displacement of capsaicin were calculated. $K_i$ values for the test substances were obtained by conversion using the Cheng-Prusoff equation (Cheng, Prusoff; Biochem. Pharmacol. 22, 3099-3108,1973).

II. Functional Investigations on Vanilloid Receptor (VR1)

The agonistic or antagonistic action of the substances to be investigated on the vanilloid receptor (VR1) may also be determined with the following assay. According to this assay, the influx of $Ca^{2+}$ through the channel is quantified with the assistance of a Ca$^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:

Chinese hamster ovary cells (CHO K1 cells, European Collection of Cell Cultures (ECACC), Great Britain) are stably transfected with the VR1 gene. For functional investigations, these cells are plated out onto poly-D-lysine-coated, black 96-hole plates with a clear base (BD Biosciences, Heidelberg, Germany) at a density of 25,000 cells/hole. The cells are incubated overnight at 37° C. and 5% $CO_2$ in a culture medium (Ham's Nutrient Mixture F12, 10 vol. % FCS (foetal calf serum), 18 µg/mL L-proline). On the following day, the cells are incubated with Fluo-4 (Fluo-4 2 µM, Pluronic F127 0.01 vol. %, Molecular Probes in HBSS (Hank's buffered saline solution), Gibco Invitrogen GmbH, Karlsruhe, Germany) for 30 minutes at 37° C. The plates are then washed 3 times with HBSS buffer and, after a further 15 minutes' incubation at room temperature, used for Ca$^{2+}$ measurement in the FLIPR. Ca$^{2+}$-dependent fluorescence is here measured before and after the addition of the substances to be investigated (wavelength $\lambda_{ex}$=488 nm, $\lambda_{em}$=540 nm).

Quantification proceeds by measuring the highest fluorescence intensity (FC, fluorescence counts) over time.

FLIPR Assay:

The FLIPR protocol consists of 2 additions of substance. The substances to be tested (10 µM) are firstly pipetted onto the cells and Ca$^{2+}$ influx is compared with the control (capsaicin 10 µM) (% activation relative to the Ca$^{2+}$ signal after addition of 10 µM of capsaicin). After 5 minutes' incubation, 100 nM of capsaicin are added and the influx of Ca$^{2+}$ is likewise determined.

Desensitising agonists and antagonists resulted in suppression of Ca$^{2+}$ influx. The percentage inhibition in comparison with the maximum achievable inhibition with 10 µM capsaicin is calculated.

On the basis of the percentage displacement by different concentrations of the compounds to be tested of the general formula I, $IC_{50}$ inhibition concentrations which bring about 50% displacement of capsaicin were calculated. $K_i$ values for the test substances were obtained by conversion using the Cheng-Prusoff equation (Cheng, Prusoff; Biochem. Pharmacol. 22, 3099-3108, 1973).

III. b. Formaldehyde Test in Mice

The investigation for determining the antinociceptive action of the compounds according to the invention is performed using the formaldehyde test on male mice (NMRI, 20 to 30 g body weight, Iffa, Credo, Belgium).

In the formaldehyde test, according to D. Dubuisson et al., Pain 1977, 4, 161-174 a distinction is drawn between the first (early) phase (0 to 15 minutes after the formaldehyde injection) and the second (late) phase (15 to 60 minutes after the formaldehyde injection). The early phase, being a direct response to the formaldehyde injection, is considered to be a model for acute pain, while the late phase is considered to be a model for persistent (chronic) pain (T. J. Coderre, et al., Pain 1993, 52, 259-285). The corresponding literature descriptions are hereby introduced as a reference and are deemed to be part of the disclosure.

The compounds according to the invention are investigated in the second phase of the formaldehyde test in order to obtain information concerning the effects of the substances on chronic/inflammatory pain.

The administration time of the compounds according to the invention prior to the formaldehyde injection is selected as a function of the mode of administration of the compounds according to the invention. Intravenous administration of 10 mg/kg body weight of the test substances proceeds 5 minutes prior to the formaldehyde injection. This is effected by a one-off subcutaneous formaldehyde injection (20 µL, 1% aqueous solution) into the dorsal side the right hand hind paw, such that, in the case of freely mobile test animals, a nociceptive reaction is induced, which manifests itself in marked licking and biting of the relevant paw.

Then, the nociceptive behaviour of the animals is observed and recorded continuously for an investigation period of three minutes in the second (late) phase of the formaldehyde test (21 to 24 minutes after the formaldehyde injection). Quantification of the pain behaviour proceeds by summation of the seconds in which the animals licked and bit the relevant paw during the investigation period.

The comparison is made in each case with control animals, which, instead of compounds according to the invention, received vehicle (0.9% aqueous sodium chloride soln.) before administration of the formaldehyde. On the basis of the quantification of the pain behaviour, the substance effect in the formaldehyde test is determined in percent as a change compared with the corresponding control.

After the injection of substances which have an antinociceptive action in the formaldehyde test, the described behaviours of the animals, i.e. licking and biting, are reduced or eliminated.

IV. c) Investigation of Analgesic Efficacy by the Writhing Test

Investigation of the compounds according to the invention of the general formula I for analgesic efficacy was performed by phenylquinone-induced writhing in the mouse, modified after I. C. Hendershot and J. Forsaith (1959) J. Pharmacol. Exp. There. 125, 237-240. The corresponding literature description is hereby introduced as a reference and is deemed to be part of the disclosure.

Male NMRI mice weighing from 25 to 30 g were used for this purpose. Groups of 10 animals per compound dose received, 10 minutes after intravenous administration of the compounds to be tested, 0.3 mL/mouse of a 0.02% aqueous solution of phenylquinone (phenylbenzoquinone, Sigma, Deisenhofen, Germany; solution prepared with addition of 5% of ethanol and stored in a water bath at 45° C.) administered intraperitoneally. The animals were placed individually in observation cages. A push button counter was used to record the number of pain-induced stretching movements (writhing reactions=straightening of the torso with stretching of the rear extremities) for 5-20 minutes after phenylquinone administration. The control was provided by animals which had received only physiological saline. All the compounds were tested at the standard dosage of 10 mg/kg.

V. Hypothermia Assay in Mice

Description of Method:

The hypothermia assay is carried out on male NMRI mice (weight 25-35 grams, breeder IFFA CREDO, Brussels, Belgium). The animals were kept under standardised conditions: light/dark cycle (06:00 to 18:00 light phase; 18:00 to 06:00 dark phase), RT 19-22° C., relative humidity 35-70%, 15 air exchanges per hour, air movement <0.2 m/sec. The animals received standard feed (ssniff R/M maintenance, ssniff Spezialdiäten GmbH, Soest, Germany) and tap water. Water and feed were withdrawn during the test. All the animals were used only once in the test. The animals had a habituation phase of at least 5 days.

Acute administration of capsaicin (VR-1 agonist) leads to a drop in core body temperature in rats and mice by stimulation of heat sensors. Only specifically acting VR-1-receptor antagonists are capable of antagonising capsaicin-induced hypothermia. Morphine-induced hypothermia, in contrast, is not antagonised by VR-1 antagonists. This model is therefore suitable for identifying substances with VR-1 antagonistic properties from their action on the body temperature.

Core body temperature was measured using a digital thermometer (Thermalert TH-5, physitemp, Clifton N.J., USA). The sensor is here inserted into the animal's rectum. Body temperature is measured twice for each animal at an interval of approx. half an hour as an individual baseline value. One group of animals (n=6 to 10) then receives intraperitoneal (i.p.) administration of capsaicin 3 mg/kg and vehicle (control group). Another group of animals receives the substance to be tested (i.v. or per os) and additionally capsaicin (3 mg/kg) i.p. The test substance is administered i.v. 10 minutes or per os 15 minutes before the capsaicin. Body temperature is then measured 7.5/15 and 30 min after capsaicin (i.v.+i.p.) or 15/30/60/90/120 min (per os+i.p.) after capsaicin. In addition, one group of animals is treated only with the test substance and one group only with vehicle. The measured values are evaluated and presented as a mean+/−SEM of the absolute values on a graph. The antagonistic action is calculated as a percentage reduction in capsaicin-induced hypothermia.

VI. Neuropathic Pain in Mice

Efficacy against neuropathic pain was investigated in the Bennett model (chronic constriction injury; Bennett and Xie, 1988, Pain 33: 87-107).

NMRI mice weighing 16-18 g are provided under Ketavet-Rompun anaesthesia with three loose ligatures of the right ischial nerve. On the paw innervated by the damaged nerve, the animals develop hypersensitivity which, after one week's convalescence, is quantified over a period of approx. three weeks by means of a cold metal plate at 4° C. (cold allodynia). The animals are observed on this plate for a period of 2 min. and the number of withdrawal responses by the damaged paw is measured. Relative to the preliminary value prior to administration of the substance, the action of the substance is determined at different occasions over a given period (for example 15, 30, 45, 60 min. after administration) and the resultant area under the curve (AUC) and/or the inhibition of cold allodynia at the individual measuring points is stated as a percentage action relative to the vehicle control (AUC) or to the initial value (individual measurement points). The size of the group is n=10, the significance of an antiallodynic action (*=p<0.05) is determined with reference to an analysis of variance with repeated measurement and post hoc Bonferroni analysis.

The invention will be explained below with reference to a number of examples. These explanations are given merely by way of example and do not restrict the general concept of the invention.

EXAMPLES

The yields of the compounds produced have not been optimized. All temperatures are uncorrected. The term "equivalents" means molar equivalents, "RT" means room temperature, "M" and "N" are concentrations stated in mol/l, "aq." means aqueous, "sat." means saturated, "soln." means solution. Other abbreviations are as follows:

| AcOH | acetic acid |
| DCM | dichloromethane |
| DMF | N,N-dimethylformamide |
| EDCl | N-ethyl-N'-(3-dimethylaminopropyl)-carbodiimide hydrochloride |
| EA | ethyl acetate |

-continued

| $H_2O$ | water |
| HOBt | N-hydroxybenzotriazole |
| MeOH | methanol |
| TEA | triethylamine |
| THF | tetrahydrofuran. |

The chemicals and solvents used were purchased from conventional suppliers (Acros, Avocado, Aldrich, Bachem, Fluka, Lancaster, Maybridge, Merck, Sigma, TCI, Oakwood etc.) or synthesized by conventional methods known to persons skilled in the art.

Silica gel 60 (0.0-0-0.063 mm) from E. Merck, Darmstadt, was used as the stationary phase for column chromatography. Thin-layer chromatography was performed with pre-coated silica gel 60 F 254 HPTLC plates from E. Merck, Darmstadt. The mixture ratios for solvents, mobile solvents or for chromatographic investigations are always stated in volume/volume. Analysis was performed by mass spectroscopy and NMR.

1. General Method of Preparing Amines of the General Formula V-A

Amines of formula V-A were prepared as illustrated in the following Scheme 1:

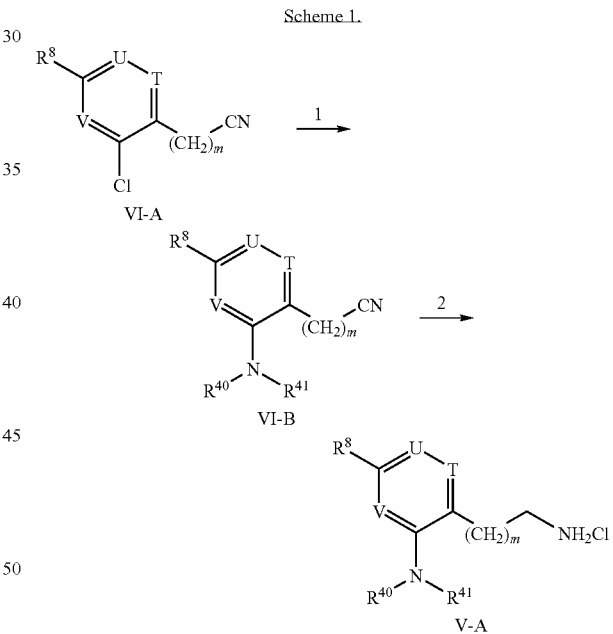

Stage 1: Preparation of Nitriles of the General Formula VI-B

Method A:

Compounds of the general formula VI-A (1 equivalent), in which $R^8$, U, T and V have the above-stated meanings and m denotes 0, 1, 2 or 3, are stirred with an amine of the general formula $HNR^{40}R^{41}$ (6 equivalents) for 48 hours at RT. The reaction mixture is combined with 1 N hydrochloric acid and extracted repeatedly with EA. The aqueous phase is saturated with NaCl and then extracted again with EA. The combined organic phases are washed with 1 N hydrochloric acid and with a sat. aq. NaCl soln., dried over $MgSO_4$ and the solvent was removed under a vacuum.

The following compound was produced using Method A.

6'-tert.-butyl-4-methyl-3,4,5,6-tetrahydro-2H-[1,2']bipyridinyl-3'-carbonitrile

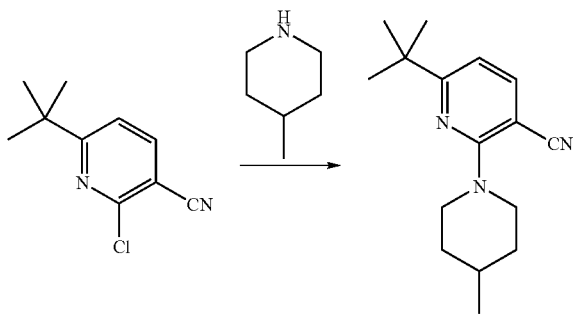

$^1$H-NMR (CDCl$_3$) δ 7.65 (d, 1H, J=7.9 Hz, Ar), 6.70 (d, 1H, J=8.0 Hz, Ar), 4.45 (m, 2H, piperidine), 2.98 (m, 2H, piperidine), 1.75-1.24 (m, 5H, piperidine), 1.29 (s, 9H, C(CH$_3$)$_3$), 0.98 (d, 3H, J=5.9 Hz, CHCH$_3$)
IR 2956, 2213, 1583, 1550, 1452, 1230, 965 cm$^{-1}$ Method B:
Compounds of the general formula VI-A (1 equivalent), in which R$^8$, U, T and V have the above-stated meanings and m denotes 0, 1, 2 or 3, are stirred with an amine of the general formula HNR$^{40}$R$^{41}$ (2 equivalents) and DBU [1,8-diaza-bicyclo[5.4.0]undec-7-ene] (2 equivalents) in acetonitrile (7 mL per mmol of the compound of formula VI-A) for 12 hours at RT. The reaction mixture is extracted repeatedly with EA. The combined organic phases are washed with sat. aq. NaCl solution, dried over MgSO$_4$ and the solvent was removed under a vacuum. The residue is purified in each case by column chromatography (SiO$_2$, different mixtures of hexane/EA).

The following compounds were produced using Method B.

6-(trifluoromethyl)-2-(4-methylpiperidin-1-yl)pyridine-3-carbonitrile

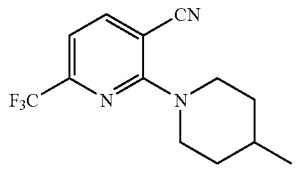

$^1$H NMR (300 MHz, CDCl$_3$) δ 7.87 (d, 1H, J=7.8 Hz), 6.95 (d, 1H, J=7.8 Hz), 4.53 (m, 2H), 3.05 (m, 2H), 1.78 (m, 2H), 1.64 (m, 1H), 1.29 (m, 2H), 1.00 (d, 3H, J=6.6 Hz); IR (pur) 2926, 2852, 2218, 1590, 1497, 1456, 1324, 1237, 1186, 1147, 1082, 963 cm$^{-1}$; MS (FAB) m/z 270 (M+H)

Stage 2
Method 1
Compounds of the general formula VI-B (5 mmol), in which R$^8$, R$^{40}$, R$^{41}$, U, T and V have the above-stated meanings and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through Celite and the filtrate is evaporated under a vacuum. The residue is purified by means of flash chromatography (SiO$_2$, EA).

Method 2:
Compounds of the general formula VI-B (2 mmol), in which R$^8$, R$^{40}$, R$^{41}$, U, T and V have the above-stated meanings and m denotes 0, 1, 2 or 3, are dissolved in THF (10 mL, 10 mL) and BH$_3$.S(CH$_3$)$_2$ [2.0 M in THF, 3 mL, 3 equivalents] is added thereto. The reaction mixture is heated to reflux for 8 hours, aq. HCl (2 N) is added thereto and the reaction mixture is again heated to reflux for 30 minutes. The reaction mixture is combined with aq. sodium hydroxide solution (2N) and washed with EA. The combined organic phases are washed with a sat. aq. NaCl solution and dried over magnesium sulfate. The solvent is removed under a vacuum and the residue is purified by column chromatography (SiO$_2$, different mixture of dichloromethane and MeOH as mobile solvent).

The following compounds were obtained using Method 2.

(6-(trifluoromethyl)-2-(4-methylpiperidin-1-yl)pyridin-3-yl)methanamine

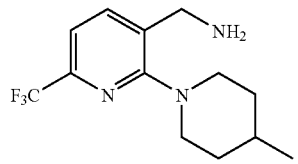

$^1$H NMR (300 MHz, CDCl$_3$) δ 7.89 (d, 1H, J=7.8 Hz), 7.33 (d, 1H, J=7.8 Hz), 3.88 (s, 2H), 3.39 (m, 2H), 2.83 (m, 2H), 1.75 (m, 2H), 1.55 (m, 1H), 1.38 (m, 2H), 1.00 (d, 3H, J=6.6 Hz); MS (FAB) m/z 274 (M+H)

C-(6'-tert.-butyl-4-methyl-3,4,5,6-tetrahydro-2H-[1,2']bipyridinyl-3'-yl)-methylamine

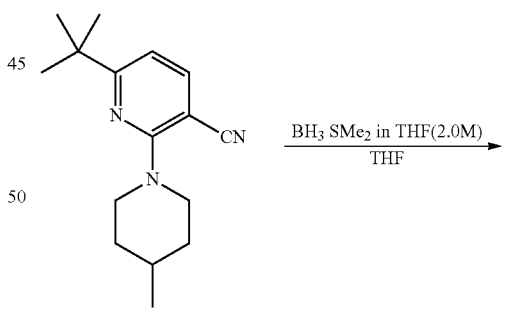

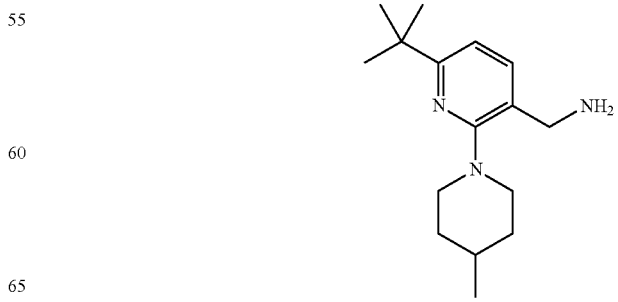

$^1$H-NMR (CDCl$_3$) δ 7.48 (d, 1H, J=7.7 Hz, Ar), 6.90 (d, 1H, J=7.7 Hz, Ar), 3.82 (s, 2H, CH$_2$NH$_2$), 3.38 (m, 2H, Piperidin), 2.81 (m, 2H, Piperidin), 1.73-1.28 (m, 5H, Piperidin), 1.31 (s, 9H, C(CH$_3$)$_3$), 0.98 (d, 3H, J=6.4 Hz, CHCH$_3$)

IR 3363, 2954, 1571, 1451, 1400, 1372, 1234, 960 cm$^{-1}$

2. General Method of Preparing Amines of the General Formula V-E

Amines of the general formula V-E are prepared as illustrated in the following Scheme 2.

Scheme 2.

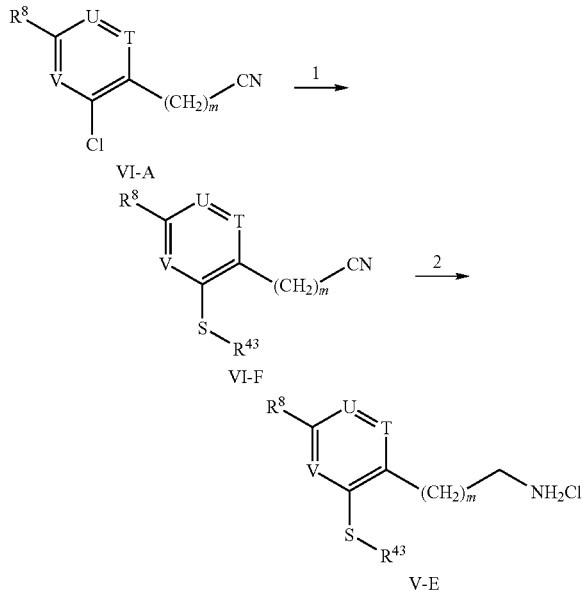

Stage 1

Synthesis of 2-(cyclohexylthio)-6-(trifluoromethyl)nicotinonitrile

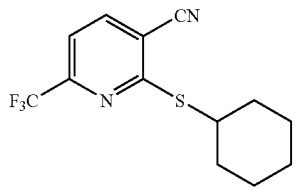

1.3 equivalents of NaH (4.9 g, 0.124 mol) were dissolved in 50 mL DMF under a nitrogen atmosphere. After the addition of 1.2 equivalents of cyclohexanethiol (14.2 mL, 0.116 mol) stirring was performed at RT for 1.5 h. The resultant suspension was cooled to 10° C. and 1 equivalent of 2-chloro-6-(trifluoromethyl)nicotinonitrile (20 g, 0.096 mol) in 50 mL DMF was added dropwise and stirred for 2 h at RT. The reaction mixture was combined with sat. aq. NH$_4$Cl soln., diluted with 1 L of water and extracted repeatedly with EA (3×200 mL). The combined organic phases were washed with a sat. aq. NaCl soln., dried over MgSO$_4$ and evaporated under a vacuum. Purification performed by column chromatography (silica gel, 100-200 mesh, eluent: 2% EA in hexane) resulted in 26 g (93.8%) of product.

$^1$H NMR (300 MHz, CDCl$_3$) δ 7.94 (d, 1H, J=7.9 Hz), 7.34 (d, 1H, J=7.9 Hz), 4.00 (m, 1H), 1.90-2.14 (m, 2H), 1.42-1.88 (m, 8H)

IR (neat) 2930, 2854, 2232, 1643, 1573, 1447, 1334, 1245, 1186, 1149, 1107, 851 cm$^{-1}$ MS (FAB) m/z 287 (M+H)

Stage 2

Synthesis of (2-(cyclohexylthio)-6-(trifluoromethyl)pyridin-3-yl)methanamine dihydrochloride The nitrile (26 g, 0.091 mol) was dissolved under a nitrogen atmosphere in 600 mL of THF and cooled to 5° C. BH$_3$ dimethyl sulfide (13.78 g, 0.182 mol) was added dropwise and refluxed for 20 h. After cooling to 5° C., the reaction batch was combined with 100 mL of MeOH and stirred for 15 minutes at RT. Then di-tert.-butyl dicarbonate (29.7 g, 0.136 mol) was added and stirring was performed 30 min at RT. After removal of the solvent under a vacuum, the crude product was purified by column chromatography (silica gel, 100-200, mesh, eluent: 10% EA in hexane) and 23.4 g (66%) of product was obtained.

The crude product was dissolved in 120 mL sat. HCl-dioxane soln. and stirred for 6 h at RT. After removal of the solvent under a vacuum, the solid was washed with 10% EA in hexane (2×100 mL) and filtered out.

Yield: 17 g (88.8%)

$^1$H NMR (DMSO-d$_6$, 400 MHz): δ 8.8 (s, 2H), 8.05 (d, 1H), 7.76 (d, 1H), 4.01 (s, 1H), 3.86-3.93 (m, 1H), 2.02-2.08 (m, 2H), 1.71-1.74 (m, 2H), 1.40-1.60 (m, 6H).

3. General Method of Preparing Amines of the General Formula V-B

Amines of the general formula V-B are prepared as illustrated in the following Scheme 3.

Scheme 3.

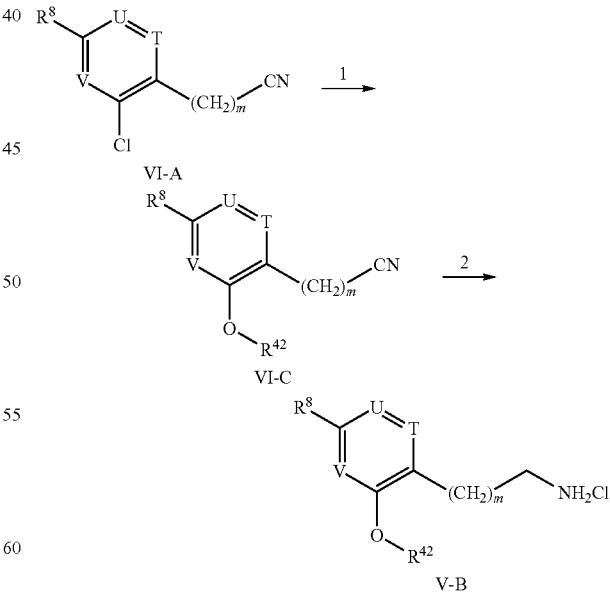

Stage 1: Preparation of Nitriles of the General Formula VI-C

Compounds of the general formula VI-A (1 equivalent), in which R$^8$, U, T and V have the above-stated meanings and m denotes 0, 1, 2 or 3, are stirred with an alcohol of the general formula HO—R$^{42}$ (3.5 equivalents) and DBU [1,8-diaza-bicyclo[5.4.0]undec-7-ene] (3.5 equivalents) in acetonitrile (7 mL per mmol of the compound of formula VI-A) for 12 hours at RT. The reaction mixture is extracted repeatedly with EA. The combined organic phases are washed with sat. aq. NaCl solution, dried over MgSO$_4$ and the solvent was removed under a vacuum. The residue is purified in each case by column chromatography (SiO$_2$, different mixtures of hexane/EA).

Method 2:

Compounds of the general formula VI-C (2 mmol), in which R$^8$, R$^{42}$, U, T and V have the above-stated meanings and m denotes 0, 1, 2 or 3, are dissolved in THF (10 mL, 10 mL) and BH$_3$.S(CH$_3$)$_2$ [2.0 M in THF, 3 mL, 3 equivalents] is added thereto. The reaction mixture is heated to reflux for 8 hours, aq. HCl (2 N) is added thereto and the reaction mixture is again heated to reflux for 30 minutes. The reaction mixture is combined with aq. sodium hydroxide solution (2N) and washed with EA. The combined organic phases are washed with a sat. aq. NaCl solution and dried over magnesium sulfate. The solvent is removed under a vacuum and the residue is purified by column chromatography (SiO$_2$, different mixture of dichloromethane and methanol as mobile solvent).

Method 3:

Compounds of the general formula VI-C (1.5 mmol), in which R$^8$, R$^{42}$, U, T and V have the above-stated meanings and m denotes 0, 1, 2 or 3, are dissolved in diethyl ether (3 ml) and a suspension of lithium aluminium hydride (3 mmol) in ether (5 ml) is added slowly dropwise at 0° C. The reaction mixture is heated to reflux for 4 hours and methanol and then 1 N aq. NaOH solution are added slowly dropwise at 0° C. The reaction mixture is diluted with methanol and filtered through Celite. The solvent is removed under a vacuum and the residue is purified by column chromatography (SiO$_2$, different mixture of dichloromethane and methanol as mobile solvent).

4. General Method of Preparing Amines of the General Formula V-C

Amines of the general formula V-C are prepared as illustrated in the following Scheme 4.

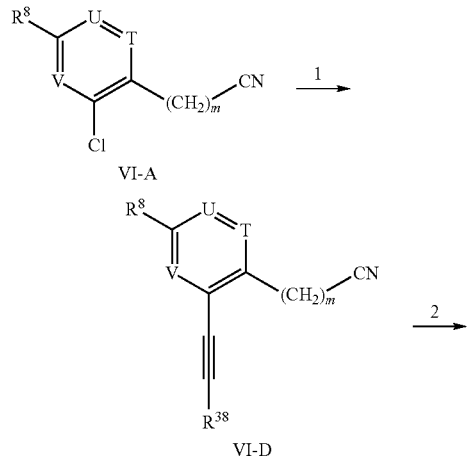

-continued

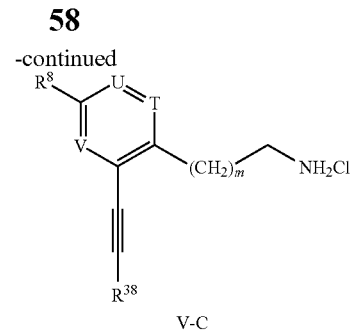

Stage 1: Preparation of Nitrites of the General Formula VI-D

Compounds of the general formula VI-A (1 equivalent), in which R$^8$, U, T and V have the above-stated meanings and m denotes 0, 1, 2 or 3, are dissolved with bis(triphenylphosphine)palladium dichloride (7 mol %) and copper(I) iodide (14 mol %) in 1-methyl-2-pyrrolidinone (7 ml per mmol of compound of the general formula VI-A). After 10 minutes the alkyne of the general formula HC≡C—R$^{38}$ (3.5 equivalents) and N, N-diisopropylethylamine (2 equivalents) are added and the reaction mixture is stirred for 12 h at a temperature of between 90 and 110° C. The reaction mixture is filtered through Celite and extracted repeatedly with EA. The combined organic phases are washed with sat. aq. NaCl solution, dried over MgSO$_4$ and the solvent was removed under a vacuum. The residue is purified in each case by column chromatography (SiO$_2$, different mixtures of hexane/EA).

5. General Method of Preparing Amines of the General Formula V-D

Amines of the general formula V-D are prepared as illustrated in the following Scheme 5.

Scheme 5.

Stage 1: Preparation of Nitrites of the General Formula VI-E

Compounds of the general formula VI-A (1 equivalent), in which R$^8$, U, T and V have the above-stated meanings and m denotes 0, 1, 2 or 3, are stirred with palladium dichloride (5 mol %) and a compound of the general formula R$^{38}$—B(OH)$_2$ (2 equivalents), in which R$^{38}$ denotes aryl, heteroaryl or cycloalkenyl, in a solvent mixture of toluene/dioxane/2 N aq.

sodium carbonate solution (20 mL per 1 mmol compounds of the general formula VI-A). The reaction mixture is heated to reflux for 12 h and filtered through Celite. The combined organic phases are dried with magnesium sulfate and the solvent is removed under a vacuum. The residue is purified by column chromatography (SiO$_2$, different solvent mixtures of hexane and EA).

Stage 2
Method 1

Compounds of the general formula VI-E (5 mmol), in which R$^8$, R$^{38}$, U, T and V have the above-stated meanings and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through Celite and the filtrate is evaporated under a vacuum. The residue is purified by means of flash chromatography (SiO$_2$, EA).

Method 2:

Compounds of the general formula VI-E (2 mmol), in which R$^8$, R$^{38}$, U, T and V have the above-stated meanings and m denotes 0, 1, 2 or 3, are dissolved in THF (10 mL, 10 mL) and BH$_3$.S(CH$_3$)$_2$ [2.0 M in THF, 3 mL, 3 equivalents] is added. The reaction mixture is heated to reflux for 8 hours, aq. HCl (2 N) is added thereto and the reaction mixture is again heated to reflux for 30 minutes. The reaction mixture is combined with aq. sodium hydroxide solution (2N) and washed with EA. The combined organic phases are washed with a sat. aq. NaCl solution and dried over magnesium sulfate. The solvent is removed under a vacuum and the residue is purified by column chromatography (SiO$_2$, different mixture of dichloromethane and methanol as mobile solvent).

6. Method of Preparing Carboxylic Acids of the General Formula VII 6.1 Preparation of 2-(benzo[d]oxazol-5-yl)propanoic acid

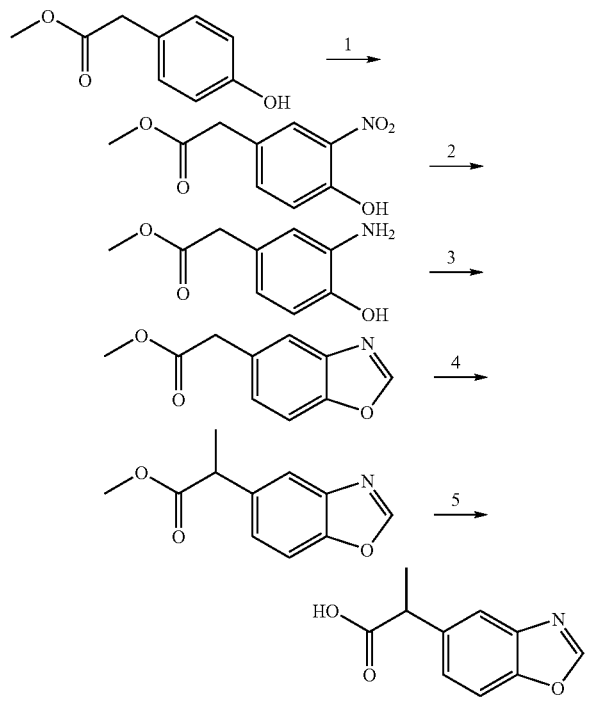

Stage 1

Synthesis of methyl-2-(4-hydroxy-3-nitrophenyl)acetate

Methyl-2-(4-hydroxyphenyl)acetate (2.0 g, 12.0 mmol) was dissolved in acetic acid (15 ml) and nitric acid (60-62%, 1.27 g, 12.1 mmol) was added at RT. The reaction mixture was stirred for 30 minutes at RT, poured into ice water (100 ml) and extracted with EA. The organic phase was dried over MgSO$_4$, the solvent removed under a vacuum and the residue purified by means of column chromatography (n-hexane/EA=4:1).

Stage 2

Synthesis of methyl-2-(3-amino-4-hydroxyphenyl)acetate

Methyl-2-(4-hydroxy-3-nitrophenyl)acetate (2.31 g, 10.9 mmol) was dissolved in THF (20 mL) and MeOH (20 mL) and 10% palladium on carbon (210 mg) was added slowly at RT. The reaction mixture was hydrogenated for 2 h at 39 psi hydrogen pressure, filtered through Celite and washed with MeOH. The solvent was removed under a vacuum and the residue purified by means of column chromatography (n-hexane/EA=2:1).

Stage 3

Synthesis of methyl-2-(benzo[d]oxazol-5-yl)acetate

Methyl-2-(3-amino-4-hydroxyphenyl)acetate (1.39 g, 7.67 mmol) was combined at RT with triethyl orthoformate (10 ml). The reaction mixture was heated to reflux for 12 h and then cooled to RT. Water (70 mL) was added thereto and the reaction mixture was extracted with EA. The combined organic phases were dried over MgSO$_4$ and filtered. The solvent was removed under a vacuum and the residue purified by means of column chromatography (n-hexane/EA=2:1).

Stage 4

Synthesis of methyl-2-(benzo[d]oxazol-5-yl) propanoate

Methyl-2-(benzo[d]oxazol-5-yl)acetate (0.90 g, 4.71 mmol) was dissolved in DMF (5 ml) and combined at 0° C. with sodium hydride (198 mg, 4.95 mmol) and methyl iodide (661 mg, 4.65 mmol). The reaction mixture was stirred for 30 min at 0° C. and then for 1 h at RT. The reaction mixture was combined with water (70 ml) and extracted with EA. The combined organic phases were dried over MgSO$_4$ and filtered. The solvent was removed under a vacuum and the residue purified by means of column chromatography (n-hexane/EA=4/1).

$^1$H-NMR (CDCl$_3$) δ 8.10 (s, 1H, Ar), 7.74 (d, 1H, J=1.7 Hz, Ar), 7.54 (d, 1H, 8.4 Hz, Ar), 7.35 (dd, 1H, J=8.6, 1.8 Hz, Ar), 3.87 (q, 1H, J=7.3 Hz, CHCH$_3$), 3.67 (s, 3H, OCH$_3$), 1.57 (d, 3H, J=7.1 Hz, CHCH$_3$)

IR 2982, 1735, 1517, 1437, 1248, 1201, 1170, 1067 cm$^{-1}$

Stage 5

Synthesis of 2-(benzo[d]oxazol-5-yl)propanoic acid

Methyl-2-(benzo[d]oxazol-5-yl) propanoate (425 mg, 2.07 mmol) was dissolved in THF (8 ml) and water (8 ml).

LiOH*H₂O (93 mg, 2.21 mmol) was added thereto at RT. The reaction mixture was stirred for 40 h at RT, combined with water (25 ml) and adjusted with acetic acid to a pH value of 3. The reaction mixture was extracted with DC M and the combined organic phases were dried over MgSO₄ and filtered. The solvent was removed under a vacuum and the residue purified by means of column chromatography (n-hexane/MeOH=15:1).

¹H-NMR (CD₃OD) δ 8.46 (s, 1H, Ar), 7.70 (d, 1H, J=1.7 Hz, Ar), 7.61 (d, 1H, 8.0 Hz, Ar), 7.42 (dd, 1H, J=8.6, 1.8 Hz, Ar), 3.87 (q, 1H, J=7.1 Hz, CHCH₃), 1.51 (d, 3H, J=7.1 Hz, CHCH₃)

6.2 Preparation of 2-(benzo[d]oxazol-6-yl)propanoic acid

The compound 2-(benzo[d]oxazol-6-yl)propanoic acid was produced in a similar manner to the synthesis of 2-(benzo[d]oxazol-5-yl)propanoic acid (see 6.1) starting from 2-(3-hydroxyphenyl)acetic acid.

¹H-NMR (CD₃OD) δ 8.44 (s, 1H, Ar), 7.67 (m, 2H, Ar), 7.38 (dd, 1H, J=8.3, 1.5 Hz, Ar), 3.88 (q, 1H, J=7.1 Hz, CHCH₃), 1.51 (d, 3H, J=7.1 Hz, CHCH₃)

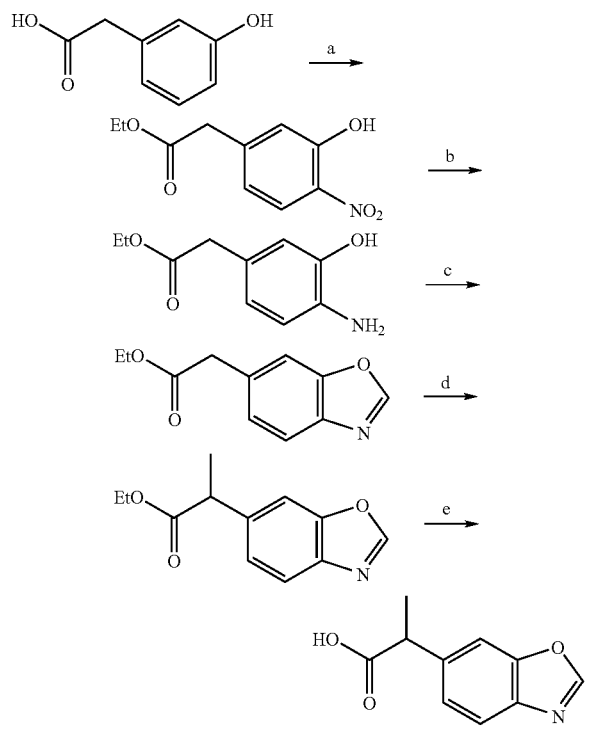

a. HNO₃, AcOH, H₂SO₄(cat.), EtOH, 26%; b. 10% Pd/C, H₂, THF/EtOH, 85%; c. CH(OEt)₃, 99%; d. NaH, CH₃I, DMF, 56%; e. LiOH H₂O, THF/H₂O, 97%

6.3 Preparation of 2-(benzo[d]oxazol-7-yl)propanoic acid

The compound 2-(benzo[d]oxazol-7-yl)propanoic acid was produced in a similar manner to the synthesis of 2-(benzo[d]oxazol-5-yl)propanoic acid (see 6.1) starting from 2-(2-hydroxyphenyl)acetic acid.

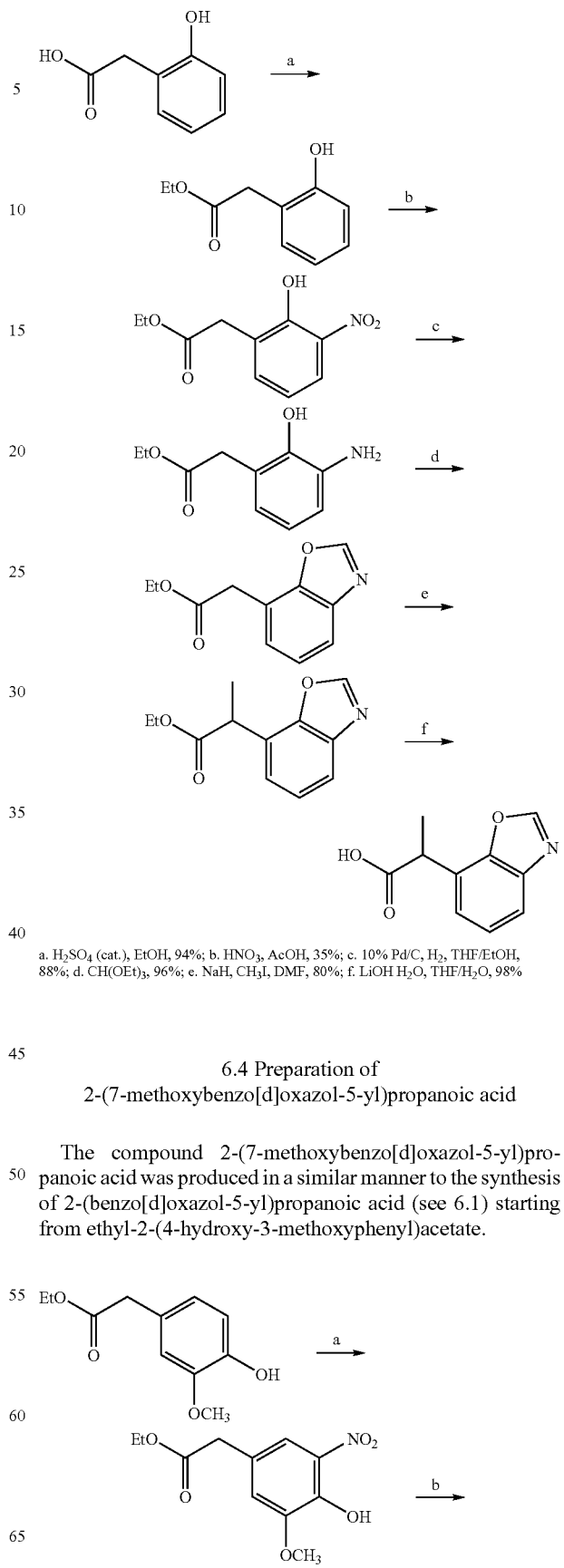

a. H₂SO₄ (cat.), EtOH, 94%; b. HNO₃, AcOH, 35%; c. 10% Pd/C, H₂, THF/EtOH, 88%; d. CH(OEt)₃, 96%; e. NaH, CH₃I, DMF, 80%; f. LiOH H₂O, THF/H₂O, 98%

6.4 Preparation of 2-(7-methoxybenzo[d]oxazol-5-yl)propanoic acid

The compound 2-(7-methoxybenzo[d]oxazol-5-yl)propanoic acid was produced in a similar manner to the synthesis of 2-(benzo[d]oxazol-5-yl)propanoic acid (see 6.1) starting from ethyl-2-(4-hydroxy-3-methoxyphenyl)acetate.

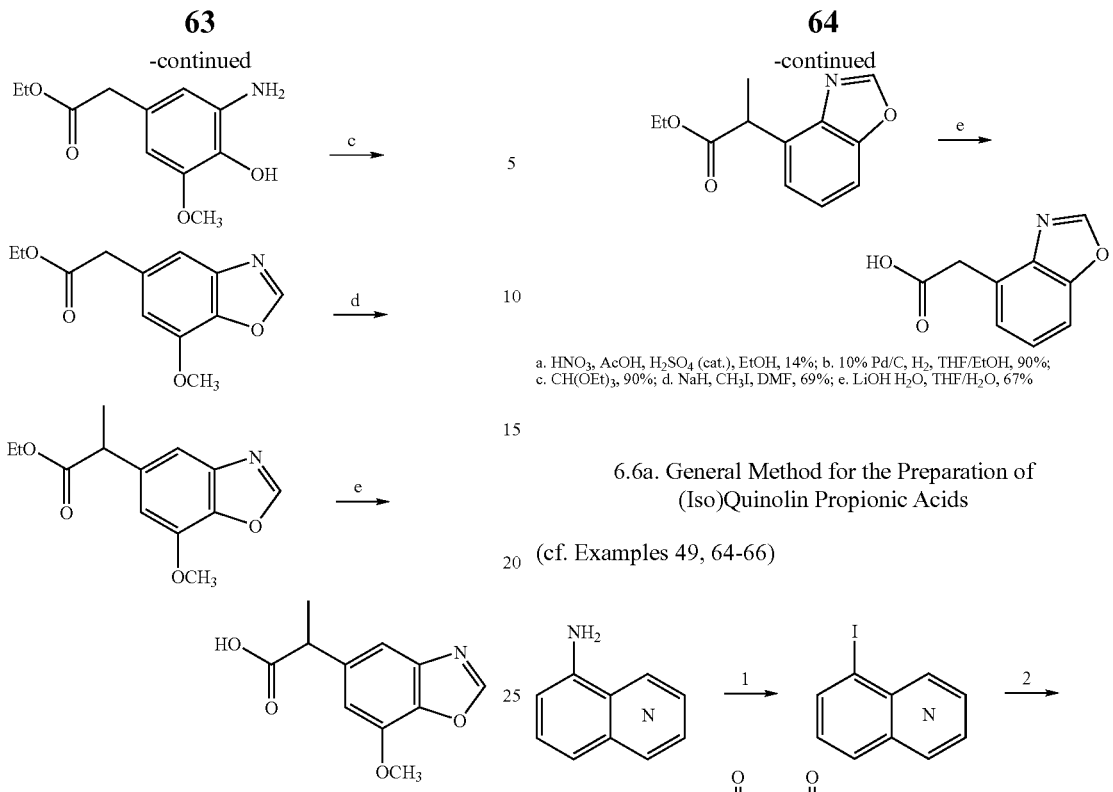

a. HNO₃, AcOH, H₂SO₄ (cat.), EtOH, 14%; b. 10% Pd/C, H₂, THF/EtOH, 90%;
c. CH(OEt)₃, 90%; d. NaH, CH₃I, DMF, 69%; e. LiOH H₂O, THF/H₂O, 67%

6.6a. General Method for the Preparation of (Iso)Quinolin Propionic Acids (cf. Examples 49, 64-66)

a. HNO₃, AcOH, 48%; b. 10% Pd/C, H₂, THF/EtOH, quantitative;
c. Triethylorthoformiate, 99%; d. NaH, CH₃I, DMF, 52%; e. LiOH H₂O, THF/H₂O, 74%

6.5 Preparation of 2-(benzo[d]oxazol-4-yl)propanoic acid

The compound 2-(benzo[d]oxazol-4-yl)propanoic acid was produced in a similar manner to the synthesis of 2-(benzo[d]oxazol-5-yl)propanoic acid (see 6.1) starting from 2-(3-hydroxyphenyl)acetic acid.

¹H-NMR (CD₃OD) δ 8.42 (s, 1H, Ar), 7.55 (dd, 1H, J=7.9, 1.1 Hz, Ar), 7.37 (m, 2H, Ar), 4.38 (q, 1H, J=7.1 Hz, CHCH₃), 1.57 (d, 3H, J=7.4 Hz, CHCH₃)

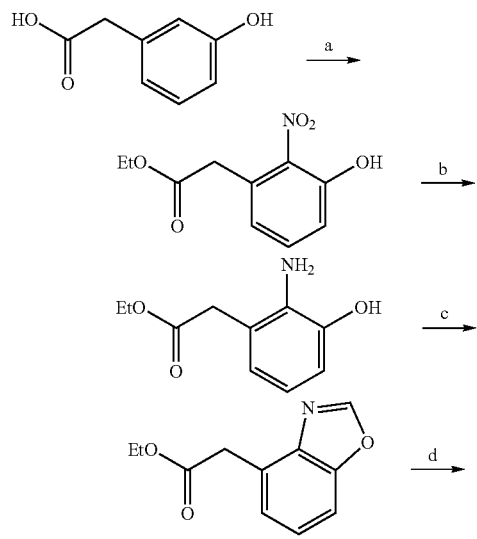

Step 1: Add to a solution of starting material (10.6 mmol) in 6 N HCl (20 mL) cooled to 0° C., a solution of NaNO₂ (730 mg, 10.6 mmol) in water (10 mL) dropwisely. Add the resulting solution to a solution of KI (7.3 g, 44 mmol) in water (15 mL), keeping the temperature at 0° C. Allow the reaction mixture to warm to room temperature and stir for 3 h, then extract with ethyl acetate. Wash the combined layers in sequence with 10% Na₂S₂O₃ and brine, then dry over Na₂SO₄ and concentrate under vacuum to afford iodo(iso)quinoline as a solid, which can use without further purification in the next step.

Step 2: Add to CuI (9.5 mg, 5.0 mol %), 2-picolinic acid (12.3 mg, 10.0 mol %), Cs₂CO₃ (0.98 g, 3.0 mmol) and 1,4-dioxane (10 ml) the distilled diethyl malonate (304 µL, 2.00 mmol) and aryl iodide (1.00 mmol). After stirring 7 hrs at 70° C. cool down the reaction mixture to rt. The reaction mixtures should extracted with ethyl acetate (20 mL×3) and saturated aqueous NH$_4$Cl (10 mL). Dry the combined organic layer over Na$_2$SO$_4$, filter and concentrate under vacuum. Purify the oily residue by flash chromatography on silica gel to give the desired α-aryl malonate product.

Step 3: Treat a cooled solution of the α-aryl malonate (1 mmol) in DMF (10 mL) at 0° C. with NaH (1.1 mmol) and MeI (1.2 mmol) and stir for 30 min at room temperature. Concentrate the reaction mixture in vacuo and purify the residue by flash column chromatography on silica gel with EtOAc/hexanes (1:4) as eluant.

Step 4: Reflux a mixture of α-aryl methyl malonate (1 mmol) and NaOH (2 mmol) in 80% aqeuous EtOH (10 mL) for 6 hrs. Neutralized the mixture with 1 N HCl, extract with ethyl acetate (20 mL×3) and concentrate in vacuo. Purified the residue by flash column chromatography on silica gel with EtOAc/hexanes (1:1) as eluant to obtain the desired (iso)quinoline propanoic acid.

6.6b. General Method for the Preparation of (Iso)quinolin Propionic Acids

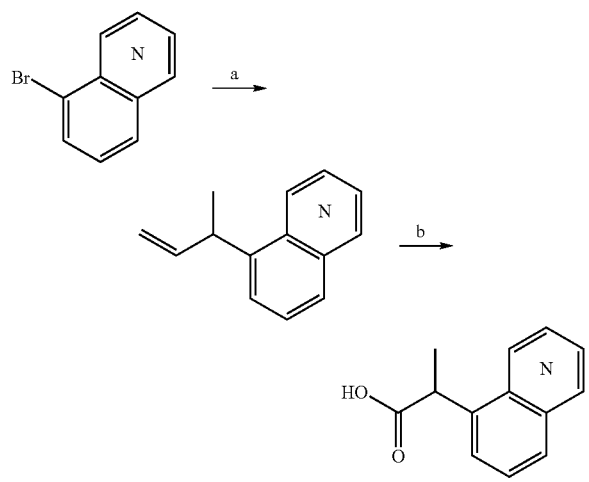

a. Potassium allyltrifluoroborane, Pd(OAc)$_2$, D-t-BPF, K$_2$CO$_3$, THF/H$_2$O; b. KMnO$_4$, NaIO$_4$ General Protocol for the Reaction of Aryl Halides with Potassium Allyl-Trifluoroborane Catalyzed by a Pd(OAc)$_2$/D-t-BPF-Complex In analogy to Yamamoto, Y. et al. (*Chem. Lett.* (2006), 35, 7, 704-705), THF (5 mL) and the corresponding aryl bromide (1 mmol) are added to a mixture of Pd(OAc)$_2$ (0.03 mmol, 3 mol %), D-t-BPF (0.036 mmol), K$_2$CO$_3$ (3 mmol) and potassium allyl-trifluoroborane (2.5 mmol) under inert gas atmosphere. The reaction mixture is refluxed for 22 h. The organic solvent can be removed under reduced pressure and the residue can be purified by column chromatography (a).

As described by Kawatsura, M. et al. (*Tetrahedron* (2000), 56, 15, 2247-2258) the obtained alkene can be converted into the corresponding propanoic acid. The obtained product from (a) (1 mmol) is dissolved in t-BuOH (18 mL) and water (45 mL). KMnO$_4$ (2.5 mmol), NaIO$_4$ (16 mmol) and K$_2$CO$_3$ (6.5 mmol) are added and the reaction mixture is alkalized with NaOH (3 N) up to pH 8 and stirred for 2 h at room temperature. HCl (conc.) is added to acidify the mixture up to pH 1 and NaHSO$_3$ is applied to reduce the generated MnO$_2$. Diethyl ether is added to the reaction mixture, the layers are separated and the organic layer is extracted with aqueous NaOH (3N). The aqueous layer is acidified with HCl (conc.) and is also extracted with diethyl ether. The combined organic layers are dried over MgSO$_4$ and concentrated in vacuo (b).

6.7 Synthesis of Benzooxocyclic Propionic and Acetic Acids (cf. Examples 9, 58-63)

Procedure for the Synthesis of Benzenedioxol Propionic Acid

Example 60

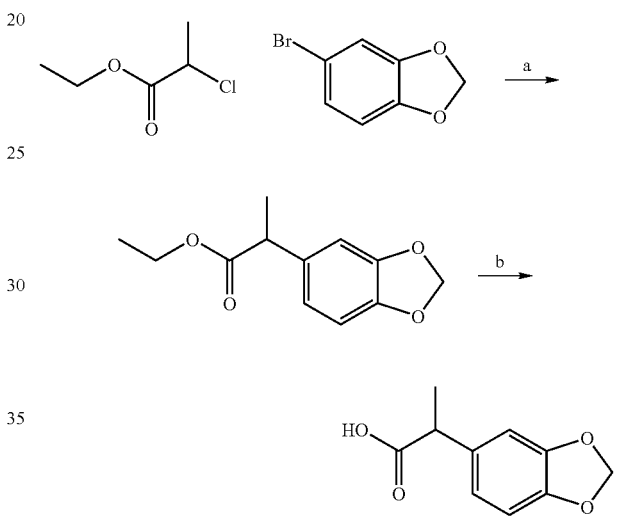

a. NBu$_4$BF$_4$, NiBr$_2$bipy, DMF, 25° C., 9% b. LiOH, THF/H$_2$O, reflux, 12 h, 97%

4-Bromo-1,2-(methylenedioxy)benzene (2 g, 10 mmol) and ethyl 2-chloropropanoate (1.6 mL, 13 mmol) were stirred in DMF (15 mL) under a nitrogen atmosphere at room temperature. Mn (1.1 g, 20 mmol), (2,2'-bipyridine)nickel(II)-dibromide (0.26 g, 0.7 mmol) and TFA (20 mL) were added and the reaction mixture was stirred for 1.5 h at 50° C. The reaction mixture was cooled and hydrolyzed by HCl (1 N, 25 mL). The resulting mixture was extracted with diethyl ether (3×25 mL) and the combined organic layers were washed with water (25 mL), saturated aqueous NaCl (25 mL), dried over MgSO$_4$ and reduced in vacuo. The precipitated solid was filtered off and washed with diethyl ether. After purification by column chromatography (n-hexane/tert-BME, 9:1), 0.198 g (Yield: 9%) of the product could be obtained as a white solid (a).

The propionate obtained from (a) was dissolved in a mixture of THF (1.6 mL, 20 mmol) and water (0.8 mL, 45 mmol). LiOH (0.058 g, 2.43 mmol) was added and the reaction mixture was refluxed over night. Water (25 mL) and diethyl ether (25 mL) were added and the layers were separated. The aqueous one was acidified with HCl and extracted with dichloromethane (3×25 mL). The combined organic layers were dried over MgSO$_4$ and concentrated in vacuo to yield the propionic acid (0.150 g, 97%) (b).

Other benzooxocyclic propanoic acids can be obtained according to this procedure:

2-(Benzo[d][1,3]dioxol)propanoic acids (i),
2-(2,3-Dihydrobenzo[b][1,4]dioxin)propanoic acids (ii),
2-(3,4-Dihydro-2H-benzo[b][1,4]dioxepin)propanoic acids (iii)

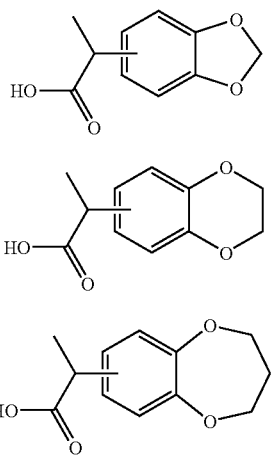

In addition, the corresponding benzooxocyclic acetic acids can also be prepared by this method:

2-(Benzo[d][1,3]dioxol)acetic acids (i),
2-(2,3-Dihydrobenzo[b][1,4]dioxin)acetic acids (ii), Ex 58, 59
2-(3,4-Dihydro-2H-benzo[b][1,4]dioxepin)acetic acids (iii)

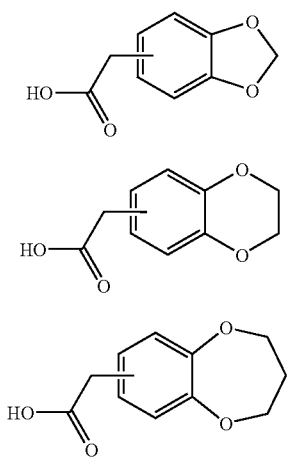

6.8 General Method for the Synthesis of Aryl Propionic Acids from Aryl Bromides In analogy to Sakamoto, T. et al., *Heterocycles* (1993), 36, 2509-2512.

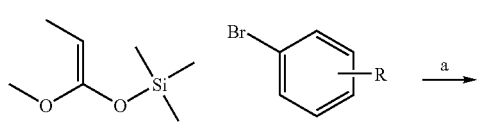

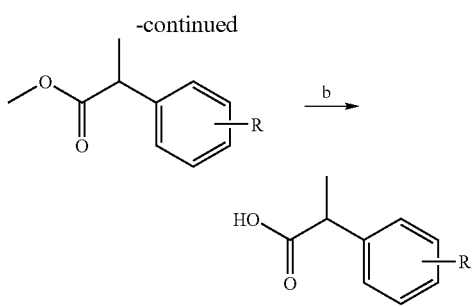

a. THF, reflux, 6 h b. LiOH, THF/H$_2$O, reflux, 12 h

Preparation of the Catalyst

Pd(dppf)Cl$_2$ (110 mg, 0.15 mmol), dppf (83 mg, 0.15 mmol) and butyl lithium (in hexane) (0.3 mmol) are added to 10 mL of dry THF. The reaction mixture is stirred for 1 minute at room temperature and can be used as palladium(0) catalyst in the following procedure.

General Protocol for the Palladium-Catalyzed Reaction of Aryl Halides with (E)-1-methoxy-1-trimethylsiloxypropane The prior in situ generated palladium(0) catalyst in dry THF (10 mL) is added to a mixture of TlOAc (90%, 1.78 g, 6 mmol) and dry THF (20 mL) under argon atmosphere. The resulting mixture is stirred for 5 minutes and then aryl halide (3 mmol) in dry THF (10 mL) and (E)-1-Methoxy-1-trimethylsiloxypropane (0.96 g, 6 mmol) are added at room temperature. The reaction mixture is then refluxed for 4-24 h. The organic solvents are removed in vacuo and water and diethyl ether are added to the residue, which is then filtered off. The filtrate is extracted with diethyl ether and the combined organic layers are dried over MgSO$_4$. After removal of the ether under reduced pressure the residue is purified by column chromatography.

6.9 General Method for the Synthesis of 2-(1H-indazol)propanoic Acids (cf. Examples 44-46, 48, 69-72)

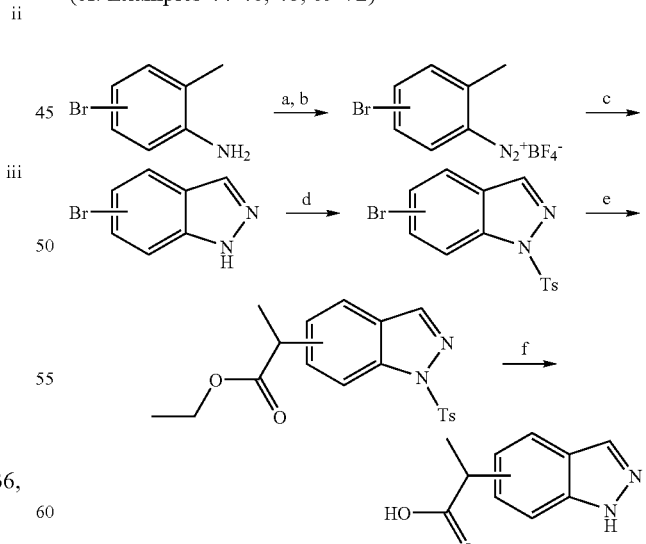

a. HBF$_4$ aq 50%; b. NaNO$_2$ aq, 0° C.; c. AcOK, 18-crown-6, CHCl$_3$, rt; d. TsCl, TEA, CH$_2$Cl$_2$; e. ethyl chloropropionate, NBu$_4$BF$_4$, NiBr$_2$bipy DMF, rt; f. TMSCl, NaI, CH$_3$CN, reflux The preparation of indazol derivatives can be performed according to the scheme above. Starting from the corresponding bromo substituted methylaniline the desired bromo-1-H-indazol can be obtained as described by Boulouard, M. et al. (*Bioorganic Medicinal Chemistry Letters* (2007), 17, 3177-3180) (a, b and c).

According to a procedure known to a person skilled in the art, the 1-H-indazol moiety can be protected utilizing a tosyl function (d). The tosyl protected bromo-indazol can be converted into the corresponding indazol propanoic acid ester applying ethyl chloropropionate according to Durandetti, M. et al. (*Tetrahedron* (2007), 63, 1146-1153) (e). The desired indazol propanoic acid can then be obtained by deprotection of the propanoic acid group as well as the indazol as it is described in Sabitha, G. et al. (*Tetrahedron Letters* (1999), 40, 1569-1570) (f).

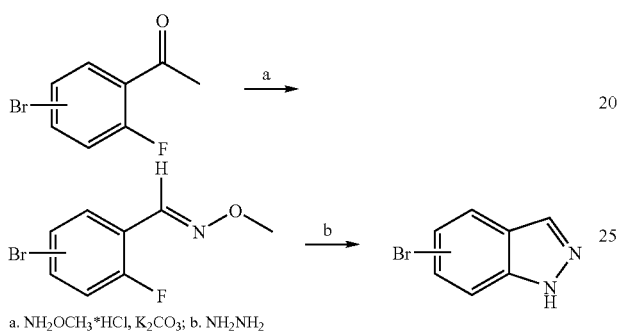

a. NH$_2$OCH$_3$*HCl, K$_2$CO$_3$; b. NH$_2$NH$_2$

Starting from bromo-substituted fluorophenyl ethanons, Lukin, K. et al. (*J. Org. Chem.* (2006), 71, 21, 8166-8172) describe an alternative access to the precursors of bromo-1-H-indazoles (a, b).

6.10 General Method for the Synthesis of 2-(1-phenyl-1H-indazol)propanoic Acids (cf. Example 73)

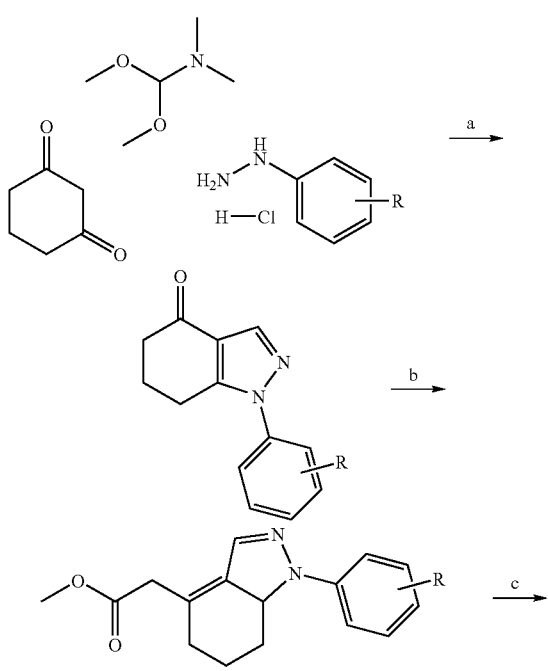

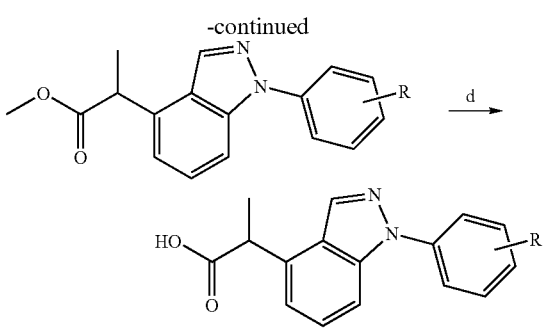

a. HOAc, H$_2$O, 2 min, 200° C., μwave; b. 2-Brompropansäure, Zn, I, HgCl$_2$, Benzen;
c. S, 190° C., 1 h, Raney-Nickel;
d. aq NaOH, reflux, 4 h The preparation of phenylindazol propanoic acids can be performed according to U.S. Pat. No. 3,657,270 (b-d). The starting material necessary for these reactions are the corresponding substituted 6,7-dihydro-1-phenyl-indazol-4(5H)-ones, which can be synthesized in a three-components-reaction under microwave radiation according to Molteni, V. et al. (*Synthesis* (2002), 12, 1669-1674) (a).

6.11. General Method for the Synthesis of 2-(indolin)propanoic Acids (cf. Examples 74-77)

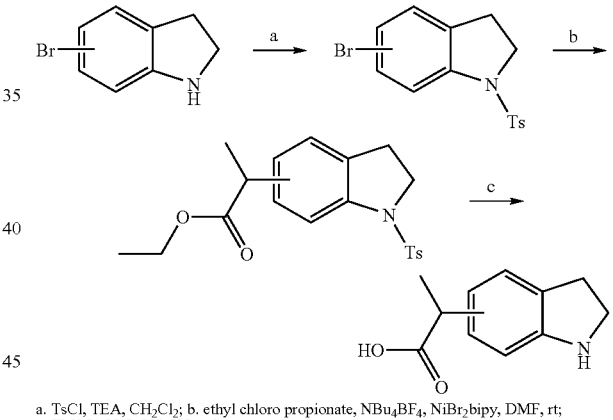

a. TsCl, TEA, CH$_2$Cl$_2$; b. ethyl chloro propionate, NBu$_4$BF$_4$, NiBr$_2$bipy, DMF, rt;
c. TMSCl, NaI, CH$_3$CN, reflux Starting from the corresponding bromo-substituted indolin a tosyl group is introduced according to a procedure known to a person skilled in the art (a). As described by Durandetti, M. et al. (*Tetrahedron* (2007), 63, 1146-1153), ethyl chloropropionate is applied for the preparation of an indolin propanoic acid ester (b). A deprotection step is performed consequently to yield the desired 2-indolin propanoic acid as described in Sabitha, G. et al. (*Tetrahedron Letters* (1999), 40, 1569-1570) (c).

In analogy to the protocols described above, the corresponding 2-(1H-indol)propanoic acids (i), 2-(2-oxoindolin)propanoic acids (ii), 2-(1,2,3,4-tetrahydrochinolin)propanoic acids (iii) and 2-(2-oxo-1,2,3,4-tetrahydrochinolin)propanoic acids (iv)

can be obtained.

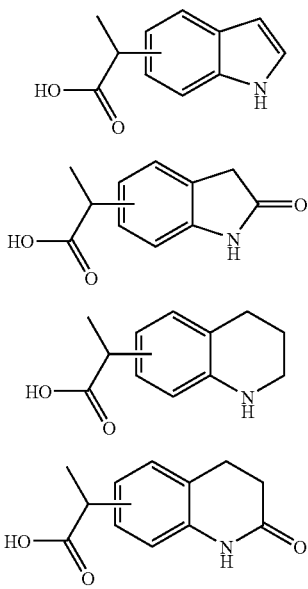

8. General Method of Reacting Amines of the General Formulae V or X with Carboxylic Acids of the General Formula VII Method A:

The acid of the general formula VII (1 equivalent), the amine of the general formulae V or X (1.2 equivalents) and EDCI (1.2 equivalents) are stirred in DMF (10 mmol acid in 20 mL) for 12 hours at RT and then water is added thereto. The reaction mixture is extracted repeatedly with EA, the aqueous phase is saturated with NaCl and then re-extracted with EA. The combined organic phases are washed with 1 N hydrochloric acid and a sat. aq. NaCl soln., dried over $MgSO_4$ and the solvent is removed under a vacuum. The residue is purified by means of flash chromatography ($SiO_2$, EA/hexane 1:2).

Method B:

The acid of the general formula VII (1 equivalent) and the amine of the general formulae V or X (1.1 equivalents) are dissolved in DCM (1 mmol acid in 6 mL) and combined at 0° C. with EDCI (1.5 equivalents), HOBt (1.4 equivalents) and triethylamine (3 equivalents). The reaction mixture is stirred for 20 h at RT and purified by means of column chromatography (n-hexane/EA=2:1).

The following example compounds were obtained according to the above-stated Method B.

Example Compound 1

2-benzooxazol-5-yl-N-(4-tert.-butyl-benzyl)-propionamide

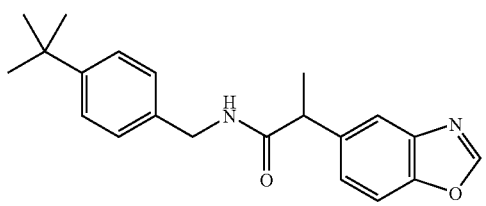

$^1$H-NMR ($CDCl_3$) δ 8.10 (s, 1H, Ar), 7.74 (d, 1H, J=1.7 Hz, Ar), 7.56 (d, 1H, J=8.4 Hz, Ar), 7.38 (dd, 1H, J=8.6, 1.8 Hz, Ar), 7.30 (d, 2H, J=8.4 Hz, Ar), 7.09 (d, 2H, J=8.4 Hz, Ar), 5.64 (bs, NH), 4.37 (m, 2H, $NHCH_2Ar$), 3.72 (q, 1H, J=7.1 Hz, COCH), 1.61 (d, 3H, J=7.1 Hz, $CHCH_3$), 1.28 (s, 9H, $C(CH_3)_3$)

Synthesis of Example Compound 2

2-benzooxazol-6-yl-N-(4-tert.-butyl-benzyl)-propionamide

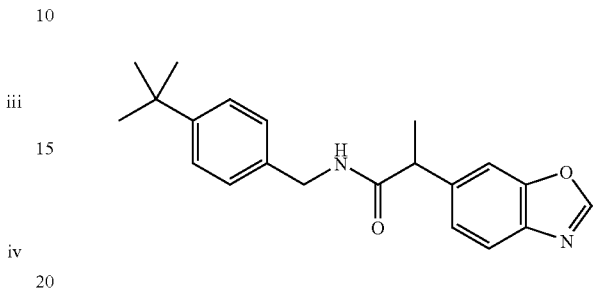

$^1$H-NMR ($CDCl_3$) δ 8.02 (d, 1H, J=2.0 Hz, Ar), 7.07 (dd, 1H, J=8.3, 1.7 Hz, Ar), 7.54 (s, 1H, Ar), 7.25 (m, 3H, Ar), 7.04 (d, 2H, J=7.0 Hz, Ar), 5.79 (bs, NH), 4.32 (m, 2H, $NHCH_2Ar$), 3.67 (q, 1H, J=7.1 Hz, COCH), 1.55 (d, 3H, J=7.1 Hz, $CHCH_3$), 1.23 (s, 9H, $C(CH_3)_3$)

IR 3296, 2963, 1649, 1518, 1479, 1434, 1247, 1067 $cm^{-1}$
Mass (FAB) m/z 337 $[M+H]^+$ Synthesis of Example Compound 3

2-benzooxazol-7-yl-N-(4-tert.-butyl-benzyl)-propionamide

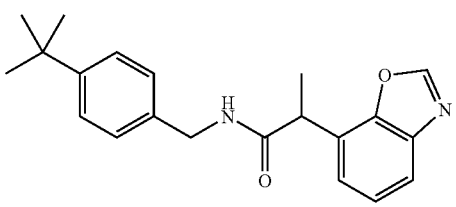

$^1$H-NMR ($CDCl_3$) δ 8.07 (s, 1H, Ar), 7.71 (m, 1H, Ar), 7.39-7.28 (m, 4H, Ar), 7.06 (d, 2H, J=8.4 Hz, Ar), 5.74 (bs, NH), 4.38 (m, 2H, $CH_2NH$), 4.06 (q, 1H, J=7.1 Hz, $CHCH_3$), 1.68 (d, 3H, J=7.1 Hz, $CHCH_3$), 1.29 (s, 9H, $C(CH_3)_3$)
Mass (FAB) m/z 337 $[M+H]^+$ Synthesis of Example Compound 4

Example 4 a) 2-(4-Aminophenyl)propanoic acid

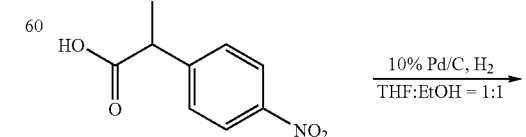

2-(4-nitrophenyl)propanoic acid
Commercially available

-continued

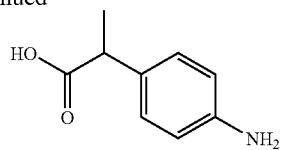

To the flask was added THF/EtOH (1:1, 100 mL) followed by starting material (10 g, 51.2 mmol) and 10% palladium carbon (0.87 g) at room temperature. The reaction mixture was hydrogenated and stirred for 1 hrs at 45 psi then filtered through celite bed, and washed with EtOH. The filtrate was concentrated in vacuo White-to-pale black solid, yield: quantitative b) 2-(4-Amino-3-nitrophenyl)propanoic acid

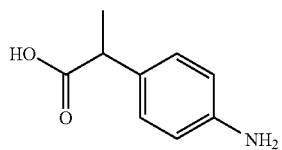

A solution of 2-(4-Aminophenyl)propanoic acid (8.45 g, 51.2 mmol) in AcOH (70 mL) was added $HNO_3$ (60%, 5.66 g) at room temperature. The reaction mixture was refluxed for 4 hrs then cooled to room temperature. The mixture was poured into iced water (200 mL), and extracted with $CH_2Cl_2$. The organic layer was dried over $MgSO_4$, filtered, and concentrated in vacuo.

c) Ethyl 2-(4-amino-3-nitrophenyl) propanoate

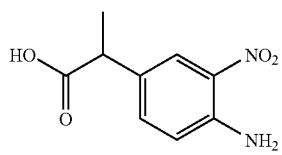

To the flask of 2-(4-Amino-3-nitrophenyl)propanoic acid residue was added EtOH (200 mL) and catalytic amounts of sulfuric acid (1 mL) at room temperature. The reaction mixture was refluxed for 6 hrs then cooled to room temperature. The mixture was diluted with $H_2O$ and extracted with EtOAc. The organic layer was dried over $MgSO_4$, filtered, and concentrated in vacuo.

Pale yellow oil, yield: 17.4% (two steps)

d) Ethyl 2-(3,4-diaminophenyl)propanoate

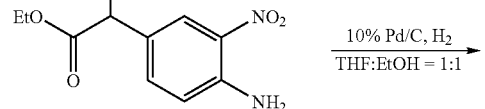

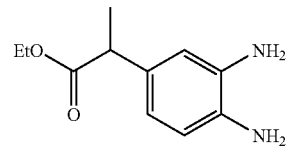

To the flask was added THF/EtOH (1:1, 50 mL) followed by Ethyl 2-(4-amino-3-nitrophenyl) propanoate (2.12 g, 8.90 mmol) and 10% palladium carbon (220 mg) at room temperature. The reaction mixture was hydrogenated and stirred for 3 hrs at 45 psi then filtered through celite bed, and washed with EtOH. The filtrate was concentrated in vacuo. The residue was purified by flash column chromatography on silica gel using EtOAc:hexanes (1:4-1:2) as eluant.

Yellow oil, yield: 74.5% e) Ethyl 2-(2,3-dihydro-2-oxo-1H-benzo[d]imidazol-5-yl)propanoate

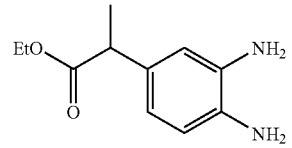

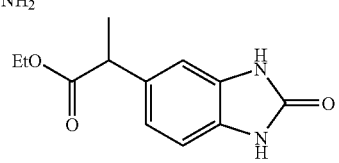

A solution of Ethyl 2-(3,4-diaminophenyl)propanoate (217 mg, 1.04 mmol) in $CH_2Cl_2$ (4 mL) was added 1,1'-carbonyldiimidazole (189 mg) and DBU (330 mg, in $CH_2Cl_2$ (4 mL)) at room temperature.

The reaction mixture was stirred for 1 hr at room temperature. The mixture was diluted with $H_2O$ (20 mL) and extracted with $CH_2Cl_2$. The organic layer was dried over $MgSO_4$, filtered, and concentrated in vacuo. The residue was purified by flash column chromatography on silica gel using EtOAc:hexanes (1:4-1:2) as eluant.

Pale yellow solid, yield: 72.7% f) 2-(2,3-Dihydro-2-oxo-1H-benzo[d]imidazol-5-yl) propanoic acid

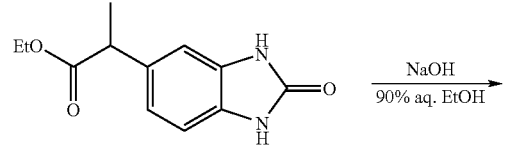

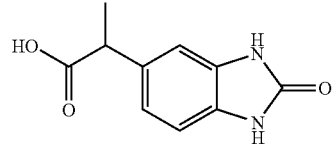

To the flask of Ethyl 2-(2,3-dihydro-2-oxo-1H-benzo[d]imidazol-5-yl)propanoate (175 mg, 0.747 mmol) was added 90% aq. EtOH (5 mL) at room temperature, and additionally added NaOH (70 mg). The reaction mixture was stirred for 10 hrs at 40° C. then cooled to room temperature. The mixture was diluted with H₂O (25 mL) and acidified with AcOH (4 mL, pH=4) then extracted with CH₂Cl₂. The organic layer was dried over MgSO₄, filtered, and concentrated in vacuo. The residue was purified by flash column chromatography on silica gel using CH₂Cl₂:MeOH (10:1) as eluant.

Pale brown solid, yield: 63.6%

Example Compound 4

N-(4-tert.-butyl-benzyl)-2-(2-oxo-2,3-dihydro-1H-benzoimidazol-5-yl)-propionamide

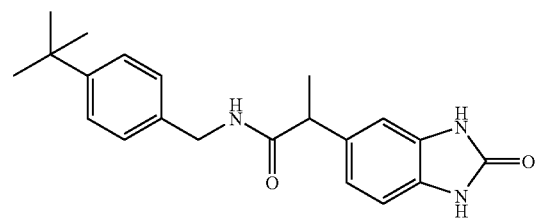

¹H NMR (300 MHz, DMSO) δ10.6-10.5 (bs, 2H), 8.33 (bt, 1H), 7.34-7.22 (m, 2H), 7.09-7.06 (m, 2H), 6.93-6.81 (m, 3H), 4.21-4.17 (m, 2H), 3.60 (q, 1H, J=7.1 Hz), 1.34-1.24 (m, 12H)
MS (EI) m/z 451 (M+H)

Synthesis of Example Compound 5 a) Ethyl 2-(3-hydroxyphenyl)acetate

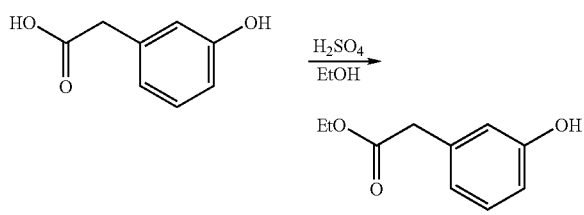

To the flask was added EtOH (100 ml) followed by starting material (9.83 g, 64.6 mmol) and sulfuric acid (catalytic amount). The mixture was refluxed for 3 hrs then cooled to room temperature. The mixture was diluted with H₂O (100 mL) and extracted with EtOAc (100 mL). The organic layer was dried over MgSO₄, filtered, and concentrated in vacuo. The residue was purified by flash column chromatography on silica gel using EtOAc:hexanes (1:4) as eluant.

Pale yellow oil, yield: 94.5%.

b) Ethyl 2-(3-(methoxymethoxy)phenyl)acetate

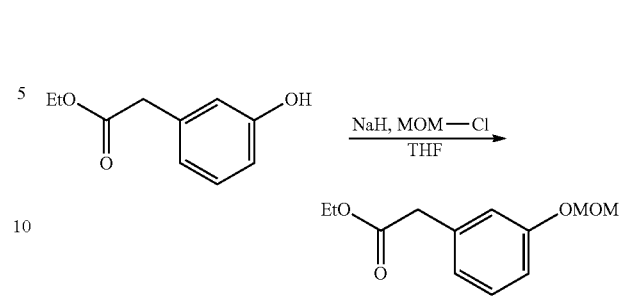

Reference: JACS, 100, 8031 (1978)

A solution of Ethyl 2-(3-hydroxyphenyl)acetate (11 g, 61 mmol) in THF (100 mL) was added NaH (2.93 g, 73.3 mmol) and MOM-Cl 5.94 g, 73.3 mmol) at 0° C. The reaction mixture was stirred for 16 hrs at 0° C. then warmed to room temperature. The reaction mixture was diluted with H₂O (200 mL) and extracted with EtOAc. The organic layer was dried over MgSO₄, filtered, and concentrated in vacuo. The residue was purified by flash column chromatography on silica gel using EtOAc:hexanes (1:10) as eluant.

Colorless oil, yield: 79.7%.

c) Ethyl 2-(3-(methoxymethoxy)phenyl)propanoate

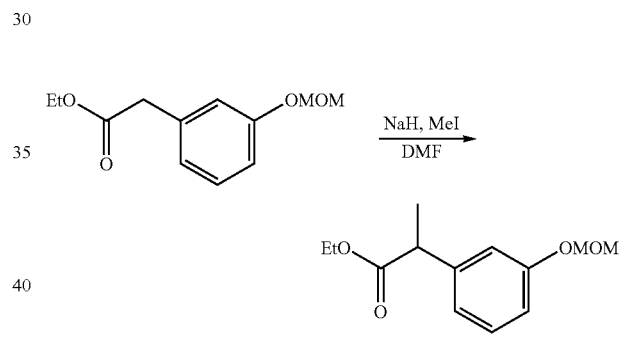

A solution of Ethyl 2-(3-(methoxymethoxy)phenyl)acetate (8.06 g, 35.9 mmol) in DMF (50 mL) was added NaH (1.74 g, 43.5 mmol) and iodomethane (6.37 g, 44.9 mmol) at 0° C. The reaction mixture was stirred for 1 hrs at 0° C. then diluted with H₂O (250 mL) and extracted with EtOAc. The organic layer was dried over MgSO₄, filtered, and concentrated in vacuo. The residue was purified by flash column chromatography on silica gel using EtOAc:hexanes (1:10) as eluant.

Colorless oil, yield: 49.1%.

d) Ethyl 2-(3-hydroxyphenyl)propanoate

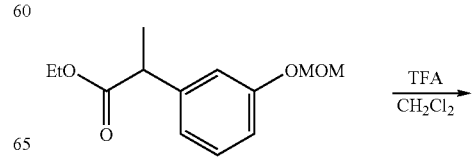

-continued

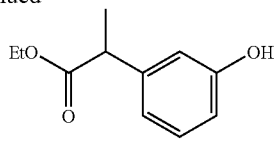

A solution of Ethyl 2-(3-(methoxymethoxy)phenyl)propanoate (4.17 g, 17.5 mmol) in $CH_2Cl_2$ (80 mL) was added trifluoroacetic acid (40 mL) at 0° C. The reaction mixture was stirred for 1 hrs at 0° C., and basified with $NaHCO_3$ (60 g). The mixture was diluted with $H_2O$ (250 mL) slowly and extracted with $CH_2Cl_2$. The organic layer was dried over $MgSO_4$, filtered, and concentrated in vacuo. The residue was purified by flash column chromatography on silica gel using EtOAc:hexanes (1:4) as eluant.

Colorless oil, yield: 74.1% e) Ethyl 2-(3-hydroxy-4-nitrophenyl)propanoate

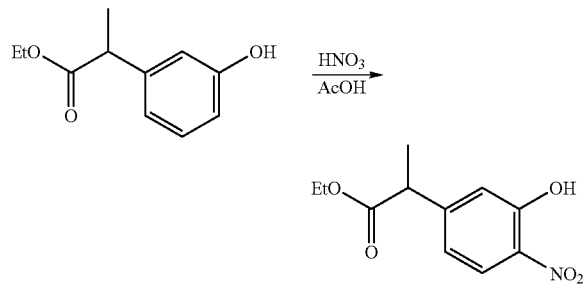

A solution of Ethyl 2-(3-hydroxyphenyl)propanoate (2.51 g, 12.9 mmol) in acetic acid (20 mL) was added nitric acid (1.45 g, 13.8 mmol) in acetic acid (2 mL) at room temperature. Then the colorless oil changed to the dark brown oil after 1~2 minutes stirred. The reaction mixture was stirred for 15 minutes at room temperature then poured into iced water (100 mL), and extracted with EtOAc. The organic layer was dried over $MgSO_4$, filtered, and concentrated in vacuo. The residue was purified by flash column chromatography on silica gel using EtOAc:hexanes (1:6) as eluant. Yellow solid (m.p. 45-47° C.), yield: 30.8% f) Ethyl 2-(4-amino-3-hydroxyphenyl)propanoate

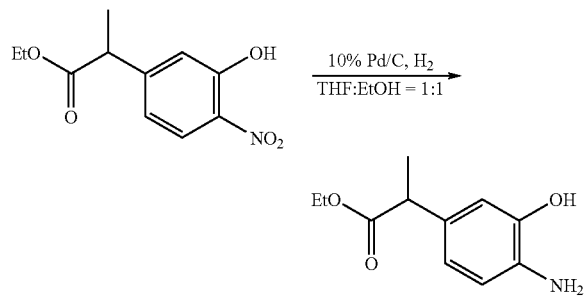

To the flask was added THF/EtOH (1:1, 30 mL) followed by Ethyl 2-(3-hydroxy-4-nitrophenyl)propanoate (900 mg, 3.76 mmol) and 10% palladium carbon (93 mg) at room temperature. The reaction mixture was hydrogenated and stirred for 1 hrs at 46 psi then filtered through celite bed, and washed with EtOAc. The filtrate was concentrated in vacuo. The residue was purified by flash column chromatography on silica gel using EtOAc:hexanes (1:2) as eluant.

White solid (m.p. 119-121° C.), yield: 80.1% e) ethyl 2-(4-(2-chloroacetamido)-3-hydroxyphenyl) propanoate

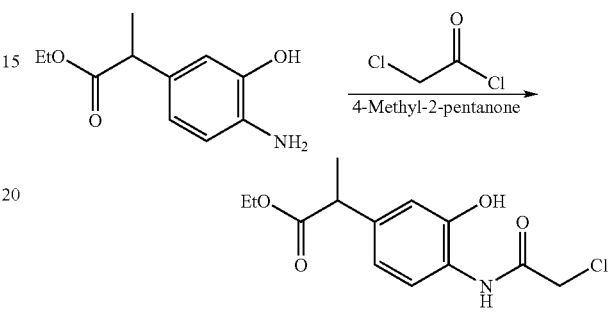

A solution of Ethyl 2-(4-amino-3-hydroxyphenyl)propanoate (101 mg, 0.483 mmol) in 4-methyl-2-pentanone (4 mL) was added chloroacetyl chloride (58 mg, 0.514 mmol) in 4-methyl-2-pentanone (2 mL) at room temperature. The reaction mixture was stirred for 12 hrs at 80° C. then cooled to room temperature. The mixture was diluted with $H_2O$ and extracted with EtOAc. The organic layer was dried over $MgSO_4$, filtered, and concentrated in vacuo. The residue was purified by flash column chromatography on silica gel using EtOAc:hexanes (1:2) as eluant.

Pale pink solid (m.p. 118-120° C.), yield: 90.6% f) Ethyl 2-(3,4-dihydro-3-oxo-2H-benzo[b][1,4]oxazin-7-yl)propanoate

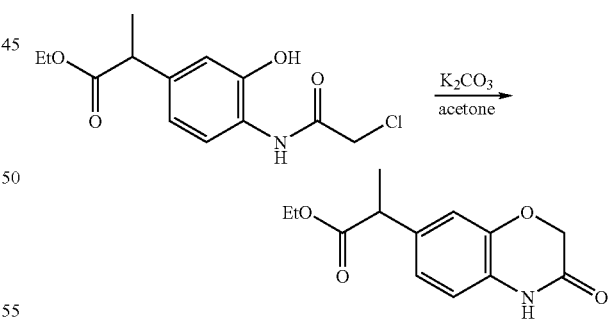

A solution of ethyl 2-(4-(2-chloroacetamido)-3-hydroxyphenyl)propanoate (110 mg, 0.385 mmol) in acetone (10 mL) was added potassium carbonate (61 mg). the reaction mixture was refluxed for 3 hrs then cooled to room temperature. The mixture was diluted with $H_2O$ and extracted with EtOAc. The organic layer was dried over $MgSO_4$, filtered, and concentrated in vacuo. The residue was purified by flash column chromatography on silica gel using EtOAc:hexanes (1:2) as eluent.

White solid (m.p. 101° C.), yield: 91.7% g) 2-(3,4-Dihydro-3-oxo-2H-benzo[b][1,4]oxazin-7-yl)propanoic acid)

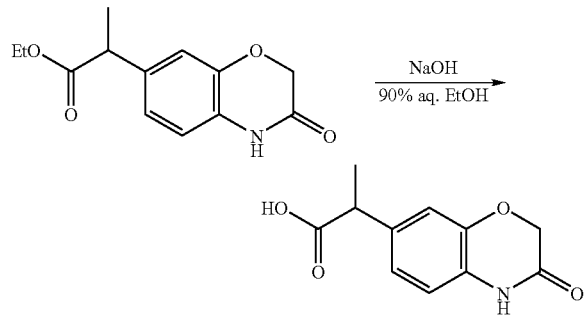

A solution of Ethyl 2-(3,4-dihydro-3-oxo-2H-benzo[b][1,4]oxazin-7-yl)propanoate (80 mg, 0.321 mmol) in 90% aq. EtOH (5 mL) was added NaOH (64 mg, 1.60 mmol) at room temperature. The reaction mixture was stirred for 12 hrs at 50° C. then cooled to room temperature. The mixture was diluted with H$_2$O (20 mL) and acidified with AcOH then extracted with CH$_2$Cl$_2$. The organic layer was dried over MgSO$_4$, filtered, and concentrated in vacuo.

White solid (m.p. 199-201° C.), yield: 98.4%

Example Compound 5

N-(4-tert.-butyl-benzyl)-2-(3-oxo-3,4-dihydro-2H-benzo[1,4]oxazin-7-yl)propionamide

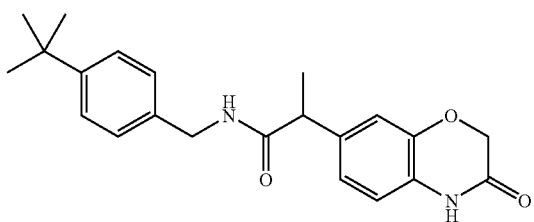

$^1$H-NMR (CDCl$_3$) δ 9.15 (bs, NH), 7.32 (d, 2H, J=8.2 Hz, Ar), 7.12 (d, 2H, J=8.2 Hz, Ar), 6.93-6.78 (m, 3H, Ar), 5.79 (bs, NH), 4.58 (s, 2H, OCH$_2$), 4.38 (m, 2H, NHCH$_2$), 3.50 (q, 1H, J=7.1 Hz, COCH), 1.51 (d, 3H, J=7.1 Hz, CHCH$_3$), 1.29 (s, 9H, C(CH$_3$)$_3$)

IR 3284, 2962, 1700, 1645, 1517, 1417 cm$^{-1}$

Mass (FAB) m/z 367 [M+H]$^+$, 389 [M+Na]$^+$

Synthesis of Example Compound 6 a) Ethyl 2-(4-(methoxymethoxy)phenyl)acetate

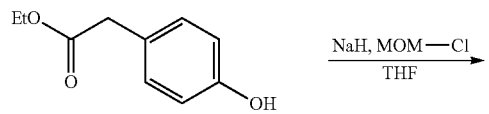

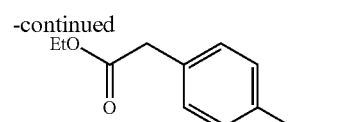

Starting material (2.14 g, 11.8 mmol) in THF (20 mL) was slowly added sodium hydride (0.50 g, 12.5 mmol) and chloromethylmethylether (1.00 g, 12.4 mmol) at 0° C. The reaction mixture was stirred for 16 hours at room temperature. The mixture was added water (50 mL) and extracted with EtOAc. The organic layer was dried with MgSO$_4$. The organic layer was filtered and the filtrate was concentrated in vacuo. The residue was purified by column chromatography eluting with n-Hexane/EtOAc=6/1.

Colorless oil, yield: 67% b) Ethyl 2-(4-(methoxymethoxy)phenyl)propanoate

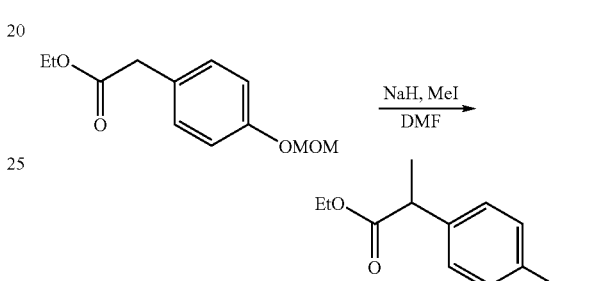

Ethyl 2-(4-(methoxymethoxy)phenyl)acetate (1.75 g, 7.80 mmol) in DMF (50 mL) was slowly added sodium hydride (330 mg, 8.25 mmol) and iodomethane (1.13 g, 7.96 mmol) at 0° C. The reaction mixture was stirred for 1 hour at 0° C. The mixture was added water (50 mL) and extracted with EtOAc. The organic layer was dried with MgSO$_4$. The organic layer was filtered and the filtrate was concentrated in vacuo. The residue was purified by column chromatography eluting with n-Hexane/EtOAc=15/1.

Colorless oil, yield: 57% c) Ethyl 2-(4-hydroxyphenyl)propanoate

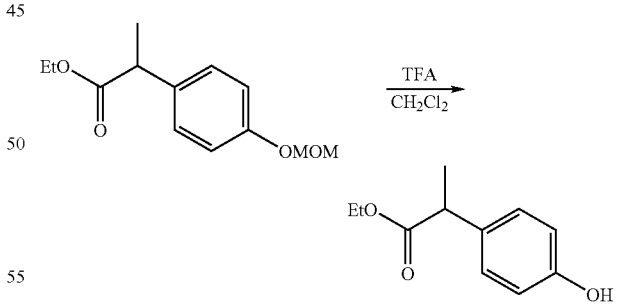

Ethyl 2-(4-(methoxymethoxy)phenyl)propanoate (485 mg, 2.04 mmol) in methylene chloride (10 mL) was added trifluoroacetic acid (5 mL) at 0° C. The mixture was stirred for 40 minutes at 0° C. and then slowly added solid sodium bicarbonate (7.14 g) and water (100 mL) at 0° C. The mixture was extracted with methylene chloride. The organic layer was dried with MgSO$_4$. The organic layer was filtered and the filtrate was concentrated in vacuo. The residue was purified by column chromatography eluting with n-Hexane/EtOAc=4/1.

Colorless oil, yield: 67% d) Ethyl 2-(4-hydroxy-3-nitrophenyl)propanoate

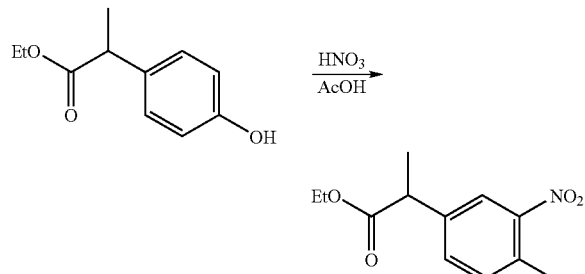

Ethyl 2-(4-hydroxyphenyl)propanoate (275 mg, 1.42 mmol) in acetic acid (2 mL) was added nitric acid (60-62%, 300 mg, 2.86 mmol) at room temperature. The mixture was stirred for 1 hour at 50° C. and cooled to room temperature. The reaction mixture was poured into ice water (20 mL) and extracted with EtOAc. The organic layer was dried with MgSO₄ and filtered. EtOAc was removed by evaporation. The residue was purified by column chromatography eluting with n-Hexane/EtOAc=6/1.

Yellow oil, yield: 87% e) Ethyl 2-(3-amino-4-hydroxyphenyl)propanoate

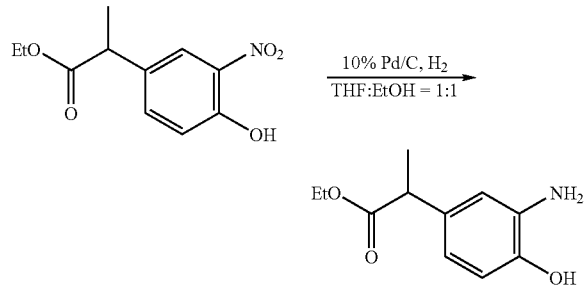

Ethyl 2-(4-hydroxy-3-nitrophenyl)propanoate (260 mg, 1.09 mmol) in THF (6 mL) and ethanol (6 mL) was slowly added 10% Pd/C (29 mg) at room temperature. The mixture was hydrogenated for 2 hours at 43 psi and then filtered with celite pad and washed with EtOAc. The filtrate was concentrated in vacuo. The residue was purified by column chromatography eluting with n-Hexane/EtOAc=1/1.

Yellow oil, yield: 86% f) ethyl 2-(3-(2-chloroacetamido)-4-hydroxyphenyl)propanoate

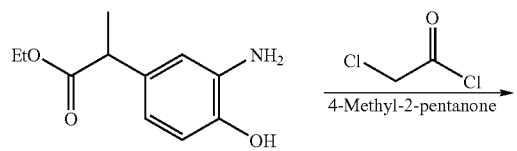

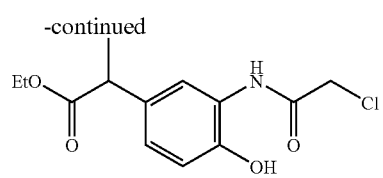

Ethyl 2-(3-amino-4-hydroxyphenyl)propanoate (104 mg, 0.497 mmol) in 4-methyl-2-pentanone (4 mL) was added chloroacetylchloride (56 mg, 0.496 mmol) at room temperature and stirred for 20 hours at 80° C. The reaction mixture was cooled to room temperature and added water (30 mL). The mixture was extracted with EtOAc. The organic layer was dried with MgSO₄ and filtered. EtOAc was removed by evaporation. The residue was purified by column chromatography eluting with n-Hexane/EtOAc=2/1.

White solid (m.p. 126-128° C.), yield: 78% g) Ethyl 2-(3,4-dihydro-3-oxo-2H-benzo[b][1,4]oxazin-6-yl)propanoate

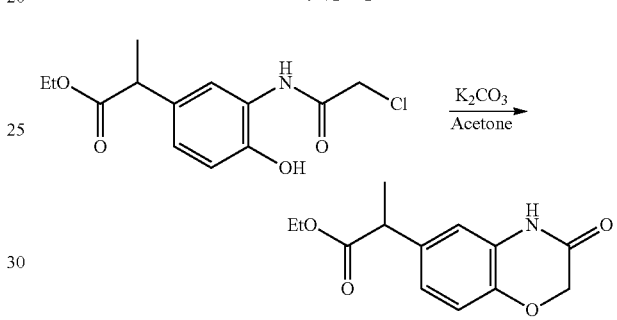

Ethyl 2-(3-(2-chloroacetamido)-4-hydroxyphenyl)propanoate (100 mg, 0.350 mmol) in acetone (10 mL) was added potassium carbonate (59 mg) at room temperature and refluxed for 3 hours. The reaction mixture was cooled to room temperature and added water (15 mL). The mixture was extracted with EtOAc. The organic layer was dried with MgSO₄ and filtered. EtOAc was removed by evaporation. The residue was purified by column chromatography eluting with n-Hexane/EtOAc=2/1.

White solid (m.p. 116-118° C.), yield: 92% h) 2-(3,4-Dihydro-3-oxo-2H-benzo[b][1,4]oxazin-6-yl)propanoic acid

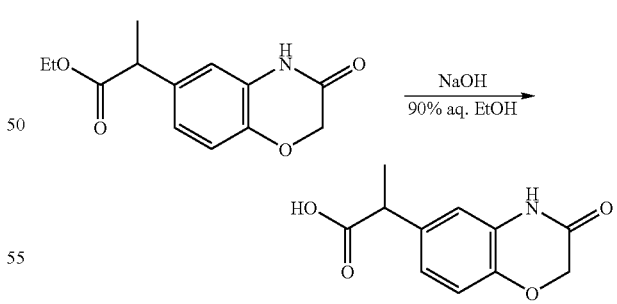

Ethyl 2-(3,4-dihydro-3-oxo-2H-benzo[b][1,4]oxazin-6-yl)propanoate (63 mg, 0.253 mmol) in 90% aq. EtOH (4.5 mL) was added sodium hydroxide (50 mg, 1.25 mmol) at room temperature. The reaction mixture was stirred for 12 hours at 50° C. and cooled to room temperature. The mixture was added water (20 mL) and acidified with acetic acid. The mixture was extracted with methylene chloride. The organic layer was dried with MgSO₄ and filtered. The filtrate was concentrated in vacuo.

white solid (m.p. 191-193° C.), yield: 95%,

Example Compound 6

N-(4-tert.-butyl-benzyl)-2-(3-oxo-3,4-dihydro-2H-benzo[1,4]oxazin-6-yl)propionamide

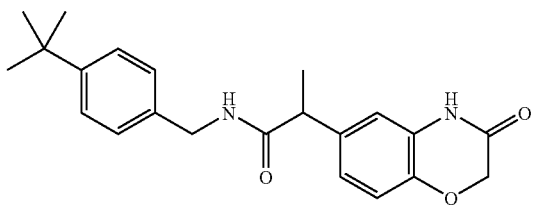

$^1$H-NMR (CDCl$_3$) δ 8.76 (bs, NH), 7.32 (d, 2H, J=8.4 Hz, Ar), 7.12 (d, 2H, J=8.3 Hz, Ar), 6.93-6.85 (m, 3H, Ar), 5.73 (bs, NH), 4.58 (s, 2H, OCH$_2$), 4.38 (m, 2H, NHCH$_2$), 3.48 (q, 1H, J=7.1 Hz, COCH), 1.51 (d, 3H, J=7.1 Hz, CHCH$_3$), 1.29 (s, 9H, C(CH$_3$)$_3$)

IR 2925, 2855, 1648, 1540, 1459 cm$^{-1}$
Mass (FAB) m/z 367 [M+H]$^+$

Synthesis of Example Compound 7

N-(4-tert.-butyl-benzyl)-2-(7-methoxy-benzooxazolyl-5-yl)-propionamide

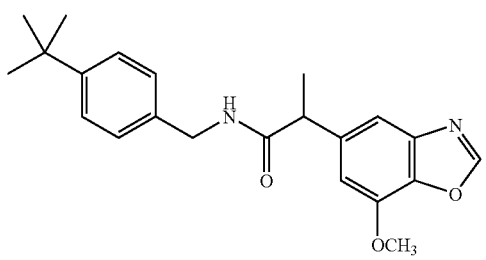

$^1$H-NMR (CDCl$_3$) δ 8.06 (s, 1H, Ar), 7.29 (m, 3H, Ar), 7.10 (d, 2H, J=8.1 Hz, Ar), 6.87 (s, 1H, Ar), 5.70 (bs, NH), 4.37 (m, 2H, NHCH$_2$Ar), 4.00 (s, 3H, OCH$_3$), 3.69 (q, 1H, J=7.1 Hz, COCH), 1.60 (d, 3H, J=7.1 Hz, CHCH$_3$), 1.28 (s, 9H, C(CH$_3$)$_3$)

IR 3297, 2963, 1647, 1519, 1316, 1110 cm$^{-1}$
Mass (FAB) m/z 367 [M+H]$^+$

Example Compound 8

2-benzooxazol-4-yl-N-(4-tert.-butyl-benzyl)-propionamide

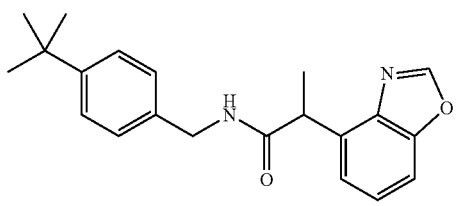

$^1$H-NMR (CDCl$_3$) δ 8.04 (s, 1H, Ar), 7.51 (m, 1H, Ar), 7.41 (m, 2H, Ar), 7.26 (d, 2H, J=8.2 Hz, Ar), 7.03 (d, 2H, J=8.3 Hz, Ar), 6.65 (bs, NH), 4.35 (m, 3H, NHCH$_2$Ar & COCH), 1.68 (d, 3H, J=7.1 Hz, CHCH$_3$), 1.29 (s, 9H, C(CH$_3$)$_3$)

IR 3304, 2962, 1658, 1519, 1428, 1242, 1076 cm$^{-1}$
Mass (FAB) m/z 337 [M+H]$^+$

Synthesis of Example Compound 9 a) Ethyl 2-(3,4-dihydroxyphenyl)acetate

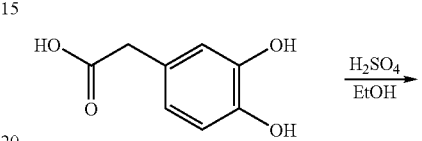

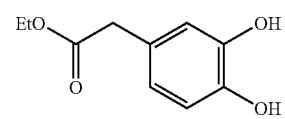

To the flask was added EtOH (15 ml) followed by starting material (1.07 g, 6.36 mmol) and sulfuric acid (catalytic amount). The mixture was refluxed for 3 hrs then cooled to room temperature. The mixture was diluted with H$_2$O (30 mL) and extracted with EtOAc (30 mL). The organic layer was dried over MgSO$_4$, filtered, and concentrated in vacuo. The residue was purified by flash column chromatography on silica gel using EtOAc:hexanes (1:1) as eluant.

Colorless oil, yield: 89.8%.

b) Ethyl 2-(2,3-dihydrobenzo[b][1,4]dioxin-7-yl)acetate

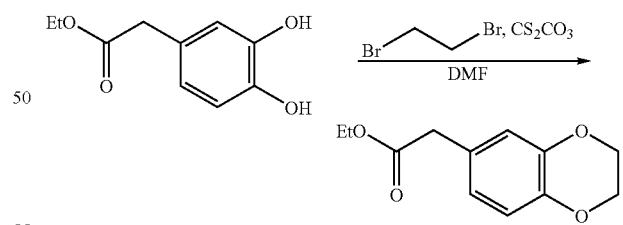

A mixture of Ethyl 2-(3,4-dihydroxyphenyl)acetate (1.11 g, 5.66 mmol) and 1,2-dibromoethane (1.07 g, 5.69 mmol) in DMF (5 mL) was added cesium carbonate (3.71 g, 11.4 mmol). The reaction mixture was stirred for 2 hrs at 80° C. then cooled to room temperature. The mixture was diluted with H$_2$O and extracted with EtOAc. The organic layer was dried over MgSO$_4$, filtered, and concentrated in vacuo. The residue was purified by flash column chromatography on silica gel using EtOAc:hexanes (1:4~1:2) as eluant.

Colorless oil, yield: 21.5%.

c) Ethyl 2-(2,3-dihydrobenzo[b][1,4]dioxin-7-yl)propanoate

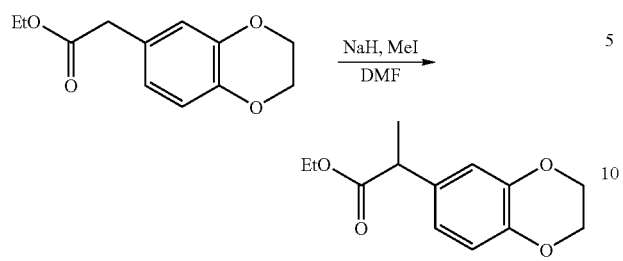

A solution of Ethyl 2-(2,3-dihydrobenzo[b][1,4]dioxin-7-yl)acetate (257 mg, 1.16 mmol) in DMF (2 mL) was added NaH (50 mg, 1.25 mmol) and iodomethane (167 mg, 1.18 mmol) in DMF (0.5 mL) at 0° C. The reaction mixture was stirred for 1 hrs at 0° C. then diluted with $H_2O$ (20 mL) and extracted with EtOAc (20 mL). The organic layer was dried over $MgSO_4$, filtered, and concentrated in vacuo. The residue was purified by flash column chromatography on silica gel using EtOAc:hexanes (1:6) as eluant.

Colorless oil, yield: 82.1%.

d) 2-(2,3-Dihydrobenzo[b][1,4]dioxin-7-yl)propanoic acid

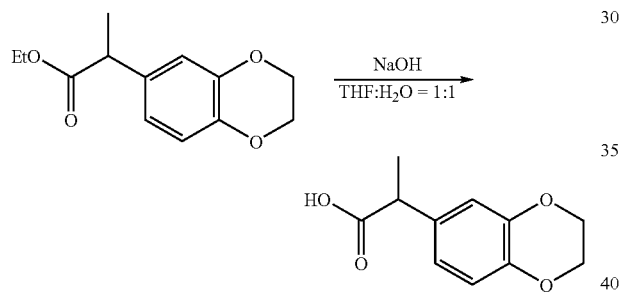

To the flask was added $THF/H_2O$ (1:1, 4 mL) followed by Ethyl 2-(2,3-dihydrobenzo[b][1,4]dioxin-7-yl)propanoate (133 mg, 0.563 mmol) and NaOH (30 mg, 0.750 mmol) at room temperature. The reaction mixture was stirred for 16 hrs at room temperature. The mixture was diluted with $H_2O$ (20 mL) and acidified with acetic acid (4 mL, pH=4) then extracted with $CH_2Cl_2$. The organic layer was dried over $MgSO_4$, filtered, and concentrated in vacuo.

Colorless oil, yield: quantitative.

Example Compound 9

N-(4-tert.-butyl-benzyl)-2-(2,3-dihydro-benzo[1,4]dioxin-6-yl)-propionamide

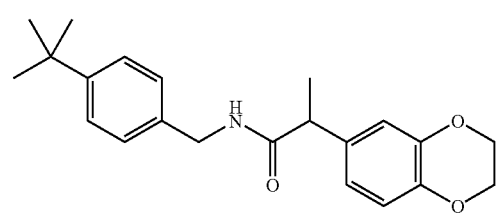

$^1$H-NMR (CDCl$_3$) δ 7.32 (d, 2H, J=8.3 Hz, Ar), 7.10 (d, 2H, J=8.3 Hz, Ar), 6.84-6.74 (m, 3H, Ar), 5.62 (bs, NH), 4.36 (m, 2H, NHCH$_2$), 4.25 (s, 4H, CH$_2$CH$_2$), 3.49 (q, 1H, J=7.1 Hz, COCH), 1.51 (d, 3H, J=7.1 Hz, CHCH$_3$), 1.30 (s, 9H, C(CH$_3$)$_3$)

IR 3298, 2963, 1648, 1507, 1287, 1255, 1068 cm$^{-1}$

Mass (FAB) m/z 354 [M+H]$^+$

Synthesis of Example Compound 10 a) 2-(4-Aminophenyl)propanoic acid

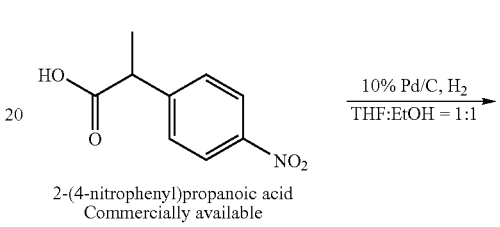

2-(4-nitrophenyl)propanoic acid
Commercially available

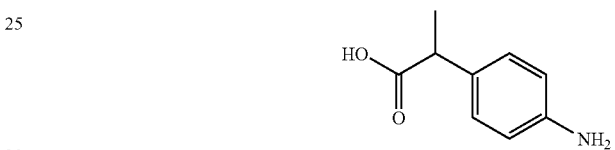

To the flask was added THF/EtOH (1:1, 100 mL) followed by starting material (10 g, 51.2 mmol) and 10% palladium carbon (0.87 g) at room temperature. The reaction mixture was hydrogenated and stirred for 1 hrs at 45 psi then filtered through celite bed, and washed with EtOH. The filtrate was concentrated in vacuo White-to-pale black solid, yield: quantitative b) 2-(4-Amino-3-nitrophenyl)propanoic acid

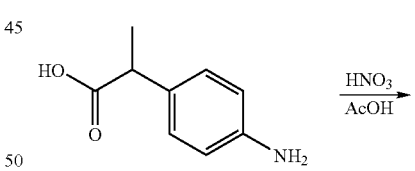

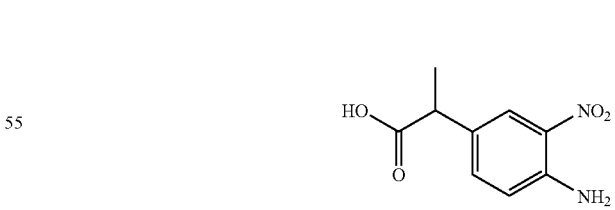

A solution of 2-(4-Aminophenyl)propanoic acid (8.45 g, 51.2 mmol) in AcOH (70 mL) was added HNO$_3$ (60%, 5.66 g) at room temperature. The reaction mixture was refluxed for 4 hrs then cooled to room temperature. The mixture was poured into iced water (200 mL), and extracted with $CH_2Cl_2$. The organic layer was dried over $MgSO_4$, filtered, and concentrated in vacuo.

c) Ethyl 2-(4-amino-3-nitrophenyl)propanoate

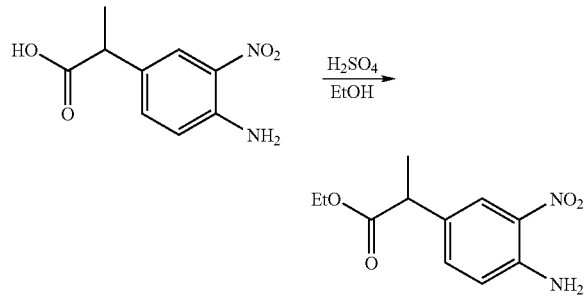

To the flask of 2-(4-Amino-3-nitrophenyl)propanoic acid residue was added EtOH (200 mL) and catalytic amounts of sulfuric acid (1 mL) at room temperature. The reaction mixture was refluxed for 6 hrs then cooled to room temperature. The mixture was diluted with H$_2$O and extracted with EtOAc. The organic layer was dried over MgSO$_4$, filtered, and concentrated in vacuo.

Pale yellow oil, yield: 17.4% (two steps)

d) Ethyl 2-(3,4-diaminophenyl)propanoate

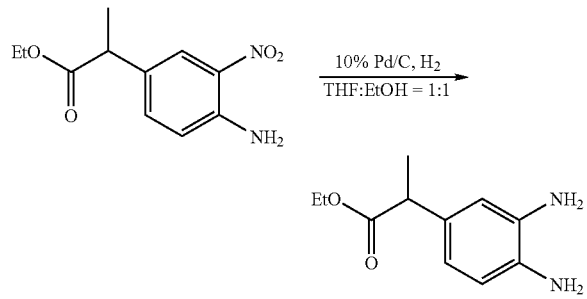

To the flask was added THF/EtOH (1:1, 50 mL) followed by Ethyl 2-(4-amino-3-nitrophenyl)propanoate (2.12 g, 8.90 mmol) and 10% palladium carbon (220 mg) at room temperature. The reaction mixture was hydrogenated and stirred for 3 hrs at 45 psi then filtered through celite bed, and washed with EtOH. The filtrate was concentrated in vacuo. The residue was purified by flash column chromatography on silica gel using EtOAc:hexanes (1:4-1:2) as eluant.

Yellow oil, yield: 74.5% e) Ethyl 2-(2,3-dihydro-2-oxo-1H-benzo[d]imidazol-5-yl)propanoate

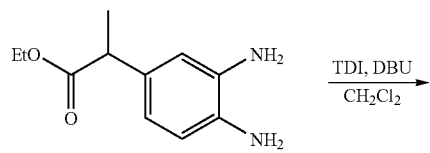

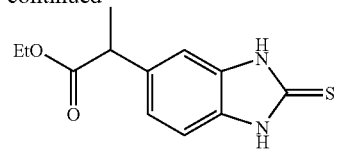

A solution of ethyl 2-(3,4-diaminophenyl)propanoate (222 mg, 1.07 mmol) in CH$_2$Cl$_2$ (4 mL) was added 1,1'-Thiocarbonyl diimidazole (241 mg) and DBU (345 mg, in CH$_2$Cl$_2$ (4 mL)) at room temperature. The reaction mixture was stirred for 1 hr at room temperature. The mixture was diluted with H$_2$O (20 mL) and extracted with CH$_2$Cl$_2$. The organic layer was dried over MgSO$_4$, filtered, and concentrated in vacuo. The residue was purified by flash column chromatography on silica gel using EtOAc:hexanes (1:4-1:2) as eluant.

Colorless oil, yield: 35.8% f) 2-(2,3-Dihydro-2-thioxo-1H-benzo[d]imidazol-5-yl)propanoic acid

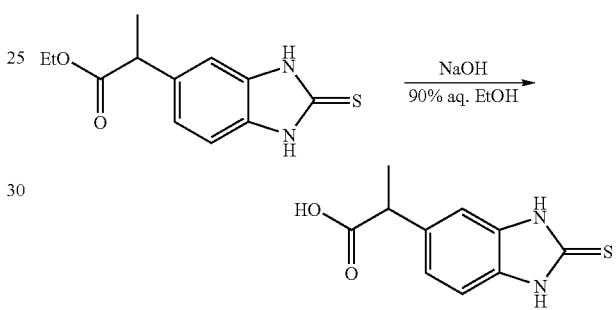

To the flask of ethyl 2-(2,3-dihydro-2-oxo-1H-benzo[d]imidazol-5-yl)propanoate (93 mg, 0.372 mmol) was added 90% aq. EtOH (5 mL) at room temperature, and additionally added NaOH (30 mg). The reaction mixture was stirred for 10 hrs at 40° C. then cooled to room temperature. The mixture was diluted with H$_2$O (25 mL) and acidified with AcOH (3 mL, pH=4) then extracted with CH$_2$Cl$_2$. The organic layer was dried over MgSO$_4$, filtered, and concentrated in vacuo. The residue was purified by flash column chromatography on silica gel using CH$_2$Cl$_2$:MeOH (10:1) as eluant.

Brown oil, yield: 94.3%

Example Compound 10

N-(4-tert.-butyl-benzyl)-2-(2-thioxo-2,3-dihydro-1H-benzoimidazol-5-yl)-propionamide

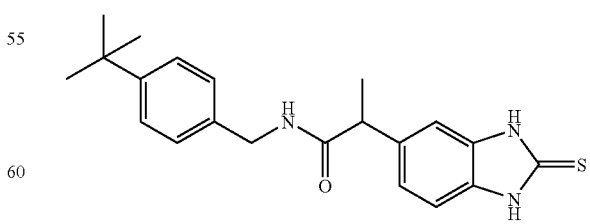

$^1$H NMR (300 MHz, CD$_3$OD) $\delta$ 7.28-6.95 (m, 7H), 4.19 (s, 2H), 3.63 (q, 1H, J=7.0 Hz), 1.38 (d, 3H, J=7.1 Hz), 1.16 (s, 9H)

MS (EI) m/z 367 (M+H)

Synthesis of Example Compound 11 a) 2-(4-Amino-phenyl)-propionitrile

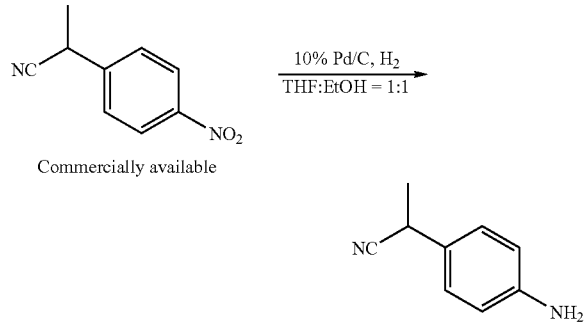

Commercially available

To the flask was added THF/EtOH (1:1, 70 mL) followed by 2-(4-nitrophenyl)-propionitrile (13.2 g, 74.9 mmol) and 10% palladium carbon (1.07 g) at room temperature. The reaction mixture was hydrogenated and stirred for 30 minutes at 47 psi to 28 psi then filtered through celite bed, and washed with EtOAc. The filtrate was concentrated in vacuo. The residue was purified by flash column chromatography on silica gel using EtOAc:hexanes (1:3) as eluant.

Yellow oil, yield: 94.1% b) N-[4-(Cyano-methyl-methyl)-phenyl]-acetamide

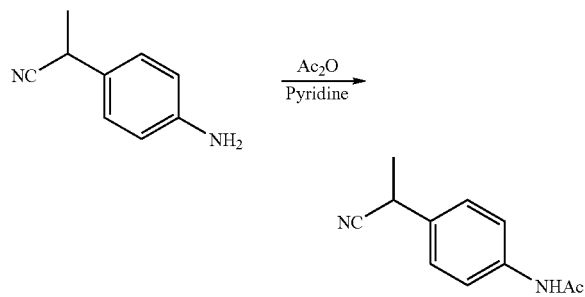

Reference: Eur. J. Med. Chem. (1975), 10, 239

A solution of 2-(4-Amino-phenyl)-propionitrile (10.2 g, 69.8 mmol) in pyridine (40 mL) was added Ac$_2$O (7.49 g, 73.4 mmol) at room temperature. The reaction mixture was refluxed for 1 hrs then cooled to room temperature, and concentrated in vacuo.

White solid (m.p. 75-77° C.), yield: 98.2% c) N-[4-(Cyano-methyl-methyl)-2-nitro-phenyl]-acetamide

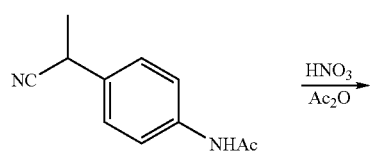

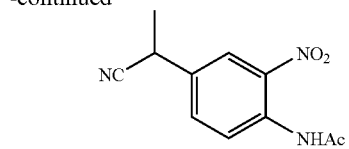

Reference: Eur. J. Med. Chem. (1975), 10, 239

To the flask of N-[4-(Cyano-methyl-methyl)-phenyl]-acetamide (12.9 g, 68.5 mmol) was added Ac$_2$O (35 mL) at 5° C. The mixture was stirred and added HNO$_3$ (7.45 g, 70.9 mmol) at 0° C. This reaction was very exothermic. The mixture was stirred for 1 hr at 0° C. and additionally stirred for 3 hrs at room temperature. The mixture was diluted with H$_2$O and extracted with EtOAc. The organic layer was dried over MgSO$_4$, filtered, and concentrated in vacuo. The residue was purified by flash column chromatography on silica gel using EtOAc:hexanes (1:2) as eluant.

Yellow solid (m.p. 84-86° C.), yield: 55.7% d) 2-(4-Amino-3-nitro-phenyl)-propionic acid

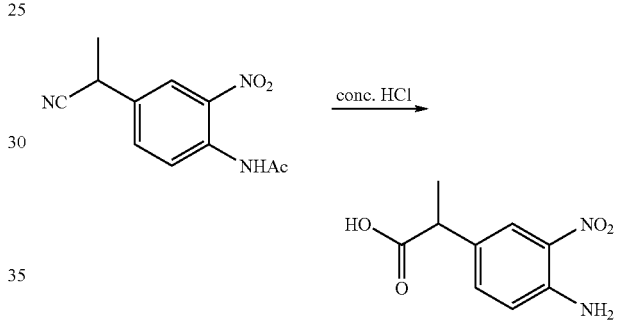

Reference: Eur. J. Med. Chem. (1975), 10, 239

To the flask of N-[4-(Cyano-methyl-methyl)-2-nitro-phenyl]-acetamide (8.90 g, 38.2 mmol) was added conc. HCl (25 mL) at room temperature. The reaction mixture was refluxed for 5 hrs then cooled to room temperature. The mixture was diluted with H$_2$O (150 mL) and extracted with CH$_2$Cl$_2$. The organic layer was dried over MgSO$_4$, filtered, and concentrated in vacuo. The residue was purified by flash column chromatography on silica gel using CH$_2$Cl$_2$:MeOH (20:1-10:1) as eluant.

Yellow solid (m.p. 118-120° C.), yield: 87.8% e) 2-(3,4-Diaminophenyl)propanoic acid

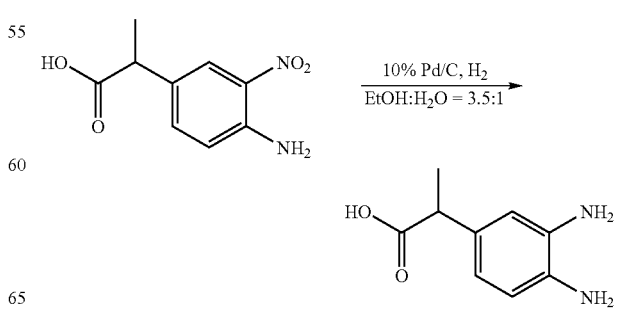

To the flask was added EtOH/H₂O (3.5:1, 45 mL) followed by 2-(4-Amino-3-nitro-phenyl)-propionic acid (5.73 g, 27.3 mmol) and 10% palladium carbon (117 mg) at room temperature. The reaction mixture was hydrogenated and stirred for 5 hrs at 64 psi then filtered through celite bed, and washed with EtOH. The filtrate was concentrated in vacuo. The residue was purified by flash column chromatography on silica gel using CH₂Cl₂:MeOH (10:1) as eluant.

Brown solid (m.p. 142-144° C.), yield: 50.0% f) N-(4-tert-Butyl-benzyl)-2-(3,4-diamino-phenyl)-propionamide

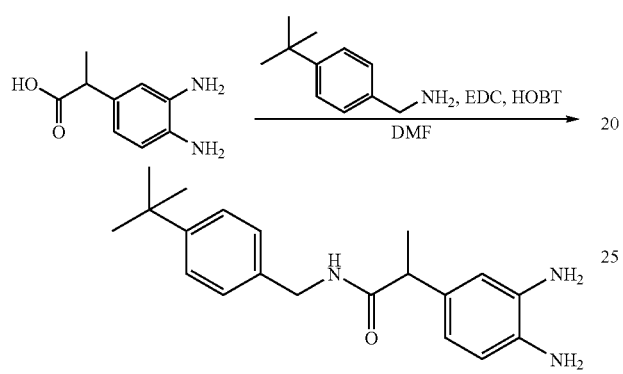

2-(3,4-Diaminophenyl)propanoic acid (436 mg, 2.42 mmol) in DMF (5 mL) was added 4-t-butylbenzylamine (399 mg, 2.44 mmol), EDC (702 mg, 3.66 mmol), HOBt (496 mg, 3.67 mmol), triethylamine (617 mg, 6.10 mmol) at 0° C. The reaction mixture was stirred for 16 hours at room temperature, and then the mixture was added water (50 mL) and extracted with methylene chloride. The organic layer was dried with MgSO₄ and filtered. Methylene chloride was removed by evaporation. The residue was purified by column chromatography eluting with CH₂Cl₂/MeOH=20/1.

Brown oil, yield: 70%, g) N-(4-tert-Butylbenzyl)-2-(quinoxalin-6-yl)propanamide

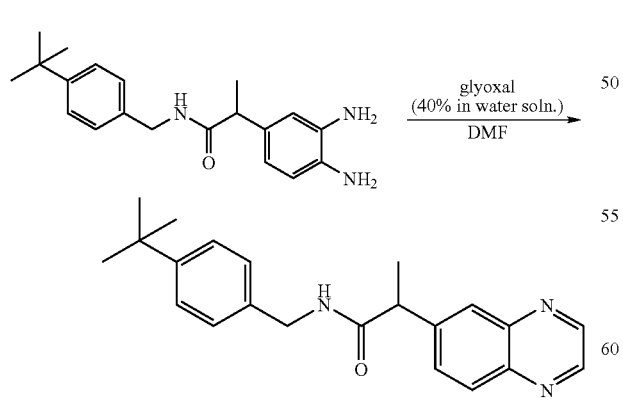

To the flask of N-(4-tert-butyl-benzyl)-2-(3,4-diaminophenyl)-propionamide (81 mg, 0.249 mmol) was added glyoxal (4 mL, 40% in water soln.) at room temperature, and additionally added DMF (4 mL) because SM was not soluble in glyoxal sufficiently. The reaction mixture was refluxed for 2 hrs then cooled to room temperature. The mixture was diluted with H₂O (25 mL) and extracted with CH₂Cl₂. The organic layer was dried over MgSO₄, filtered, and concentrated in vacuo. The residue was purified by flash column chromatography on silica gel using EtOAc:hexanes (1:1) as eluant.

Brown solid (m.p. 53-55° C.). yield: 55.5%

Example Compound 11

N-(4-tert.-butyl-benzyl)-2-quinoxalin-6-yl-propionamide

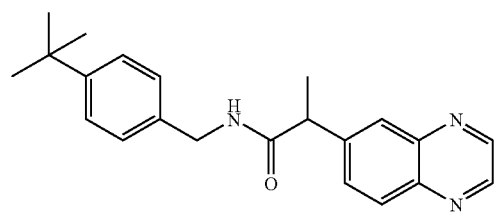

¹H NMR (300 MHz, CDCl₃) δ 8.84 (m, 2H), 8.10 (d, 1H, J=8.8 Hz), 7.81 (dd, 1H, J=8.8 Hz, 2.0 Hz), 7.30 (d, 2H, J=8.3 Hz), 7.11 (d, 2H, J=8.3 Hz), 5.68 (bt, 1H), 4.40 (m, 2H), 3.84 (q, 1H, J=7.1 Hz), 1.68 (d, 3H, J=7.1 Hz), 1.28 (s, 9H)

MS (FAB) m/z 348 (M+H)

Example Compound 15

2-(1H-benzotriazol-5-yl)-N-(4-methyl-6'-trifluoromethyl-3,4,5,6-tetrahydro-2H-[1,2']bipyridinyl-3'-ylmethyl)-propionamide

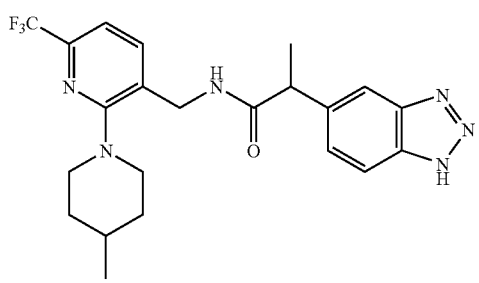

¹H-NMR (CDCl₃) δ 7.81 (m, 2H), 7.49 (d, 1H, J=7.7 Hz), 7.35 (m, 1H), 7.14 (d, 1H, J=7.5 Hz), 6.77 (bs, NH), 4.52 (d, 2H), 3.84 (q, 1H, J=7.0 Hz), 3.25 (m, 2H), 2.76 (m, 2H), 1.77 (m, 2H), 1.64 (d, 3H, J=7.0 Hz), 1.15-1.10 (m, 2H), 0.90 (d, 3H, J=6.4 Hz)

IR 3295, 2921, 1650, 1539, 1458, 1419, 1177, 1136 cm⁻¹

Mass (FAB) m/z 447 [M+H]⁺ (base), 469 [M+Na]⁺

Synthesis of Example Compound 16 a) Ethyl 2-(3-hydroxyphenyl)acetate

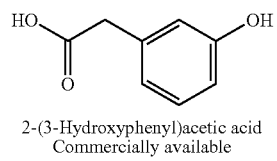

2-(3-Hydroxyphenyl)acetic acid
Commercially available

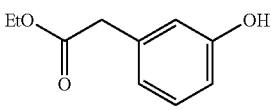

A solution of starting material (9.83 g, 64.6 mmol) in ethanol (100 mL) was added catalytic amounts of sulfuric acid. The mixture was refluxed for 3 hrs then cooled to room temperature. The mixture was diluted with H$_2$O (100 µL) and extracted with EtOAc. The organic layer was dried over MgSO$_4$, filtered, and concentrated in vacuo. The residue was purified by flash column chromatography on silica gel using EtOAc:hexanes (1:4) as eluant.

Pale yellow oil, yield: 94.5% b) Ethyl 2-(3-(methoxymethoxy)phenyl)acetate

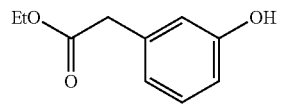

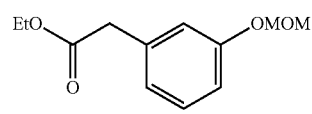

Ethyl 2-(3-hydroxyphenyl)acetate (24 g, 80.51 mmol) in THF (100 mL) was slowly added sodium hydride (2.93 g, 73.3 mmol) and chloromethylmethylether (5.94 g, 73.7 mmol) at 0° C. The reaction mixture was stirred for 16 hours at room temperature. The mixture was added water (200 mL) and extracted with EtOAc. The organic layer was dried with MgSO$_4$. The organic layer was filtered and the filtrate was concentrated in vacuo. The residue was purified by column chromatography eluting with n-Hexane/EtOAc=10/1.

Colorless oil, yield: 79.7% c) Ethyl 2-(3-(methoxymethoxy)phenyl)propanoate

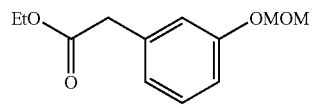

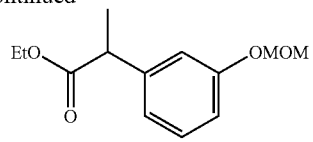

Ethyl 2-(3-(methoxymethoxy)phenyl)acetate (8.06 g, 35.9 mmol) in DMF (50 mL) was slowly added sodium hydride (1.74 g, 43.5 mmol) and iodomethane (6.37 g, 44.9 mmol) at 0° C. The reaction mixture was stirred for 1 hour at 0° C. The mixture was added water (250 mL) and extracted with EtOAc. The organic layer was dried with MgSO$_4$. The organic layer was filtered and the filtrate was concentrated in vacuo. The residue was purified by column chromatography eluting with n-Hexane/EtOAc=10/1.

Colorless oil, yield: 49% d) Ethyl 2-(3-hydroxyphenyl)propanoate

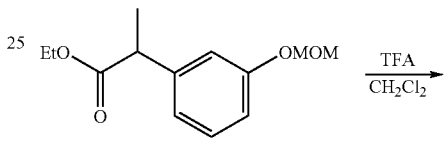

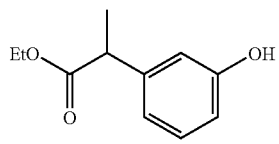

Ethyl 2-(3-(methoxymethoxy)phenyl)propanoate (4.17 g, 17.5 mmol) in methylene chloride (80 mL) was added trifluoroacetic acid (40 mL) at 0° C. The mixture was stirred for 1 hr at 0° C. and then slowly added solid sodium bicarbonate (60 g) and water (250 mL) at 0° C. The mixture was extracted with methylene chloride. The organic layer was dried with MgSO$_4$. The organic layer was filtered and the filtrate was concentrated in vacuo. The residue was purified by column chromatography eluting with n-Hexane/EtOAc=4/1.

Colorless oil, yield: 74% e) Ethyl 2-(3-hydroxy-4-nitrophenyl)propanoate

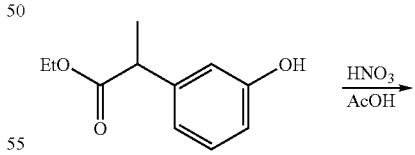

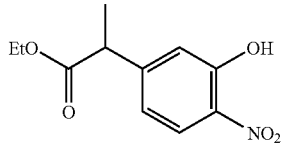

Ethyl 2-(3-hydroxyphenyl)propanoate (2.51 g, 12.9 mmol) in acetic acid (20 mL) was added nitric acid (60-62%, 1.45 g, 13.8 mmol) at room temperature. The mixture was stirred for 15 minutes at room temperature. The reaction mixture was poured into ice water (100 mL) and extracted with EtOAc.

The organic layer was dried with MgSO₄ and filtered. EtOAc was removed by evaporation. The residue was purified by column chromatography eluting with n-Hexane/EtOAc=6/1.

Yellow solid (m.p. 44° C.), yield: 30.8% f) Ethyl 2-(4-amino-3-hydroxyphenyl)propanoate

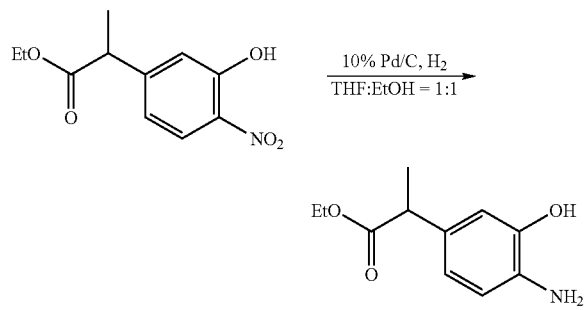

A solution of Ethyl 2-(3-hydroxy-4-nitrophenyl)propanoate (900 mg, 3.76 mmol) in THF/ethanol (1:1, 30 mL) was slowly added 10% Pd/C (93 mg) at room temperature. The mixture was hydrogenated for 1 hour at 46 psi and then filtered with celite pad and washed with EtOAc. The filtrate was concentrated in vacuo. The residue was purified by column chromatography eluting with n-Hexane/EtOAc=2/1.

White solid (m.p. 119-121° C.), yield: 80.1% g) Ethyl 2-(2,3-dihydro-2-oxobenzo[d]oxazol-6-yl)propanoate

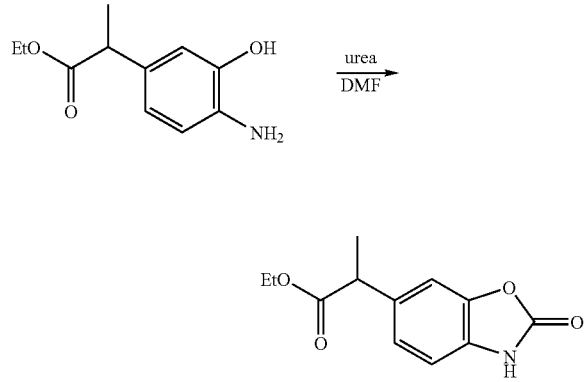

Reference: Heterocycles, Vol. 51, No. 8, 1929-1943

A solution of Ethyl 2-(4-amino-3-hydroxyphenyl)propanoate (205 mg, 0.978 mmol) in DMF (5 mL) was added urea (305 mg, 5.19 mmol) and refluxed for 5 hrs. The reaction mixture was cooled to room temperature and added water (30 mL). The mixture was acidified with conc. HCl (1 ml) and extracted with EtOAc. The organic layer was dried over MgSO₄, filtered, and concentrated in vacuo. The residue was purified by flash column chromatography on silica gel using EtOAc:hexanes (1:2) as eluant.

Brown oil, yield: 88.2% h) 2-(2,3-Dihydro-2-oxobenzo[d]oxazol-6-yl)propanoic acid

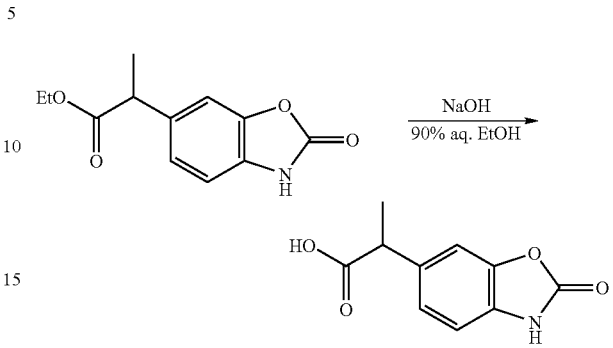

A solution of Ethyl 2-(2,3-dihydro-2-oxobenzo[d]oxazol-6-yl)propanoate (95 mg, 0.404 mmol) in 90% aq. EtOH (5 mL) was added sodium hydroxide (82 mg, 2.05 mmol) at room temperature. The reaction mixture was stirred for 24 hours at 45° C. and cooled to room temperature. The mixture was added water (10 mL) and acidified with acetic acid (pH=4). The mixture was extracted with methylene chloride. The organic layer was dried with MgSO₄ and filtered. The filtrate was concentrated in vacuo.

White solid (m.p. 169-171° C.), yield: 83.6%,

Example Compound 16

N-(4-tert.-butyl-benzyl)-2-(2-oxo-2,3-dihydro-benzooxazol-6-yl)-propionamide

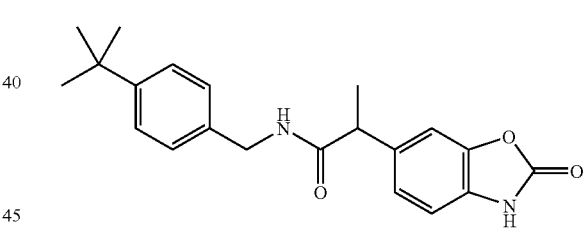

¹H-NMR (CDCl₃) δ 9.46 (bs, NH), 7.32 (d, 2H, J=8.2 Hz, Ar), 7.11 (m, 4H, Ar), 6.90 (d, 1H, J=8.0 Hz, Ar), 5.99 (bs, NH), 4.40 (m, 2H, NHCH₂), 3.61 (q, 1H, J=7.1 Hz, COCH), 1.54 (d, 3H, J=7.1 Hz, CHCH₃), 1.28 (s, 9H, C(CH₃)₃)

IR 3301, 2963, 1767, 1649, 1501, 1264, 937, 733 cm⁻¹

Mass (FAB) m/z 353 [M+H]⁺, 375 [M+Na]⁺

Synthesis of Example Compound 17 a) 2-(4-Hydroxy-phenyl)-propionic acid ethyl ester

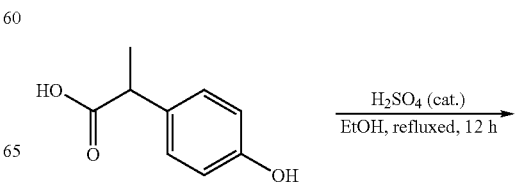

-continued

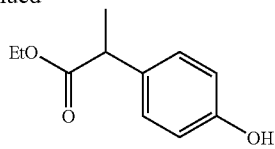

A solution of starting material (8.60 g) in ethanol (70 mL) was added sulfuric acid (10 drops) and refluxed for 12 hours. The reaction mixture was cooled to room temperature. The mixture was added water and extracted with EtOAc. The organic layer was dried over magnesium sulfate, filtered and concentrated in vacuo. (9.0 g, brown oil)

b) 2-(4-Hydroxy-3-nitro-phenyl)-propionic acid ethyl ester

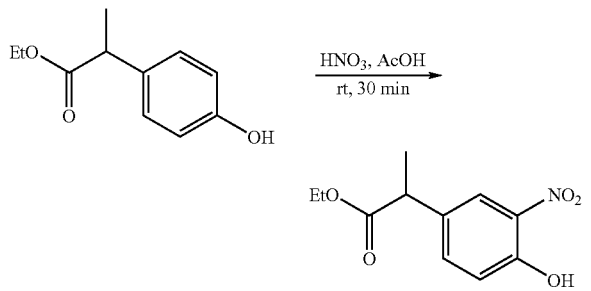

A solution of 2-(4-hydroxy-phenyl)-propionic acid ethyl ester (9.02 g) in acetic acid (75 mL) was added nitric acid (60%, 5.24 g in AcOH) at room temperature. The reaction mixture was stirred for 30 minutes at room temperature and added water. The mixture was extracted with EtOAc and the organic layer was dried over magnesium sulfate, filtered and concentrated in vacuo. The resulting residue was chromatographed on silica gel (n-Hex:EtOAc=10:1) to afford the product as yellow oil. (9.71 g)

c) 2-(3-Amino-4-hydroxy-phenyl)-propionic acid ethyl ester

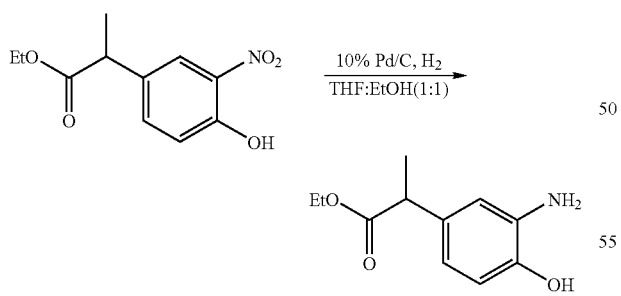

To a stirred solution of 2-(4-hydroxy-3-nitro-phenyl)-propionic acid ethyl ester (9.71 g) in THF (40 mL) and EtOH (40 mL) was slowly added 10% Pd/C (0.89 g) at room temperature. After being hydrogenated for 0.5 h with H2 balloon, the reaction mixture was filtered through celite pad and washed with EtOAc. The organic layer was dried over magnesium sulfate, filtered and concentrated in vacuo. The resulting residue was chromatographed on silica gel (n-Hex:EtOAc=2:1) to afford the product as pale yellow solid.

d) 2-(2-Thioxo-2,3-dihydro-benzooxazol-5-yl)-propionic acid ethyl ester

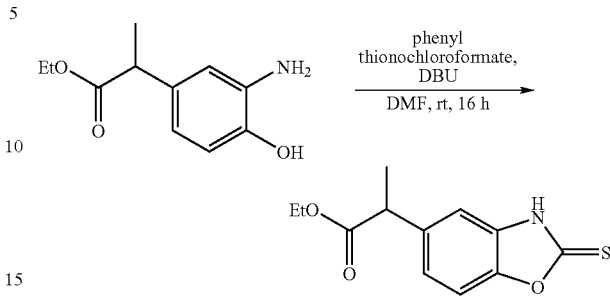

A solution of 2-(3-amino-4-hydroxy-phenyl)-propionic acid ethyl ester (370 mg) in DMF (2 mL) was added phenyl chlorothionoformate (380 mg in DMF), and DBU (540 mg, in DMF) at room temperature. The reaction mixture was stirred for 16 h at room temperature and water was added to this mixture. The resulting mixture was extracted with ethyl ether. The combined organic layer was dried over magnesium sulfate, filtered and concentrated in vacuo. The resulting residue was chromatographed on silica gel (n-Hex:EtOAc=4:1) to afford the product as white solid. (130 mg, 29.2%)

e) 2-(2-Thioxo-2,3-dihydro-benzooxazol-5-yl)-propionic acid

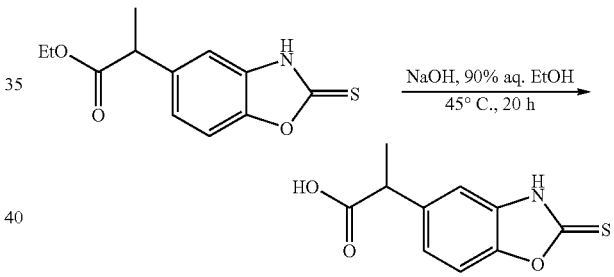

To a stirred solution of 2-(2-Thioxo-2,3-dihydro-benzooxazol-5-yl)-propionic acid ethyl ester (124 mg) in 90% aq. EtOH was added NaOH (102 mg) at room temperature. After stirred for 20 h at 45, the reaction mixture was cooled to room temperature, diluted with water. The resulting aqueous layer was acidified with acetic acid and then extracted with dichloromethane. The combined organic layer was dried over magnesium sulfate, filtered and concentrated in vacuo. (105 mg, 95.4%)

Example Compound 17

N-(4-tert.-butyl-benzyl)-2-(2-thioxo-2,3-dihydro-benzooxazol-5-yl)-propionamide

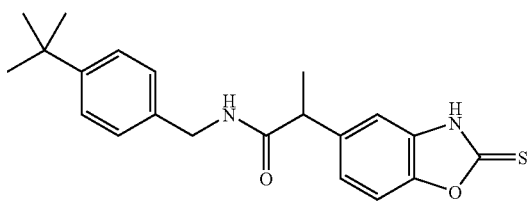

$^1$H-NMR (CDCl$_3$) δ 7.34-7.05 (m, 7H, Ar), 5.99 (bt, NH), 4.52 (m, 2H, NHCH$_2$), 3.61 (q, 1H, J=7.1 Hz, COCH), 1.58 (d, 3H, J=7.0 Hz, CHCH$_3$), 1.27 (s, 9H, C(CH$_3$)$_3$)

IR 3297, 2963, 1646, 1534, 1460, 1428, 1267, 1105 cm$^{-1}$

Mass (FAB) m/z 369 [M+H]$^+$

Synthesis of Example Compound 18 a) (3-Hydroxy-phenyl)-acetic acid ethyl ester

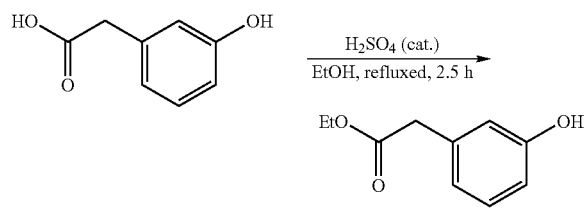

A solution of 3-hydroxyphenylacetic acid (15.5 g) in ethanol (200 mL) was added sulfuric acid (1 mL) and refluxed for 2.5 hours. The reaction mixture was cooled to room temperature. The mixture was added water and extracted with EtOAc. The organic layer was dried over magnesium sulfate, filtered and concentrated in vacuo. (18.2 g, 99.0%, pale brown oil)

b) (3-Methoxymethoxy-phenyl)-acetic acid ethyl ester

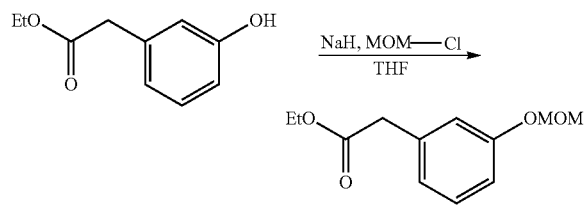

To a solution of (3-Hydroxy-phenyl)-acetic acid ethyl ester (27.6 g) in THF was added NaH (7.35 g), MOM-Cl (14.8 g) slowly at 0°. After stirred for 14 h at the same temperature, the reaction mixture was warmed to room temperature. The resulting mixture was diluted with water and extracted with EtOAc. The combined organic layer was dried over magnesium sulfate, filtered and concentrated in vacuo. The resulting residue was chromatographed on silica gel (n-Hex:EtOAc=15:1 to 10:1) to afford the product as colorless oil. (31.2 g, 90.9%)

c) 2-(3-Methoxymethoxy-phenyl)-propionic acid ethyl ester

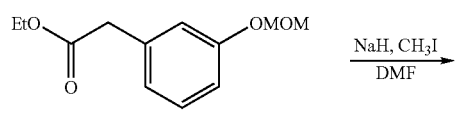

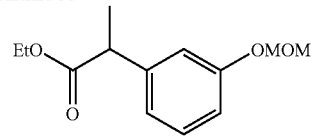

To a stirred solution of (3-Methoxymethoxy-phenyl)-acetic acid ethyl ester (31.2 g) in DMF (200 mL) was slowly added sodium hydride (6.21 g) and iodomethane (22.3 g) at 0°. After stirred for 20 h at 0°, this reaction mixture was quenched with water. This mixture was extracted with EtOAc, and combined organic layer was dried over magnesium sulfate, filtered and concentrated in vacuo. The resulting residue was chromatographed on silica gel (n-Hex:EtOAc=10:1) to afford the product as colorless oil.

d) 2-(3-Hydroxy-phenyl)-propionic acid ethyl ester

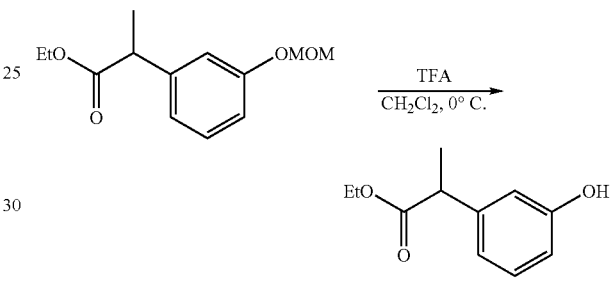

To a stirred solution of 2-(3-methoxymethoxy-phenyl)-propionic acid ethyl ester in the dichloromethane was added dropwise TFA (150 mL) at 0°. The reaction mixture was stirred 1 h at 0°, and solid sodium bicarbonate (200 g) was added very slowly. The resulting mixture was poured into ice water very slowly and extracted with EtOAc. The combined organic layer was dried over magnesium sulfate, filtered and concentrated in vacuo. The resulting residue was chromatographed on silica gel (n-Hex:EtOAc=10:1 to 4:1) to afford the product as colorless oil. (19.0 g, 70.4% 2 steps)

e) 2-(3-Hydroxy-4-nitro-phenyl)-propionic acid ethyl ester

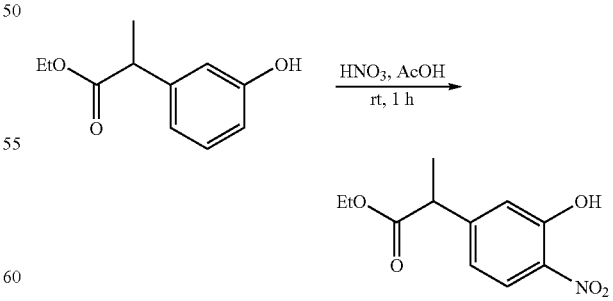

A solution of 2-(3-Hydroxy-phenyl)-propionic acid ethyl ester (19.0 g) in acetic acid (150 mL) was added nitric acid (11.3 g) at room temperature. The reaction mixture was stirred for 1 h at room temperature and added water. The mixture was extracted with EtOAc and the organic layer was dried over magnesium sulfate, filtered and concentrated in vacuo. The resulting residue was chromatographed on silica gel (n-Hex:EtOAc=10:1) to afford the product as yellow solid. (6.08 g, 26.0%)

f) 2-(3-Hydroxy-4-nitro-phenyl)-propionic acid

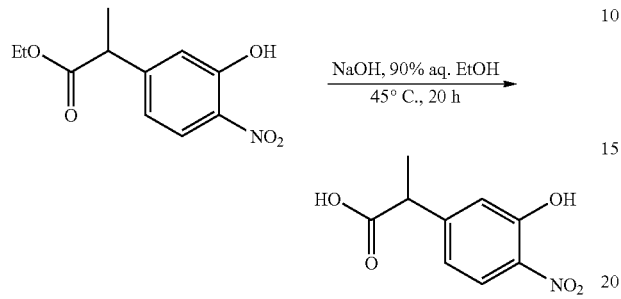

To a stirred solution of 2-(3-Hydroxy-4-nitro-phenyl)-propionic acid ethyl ester (1.48 g) in 90% aq. EtOH was added NaOH (1.24 g) at room temperature. After stirred for 14 h at 45° C., the reaction mixture was cooled to room temperature, diluted with water. The resulting aqueous layer was acidified with acetic acid and then extracted with dichloromethane. The combined organic layer was dried over magnesium sulfate, filtered and concentrated in vacuo. (1.30 mg, 99.5%, yellow solid)

g) 2-(4-Amino-3-hydroxy-phenyl)-propionic acid

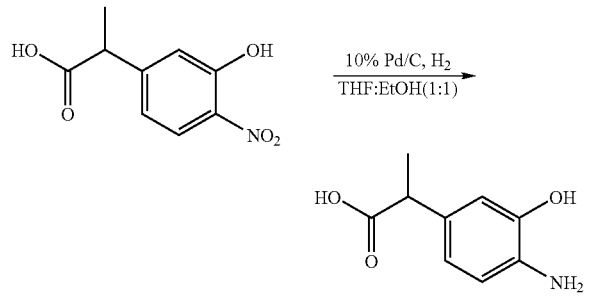

To a stirred solution of 2-(3-hydroxy-4-nitro-phenyl)-propionic acid (1.28 g) in THF (20 mL) and EtOH (20 mL) was slowly added 10% Pd/C (0.12 g) at room temperature. After being hydrogenated for 3 h with H₂ balloon, the reaction mixture was filtered through celite pad and washed with EtOH. The filtrate was concentrated in vacuo to afford the product as yellow solid. (1.08 g, 98.4%)

h) 2-(2-Amino-benzooxazol-6-yl)-propionic acid

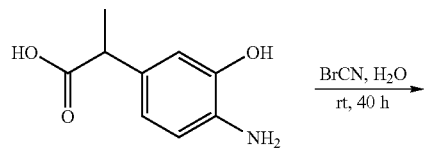

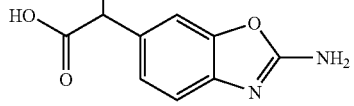

To a stirred solution of 2-(4-Amino-3-hydroxy-phenyl)-propionic acid (1.02 g) in H2O was added BrCN (648 mg) at room temperature. After stirred for 40 h at room temperature, the reaction mixture was neutralized with 30% aq. NaOH to pH 6~7 and then stirred for 1 hour. The solid was filtered, washed with water and dried under reduced vacuum to afford the product as yellow solid. (760 mg, 65.5%)

Example Compound 18

2-(2-amino-benzooxazol-6-yl)-N-(4-tert.-butyl-benzyl)-propionamide

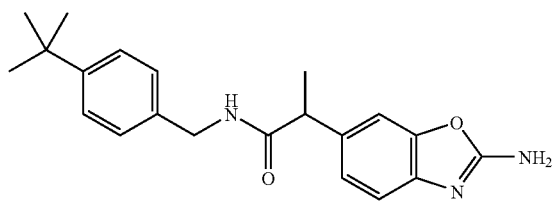

¹H-NMR (CDCl₃) δ 7.32-7.28 (m, 4H, Ar), 7.12-7.07 (m, 3H, Ar), 5.61 (bt, NH), 5.01 (bs, NH₂), 4.37 (m, 2H, NHCH₂), 3.63 (q, 1H, J=7.1 Hz, COCH), 1.57 (d, 3H, J=7.2 Hz, CHCH₃), 1.29 (s, 9H, C(CH₃)₃)

Synthesis of Example Compound 19 a) 2-(4-Amino-3-hydroxy-phenyl)-propionic acid ethyl ester

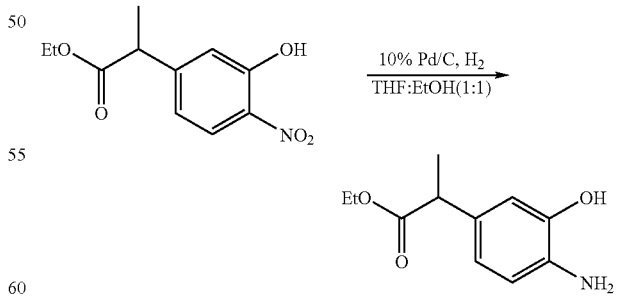

To a stirred solution of starting material (4.63 g) in THF (50 mL) and EtOH (50 mL) was slowly added 10% Pd/C (0.42 g) at room temperature. After hydrogenated for 2 h with H₂ balloon, the reaction mixture was filtered through celite pad and washed with EtOH. The filtrate was concentrated in vacuo. The resulting residue was chromatographed on silica gel (n-Hex:EtOAc=4:1) to afford the product as white-to-pale pink solid. (3.86 g, 95.1%)

b) 2-(2-Thioxo-2,3-dihydro-benzooxazol-6-yl)-propionic acid ethyl ester

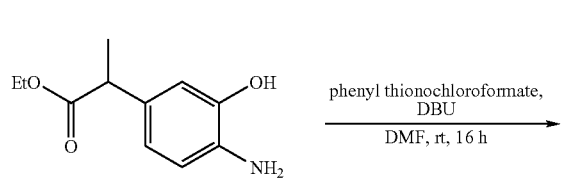

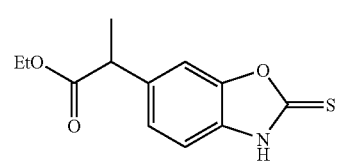

Solution of 2-(4-Amino-3-hydroxy-phenyl)-propionic acid ethyl ester (570 mg) in DMF (5 mL) was added phenyl chlorothionoformate (563 mg in DMF), and DBU (829 mg, in DMF) at room temperature. The reaction mixture was stirred for 14 h at room temperature and water was added to this mixture. The resulting mixture was extracted with ethyl ether. The combined organic layer was dried over magnesium sulfate, filtered and concentrated in vacuo. The resulting residue was chromatographed on silica gel (n-Hex:EtOAc=10:1 to 4:1) to afford the product as yellow oil. (90 mg, 13.2%)

c) 2-(2-Thioxo-2,3-dihydro-benzooxazol-6-yl)-propionic acid

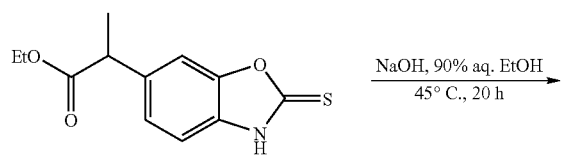

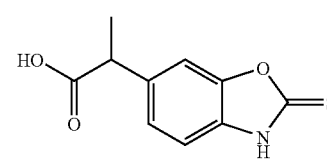

To a stirred solution of 2-(2-Thioxo-2,3-dihydro-benzooxazol-6-yl)-propionic acid ethyl ester (76 mg) in 90% aq. EtOH was added NaOH (48 mg) at room temperature. After stirred for 16 h at room temperature, the reaction mixture was cooled to room temperature, diluted with water. The resulting aqueous layer was acidified with acetic acid and then extracted with dichloromethane. The combined organic layer was dried over magnesium sulfate, filtered and concentrated in vacuo. (58 mg, 86.0%, brown solid)

Example Compound 19

N-(4-tert.-butyl-benzyl)-2-(2-thioxo-2,3-dihydro-benzooxazol-6-yl)-propionamide

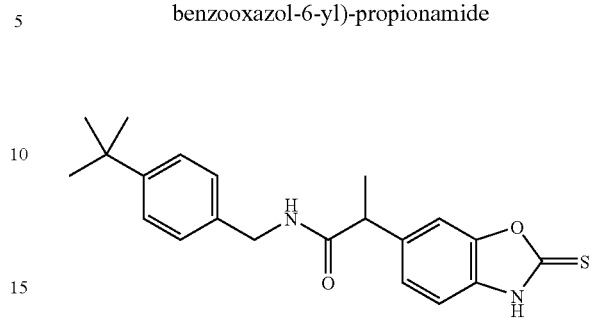

$^1$H-NMR (CDCl$_3$) δ 7.36 (d, 2H, J=8.4 Hz, Ar), 7.25 (d, 1H, J=1.5 Hz, Ar), 7.20 (d, 2H, J=8.3 Hz, Ar), 7.13 (dd, 1H, J=8.3, 1.5 Hz, Ar), 6.79 (d, 1H, J=8.1 Hz, Ar), 6.09 (bt, NH), 4.47 (m, 2H, NHCH$_2$), 3.68 (q, 1H, J=7.1 Hz, COCH), 1.57 (d, 3H, J=7.1 Hz, CHCH$_3$), 1.29 (s, 9H, C(CH$_3$)$_3$)

IR 3300, 2962, 1645, 1496, 1418, 1362, 1150 cm$^{-1}$

Mass (FAB) m/z 369 [M+H]$^+$

Synthesis of Example Compound 20 a) 2-(3,4-Dihydro-2H-benzo[1,4]oxazin-7-yl)-propionic acid ethyl ester

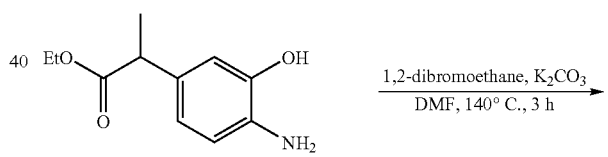

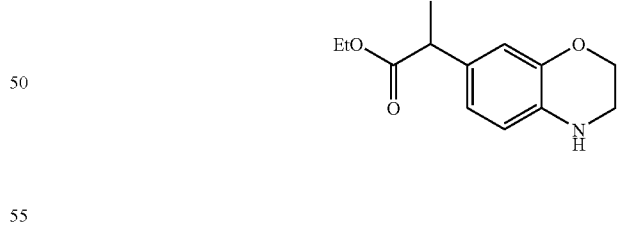

To a stirred solution of starting material (2.01 g) in DMF (25 mL) was added potassium carbonate (2.68 g) and 1,2-dibromoethane (1.90 g) at room temperature. After stirred for 3 h at 140° C., the reaction mixture was cooled to room temperature and diluted with EtOAc. The resulting mixture was washed with water and the organic layer was dried over magnesium sulfate, filtered and concentrated in vacuo. The resulting residue was chromatographed on silica gel (n-Hex:EtOAc=4:1) to afford the product as a brown oil. (265 mg, 11.7%)

b)
2-(3,4-Dihydro-2H-benzo[1,4]oxazin-7-yl)-propionic acid

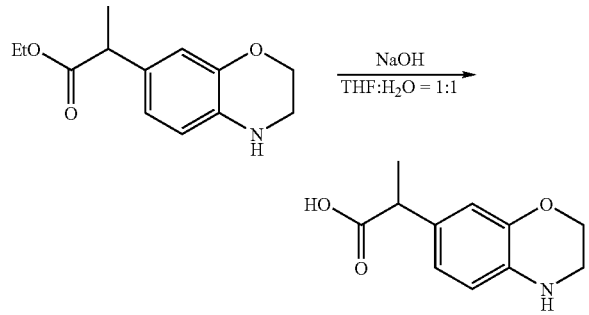

To a stirred solution of 2-(3,4-dihydro-2H-benzo[1,4]oxazin-7-yl)-propionic acid ethyl ester (258 mg) in THF (3 mL) and H2O (3 mL) was added NaOH (134 mg) at room temperature. After being stirred for 20 h at room temperature, the reaction mixture was acidified with AcOH (pH=4) and diluted with water. The resulting mixture extracted with dichloromethane and the combined organic layer was dried magnesium sulfate, filtered and concentrated in vacuo. The resulting residue was chromatographed on silica gel (CH$_2$Cl$_2$:MeOH=15:1) to afford the product as a brown oil. (150 mg, 65.8%)

Example Compound 20

N-(4-tert.-butylbenzyl)-2-(3,4-dihydro-2H-benzo[b][1,4]oxazin-7-yl)propionamide

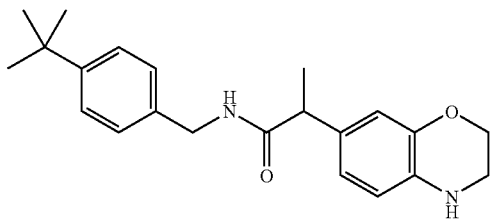

$^1$H-NMR (CDCl$_3$) δ 7.31 (d, 2H, J=8.4 Hz, Ar), 7.10 (d, 2H, J=8.2 Hz, Ar), 6.70 (m, 2H, Ar), 6.55 (d, 1H, J=7.9 Hz, Ar), 5.68 (bt, NH), 4.44-4.23 (m, 4H, OCH$_2$ & NHCH$_2$), 3.75 (bt, NH), 3.50-3.39 (m, 3H, NHCH$_2$ & COCH), 1.50 (d, 3H, J=7.1 Hz, CHCH$_3$), 1.30 (s, 9H, C(CH$_3$)$_3$)

IR 3304, 2963, 1649, 1516, 1357, 1305 cm$^{-1}$

Mass (FAB) m/z 353 [M+H]$^+$

Synthesis of Example Compound 21 a) 2-(4-Amino-phenyl)-propionic acid

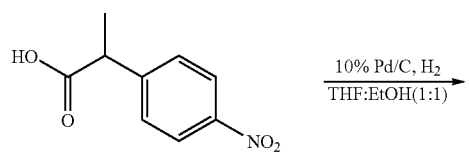

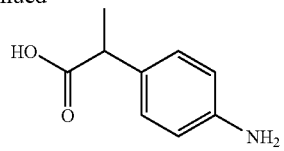

To a stirred solution of 2-(4-nitrophenyl)propionic acid (2.05 g) in THF (20 mL) and EtOH (20 mL) was slowly added 10% Pd/C (0.21 g) at room temperature. After hydrogenated for 2 h with H$_2$ balloon, the reaction mixture was filtered through celite pad and washed with EtOH. The filtrate was concentrated in vacuo to afford the product as pale brown solid. (1.75 g, quantitative)

d) 2-Quinolin-6-yl-propionic acid

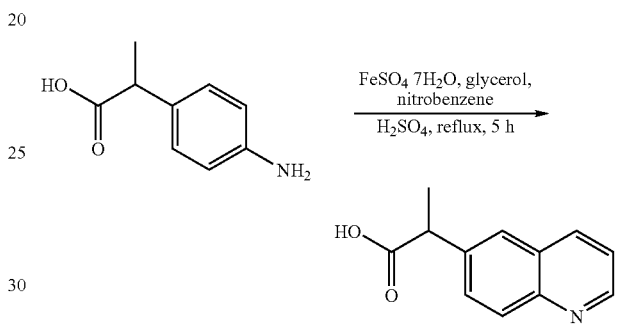

The mixture of 2-(4-Amino-phenyl)-propionic acid (1.70 g), FeSO$_4$ 7H$_2$O (0.30 g), glycerol (4.04 g) and sulfuric acid (2 mL) was refluxed with stirring for 5 h. After cooled to room temperature, the reaction mixture was concentrated under reduced vacuum. The aqueous solution was treated with 12N—NaOH solution. The precipitated solid was filtered and the filtrate was acidified with AcOH. The resulting mixture was extracted and the combined organic layer was dried over magnesium sulfate, filtered, concentrated in vacuo. The resulting residue was chromatographed on silica gel (CH$_2$Cl$_2$:MeOH=15:1 to 10:1) to afford the product as a brown solid. (0.83 g, 40.0%)

Example Compound 21

N-(4-tert.-butyl-benzyl)-2-quinolin-6-yl-propionamide

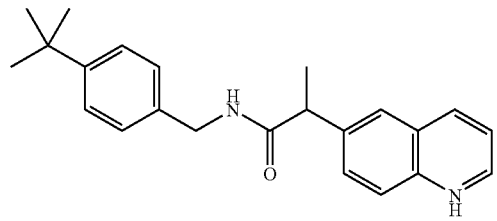

$^1$H-NMR (CDCl$_3$) δ 8.89 (dd, 1H, J=4.2, 1.4 Hz, Ar), 8.10 (m, 2H, Ar), 7.74 (d, 1H, J=1.8 Hz, Ar), 7.67 (dd, 1H, J=8.6, 1.8 Hz, Ar), 7.41 (m, 1H, Ar), 7.29 (d, 2H, J=8.3 Hz, Ar), 7.09 (d, 2H, J=8.1 Hz, Ar), 5.74 (bt, NH), 4.39 (m, 2H, NHCH$_2$), 3.77 (q, 1H, J=7.1 Hz, COCH), 1.64 (d, 3H, J=7.1 Hz, CHCH₃), 1.28 (s, 9H, C(CH₃)₃)

IR 3294, 2962, 1651, 1544, 1366, 1232, 1117 cm⁻¹

Example Compound 22

2-(1H-benzotriazol-5-yl)-N-(2-butoxy-6-tert.-butyl-pyridin-3-ylmethyl)-propionamide

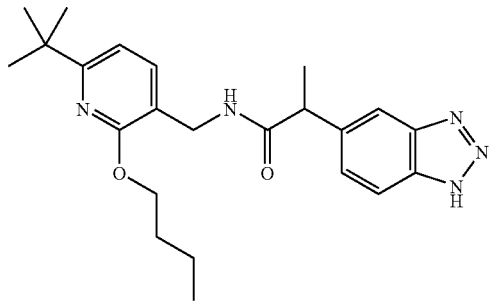

¹H-NMR (CDCl₃) δ 7.80 (m, 2H, Ar), 7.37-7.30 (m, 2H, Ar), 6.75 (d, 1H, J=7.5 Hz, Ar), 6.24 (bt, NH), 4.43-4.18 (m, 4H, OCH₂ & CH₂NH), 3.74 (q, 1H, J=7.1 Hz, CHCH₃), 1.61-1.52 (m, 5H, CHCH₃ & OCH₂CH₂), 1.35 (m, 2H, CH₂CH₃), 1.27 (s, 9H, C(CH₃)₃), 0.90 (t, 3H, J=7.4 Hz, CH₂CH₃)

IR 3300, 2960, 1648, 1543, 1457, 1413, 1255 cm⁻¹

Mass (FAB) m/z 410 [M+H]⁺, 432 [M+Na]⁺

Example Compound 23

2-(1H-benzoimidazol-5-yl)-N-(2-butoxy-6-tert.-butyl-pyridin-3-ylmethyl)-propionamide

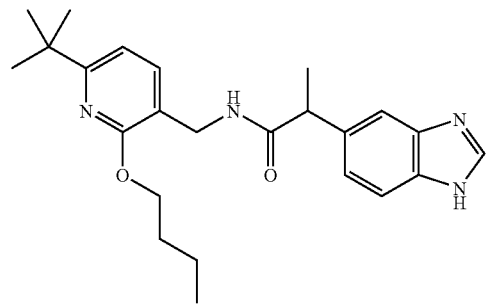

¹H-NMR (CDCl₃) δ 8.00 (s, 1H, Ar), 7.59 (m, 2H, Ar), 7.30 (d, 1H, J=7.5 Hz, Ar), 7.17 (dd, 1H, J=8.3, 1.5 Hz, Ar), 6.73 (d, 1H, J=7.5 Hz, Ar), 6.17 (bt, NH), 4.38-4.14 (m, 4H, OCH₂ & CH₂NH), 3.70 (q, 1H, J=7.1 Hz, CHCH₃), 1.58-1.47 (m, 5H, CHCH₃ & OCH₂CH₂), 1.38-1.25 (m, 11H, CH₂CH₃ & C(CH₃)₃), 0.89 (t, 3H, J=7.3 Hz, CH₂CH₃)

IR 3270, 2961, 1650, 1544, 1456, 1412, 1357, 1254 cm⁻¹

Mass (FAB) m/z 409 [M+H]⁺, 431 [M+Na]⁺

Example Compound 24

2-(1H-benzotriazol-5-yl)-N-(6'-tert.-butyl-4-methyl-3,4,5,6-tetrahydro-2H-[1,2']bipyridinyl-3'-ylmethyl)-propionamide

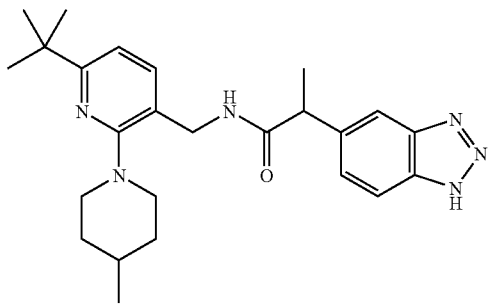

¹H-NMR (CDCl₃+CD₃OD) δ 7.77 (m, 2H, Ar), 7.37-7.26 (m, 2H, Ar), 6.85 (d, 1H, J=7.7 Hz, Ar), 4.40 (m, 2H, CH₂NH), 3.75 (q, 1H, J=7.0 Hz, CHCH₃), 3.18 (m, 2H, piperidine), 2.72 (m, 2H, piperidine), 1.65-1.00 (m, 5H, piperidine), 1.60 (d, 3H, J=7.1 Hz, CHCH₃), 1.27 (s, 9H, C(CH₃)₃), 0.88 (d, 3H, J=6.6 Hz, piperidine CH₃)

IR 3300, 2956, 1646, 1565, 1450, 1371, 1234 cm⁻¹

Mass (FAB) m/z 435 [M+H]⁺

Example Compound 25

2-(1H-benzoimidazol-5-yl)-N-(6'-tert.-butyl-4-methyl-3,4,5,6-tetrahydro-2H-[1,2']bipyridinyl-3'-ylmethyl)-propionamide

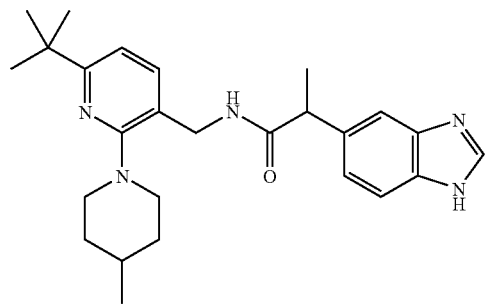

¹H-NMR (CDCl₃) δ 8.02 (s, 1H, Ar), 7.60 (bs, 2H, Ar), 7.26-7.19 (m, 2H, Ar), 6.83 (d, 1H, J=7.7 Hz, Ar), 6.73 (bs, NH), 4.40 (m, 2H, CH₂NH), 3.71 (q, 1H, J=6.8 Hz, CHCH₃), 3.18 (m, 2H, piperidine), 2.69 (m, 2H, piperidine), 1.65-1.00 (m, 5H, piperidine), 1.60 (d, 3H, J=7.1 Hz, CHCH₃), 1.27 (s, 9H, C(CH₃)₃), 0.88 (d, 3H, J=6.6 Hz, piperidine CH₃)

IR 3280, 2955, 1649, 1566, 1451, 1401, 1371, 1252 cm⁻¹

Mass (FAB) m/z 434 [M+H]⁺

Example Compound 26

2-(1H-benzotriazol-5-yl)-N-(6-tert.-butyl-2-cyclo-hexyl-sulfanyl-pyridin-3-ylmethyl)-propionamide

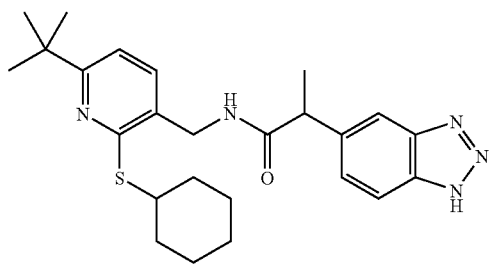

$^1$H-NMR (CDCl$_3$) δ 7.79 (bs, 2H, Ar), 7.36-7.30 (m, 2H, Ar), 6.88 (d, 1H, J=7.9 Hz, Ar), 6.29 (bt, NH), 4.36 (m, 2H, CH$_2$NH), 3.92 (m, 1H, SCH), 3.78 (q, 1H, J=7.1 Hz, CHCH$_3$), 2.05-1.20 (m, 10H, cyclohexyl), 1.60 (d, 3H, J=7.1 Hz, CHCH$_3$), 1.28 (s, 9H, C(CH$_3$)$_3$)

IR 3278, 2929, 2854, 1649, 1553, 1450, 1370, 1203, 734 cm$^{-1}$

Mass (FAB) m/z 452 [M+H]$^+$, 474 [M+Na]$^+$

Example Compound 27

2-(1H-benzoimidazol-5-yl)-N-(6-tert.-butyl-2-cyclo-hexyl-sulfanyl-pyridin-3-ylmethyl)-propionamide

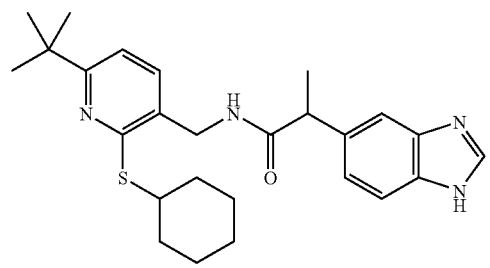

$^1$H-NMR (CDCl$_3$) δ 8.03 (s, 1H, Ar), 7.60 (bs, 2H, Ar), 7.25 (m, 2H, Ar), 6.88 (d, 1H, J=7.7 Hz, Ar), 5.94 (bt, NH), 4.28 (m, 2H, CH$_2$NH), 3.92 (m, 1H, SCH), 3.72 (q, 1H, J=7.3 Hz, CHCH$_3$), 2.01 (m, 2H, cyclohexyl), 1.77-1.20 (m, 8H, cyclohexyl), 1.59 (d, 3H, J=7.1 Hz, CHCH$_3$), 1.29 (s, 9H, C(CH$_3$)$_3$)

IR 3270, 2928, 2854, 1652, 1554, 1449, 733 cm$^{-1}$

Mass (FAB) m/z 451 [M+H]$^+$, 473 [M+Na]$^+$

Synthesis of Example Compound 29

Example 29

N-(2-Butoxy-6-tert-butyl-pyridin-3-ylmethyl)-2-(2-ethylsulfanyl-2,3-dihydro-benzothiazol-6-yl)-propionamide

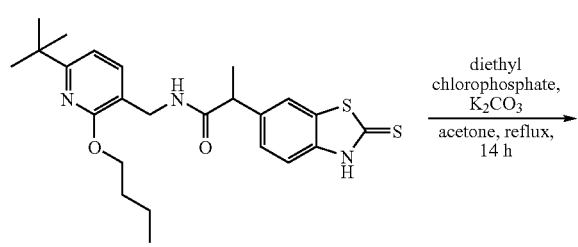

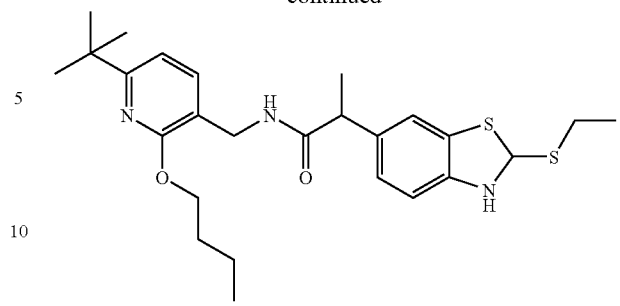

To a stirred solution of starting material (146 mg) in acetone was added diethyl chlorophosphate (87 mg) and potassium carbonate (111 mg) at room temperature. After refluxed for 14 h, the reaction mixture was cooled to rt. The resulting mixture was diluted with water and extracted with EtOAc. The combined organic layer was dried over magnesium sulfate, filtered and concentrated in vacuo. The resulting residue was chromatographed on silica gel (n-Hex: EtOAc=4:1 to 2:1) to afford the product as white solid. (122 mg, 78.7%)

Example Compound 29

N-(2-butoxy-6-tert.-butyl-pyridin-3-ylmethyl)-2-(2-ethylsulfanyl-benzothiazol-6-yl)-propionamide

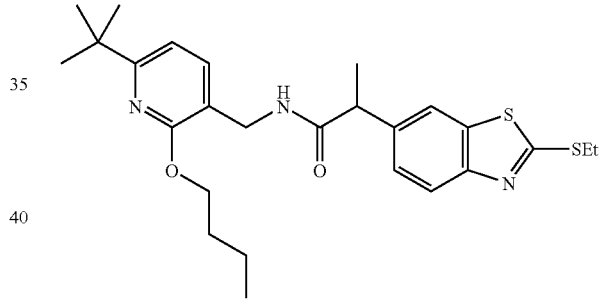

$^1$H-NMR (CDCl$_3$) δ 7.80 (d, 1H, J=8.4 Hz, Ar), 7.67 (d, 1H, J=1.7 Hz, Ar), 7.34 (d, 1H, J=7.5 Hz, Ar), 7.29 (dd, 1H, J=8.4, 1.8 Hz, Ar), 6.76 (d, 1H, J=7.3 Hz, Ar), 5.98 (bs, NH), 4.35-4.13 (m, 4H, OCH$_2$ & CH$_2$NH), 3.63 (q, 1H, J=7.1 Hz, CHCH$_3$), 3.35 (q, 2H, J=7.5 Hz, SCH$_2$CH$_3$), 1.59-1.47 (m, 8H), 1.32 (m, 2H, CH$_2$CH$_3$), 1.28 (s, 9H, C(CH$_3$)$_3$), 0.90 (t, 3H, J=7.3 Hz, CH$_2$CH$_3$)

IR 3296, 2960, 1648, 1543, 1450, 1412, 1254, 1002 cm$^{-1}$

Mass (FAB) m/z 486 [M+H]$^+$, 508 [M+Na]$^+$

Synthesis of Example Compound 30

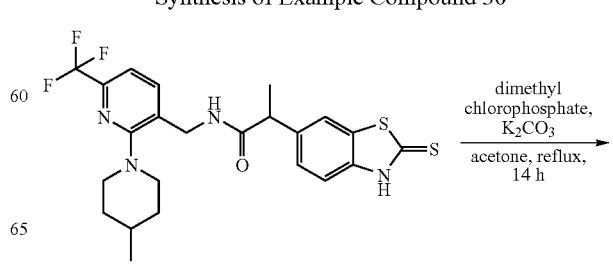

-continued

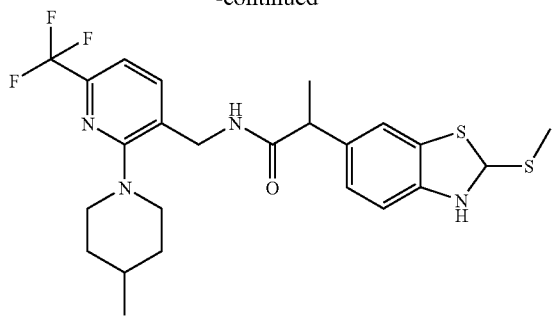

To a stirred solution of starting material (188 mg) in acetone was added dimethyl chlorophosphate (92 mg) and potassium carbonate (140 mg) at room temperature. After refluxed for 14 h, the reaction mixture was cooled to rt. The resulting mixture was diluted with water and extracted with EtOAc. The combined organic layer was dried over magnesium sulfate, filtered and concentrated in vacuo. The resulting residue was chromatographed on silica gel (n-Hex:EtOAc=2:1) to afford the product as white solid. (164 mg, 84.9%)

Example Compound 30

2-(2-methylsulfanyl-benzothiazol-6-yl)-N-(4-methyl-6'-trifluoromethyl-3,4,5,6-tetrahydro-2H-[1,2']bipyridinyl-3'-ylmethyl)-propionamide

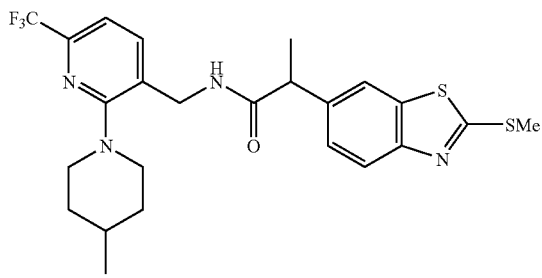

$^1$H-NMR (CDCl$_3$) δ 7.82 (d, 1H, J=8.4 Hz, Ar), 7.71 (d, 1H, J=1.7 Hz, Ar), 7.43 (d, 1H, J=7.9 Hz, Ar), 7.32 (dd, 1H, J=8.4, 1.8 Hz, Ar), 7.16 (d, 1H, J=7.7 Hz, Ar), 6.19 (bt, NH), 4.45 (m, 2H, CH$_2$NH), 3.70 (q, 1H, J=7.1 Hz, CHCH$_3$), 3.25 (m, 2H, piperidine), 2.79 (s, 3H, SCH$_3$), 2.76 (m, 2H, piperidine), 1.70-1.05 (m, 5H, piperidine), 1.60 (d, 3H, J=7.1 Hz, CHCH$_3$), 0.92 (d, 3H, J=6.6 Hz, piperidine CH$_3$)

IR 3295, 2925, 1651, 1540, 1453, 1177, 1136 cm$^{-1}$
Mass (FAB) m/z 509 [M+H]$^+$ Synthesis of Example Compound 32 a) (4-Nitro-phenyl)-acetic acid ethyl ester

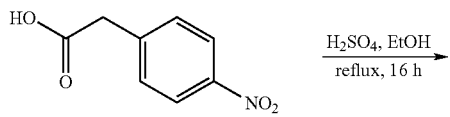

-continued

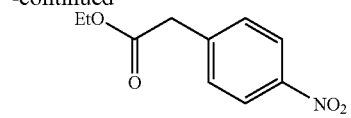

The solution of starting material (3.42 g) in ethanol (30 mL) was added sulfuric acid (0.3 mL) at room temperature. The reaction mixture was stirred under reflux for 16 h and then cooled to room temperature. Ethanol was removed under reduced vacuum and water was added to the residue. The aqueous layer was extracted with EtOAc and then the organic layer was dried over magnesium sulfate, filtered and concentrated in vacuo. The resulting residue was chromatographed on silica gel (n-Hex:EtOAc=4:1) to afford the product as a white solid.

b) 2-(4-Nitro-phenyl)-propionic acid ethyl ester

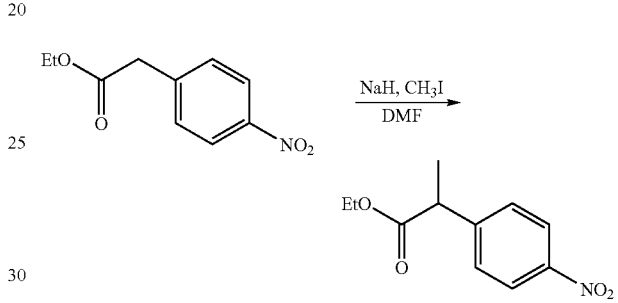

To a stirred solution of (4-Nitro-phenyl)-acetic acid ethyl ester (3.88 g) in DMF (15 mL) was slowly added sodium hydride (0.78 g) and iodomethane (1.21 mL) at 0□. After stirred for 14 h at room temperature, this reaction mixture was quenched with water. This mixture was extracted with diethyl ether, and combined organic layer was dried over magnesium sulfate, filtered and concentrated in vacuo. The resulting residue was chromatographed on silica gel (n-Hex:EtOAc=10:1 to 4:1) to afford the product as pale yellow oil. (89.1%)

c) 2-(4-Amino-phenyl)-propionic acid ethyl ester

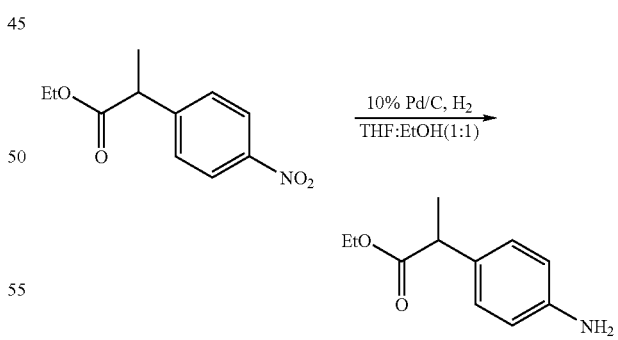

To a stirred solution of 2-(4-Nitro-phenyl)-propionic acid ethyl ester (3.67 g) in THF (40 mL) and EtOH (40 mL) was slowly added 10% Pd/C (405 mg) at room temperature. After hydrogenated for 20 h with H$_2$ balloon, the reaction mixture was filtered through celite pad and washed with EtOAc. The organic layer was dried over magnesium sulfate, filtered and concentrated in vacuo. The resulting residue was chromatographed on silica gel (n-Hex:EtOAc=4:1) to afford the product as pale yellow oil. (99.7%)

d) 2-(4-Amino-3-bromo-phenyl)-propionic acid ethyl ester

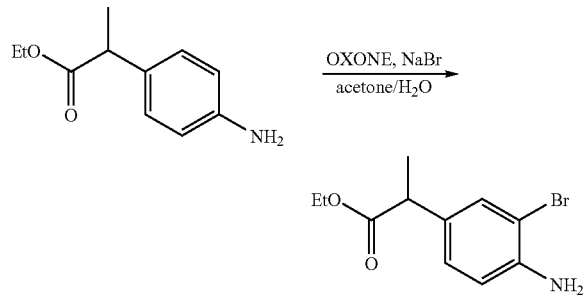

To a stirred solution of 2-(4-Amino-phenyl)-propionic acid ethyl ester (3.16 g) in acetone and water was added OXONE (10.0 g) and NaBr (6.75 g) at room temperature. After stirred for 2 minutes at room temperature, the reaction mixture was diluted with EtOAc and poured into 5% aq. Na₂S₂O₃ solution. The organic layer was dried over magnesium sulfate, filtered and concentrated in vacuo. The resulting residue was chromatographed on silica gel (n-Hex:EtOAc=6:1) to afford the product as white solid. (49.6%)

e) 2-(2-Thioxo-2,3-dihydro-benzothiazol-6-yl)-propionic acid ethyl ester

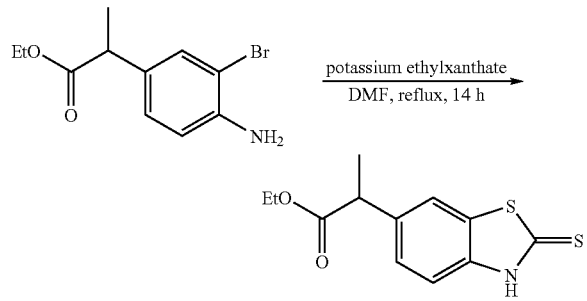

To a stirred solution of 2-(4-Amino-3-bromo-phenyl)-propionic acid ethyl ester (1.58 g) in DMF was added potassium ethylxanthate (1.86 g) at room temperature. After stirred with reflux for 14 h, the reaction mixture was cooled to room temperature and diluted with EtOAc. The organic layer was washed with water, brine, dried over magnesium sulfate and concentrated in vacuo. The resulting residue was chromatographed on silica gel (n-Hex:EtOAc=6:1 to 4:1) to afford the product as yellow oil. (595 mg, 38.3%)

f) 2-(2-Thioxo-2,3-dihydro-benzothiazol-6-yl)-propionic acid

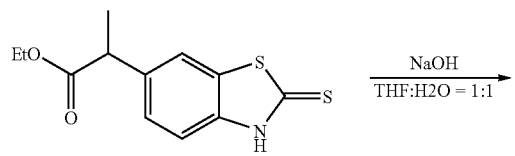

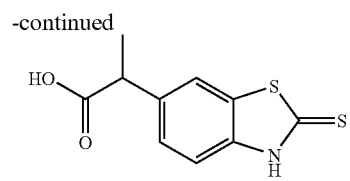

To a stirred solution of 2-(2-Thioxo-2,3-dihydro-benzothiazol-6-yl)-propionic acid ethyl ester (587 mg) in THF (4 mL) and H₂O (4 mL) was added NaOH (229 mg) at room temperature. After stirred for 14 h at room temperature, the reaction mixture was acidified with AcOH (pH=4) and diluted with water. The resulting mixture extracted with dichloromethane and the combined organic layer was dried magnesium sulfate, filtered and concentrated in vacuo. (511 mg, 97%, pale yellow solid)

Example Compound 32

N-(4-methyl-6'-trifluoromethyl-3,4,5,6-tetrahydro-2H-[1,2']bipyridinyl-3'-ylmethyl)-2-(2-thioxo-2,3-dihydro-benzothiazol-6-yl)-propionamide

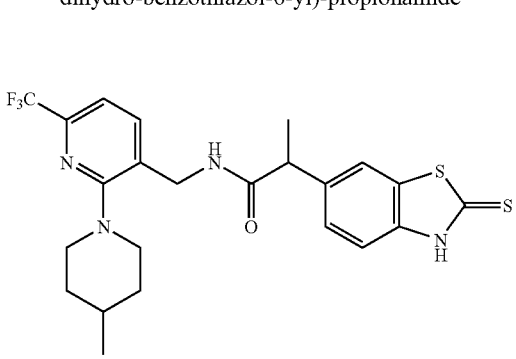

¹H-NMR (CDCl₃) δ 7.51 (d, 1H, J=7.9 Hz, Ar), 7.41 (d, 1H, J=1.3 Hz, Ar), 7.25-7.19 (m, 2H, Ar), 7.12 (d, 1H, J=8.4 Hz, Ar), 6.42 (bt, NH), 4.51 (m, 2H, CH₂NH), 3.64 (q, 1H, J=7.1 Hz, CHCH₃), 3.31 (m, 2H, piperidine), 2.81 (m, 2H, piperidine), 1.78-1.10 (m, 5H, piperidine), 1.57 (d, 3H, J=7.1 Hz, CHCH₃), 0.96 (d, 3H, J=6.6 Hz, piperidine CH₃)

IR 3300, 2924, 1650, 1534, 1472, 1416, 1332, 1177, 1136, 1035 cm⁻¹

Mass (FAB) m/z 495 [M+H]⁺

Example Compound 33

N-(6'-tert.-butyl-4-methyl-3,4,5,6-tetrahydro-2H-[1,2']bipyridinyl-3'-ylmethyl)-2-(2-thioxo-2,3-dihydro-benzothiazol-6-yl)-propionamide

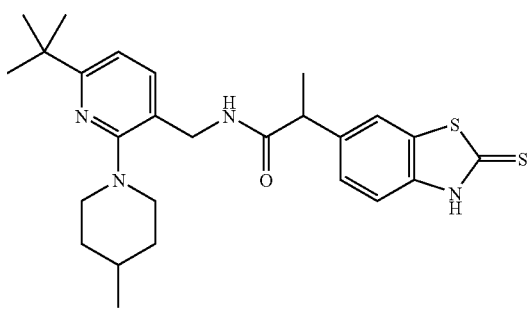

¹H-NMR (CDCl₃) δ 7.40-7.21 (m, 3H, Ar), 7.06 (d, 1H, J=8.4 Hz, Ar), 7.05 (bs, NH), 6.90 (d, 1H, J=7.7 Hz, Ar), 4.46 (m, 2H, CH₂NH), 3.61 (q, 1H, J=7.1 Hz, CHCH₃), 3.25 (m, 2H, piperidine), 2.83-2.71 (m, 2H, piperidine), 1.75-1.50 (m, 3H, piperidine), 1.55 (d, 3H, J=7.1 Hz, CHCH₃), 1.30 (s, 9H, C(CH₃)₃), 1.30-1.10 (m, 2H, piperidine), 0.95 (d, 3H, J=6.4 Hz, piperidine CH₃)

IR 3295, 2923, 1647, 1536, 1475, 1400, 1034 cm⁻¹

Mass (FAB) m/z 483 [M+H]⁺

Example Compound 34

N-(6'-tert.-butyl-4-methyl-3,4,5,6-tetrahydro-2H-[1,2']bipyridinyl-3'-ylmethyl)-2-(2-methylsulfanyl-benzothiazol-6-yl)-propionamide

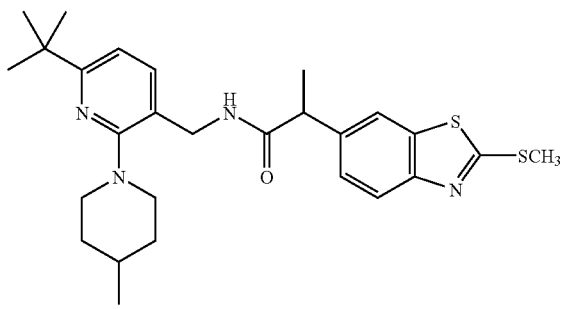

¹H-NMR (CDCl₃) δ 7.80 (d, 1H, J=8.3 Hz, Ar), 7.72 (s, 1H, Ar), 7.34-7.25 (m, 2H, Ar), 6.85 (d, 1H, J=8.0 Hz, Ar), 6.68 (bt, NH), 4.40 (m, 2H, CH₂NH), 3.66 (q, 1H, J=6.8 Hz, CHCH₃), 3.18 (m, 2H, piperidine), 2.79 (s, 3H, SCH₃), 2.71 (m, 2H, piperidine), 1.65-1.40 (m, 6H, piperidine & CHCH₃), 1.28 (s, 9H, C(CH₃)₃), 1.20-1.00 (m, 2H, piperidine), 0.89 (d, 3H, J=6.4 Hz, piperidine CH₃)

IR 3293, 2955, 1648, 1543, 1450, 1238, 1013 cm⁻¹

Mass (FAB) m/z 497 [M+H]⁺

Synthesis of Example Compound 35 a) 2-(4-Hydroxy-3-nitro-phenyl)-propionic acid (1)

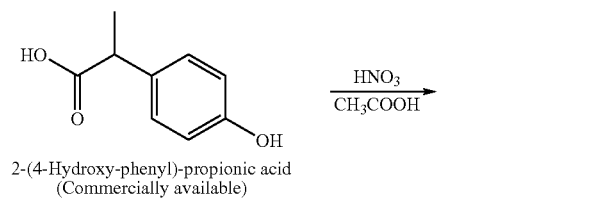

2-(4-Hydroxy-phenyl)-propionic acid (788 mg, 1 mmol) in CH₃COOH (10 ml) is added to 60% Nitric acid (552 mg, 1.11 mmol) at room temperature. The reaction mixture is stirred for 1 h. The iced water (50 ml) added to the reaction mixture. The mixture is extracted with ethyl acetate. The extracts are washed with water, dried over magnesium sulfate, filtered and concentrated in vacuo.

The residue was purified by flash column chromatography (CH₂Cl₂:MeOH).

Pale yellow solid, yield: 86.9%.

b) 2-(3-Amino-4-hydroxy-phenyl)-propionic acid (2)

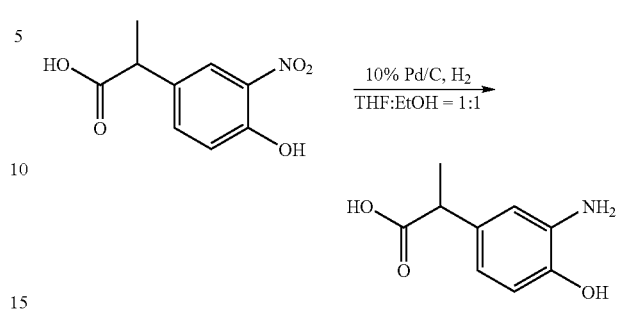

A mixture of (1) (810 mg, 1 mmol) in THF (20 ml) and EtOH (20 ml) is slowly added to 10% Pd/C (90 mg) at room temperature. The reaction mixture is hydrogenated for 3 h with H2 balloon at 45 psi. The mixture is filtered through celite pad and washed with EtOH. The filtrate is concentrated in vacuo.

Pale black solid, yield: 99.2% c) 2-(2-Amino-benzooxazol-5-yl)-propionic acid (3)

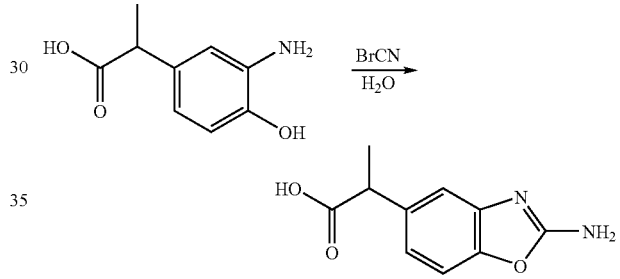

Reference: DE 2,324,443

A mixture of (2) (630 mg, 1 mmol) in H₂O (33 ml) was added BrCN (383 mg, 1.04 mmol) at room temperature. The reaction mixture is stirred for 40 h at room temperature. The reaction mixture is neutralized to pH 6□7 with 40% aq. NaOH and filtered. The solid was recrystallized with 50% aq. MeOH and filtered. The solid is dried under vacuum.

Pale brown solid, yield: 48.8%.

Example Compound 35

2-(2-amino-benzooxazol-5-yl)-N-(4-methyl-6'-trifluoromethyl-3,4,5,6-tetrahydro-2H-[1,2']bipyridinyl-3'-ylmethyl)-propionamide

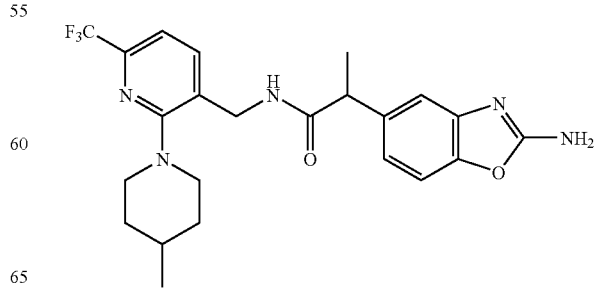

¹H-NMR (CDCl₃) δ 7.43 (d, 1H, J=7.5 Hz, Ar), 7.28-6.97 (m, 4H, Ar), 6.09 (bt, NH), 5.35 (bs, NH₂), 4.43 (d, 2H, J=5.7 Hz, CH₂NH), 3.68 (q, 1H, J=7.3 Hz, CHCH₃), 3.26 (m, 2H, piperidine), 2.76 (m, 2H, piperidine), 1.72-1.45 (m, 6H, piperidine & CHCH₃), 1.14 (m, 2H, piperidine), 0.93 (d, 3H, J=6.4 Hz, CHCH₃)

IR 3298, 2925, 1660, 1573, 1419, 1178, 1138, 951 cm⁻¹

Mass (FAB) m/z 462 [M+H]⁺

Synthesis of Example Compound 36 a) 2-(4-Amino-phenyl)-propionic acid (1)

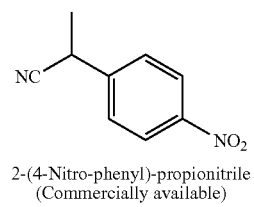

2-(4-Nitro-phenyl)-propionitrile
(Commercially available)

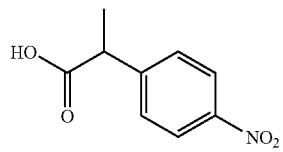

2-(4-nitro-phenyl)-propionitrile (6.03 g) is added to conc. hydrochloric acid (50 ml) at room temperature. The reaction mixture is refluxed for 14 h. The mixture is cooled to room temperature. The mixture is extracted with dichloromethane. The extracts are washed with water, dried over magnesium sulfate, filtered and concentrated in vacuo.

Pale yellow solid, yield: quantitative.

b) 2-(4-Nitro-phenyl)-propionic acid ethyl ester (2)

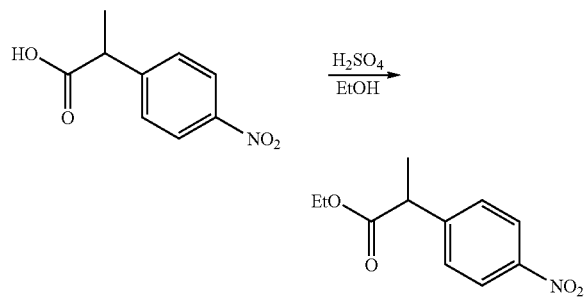

A mixture of 1 (6.7 g, 1 mmol) in EtOH (100 ml) is stirred at room temperature. A sulfuric acid (0.5 ml; catalytic amount) is slowly added to the mixture. The reaction mixture is refluxed for 15 h. the mixture is extracted with ethyl acetate. The extracts are washed with water, brine, dried over magnesium sulfate, filtered and concentrated in vacuo. The residue was purified by flash column chromatography (n-Hexane:EtOAc).

Pale yellow oil, yield: 88%.

c) 2-(4-Amino-phenyl)-propionic acid ethyl ester (3)

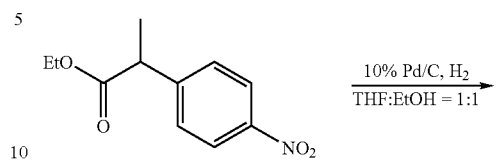

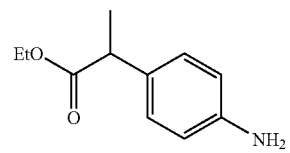

A mixture of 2 (6.7 g, 1 mmol) in THF (100 ml) and EtOH (100 ml) is slowly added 10% Pd/C (680 mg) at room temperature. The reaction mixture is hydrogenated for 24 h with H2 balloon at room temperature. The mixture is filtered through celite pad and washed with EtOH. The filtrate is concentrated in vacuo.

Pale yellow oil, yield: 54% d) 2-(2-Amino-benzothiazole-6-yl)-propionic acid ethyl ester (4)

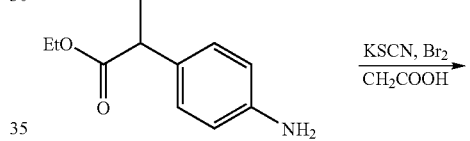

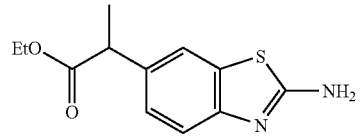

Reference: Indian Journal of Chemistry, Vol. 16B, pp 605-609

A mixture of 3 (3.13 g, 1 mmol) in CH₃COOH (15 ml) was cooled to −5° in iced bath. A mixture KSCN (6.36 g, 4.04 mmol) in CH₃COOH (15 ml) added to the flask that contained 4 and CH₃COOH at −5° in iced bath. A solution of bromine (0.80 ml) in CH₃COOH (10 ml) is added dropwise to a stirred mixture of 4, KSCN and CH₃COOH at −5° in iced bath. The reaction mixture is stirred for 1 h at room temperature. The mixture is extracted with ethyl acetate. The extracts are washed with water, brine, dried over magnesium sulfate, filtered and concentrated in vacuo. The residue was purified by flash column chromatography (n-Hexane:EtOAc).

Pale yellow solid.

e) 2-(2-Acethlamino-benzothiazol-6-yl)-propionic acid ethyl ester (5)

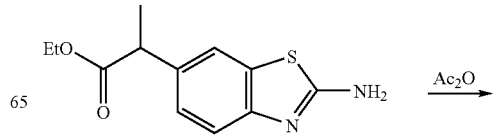

-continued

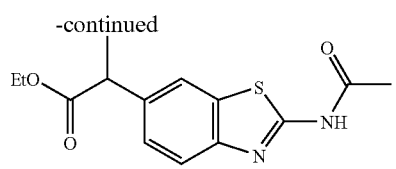

A mixture of 4 (278 mg) in acetic anhydride (4 ml) is refluxed for 3 h. The mixture is cooled to room temperature. Water (30 ml) is added to the mixture and extracted with ethyl acetate. The extracts are washed with water, brine, dried over magnesium sulfate, filtered and concentrated in vacuo.

Yield: 88%.

f) 2-(2-Acetylamino-benzothiazol-6-yl)-propionic acid (6)

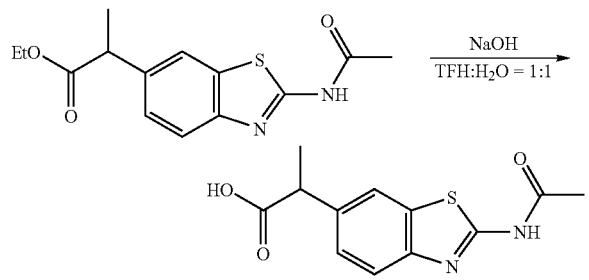

A mixture of 5 (276 mg, 1 mmol) in THF (10 ml) and H$_2$O (10 ml) is stirred at room temperature. Sodium hydroxide (96 mg) is added to the mixture. The reaction mixture is stirred for 15 h at room temperature. The reaction mixture is acidified to pH 3~4 with acetic acid. Water is added to the mixture and extracted with dichloromethane. The organic layer is dried over magnesium sulfate, filtered and concentrated in vacuo.

Pale yellow solid, yield: 99.8%.

Example Compound 36

2-(2-acetylamino-benzothiazol-6-yl)-N-(4-tert.-butyl-benzyl)-propionamide

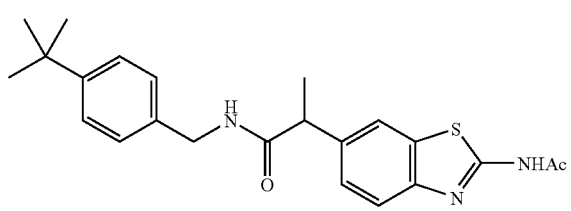

$^1$H-NMR (CDCl$_3$) δ 11.17 (bs, NH), 7.78-7.68 (m, 2H, Ar), 7.42-7.21 (m, 3H, Ar), 7.11 (d, 2H, J=8.2 Hz, Ar), 5.75 (bt, NH), 4.39 (m, 2H, CH$_2$NH), 3.71 (q, 1H, J=7.1 Hz, CHCH$_3$), 2.27 (s, 3H, COCH$_3$), 1.61 (d, 3H, J=7.1 Hz, CHCH$_3$), 1.28 (s, 9H, C(CH$_3$)$_3$)

IR 3298, 2963, 1649, 1548, 1462, 1369, 1275 cm$^{-1}$

Mass (FAB) m/z 410 [M+H]$^+$, 432 [M+Na]$^+$

Example Compound 37

2-(2-acetylamino-benzothiazol-6-yl)-N-(4-methyl-6'-trifluoromethyl-3,4,5,6-tetrahydro-2H-[1,2']bipyridinyl-3'-ylmethyl)-propionamide

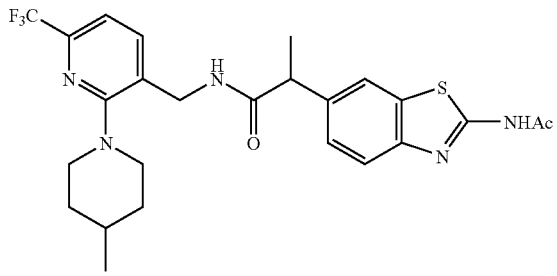

$^1$H-NMR (CDCl$_3$) δ 7.80-7.63 (m, 2H, Ar), 7.39 (m, 2H, Ar), 7.13 (d, 1H, J=7.5 Hz, Ar), 4.43 (m, 2H, CH$_2$NH), 3.78 (m, 1H, CHCH$_3$), 3.30 (m, 2H, piperidine), 2.79 (m, 2H, piperidine), 2.31 (s, 3H, COCH$_3$), 1.80-1.20 (m, 8H, CHCH$_3$ & piperidine), 0.94 (d, 3H, J=6.2 Hz, piperidine CH$_3$)

IR 3189, 2923, 2455, 1644, 1548, 1458, 1418, 1372, 1335, 1270, 1175, 1135 cm$^{-1}$

Mass (FAB) m/z 520 [M+H]$^+$

Synthesis of Example Compound 38 a) 2-(4-Nitro-phenyl)-propionic acid (1)

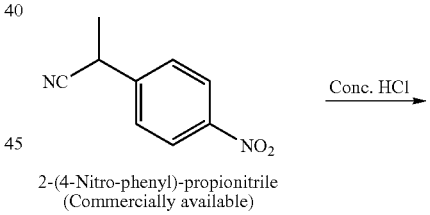

2-(4-Nitro-phenyl)-propionitrile
(Commercially available)

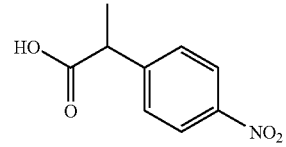

2-(4-nitro-phenyl)-propionitrile (6.03 g) is added to conc. hydrochloric acid (50 ml) at room temperature. The reaction mixture is refluxed for 14 h. The mixture is cooled to room temperature. The mixture is extracted with dichloromethane.

The extracts are washed with water, dried over magnesium sulfate, filtered and concentrated in vacuo.

Pale white solid, yield: 99%.

b) 2-(4-Amino-phenyl)-propionic acid (2)

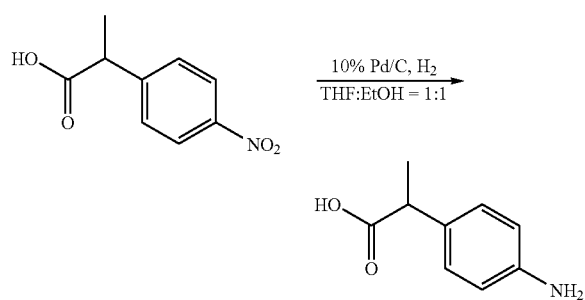

A mixture of 1 (6.7 g, 1 mmol) in THF (100 ml) and EtOH (100 ml) is slowly added 10% Pd/C (680 mg) at room temperature. The reaction mixture is hydrogenated for 24 h with H2 balloon at room temperature. The mixture is filtered through celite pad and washed with EtOH. The filtrate is concentrated in vacuo.
Pale yellow solid, yield: 99.8% c) 2-(2-Amino-benzothiazole-6-yl)-propionic acid (3)

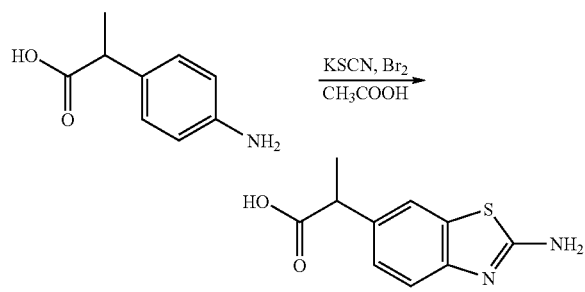

Reference: Indian Journal of Chemistry, Vol. 16B, pp 605-609

A mixture of 2 (3.13 g, 1 mmol) in CH₃COOH (15 ml) was cooled to −5° in iced bath. A mixture KSCN (6.36 g, 4.04 mmol) in CH₃COOH (15 ml) added to the flask that contained 4 and CH₃COOH at −5° in iced bath. A solution of bromine (0.80 ml) in CH₃COOH (10 ml) is added dropwise to a stirred mixture of 4, KSCN and CH₃COOH at −5° in iced bath. The reaction mixture is stirred for 1 h at room temperature. The mixture is extracted with ethyl acetate. The extracts are washed with water, brine, dried over magnesium sulfate, filtered and concentrated in vacuo.

The residue was purified by flash column chromatography (n-Hexane:EtOAc).
Pale yellow solid.

Synthesis of Example Compound 39 a) 2-(4-Amino-phenyl)-propionic acid (1)

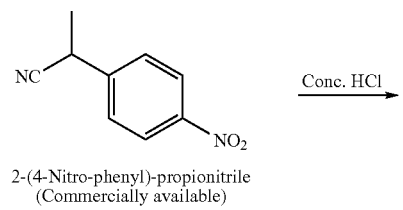

2-(4-Nitro-phenyl)-propionitrile
(Commercially available)

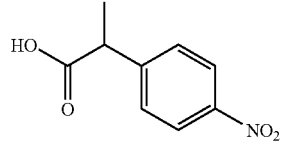

2-(4-nitro-phenyl)-propionitrile (6.03 g) is added to conc. hydrochloric acid (50 ml) at room temperature. The reaction mixture is refluxed for 14 h. The mixture is cooled to room temperature. The mixture is extracted with dichloromethane. The extracts are washed with water, dried over magnesium sulfate, filtered and concentrated in vacuo.
Pale yellow solid, yield: quantitative.

b) 2-(4-Nitro-phenyl)-propionic acid ethyl ester (2)

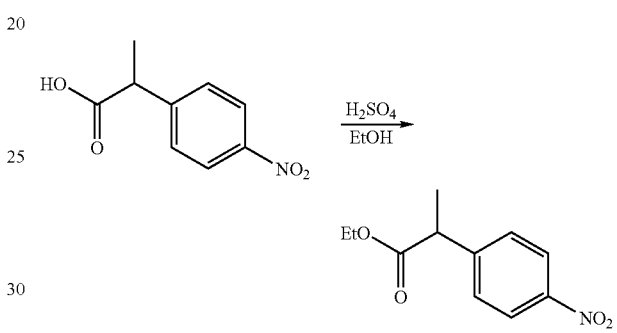

A mixture of 1 (6.7 g, 1 mmol) in EtOH (100 ml) is stirred at room temperature. A sulfuric acid (0.5 ml; catalytic amount) is slowly added to the mixture. The reaction mixture is refluxed for 15 h. The mixture is extracted with ethyl acetate.

The extracts are washed with water, brine, dried over magnesium sulfate, filtered and concentrated in vacuo.

The residue was purified by flash column chromatography (n-Hexane:EtOAc).
Pale yellow oil, yield: 88%.

c) 2-(4-Amino-phenyl)-propionic acid ethyl ester (3)

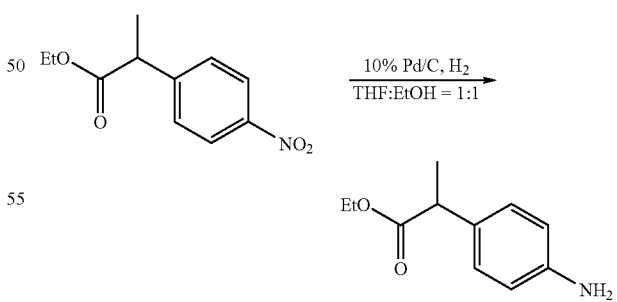

A mixture of 2 (6.7 g, 1 mmol) in THF (100 ml) and EtOH (100 ml) is slowly added 10% Pd/C (680 mg) at room temperature. The reaction mixture is hydrogenated for 24 h with H2 balloon at room temperature. The mixture is filtered through celite pad and washed with EtOH. The filtrate is concentrated in vacuo.
Pale yellow oil, yield: 54% d) 2-(2-Amino-benzothiazole-6-yl)-propionic acid ethyl ester (4)

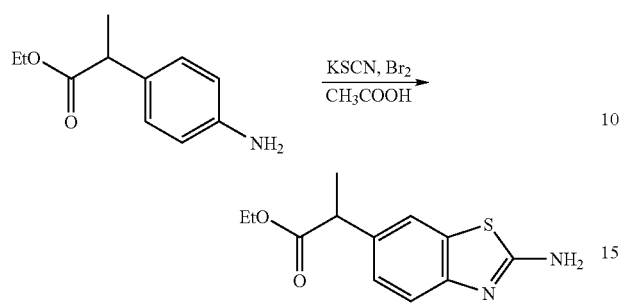

Reference: Indian Journal of Chemistry, Vol. 16B, pp 605-609

A mixture of 3 (3.13 g, 1 mmol) in CH$_3$COOH (15 ml) was cooled to −5□ in iced bath. A mixture KSCN (6.36 g, 4.04 mmol) in CH$_3$COOH (15 ml) added to the flask that contained 4 and CH$_3$COOH at −5° in iced bath. A solution of bromine (0.80 ml) in CH$_3$COOH (10 ml) is added dropwise to a stirred mixture of 4, KSCN and CH$_3$COOH at −5° in iced bath. The reaction mixture is stirred for 1 h at room temperature. The mixture is extracted with ethyl acetate. The extracts are washed with water, brine, dried over magnesium sulfate, filtered and concentrated in vacuo.

The residue was purified by flash column chromatography (n-Hexane:EtOAc).

Pale yellow solid.

e) 2-(2-Methanesulfonylamino-benzothiazole-6-yl)-propionic acid ethyl ester (5)

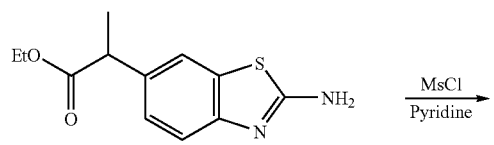

A mixture of 4 (347 mg, 1 mmol) in pyridine (3 ml) is added to MsCl (0.13 ml, 1.21 mmol) at room temperature. The reaction mixture is stirred for 14 h at room temperature. 1 N HCl (30 ml) is added to the mixture. The mixture extracted with ethyl acetate. The organic layer is dried over magnesium sulfate. The filtrate was concentrated in vacuo. The residue was purified by flash column chromatography (n-Hexane:EtOAc).

Pale yellow oil, yield: 35%.

f) 2-(2-Methanesulfonylamino-benzothiazole-6-yl)-propionic acid (6)

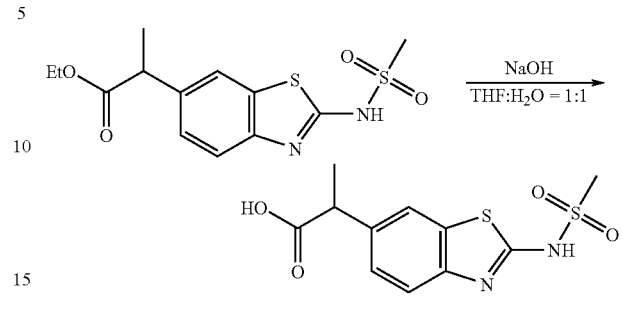

A mixture of 5 (156 mg, 1 mmol) in THF (10 ml) and H$_2$O (10 ml) is stirred at room temperature. Sodium hydroxide (50 mg, 2.5 mmol) is added to the mixture. The reaction mixture is stirred for 15 h at room temperature. The reaction mixture is acidified to pH 3~4 with acetic acid. Water is added to the mixture and extracted with dichloromethane. The organic layer is dried over magnesium sulfate, filtered and concentrated in vacuo. Yield: quantitative.

Synthesis of Example Compound 40 a) 2-(4-Amino-phenyl)-propionic acid (1)

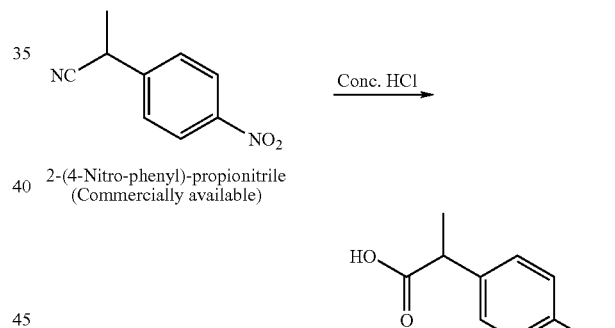

2-(4-nitro-phenyl)-propionitrile (6.03 g) is added to conc. hydrochloric acid (50 ml) at room temperature. The reaction mixture is refluxed for 14 h. The mixture is cooled to room temperature. The mixture is extracted with dichloromethane. The extracts are washed with water, dried over magnesium sulfate, filtered and concentrated in vacuo.

Pale yellow solid, yield: quantitative.

b) 2-(4-nitro-phenyl)-propionic acid ethyl ester (2)

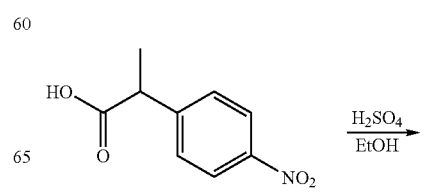

-continued

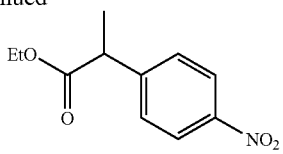

A mixture of 1 (6.7 g, 1 mmol) in EtOH (100 ml) is stirred at room temperature. A sulfuric acid (0.5 ml; catalytic amount) is slowly added to the mixture. The reaction mixture is refluxed for 15 h. The mixture is extracted with ethyl acetate. The extracts are washed with water, brine, dried over magnesium sulfate, filtered and concentrated in vacuo. The residue was purified by flash column chromatography (n-Hexane:EtOAc).

Pale yellow oil, yield: 88%.

c) 2-(4-Amino-phenyl)-propionic acid ethyl ester (3)

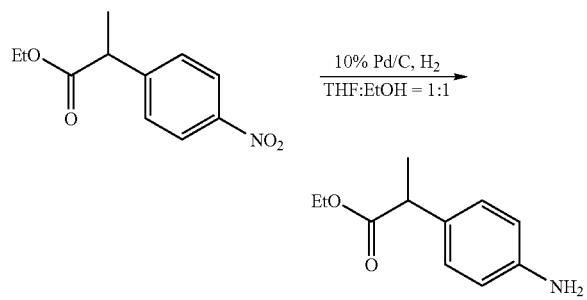

A mixture of 2 (6.7 g, 1 mmol) in THF (100 ml) and EtOH (100 ml) is slowly added 10% Pd/C (680 mg) at room temperature. The reaction mixture is hydrogenated for 24 h with H2 balloon at room temperature. The mixture is filtered through celite pad and washed with EtOH. The filtrate is concentrated in vacuo.

Pale yellow oil, yield: 54% d) 2-(2-Amino-benzothiazole-6-yl)-propionic acid ethyl ester (4)

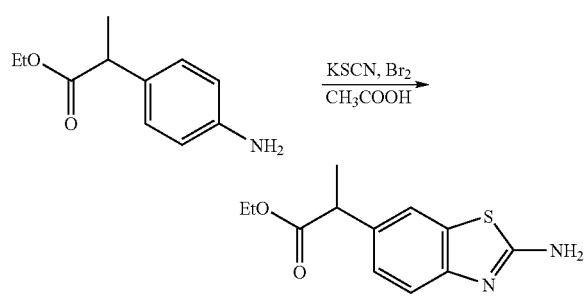

Reference: Indian Journal of Chemistry, Vol. 16B, pp 605-609

A mixture of 3 (3.13 g, 1 mmol) in CH$_3$COOH (15 ml) was cooled to −5° in iced bath. A mixture KSCN (6.36 g, 4.04 mmol) in CH$_3$COOH (15 ml) added to the flask that contained 4 and CH$_3$COOH at −5° in iced bath. A solution of bromine (0.80 ml) in CH$_3$COOH (10 ml) is added dropwise to a stirred mixture of 4, KSCN and CH$_3$COOH at −5° in iced bath. The reaction mixture is stirred for 1 h at room temperature. The mixture is extracted with ethyl acetate. The extracts are washed with water, brine, dried over magnesium sulfate, filtered and concentrated in vacuo. The residue was purified by flash column chromatography (n-Hexane:EtOAc).

Pale yellow solid.

e) 2-(2-tert-Butoxycarbonylamino-benzothiazole-6-yl)-propionic acid ethyl ester (5)

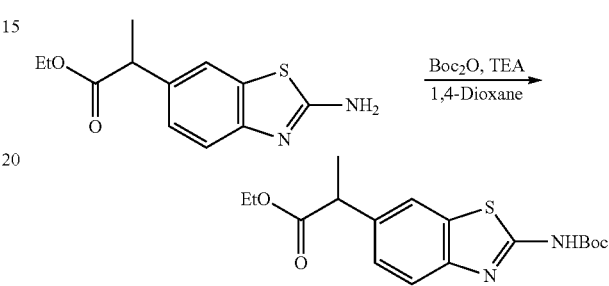

A mixture of 4 (793 mg, 1 mmol) in 1,4-Dioxane is added to Boc$_2$O (3.5 g, 5 mmol) and TEA (2.21 ml, 5 mmol) at room temperature. The reaction mixture is refluxed for 14 h. The mixture is cooled to room temperature. Water is added to the mixture and extracted with dichloromethane. The organic layer is dried over magnesium sulfate, filtered and concentrated in vacuo. The residue was purified by flash column chromatography (n-Hexane:EtOAc).

Pale white solid, yield: 22%.

f) 2-(2-tert-Butoxycarbonylamino-benzothiazole-6-yl)-propionic acid (6)

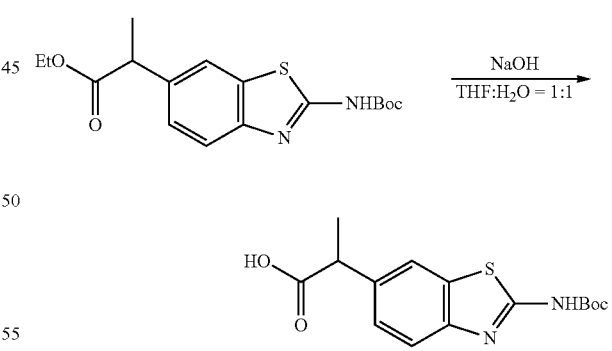

A mixture of 5 (239 mg, 1 mmol) in THF (10 ml) and H$_2$O (10 ml) is stirred at room temperature. Sodium hydroxide (68.2 mg, 2.5 mmol) is added to the mixture. The reaction mixture is stirred for 15 h at room temperature. The reaction mixture is acidified to pH 3~4 with acetic acid. Water is added to the mixture and extracted with dichloromethane. The organic layer is dried over magnesium sulfate, filtered and concentrated in vacuo. Yield: quantitative.

Synthesis of Example Compound 44 a)

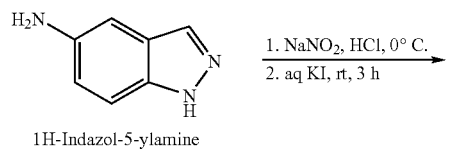

1H-Indazol-5-ylamine

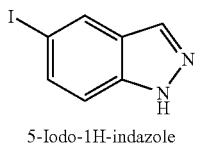

5-Iodo-1H-indazole

To a solution of 1H-indazol-5-amine (1.41 g, 10.6 mmol) in 6 N HCl (20 mL) cooled to 0° C., a solution of NaNO$_2$ (730 mg, 10.6 mmol) in water (10 mL) was added dropwisely. The resulting solution was added to a solution of KI (7.3 g, 44 mmol) in water (15 mL), keeping the temperature at 0° C. The reaction mixture was allowed to warm to room temperature and stirred for 3 h, then extracted with ethyl acetate. The combined layers were washed in sequence with 10% Na$_2$S$_2$O$_3$ and brine, then dried over Na$_2$SO$_4$ and concentrated under vacuum to afford product as a pale brown solid (1.90 g, 75%), which was used without further purification in the next step.

b)

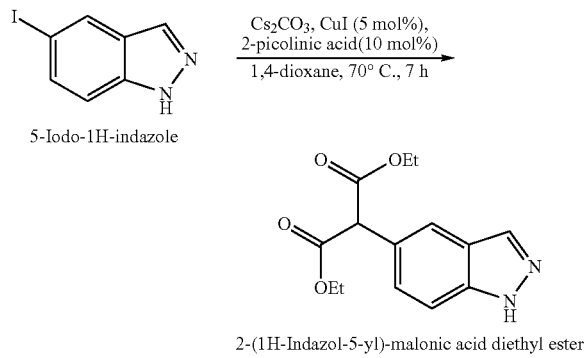

2-(1H-Indazol-5-yl)-malonic acid diethyl ester

CuI (9.5 mg, 5.0 mol %), 2-picolinic acid (12.3 mg, 10.0 mol %), Cs$_2$CO$_3$ (0.98 g, 3.0 mmol), and aryl iodide (1.0 mmol) in 1,4-dioxane (10 ml) was added distilled diethyl malonate (304 µL, 2.00 mmol) and 5-iodo-1H-indazole (1.00 mmol). After stirring 7 hrs at 70° C., the reaction mixture was cooled to rt. The reaction mixtures were extracted with ethyl acetate (20 mL×3) and saturated aqueous NH$_4$Cl (10 mL). The combined organic layer was dried over Na$_2$SO$_4$, filtered and concentrated under vacuum. The oily residue was purified by flash chromatography on silica gel to give the desired product as a colorless oil (60%)

c)

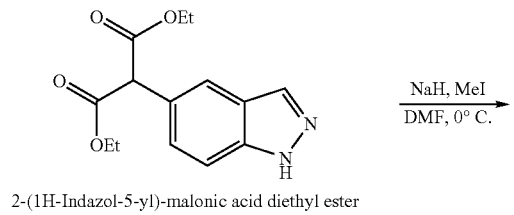

2-(1H-Indazol-5-yl)-malonic acid diethyl ester

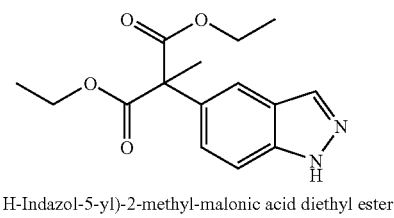

2-(1H-Indazol-5-yl)-2-methyl-malonic acid diethyl ester

A cooled solution of diethyl 2-(1H-indazol-5-yl)malonate (1 mmol) in DMF (10 mL) at 0° C. was treated with NaH (1.1 mmol) and MeI (1.2 mmol) and stirred for 30 min at room temperature. The reaction mixture was concentrated in vacuo and the residue was purified by flash column chromatography on silica gel with EtOAc/hexanes (1:4) as eluant. (65%)

d)

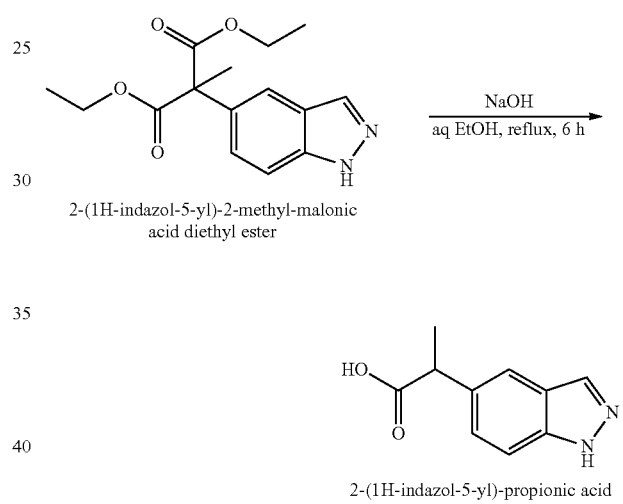

2-(1H-indazol-5-yl)-2-methyl-malonic acid diethyl ester 2-(1H-indazol-5-yl)-propionic acid A mixture of diethyl 2-(1H-indazol-5-yl)-2-methylmalonate (1 mmol) and NaOH (2 mmol) in 80% aqueous EtOH (10 mL) was refluxed for 6 hrs. The mixture was neutralized with 1 N HCl, The reaction mixture was extracted with ethyl acetate (20 mL×3) and concentrated in vacuo. The residue was purified by flash column chromatography on silica gel with EtOAc/hexanes (1:1) as eluant. 53% e)

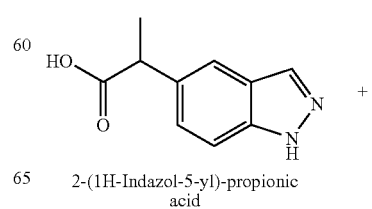

2-(1H-Indazol-5-yl)-propionic acid

-continued

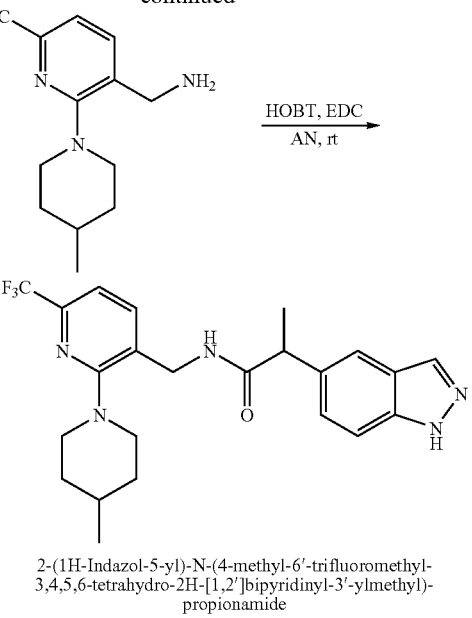

2-(1H-Indazol-5-yl)-N-(4-methyl-6'-trifluoromethyl-3,4,5,6-tetrahydro-2H-[1,2']bipyridinyl-3'-ylmethyl)-propionamide A mixture of acid (10 mmol), amine (12 mmol) and 1-(3-dimethylaminopropyl)-3-ethyl-carbodiimide hydrochloride (12 mmol) in DMF (20 mL) was stirred for 12 h at room temperature. The reaction mixture was extracted with EtOAc (50 mL). The aqueous phase was saturated with NaCl and extracted again with EtOAc (25 mL). The combined organic extracts were washed with 1 N HCl (25 mL) and brine (25 mL), dried over MgSO$_4$, filtered, and concentrated in vacuo. The residue was purified by flash column chromatography on silica gel using EtOAc:hexanes (1:2) as eluant. 75%, white solid, mp=113-115° C.

Synthesis of Example Compound 45

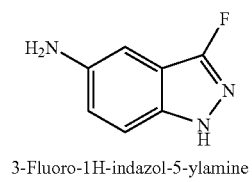

3-Fluoro-1H-indazol-5-ylamine

1. NaNO$_2$, HCl, 0° C.
2. aq. KI, rt, 3 h

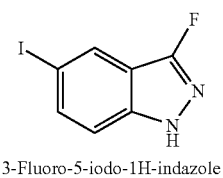

3-Fluoro-5-iodo-1H-indazole

Same as general procedure
56% colorless oil

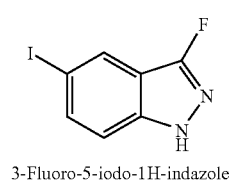

3-Fluoro-5-iodo-1H-indazole

Cs$_2$CO$_3$, CuI (5 mol%), 2-picolinic acid(10 mol%)
1,4-dioxane, 70° C., 7 h

-continued

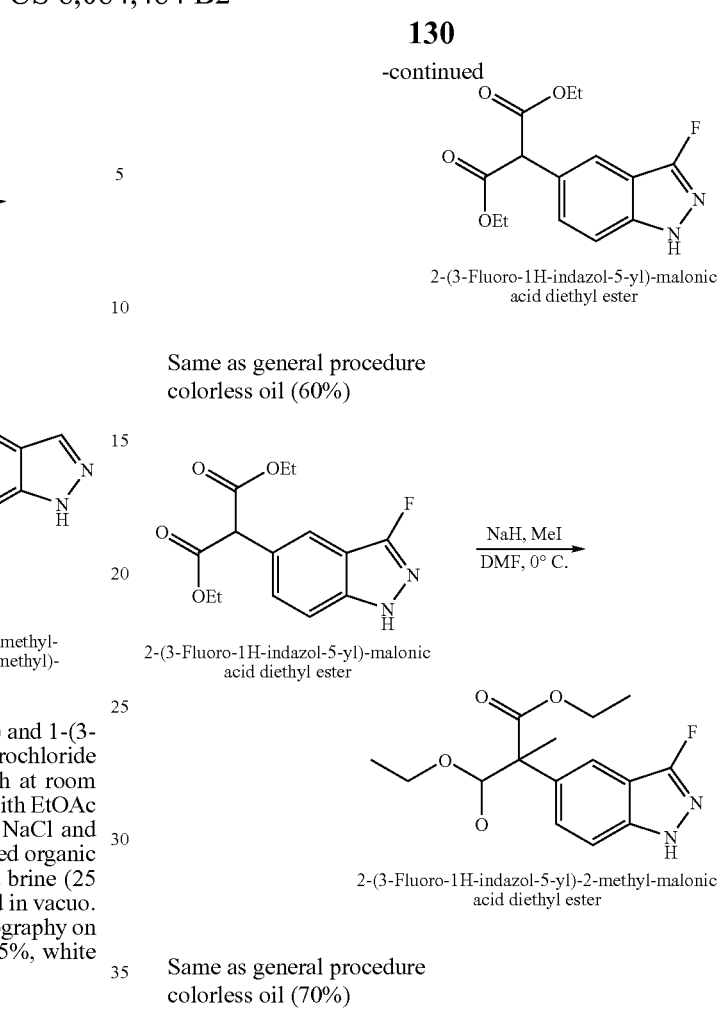

2-(3-Fluoro-1H-indazol-5-yl)-malonic acid diethyl ester

Same as general procedure
colorless oil (60%)

2-(3-Fluoro-1H-indazol-5-yl)-malonic acid diethyl ester

NaH, MeI
DMF, 0° C.

2-(3-Fluoro-1H-indazol-5-yl)-2-methyl-malonic acid diethyl ester

Same as general procedure
colorless oil (70%)

2-(3-Fluoro-1H-indazol-5-yl)-2-methyl-malonic acid diethyl ester

NaOH
aq EtOH, reflux, 6 h 2-(3-Fluoro-1H-indazol-5-yl)-propionic acid

Same as general procedure
colorless oil (53%)

2-(3-Fluoro-1H-indazol-5-yl)-propionic acid            +

-continued

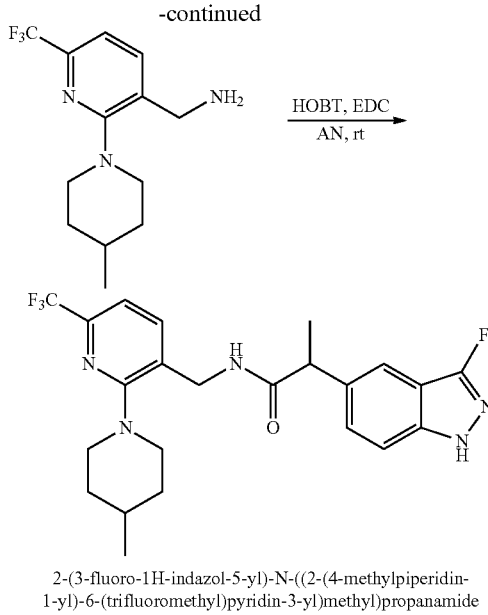

2-(3-fluoro-1H-indazol-5-yl)-N-((2-(4-methylpiperidin-1-yl)-6-(trifluoromethyl)pyridin-3-yl)methyl)propanamide Same as general procedure
0.70%, white solid, mp=123-127° C.

Synthesis of Example Compound 46 a)

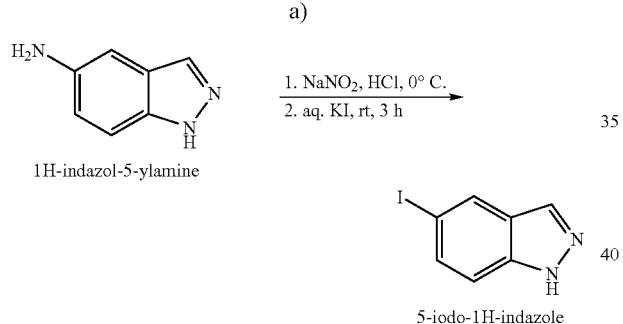

1H-indazol-5-ylamine 5-iodo-1H-indazole

To a solution of 1H-indazol-5-amine (1.41 g, 10.6 mmol) in 6 N HCl (20 mL) cooled to 0° C., a solution of NaNO$_2$ (730 mg, 10.6 mmol) in water (10 mL) was added dropwisely. The resulting solution was added to a solution of KI (7.3 g, 44 mmol) in water (15 mL), keeping the temperature at 0° C. The reaction mixture was allowed to warm to room temperature and stirred for 3 h, then extracted with ethyl acetate. The combined layers were washed in sequence with 10% Na$_2$S$_2$O$_3$ and brine, then dried over Na$_2$SO$_4$ and concentrated under vacuum to afford product as a pale brown solid (1.90 g, 75%), which was used without further purification in the next step.

b)

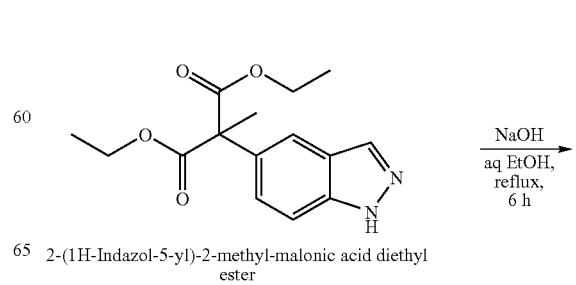

5-Iodo-1H-indazole

-continued

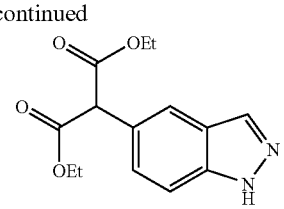

2-(1H-Indazol-5-yl)-malonic acid diethyl ester

CuI (9.5 mg, 5.0 mol %), 2-picolinic acid (12.3 mg, 10.0 mol %), Cs$_2$CO$_3$ (0.98 g, 3.0 mmol), and aryl iodide (1.0 mmol) in 1,4-dioxane (10 ml) was added distilled diethyl malonate (304 µL, 2.00 mmol) and 5-iodo-1H-indazole (1.00 mmol). After stirring 7 hrs at 70° C., the reaction mixture was cooled to rt. The reaction mixtures were extracted with ethyl acetate (20 mL×3) and saturated aqueous NH$_4$Cl (10 mL). The combined organic layer was dried over Na$_2$SO$_4$, filtered and concentrated under vacuum. The oily residue was purified by flash chromatography on silica gel to give the desired product as a colorless oil (60%)

c)

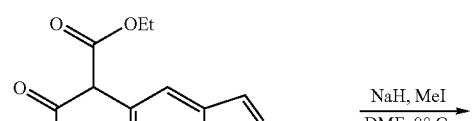

2-(1H-Indazol-5-yl)-malonic acid diethyl ester

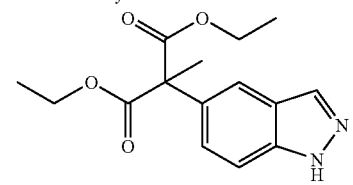

2-(1H-Indazol-5-yl)-2-methyl-malonic acid diethyl ester

A cooled solution of diethyl 2-(1H-indazol-5-yl)malonate (1 mmol) in DMF (10 mL) at 0° C. was treated with NaH (1.1 mmol) and MeI (1.2 mmol) and stirred for 30 min at room temperature. The reaction mixture was concentrated in vacuo and the residue was purified by flash column chromatography on silica gel with EtOAc/hexanes (1:4) as eluant. (65%)

d)

2-(1H-Indazol-5-yl)-2-methyl-malonic acid diethyl ester

-continued

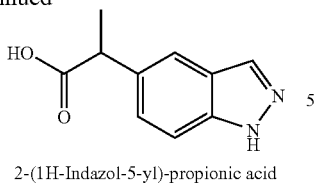
2-(1H-Indazol-5-yl)-propionic acid

A mixture of diethyl 2-(1H-indazol-5-yl)-2-methylmalonate (1 mmol) and NaOH (2 mmol) in 80% aqueous EtOH (10 mL) was refluxed for 6 hrs. The mixture was neutralized with 1 N HCl, The reaction mixture was extracted with ethyl acetate (20 mL×3) and concentrated in vacuo. The residue was purified by flash column chromatography on silica gel with EtOAc/hexanes (1:1) as eluant. 53% e)

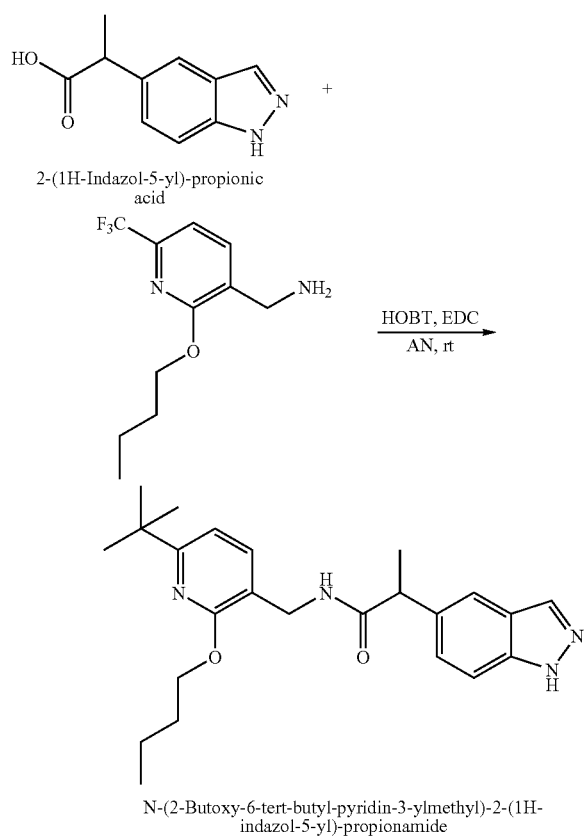
N-(2-Butoxy-6-tert-butyl-pyridin-3-ylmethyl)-2-(1H-indazol-5-yl)-propionamide Same as general procedure
0.60%, white solid, mp=103-107° C.

Synthesis of Example Compound 48 a)

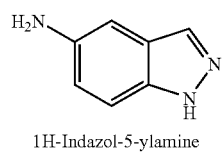
1H-Indazol-5-ylamine

1. NaNO₂, HCl, 0° C.
2. aq KI, rt, 3 h

-continued

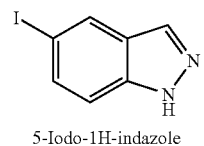
5-Iodo-1H-indazole

To a solution of 1H-indazol-5-amine (1.41 g, 10.6 mmol) in 6 N HCl (20 mL) cooled to 0° C., a solution of NaNO₂ (730 mg, 10.6 mmol) in water (10 mL) was added dropwisely. The resulting solution was added to a solution of KI (7.3 g, 44 mmol) in water (15 mL), keeping the temperature at 0° C. The reaction mixture was allowed to warm to room temperature and stirred for 3 h, then extracted with ethyl acetate. The combined layers were washed in sequence with 10% Na₂S₂O₃ and brine, then dried over Na₂SO₄ and concentrated under vacuum to afford product as a pale brown solid (1.90 g, 75%), which was used without further purification in the next step.

b)

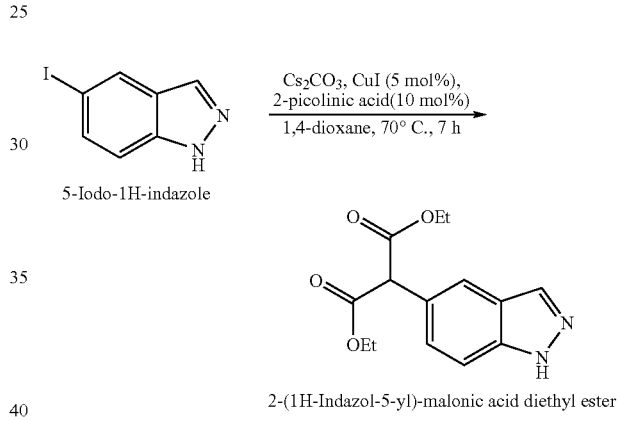

CuI (9.5 mg, 5.0 mol %), 2-picolinic acid (12.3 mg, 10.0 mol %), Cs₂CO₃ (0.98 g, 3.0 mmol), and aryl iodide (1.0 mmol) in 1,4-dioxane (10 ml) was added distilled diethyl malonate (304 µL, 2.00 mmol) and 5-iodo-1H-indazole (1.00 mmol). After stirring 7 hrs at 70° C., the reaction mixture was cooled to rt. The reaction mixtures were extracted with ethyl acetate (20 mL×3) and saturated aqueous NH₄Cl (10 mL). The combined organic layer was dried over Na₂SO₄, filtered and concentrated under vacuum. The oily residue was purified by flash chromatography on silica gel to give the desired product as a colorless oil (60%)

c)

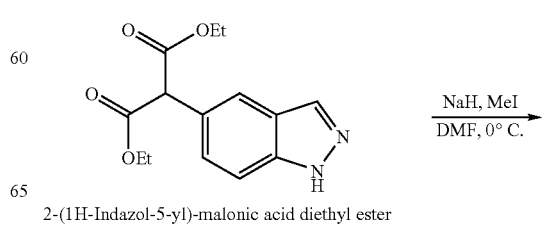
2-(1H-Indazol-5-yl)-malonic acid diethyl ester

NaH, MeI
DMF, 0° C.

-continued

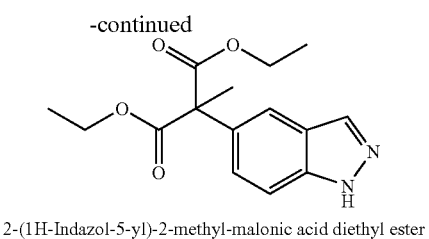

2-(1H-Indazol-5-yl)-2-methyl-malonic acid diethyl ester

A cooled solution of diethyl 2-(1H-indazol-5-yl)malonate (1 mmol) in DMF (10 mL) at 0° C. was treated with NaH (1.1 mmol) and MeI (1.2 mmol) and stirred for 30 min at room temperature. The reaction mixture was concentrated in vacuo and the residue was purified by flash column chromatography on silica gel with EtOAc/hexanes (1:4) as eluant. (65%)

d)

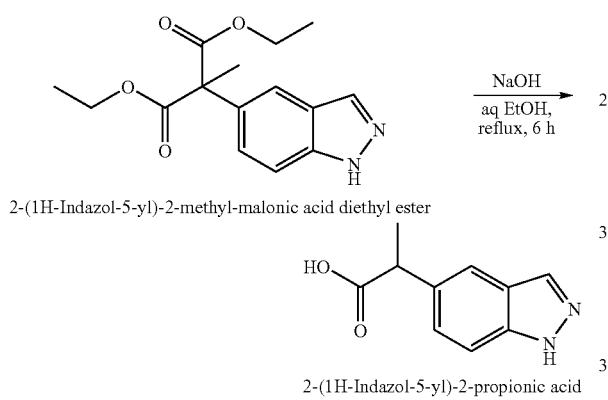

2-(1H-Indazol-5-yl)-2-methyl-malonic acid diethyl ester 2-(1H-Indazol-5-yl)-2-propionic acid A mixture of diethyl 2-(1H-indazol-5-yl)-2-methylmalonate (1 mmol) and NaOH (2 mmol) in 80% aqueous EtOH (10 mL) was refluxed for 6 hrs. The mixture was neutralized with 1 N HCl, The reaction mixture was extracted with ethyl acetate (20 mL×3) and concentrated in vacuo. The residue was purified by flash column chromatography on silica gel with EtOAc/hexanes (1:1) as eluant. 53% e)

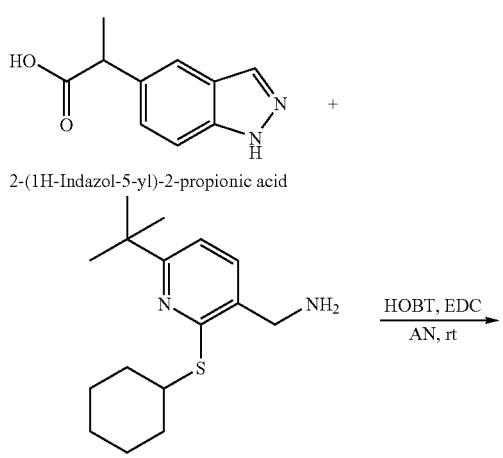

2-(1H-Indazol-5-yl)-2-propionic acid

-continued

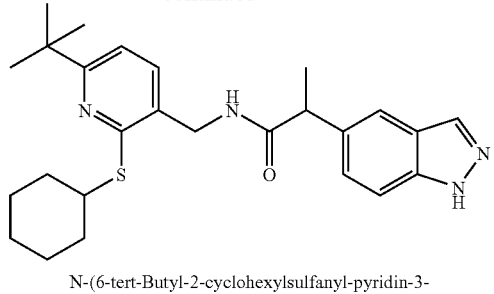

N-(6-tert-Butyl-2-cyclohexylsulfanyl-pyridin-3-ylmethyl)-2-(1H-indazol-5-yl)-propionamide Same as general procedure
76%, white solid, mp=105-108° C.

Example Compound 49

N-(2-butoxy-6-tert.-butyl-pyridin-3-ylmethyl)-2-(2-thioxo-2,3-dihydro-benzothiazol-6-yl)-propionamide

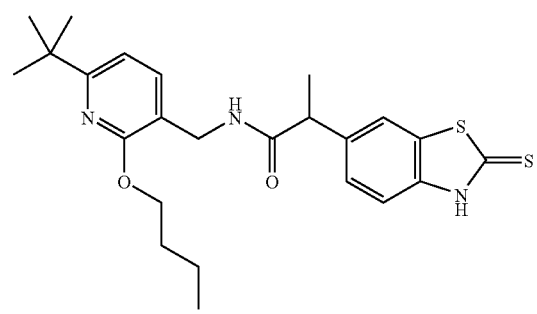

$^1$H-NMR (CDCl$_3$) δ 7.38 (m, 2H, Ar), 7.21-7.03 (m, 2H, Ar), 6.79 (d, 1H, J=7.5 Hz, Ar), 6.16 (bs, NH), 4.33 (m, 4H, OCH$_2$ & CH$_2$NH), 3.58 (q, 1H, J=7.1 Hz, CHCH$_3$), 1.65 (m, 2H, OCH$_2$CH$_2$), 1.52 (d, 3H, J=7.1 Hz, CHCH$_3$), 1.40 (m, 2H, CH$_2$CH$_3$), 1.30 (s, 9H, C(CH$_3$)$_3$), 0.95 (t, 3H, J=7.3 Hz, CH$_2$CH$_3$)
IR 2958, 1648, 1537, 1475, 1405, 1254, 1033 cm$^{-1}$
Mass (FAB) m/z 458 [M+H]$^+$ Example Compound 50 tert.-butyl 6-(1-(4-tert.-butylbenzylamino)-1-oxopropan-2-yl)benzo[d]thiazol-2-ylcarbamate The compound was prepared by methods described for example compound 40.

Example Compound 51 tert.-butyl 6-(1-(4-tert.-butylbenzylamino)-1-oxopropan-2-yl)benzo[d]thiazol-2-ylcarbamate The compound was prepared by methods described for example compound 38.

Example Compound 52 tert.-butyl 6-(1-(4-tert.-butylbenzylamino)-1-oxopropan-2-yl)benzo[d]thiazol-2-ylcarbamate The compound was prepared by methods described for example compound 38.

Example Compound 55 tert.-butyl 6-(1-(4-tert.-butylbenzylamino)-1-oxopropan-2-yl)benzo[d]thiazol-2-ylcarbamate The compound was prepared by methods described for example compound 40.

Example Compound 56 tert.-butyl 6-(1-(4-tert.-butylbenzylamino)-1-oxopropan-2-yl)benzo[d]thiazol-2-ylcarbamate The compound was prepared by methods described for example compound 38.

Example Compound 57 tert.-butyl 6-(1-(4-tert.-butylbenzylamino)-1-oxopropan-2-yl)benzo[d]thiazol-2-ylcarbamate The compound was prepared by methods described for example compound 39.

Compounds 61-77 and 43-49 may also be obtained by the methods described herein.

Synthesis of Further Example Compounds

Synthesis of Example Compound 12 a) 2-(4-Amino-phenyl)-propionitrile

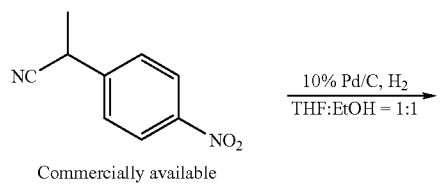

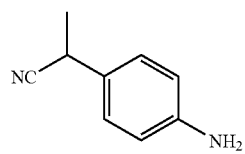

To the flask was added THF/EtOH (1:1, 70 mL) followed by 2-(4-nitrophenyl)-propionitrile (13.2 g, 74.9 mmol) and 10% palladium carbon (1.07 g) at room temperature. The reaction mixture was hydrogenated and stirred for 30 minutes at 47 psi to 28 psi then filtered through celite bed, and washed with EtOAc. The filtrate was concentrated in vacuo. The residue was purified by flash column chromatography on silica gel using EtOAc:hexanes (1:3) as eluant.

Yellow oil, yield: 94.1% b) N-[4-(Cyano-methyl-methyl)-phenyl]-acetamide

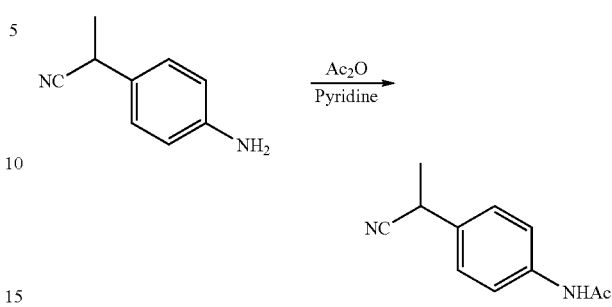

Reference: Eur. J. Med. Chem. (1975), 10, 239

A solution of 2-(4-Amino-phenyl)-propionitrile (10.2 g, 69.8 mmol) in pyridine (40 mL) was added Ac$_2$O (7.49 g, 73.4 mmol) at room temperature. The reaction mixture was refluxed for 1 hrs then cooled to room temperature, and concentrated in vacuo.

White solid (m.p. 75-77° C.), yield: 98.2% c) N-[4-(Cyano-methyl-methyl)-2-nitro-phenyl]-acetamide

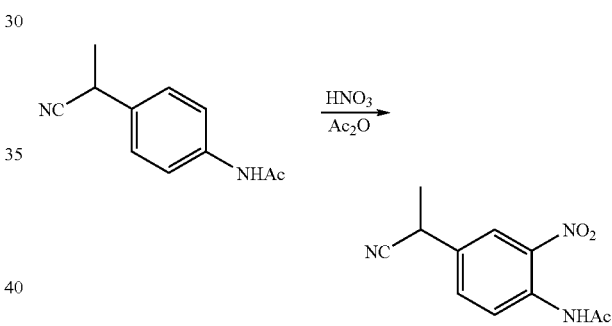

Reference: Eur. J. Med. Chem. (1975), 10, 239

To the flask of N-[4-(Cyano-methyl-methyl)-phenyl]-acetamide (12.9 g, 68.5 mmol) was added Ac$_2$O (35 mL) at 5° C. The mixture was stirred and added HNO$_3$ (7.45 g, 70.9 mmol) at 0° C. This reaction was very exothermic. The mixture was stirred for 1 hr at 0° C. and additionally stirred for 3 hrs at room temperature. The mixture was diluted with H$_2$O and extracted with EtOAc. The organic layer was dried over MgSO$_4$, filtered, and concentrated in vacuo. The residue was purified by flash column chromatography on silica gel using EtOAc:hexanes (1:2) as eluant.

Yellow solid (m.p. 84-86° C.), yield: 55.7% d) 2-(4-Amino-3-nitro-phenyl)-propionic acid

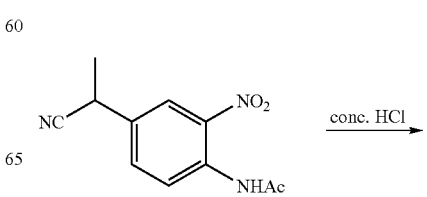

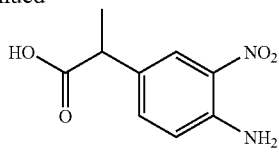

Reference: Eur. J. Med. Chem. (1975), 10, 239

To the flask of N-[4-(Cyano-methyl-methyl)-2-nitro-phenyl]-acetamide (8.90 g, 38.2 mmol) was added conc. HCl (25 mL) at room temperature. The reaction mixture was refluxed for 5 hrs then cooled to room temperature. The mixture was diluted with $H_2O$ (150 mL) and extracted with $CH_2Cl_2$. The organic layer was dried over $MgSO_4$, filtered, and concentrated in vacuo. The residue was purified by flash column chromatography on silica gel using $CH_2Cl_2$:MeOH (20:1-10:1) as eluant.

Yellow solid (m.p. 118-120° C.), yield: 87.8% e) 2-(3,4-Diaminophenyl)propanoic acid

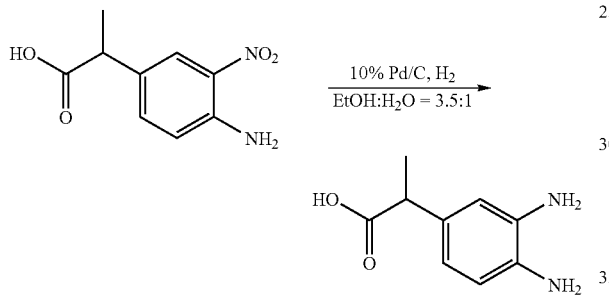

To the flask was added $EtOH/H_2O$ (3.5:1, 45 mL) followed by 2-(4-Amino-3-nitro-phenyl)-propionic acid (5.73 g, 27.3 mmol) and 10% palladium carbon (117 mg) at room temperature. The reaction mixture was hydrogenated and stirred for 5 hrs at 64 psi then filtered through celite bed, and washed with EtOH. The filtrate was concentrated in vacuo. The residue was purified by flash column chromatography on silica gel using $CH_2Cl_2$:MeOH (10:1) as eluant.

Brown solid (m.p. 142-144° C.), yield: 50.0% f) N-(4-tert-Butyl-benzyl)-2-(3,4-diamino-phenyl)-propionamide

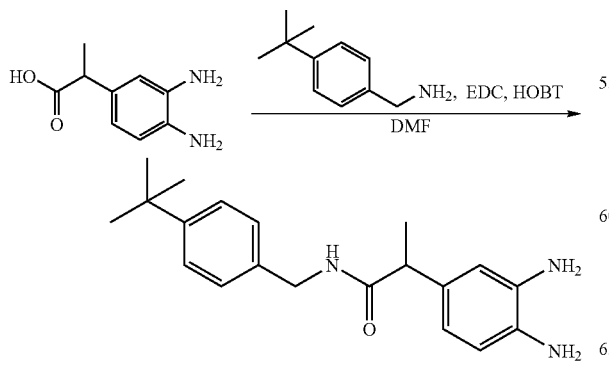

2-(3,4-Diaminophenyl)propanoic acid (436 mg, 2.42 mmol) in DMF (5 mL) was added 4-t-butylbenzylamine (399 mg, 2.44 mmol), EDC (702 mg, 3.66 mmol), HOBt (496 mg, 3.67 mmol), triethylamine (617 mg, 6.10 mmol) at 0° C. The reaction mixture was stirred for 16 hours at room temperature, and then the mixture was added water (50 mL) and extracted with methylene chloride. The organic layer was dried with $MgSO_4$ and filtered. Methylene chloride was removed by evaporation. The residue was purified by column chromatography eluting with $CH_2Cl_2$/MeOH=20/1.

Brown oil, yield: 70% g) N-(4-tert-butylbenzyl)-2-(1H-benzo[d][1,2,3]triazol-5-yl)propanamide

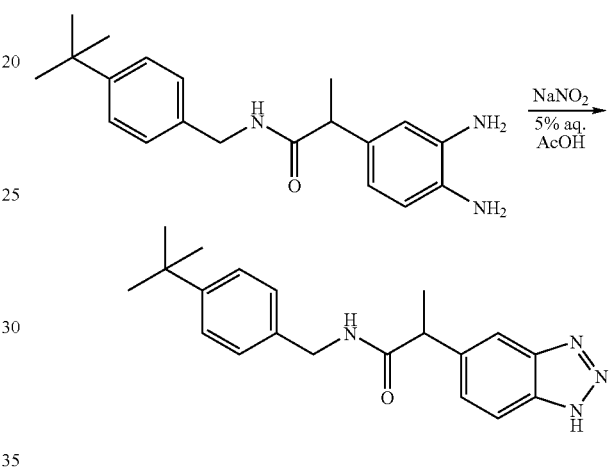

N-(4-tert-Butyl-benzyl)-2-(3,4-diamino-phenyl)-propionamide (110 mg, 0.338 mmol) in 5% aq. acetic acid (3 mL) and DMF (2.5 mL) was added sodium nitrite (30 mg, 0.435 mmol) at 0° C. The reaction mixture was stirred for 14 hours at room temperature. The mixture was added water (20 mL) and extracted with methylene chloride. The organic layer was dried with $MgSO_4$ and filtered. Methylene chloride was removed by evaporation. The residue was purified by column chromatography eluting with $CH_2Cl_2$/MeOH=10/1.

Pale brown solid (m.p. 126-128° C.), yield: quantitative

Example Compound 12

2-(1H-benzotriazol-5-yl)-N-(4-tert.-butyl-benzyl)-propanamide $^1$H-NMR (CDCl$_3$) δ 7.82 (m, 2H, Ar), 7.48 (dd, 1H, Ar), 7.26 (d, 2H, J=8.4 Hz, Ar), 7.08 (d, 2H, J=8.4 Hz, Ar), 4.30 (s, 2H, NHCH$_2$), 3.87 (q, 1H, J=7.1 Hz, CHCH$_3$), 1.54 (d, 3H, J=7.1 Hz, CHCH$_3$), 1.26 (s, 9H, C(CH$_3$)$_3$)

Mass (FAB) m/z 338 [M+H]$^+$

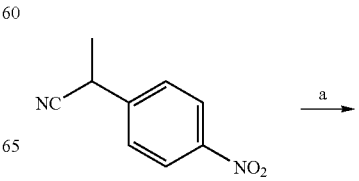

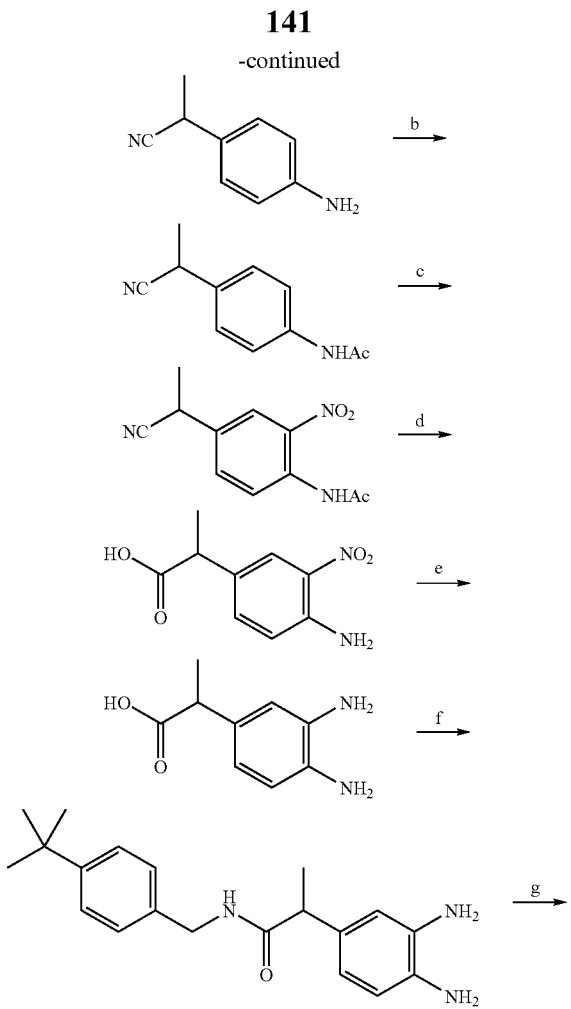

a. 10% Pd/C, H₂, THF/EtOH, 94%; b. Ac₂O, Pyridine, 98%; c. Ac₂O, HNO₃, 56%;
d. conz. HCl, 88%; e. 10% Pd/C, H₂, H₂O/EtOH, 50%;
f. 4-t-Butylbenzylamine, EDCl, HOBt, TEA, DMF, 70%; g. NaNO₂, 5% aq. AcOH, quantitative Example Compound 13

2-(1H-benzoimidazol-5-yl)-N-(4-methyl-6'-trifluoromethyl-3,4,5,6-tetrahydro-2H-[1,2']bipyridinyl-3'-ylmethyl)-propionamide

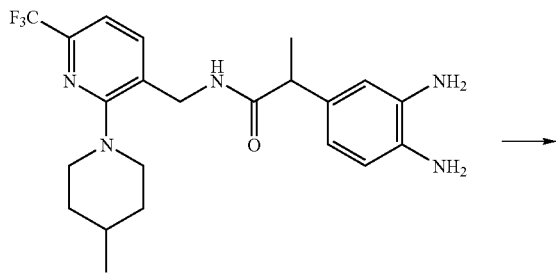

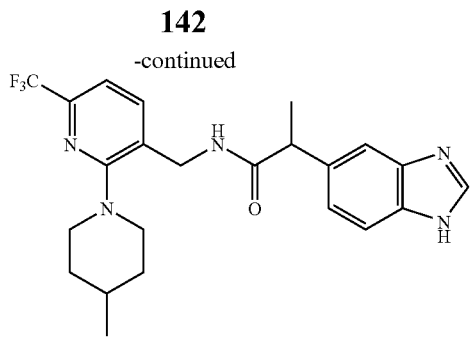

2-(3,4-diaminophenyl)-N-(4-methyl-6'-trifluoromethyl-3,4,5,6-tetrahydro-2H-[1,2']bipyridinyl-3'-ylmethyl)-propionamide (48 mg, 0.110 mmol) was combined at RT with triethyl orthoformate (2 ml). The reaction mixture was heated to reflux for 2 h and cooled to RT. The reaction mixture was combined with water and repeatedly extracted with DCM. The combined organic phases were dried over MgSO₄ and filtered. The solvent was removed under a vacuum and the residue purified by means of column chromatography (DCM/MeOH=10:1).

¹H-NMR (CD₃OD) δ 8.16 (s, 1H), 7.61-7.56 (m, 2H), 7.39 (d, 1H, J=7.3 Hz), 7.28 (dd, 1H, J=8.3, 1.7 Hz), 7.08 (d, 1H, J=7.7 Hz), 4.46-4.27 (m, 2H), 3.84 (q, 1H, J=7.0 Hz), 3.37-3.30 (m, 2H), 2.81-2.70 (m, 2H), 1.65 (m, 2H), 1.54 (d, 3H, J=7.0 Hz), 1.52-1.45 (m, 1H), 1.32-1.21 (m, 2H), 0.94 (d, 3H, J=6.6 Hz)

IR 3310, 2921, 1650, 1539, 1457, 1418, 1134, 759 cm⁻¹

Mass (FAB) m/z 447 [M+H]⁺

Example Compound 14

2-(1H-benzoimidazol-5-yl)-N-(4-tert.-butyl-benzyl)-propionamide

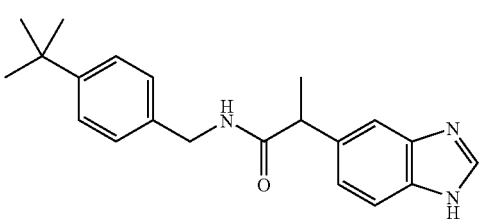

The compound was obtained by reacting N-(4-tert.-butyl-benzyl)-2-(3,4-diaminophenyl)propanamide with triethyl orthoformate in a similar manner to example compound 13.

¹H-NMR (CD₃OD) δ 8.13 (s, 1H), 7.61-7.53 (m, 2H), 7.29-7.24 (m, 3H), 7.06 (d, 1H, J=8.6 Hz), 4.29 (s, 2H), 3.78 (q, 1H, J=7.1 Hz), 1.52 (d, 3H, J=7.1 Hz), 1.25 (s, 9H)

IR 3272, 2965, 1649, 1515, 1266, 1113, 756 cm⁻¹

Mass (FAB) m/z 337 [M+H]⁺

Pharmacological Data

The affinity of the compounds according to the invention for the vanilloid receptor 1 (VR1/TRPV1 receptor) was determined as described above (Pharmacological methods I or II). The compounds according to the invention of the above-stated formula I exhibit excellent affinity for the VR1/TRPV1 receptor (Table 1).

TABLE 1

| Compound according to Example | $K_i$ (Rat) Capsaicin [nM] | $K_i$ (human) Capsaicin [nM] | $IC_{50}$ (Human) [nM] following pH-stimulus |
|---|---|---|---|
| 1 |  | 579 | Ne |
| 7 |  | 2173 | Ne |
| 9 |  | 1075 | Ne |
| 11 |  | ne |  |
| 13 |  | 7 | Ne |
| 14 |  | ne |  |
| 20 |  | 9% @ 5 μM; 0% @ 1 μM | Ne |
| 23 |  | 15.3 | Ne |
| 34 |  | 38% @ 5 μM; 3% @ 1 μM | Ne |
| 38 |  | 28.4 | Ne |
| 39 |  | 15% @ 1 μM; 0% @ 0.1 μM | Ne |
| 40 |  | 34% @ 5 μM; 14% @ 1 μM; 0% @ 0.1 μM | 37% @ 10 μM; 21% @ 5 μM 0% @ 1 μM |
| 41 |  | 18% @ 1 μM 5% @ 0.1 μM | Ne |
| 50 |  | 10% @ 5 μM 6% @ 1 μM 0% @ 0.1 μM | 53% @ 10 μM 25% @ 5 μM 10% @ 1 μM |
| 51 |  | 27% @ 1 μM 3% @ 0.1 μM | 39% @ 5 μM 27% @ 5 μM 10% @ 0.1 μM |
| 52 |  | 18% @ 1 μM 5% @ 0.1 μM | Ne |
| 55 |  | 12% @ 5 μM 0% @ 1 μM | 27% @ 5 μM 5% @ 1 μM |
| 56 |  | 18.7 | 12% @ 10 μM 2% @ 5 μM |
| 57 |  | 32.8 | 32% @ 10 μM 3% @ 5 μM |
| 58 | 60 | 27.8 | ne |
| 59 | 5.7 | 3.5 | ne |
| 60 | 45.8 | 26 | ne | ne means in each case "no effect", i.e. no response was observed.

The value after the sign "@" indicates the concentration at which inhibition (in percent) was determined in each case.

The action of the compound according to the invention was likewise determined using the formaldehyde test (Pharmacological methods III) in mice.

| Compound according to Example | Inhibition Formaldehyde test |
|---|---|
| 13 | 0.3 per os 25% |
| 23 | 0.3 per os 13% | per os (perorally)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A compound corresponding to formula I:

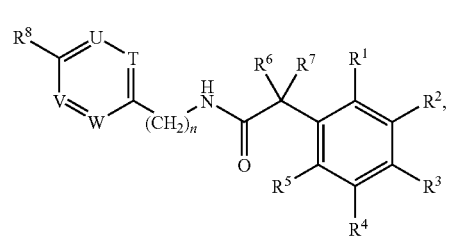

wherein
n is 0, 1, 2, 3 or 4;
R² and R³ together denote —N=CH—NH—; or —N=CH—NR⁶⁴, which is attached in any desired direction to the parent structure; or
R³ and R⁴ together denote —N=CH—NH—; or —N=CH—NR⁶⁴, which is attached in any desired direction to the parent structure;
and
the remaining residues of $R^1$, $R^2$, $R^3$, $R^4$ and $R^5$ each independently represent H; F; Cl; Br; I; —SF₅; —NO₂; —CN; —NH₂; —OH; —SH; —C(=O)—NH₂; —S(=O)₂—NH₂; —C(=O)—NH—OH; —C(=O)—OH; —C(=O)—H; —S(=O)₂—OH; —C(=NH)—NH₂; —C(=NH)—NH—R⁹; —N=C(NH₂)₂; —N=C(NHR¹⁰)(NHR¹¹); —O—P(=O)₂—O—R¹²; —NHR¹³; —NR¹⁴R¹⁵; —NH—C(=O)—R¹³; —OR¹⁶; —SR¹⁷; —C(=O)—NHR¹⁸; —C(=O)—NR¹⁹R²⁰; —S(=O)₂—NHR²¹; —S(=O)₂—NR²²R²³; —C(=O)—OR²⁴; —C(=O)—R²⁵; —S(=O)—R²⁶; —S(=O)₂—R²⁷ or a linear or branched, saturated or unsaturated, unsubstituted, monosubstituted or polysubstituted aliphatic $C_{1-10}$ residue;
R⁶ denotes H or a linear or branched, saturated or unsaturated, unsubstituted, monosubstituted or polysubstituted aliphatic $C_{1-10}$ residue;
R⁷ denotes hydrogen or —OH; or
R⁶ and R⁷ together with the carbon atom to which they are attached form a saturated or unsaturated, unsubstituted, monosubstituted or polysubstituted 3-, 4-, 5-, 6- or 7-membered cycloaliphatic residue;
R⁸ denotes —SF₅; —O—CF₃; —CF₃; —O—CFH₂; —O—CF₂H; —CFH₂; —CF₂H; or an unsubstituted, monosubstituted or polysubstituted tert.-butyl residue;
T denotes C—R³⁵; U denotes C—R³⁶; V denotes N, and W denotes C—R³⁸; or
T denotes C—R³⁵; U denotes N; V denotes C—R³⁷, and W denotes C—R³⁸; or
T denotes N; U denotes C—R³⁶; V denotes C—R³⁷, and W denotes C—R³⁸; or
T denotes N; U denotes N; V denotes C—R³⁷, and W denotes C—R³⁸; or
T denotes N; U denotes C—R³⁶; V denotes N, and W denotes C—R³⁸; or
T denotes C—R³⁵; U denotes N; V denotes N, and W denotes C—R³⁸; or
T denotes C—R³⁵; U denotes C—R³⁶; V denotes C—R³⁷, and W denotes C—R³⁸;
$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ each independently denote a linear or branched, saturated or unsaturated, unsubstituted, monosubstituted or polysubstituted aliphatic $C_{1-10}$ residue; or an unsaturated or saturated, unsubstituted, monosubstituted or polysubstituted 3-, 4-, 5-, 6-, 7-, 8- or 9-membered cycloaliphatic residue optionally comprising at least one heteroatom as a ring member, wherein said cycloaliphatic residue optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or 2- to 6-membered heteroalkylene group, or both; or an unsubstituted, monosubstituted or polysubstituted 5- to 14-membered aryl or heteroaryl residue, which optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or 2- to 6-membered heteroalkylene group, or both;

$R^{35}$, $R^{36}$ and $R^{37}$ each independently denote H; F; Cl; Br; I; —$SF_5$; —$NO_2$; —$CF_3$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; —S(=O)$_2$—$R^{27}$; or a linear or branched, saturated or unsaturated, unsubstituted, monosubstituted or polysubstituted aliphatic $C_{1-10}$ residue; or an unsubstituted, monosubstituted or polysubstituted 5- to 14-membered aryl or heteroaryl residue, which optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or $C_{2-6}$ alkenylene group or $C_{2-6}$ alkynylene group, or both;

$R^{38}$ denotes H; F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{39}$; —$NR^{40}R^{41}$; —$OR^{42}$; —$SR^{43}$; —C(=O)—$NHR^{44}$; —C(=O)—$NR^{45}R^{46}$; —S(=O)$_2$—$NHR^{47}$; —S(=O)$_2$—$NR^{48}R^{49}$; —C(=O)—$OR^{50}$; —C(=O)—$R^{51}$; —S(=O)—$R^{52}$; —S(=O)$_2$—$R^{53}$; —C(=NH)—$NH_2$; —C(=NH)—NH—$R^{54}$; —N=C($NH_2$)$_2$; —N=C($NHR^{55}$)($NHR^{56}$); or a linear or branched, saturated or unsaturated, unsubstituted, monosubstituted or polysubstituted aliphatic $C_{1-10}$ residue; or an unsaturated or saturated, unsubstituted, monosubstituted or polysubstituted 3-, 4-, 5-, 6-, 7-, 8- or 9-membered cycloaliphatic residue optionally comprising one or more heteroatoms as ring member(s), wherein said cycloaliphatic residue is attached to the parent structure via a carbon atom in the ring of the cycloaliphatic residue, and wherein said cycloaliphatic residue optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or $C_{2-6}$ alkenylene group or $C_{2-6}$ alkynylene group, or both; or an unsubstituted, monosubstituted or polysubstituted 5- to 14-membered aryl or heteroaryl residue, which optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or $C_{2-6}$ alkenylene group or $C_{2-6}$ alkynylene group, or both;

$R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$ and $R^{56}$ each independently denote a linear or branched, saturated or unsaturated, unsubstituted, monosubstituted or polysubstituted aliphatic $C_{1-10}$ residue; or an unsaturated or saturated, unsubstituted, monosubstituted or polysubstituted 3-, 4-, 5-, 6-, 7-, 8- or 9-membered cycloaliphatic residue optionally comprising one or more heteroatom(s) as ring member(s), wherein said cycloaliphatic residue optionally be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or 2- to 6-membered heteroalkylene group, or both; or an unsubstituted, monosubstituted or polysubstituted 5- to 14-membered aryl or heteroaryl residue, which optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or 2- to 6-membered heteroalkylene group, or both; or $R^{40}$ and $R^{41}$ together with the nitrogen atom to which they are attached form a saturated or unsaturated or unsubstituted heterocycloaliphatic residue or a 4-, 5-, 6-, 7-, 8- or 9-membered heterocycloaliphatic residue substituted with 1, 2, 3, 4 or 5 residues $R^{57}$ and optionally comprising one or more further heteroatom(s) as ring member(s), wherein said heterocycloaliphatic residue optionally may be fused with a saturated or unsaturated, unsubstituted, monosubstituted or polysubstituted mono- or polycyclic ring system;

$R^{57}$ denotes —$NHR^{58}$, —$NR^{59}R^{60}$; or a linear or branched, saturated or unsaturated, unsubstituted, monosubstituted or polysubstituted aliphatic $C_{1-10}$ residue;

$R^{58}$, $R^{59}$ and $R^{60}$ each independently denote —C(=O)—$R^{61}$; or a linear or branched, saturated or unsaturated, unsubstituted, monosubstituted or polysubstituted aliphatic $C_{1-10}$ residue; or an unsubstituted, monosubstituted or polysubstituted 5- to 14-membered aryl or heteroaryl residue, which optionally may be fused with a saturated or unsaturated, unsubstituted, monosubstituted or polysubstituted mono- or polycyclic ring system, or optionally may be attached via a linear or branched, unsubstituted, monosubstituted or polysubstituted $C_{1-6}$ alkylene group or $C_{2-6}$ alkenylene group or $C_{2-6}$ alkynylene group, or both;

$R^{61}$ denotes a linear or branched, saturated or unsaturated, unsubstituted, monosubstituted or polysubstituted aliphatic $C_{1-10}$ residue; and $R^{64}$ denotes a linear or branched, saturated or unsaturated, unsubstituted, monosubstituted or polysubstituted aliphatic $C_{1-10}$ residue;

or a salt thereof;

wherein:
- said aliphatic $C_{1-10}$ residues and tert.-butyl residues each optionally may be substituted with 1, 2, 3, 4, 5, 6, 7, 8 or 9 substituents independently selected from the group consisting of F, Cl, Br, I, —CN, —NO$_2$, —OH, —NH$_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —C(=O)—O—$C_{1-5}$-alkyl, —O—C(=O)—$C_{1-5}$-alkyl, —O-phenyl, phenyl, —OCF$_3$ and —SCF$_3$;
- said 2- to 6-membered heteroalkylene groups, $C_{1-6}$ alkylene groups, $C_{2-6}$ alkenylene groups and $C_{2-6}$ alkynylene groups each optionally may be substituted with 1, 2, 3, 4, 5, 6, 7, 8 or 9 substituents independently selected from the group consisting of F, Cl, Br, I, —CN, —NO$_2$, —OH, —NH$_2$, —SH, —O($C_{1-5}$-alkyl), —S($C_{1-5}$-alkyl), —NH($C_{1-5}$-alkyl), —N($C_{1-5}$-alkyl)($C_{1-5}$-alkyl), —OCF$_3$ and —SCF$_3$;
- said heteroalkylene groups each optionally may comprise 1, 2 or 3 heteroatom(s) independently selected from the group consisting of oxygen, nitrogen as NH, and sulfur as chain link(s);
- said (hetero)cycloaliphatic residues each optionally may be substituted with 1, 2, 3, 4 or 5 substituents independently selected from the group consisting of —$C_{1-6}$-alkylene-OH, =CH$_2$, —O—$C_{1-5}$-alkylene-oxetanyl, —$C_{1-5}$-alkylene-O—$C_{1-5}$-alkylene-oxetanyl, —CH$_2$—NH—$C_{1-5}$-alkyl, —CH$_2$—N($C_{1-5}$-alkyl)$_2$, —N[—C(=O)—$C_{1-5}$-alkyl]-phenyl, —CH$_2$—O—$C_{1-5}$-alkyl, oxo (=O), thioxo (=S), F, Cl, Br, I, —CN, —CF$_3$, —SF$_5$, —OH, —O—$C_{1-5}$-alkyl, —O—C(=O)—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH-phenyl, —N(—$C_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)-pyridinyl, pyridinyl, —O-phenyl, —O-benzyl, phenyl and benzyl, wherein the cyclic moiety of the oxetanyl, (4,5)-dihydroisoxazolyl, thiazolyl, (1,2,5)-thiadiazolyl, thiophenyl, phenethyl, —N[—C(=O)—$C_{1-5}$-alkyl]-phenyl, —NH-phenyl, —N(—$C_{1-5}$-alkyl)-phenyl, —(CH$_2$)-pyridinyl, pyridinyl, —O-phenyl, —O-benzyl, phenyl and benzyl residues optionally may be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$-alkyl, —O—CF$_3$, —S—CF$_3$, phenyl and —O-benzyl;
- unless otherwise stated, said (hetero)cycloaliphatic residues each optionally may comprise 1, 2 or 3 (further) heteroatom(s) independently selected from the group consisting of oxygen, nitrogen and sulfur;
- the rings of said mono- or polycyclic ring systems each optionally may be substituted with 1, 2, 3, 4 or 5 substituents independently selected from the group consisting of oxo (=O), thioxo (=S),), F, Cl, Br, I, —CN, —CF$_3$, —SF$_5$, —OH, —O—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, wherein the cyclic moiety of the —O-phenyl, —O-benzyl, phenyl and benzyl residues optionally may be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$-alkyl, —O—CF$_3$, —S—CF$_3$, phenyl and —O-benzyl;
- the rings of said mono- or polycyclic ring systems each are 5-, 6- or 7-membered and optionally may comprise 1, 2, 3, 4 or 5 heteroatom(s) as ring member(s), which are independently selected from the group consisting of oxygen, nitrogen and sulfur;
- said aryl or heteroaryl residues each optionally may be substituted with 1, 2, 3, 4 or 5 substituents independently selected from the group consisting of F, Cl, Br, I, —CN, —CF$_3$, —SF$_5$, —OH, —O—$C_{1-5}$-alkyl, —NH$_2$, —NO$_2$, —O—CF$_3$, —S—CF$_3$, —SH, —S—$C_{1-5}$-alkyl, —$C_{1-5}$-alkyl, —C(=O)—OH, —C(=O)—$C_{1-5}$-alkyl, —NH—$C_{1-5}$-alkyl, —N($C_{1-5}$-alkyl)$_2$, —NH—S(=O)$_2$—$C_{1-5}$-alkyl, —NH—C(=O)—O—$C_{1-5}$-alkyl, —C(=O)—H, —C(=O)—$C_{1-5}$-alkyl, —C(=O)—NH$_2$, —C(=O)—NH—$C_{1-5}$-alkyl, —C(=O)—N—($C_{1-5}$-alkyl)$_2$, —O-phenyl, —O-benzyl, phenyl and benzyl, wherein the cyclic moiety of the —O-phenyl, —O-benzyl, phenyl and benzyl residues optionally may be substituted with 1, 2, 3, 4 or 5 substituents independently selected from the group consisting of F, Cl, Br, —OH, —CF$_3$, —SF$_5$, —CN, —NO$_2$, —$C_{1-5}$ alkyl, —O—$C_{1-5}$-alkyl, —O—CF$_3$, —S—CF$_3$, phenyl and —O-benzyl; and
- said heteroaryl residues each optionally may comprise 1, 2, 3, 4 or 5 heteroatom(s) independently selected from the group consisting of oxygen, nitrogen and sulfur as ring member(s).

2. A compound according to claim 1, wherein said compound is present in the form of an isolated stereoisomer.

3. A compound according to claim 1, wherein said compound is present in the form of a mixture of stereoisomers in any mixing ratio.

4. A compound according to claim 1, wherein said compound is present in the form of a racemic mixture.

5. A compound according to claim 1, wherein:
- n is 0, 1, 2, 3 or 4;
- $R^2$ and $R^3$ together denote —N=CH—NH—; or —N=CH—NR$^{64}$, which is attached in any desired direction to the parent structure; or
- $R^3$ and $R^4$ together denote —N=CH—NH—; or —N=CH—NR$^{64}$, which is attached in any desired direction to the parent structure;
- and
- the remaining residues of $R^1$, $R^2$, $R^3$, $R^4$ and $R^5$ each independently denote H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—R$^{26}$; —S(=O)$_2$—R$^{27}$; methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec.-butyl, isobutyl, or tert.-butyl;
- $R^6$ denotes H or an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec.-butyl, isobutyl, tert-butyl, methyl, ethyl and n-propyl;
- $R^7$ denotes hydrogen or —OH; or R$^6$ and R$^7$ together with the carbon atom to which they are attached form a residue selected from the group consisting of cyclopropyl, cyclobutyl, cyclopentyl, cyclohexyl and cycloheptyl;

R$^8$ denotes —SF$_5$; —O—CF$_3$; —O—CFH$_2$; —O—CF$_2$H; —CFH$_2$; —CF$_2$H; —CF$_3$; or a tert.-butyl-residue, which may be unsubstituted or optionally substituted with 1, 2, 3, 4, 5, 6, 7, 8 or 9 substituents independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —NH—CH$_3$ and —NH—C$_2$H$_5$;

T denotes C—R$^{35}$; U denotes C—R$^{36}$; V denotes N, and W denotes C—R$^{38}$; or T denotes C—R$^{35}$; U denotes N; V denotes C—R$^{37}$, and W denotes C—R$^{38}$; or T denotes N; U denotes C—R$^{36}$; V denotes C—R$^{37}$, and W denotes C—R$^{38}$; or T denotes N; U denotes N; V denotes C—R$^{37}$, and W denotes C—R$^{38}$; or T denotes N; U denotes C—R$^{36}$; V denotes N, and W denotes C—R$^{38}$; or T denotes C—R$^{35}$; U denotes N; V denotes N, and W denotes C—R$^{38}$; or T denotes C—R$^{35}$; U denotes C—R$^{36}$; V denotes C—R$^{37}$, and W denotes C—R$^{38}$;

R$^{13}$, R$^{14}$, R$^{15}$, R$^{16}$, R$^{17}$, R$^{26}$ and R$^{27}$ each independently denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl and 3-pentenyl; or a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which optionally may be attached via a —CH$_2$—O, —CH$_2$—CH$_2$—O, —CH$_2$—CH$_2$—O—CH$_2$, —CH$_2$—CH(CH$_3$)—O—CH$_2$, —(CH$_2$), —(CH$_2$)$_2$ or —(CH$_2$)$_3$ group, or which may be unsubstituted or optionally substituted with 1, 2, 3, 4 or 5 substituents independently selected from the group consisting of oxo (═O), thioxo (═S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(═O)—CH$_3$, —C(═O)—C$_2$H$_5$, —C(═O)—CH(CH$_3$)$_2$, —C(═O)—C(CH$_3$)$_3$, —C(═O)—OH, —C(═O)—O—CH$_3$, —C(═O)—O—C$_2$H$_5$, —C(═O)—O—CH(CH$_3$)$_2$ and —C(═O)—O—C(CH$_3$)$_3$; or a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein said residue optionally may be attached via a —(CH$_2$)—, —(CH$_2$)$_2$— or —(CH$_2$)$_3$— group, and wherein said residue may be unsubstituted or optionally substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(═O)—OH, —C(═O)—O—CH$_3$, —C(═O)—O—C$_2$H$_5$, —C(═O)—O—CH(CH$_3$)$_2$, —C(═O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(═O)—O—CH$_3$, —NH—C(═O)—O—C$_2$H$_5$, —NH—C(═O)—O—C(CH$_3$)$_3$, —C(═O)—H, —C(═O)—CH$_3$, —C(═O)—C$_2$H$_5$, —C(═O)—CH(CH$_3$)$_2$, —C(═O)—C(CH$_3$)$_3$, —C(═O)—NH$_2$, —C(═O)—NH—CH$_3$, —C(═O)—NH—C$_2$H$_5$, —C(═O)—N(CH$_3$)$_2$, —C(═O)—N(C$_2$H$_5$)$_2$, —O-phenyl, —O-benzyl, phenyl and benzyl;

R$^{35}$, R$^{36}$ and R$^{37}$ each independently denote H; F; Cl; Br; I; —SF$_5$; —NO$_2$; —CN; —NH$_2$; —OH; —SH; —C(═O)—NH$_2$; —S(═O)$_2$—NH$_2$; —C(═O)—NH—OH; —C(═O)—OH; —C(═O)—H; —S(═O)$_2$—OH; —NHR$^{13}$; —NR$^{14}$R$^{15}$; —OR$^{16}$; —SR$^{17}$; —S(═O)—R$^{25}$; —S(═O)$_2$—R$^{26}$; or a residue selected from the group consisting of —CH$_2$—OH, methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec.-butyl, isobutyl and tert.-butyl; or a phenyl residue, which may be unsubstituted or optionally substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl and n-pentyl.

R$^{38}$ denotes H; —SF$_5$; —NO$_2$; —CN; —NH$_2$; —OH; —SH; —C(═O)—NH$_2$; —S(═O)$_2$—NH$_2$; —C(═O)—NH—OH; —C(═O)—OH; —C(═O)—H; —S(═O)$_2$—OH; —NHR$^{39}$; —NR$^{40}$R$^{41}$; —OR$^{42}$; —SR$^{43}$; —C(═O)—OR$^{50}$; —S(═O)—R$^{52}$; —S(═O)$_2$—R$^{53}$; —C(═NH)—NH$_2$; —C(═NH)—NH—R$^{54}$; —N═C(NH$_2$)$_2$; —N═C(NHR$^{55}$)(NHR$^{56}$); or a residue selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, wherein said residue is attached via a carbon atom of the ring thereof or via a —(CH═CH), —C═C or —C≡C—CH$_2$ group to the parent structure, and wherein said residue may be unsubstituted or optionally substituted with 1, 2, 3, 4 or 5 substituents independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —NC(=O)—C$_2$H$_5$]-phenyl, —NC(=O)—CH$_3$]-phenyl, oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$; or a residue selected from the group consisting of (1,3)-benzodioxolyl, (1,4)-benzodioxanyl, tetrazolyl, (2,3)-dihydrothieno[3,4-b][1,4]dioxinyl, benzo[b]furanyl, phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl and isoquinolinyl, wherein said residue optionally may be attached via a —(CH=CH)—, —C≡C—, —(CH$_2$)—, —(CH$_2$)$_2$— or —(CH$_2$)$_3$— group, and wherein said residue may be unsubstituted or optionally substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O)$_2$—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{39}$, R$^{40}$, R$^{41}$, R$^{42}$, R$^{43}$, R$^{50}$, R$^{52}$, R$^{53}$, R$^{54}$, R$^{55}$ and R$^{56}$ each independently denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec.-butyl, isobutyl, tert.-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl and 3-pentenyl; or a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which optionally may be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$— group, and which may be unsubstituted or optionally substituted with 1, 2, 3, 4 or 5 substituents independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$; or a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein said residue optionally may be attached via a —(CH$_2$)—, —(CH$_2$)$_2$— or —(CH$_2$)$_3$— group, and wherein said residue may be unsubstituted or optionally substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl; or R$^{40}$ and R$^{41}$ together with the nitrogen atom to which they are attached form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, wherein the heterocycloaliphatic moiety may be unsubstituted or optionally substituted with 1, 2, 3, 4 or 5 residues R$^{57}$;

R$^{57}$ denotes —NHR$^{58}$, —NR$^{59}$R$^{60}$; or an alkyl residue selected from the group consisting of —CF$_3$, —CH$_2$—CF$_3$, methyl, ethyl, n-propyl, isopropyl, tert.-butyl, n-butyl, sec.-butyl, and isobutyl;

R$^{58}$, R$^{59}$ and R$^{60}$ each independently denote —C(=O)—R$^{61}$; or an alkyl residue selected from the group consisting of —CF$_3$, —CH$_2$—CF$_3$, methyl, ethyl, n-propyl, isopropyl, tert.-butyl, n-butyl, sec.-butyl, and isobutyl; or a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein said residue optionally may be attached via a —(CH$_2$)—, —(CH$_2$)$_2$— or —(CH$_2$)$_3$— group, and may be unsubstituted or optionally substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{61}$ denotes an alkyl residue selected from the group consisting of —CF$_3$, —CH$_2$—CF$_3$, methyl, ethyl, n-propyl, isopropyl, tert.-butyl, n-butyl, sec.-butyl and isobutyl; and R$^{64}$ denotes an alkyl residue selected from the group consisting of methyl, ethyl, n-propyl, isopropyl, n-butyl, sec.-butyl, isobutyl, tert.-butyl, and n-pentyl, which may be unsubstituted or optionally substituted with 1, 2, 3, 4, 5, 6, 7, 8, or 9 substituents independently selected from the group consisting of F, Cl, Br, I, —CN, —NO$_2$, —OH, —NH$_2$ and —SH;

or a salt thereof.

6. A compound according to claim 1, wherein:
n is 0, 1 or 2;
R$^2$ and R$^3$ together denote —N=CH—NH—; or —N=CH—NR$^{64}$, which may be attached in any desired direction to the parent structure; or
R$^3$ and R$^4$ together denote —N=CH—NH—; or —N=CH—NR$^{64}$, which may be attached in any desired direction to the parent structure; and the remaining residues of R$^1$, R$^2$, R$^3$, R$^4$ and R$^5$ each independently denote H; F; Cl; Br; I; —CF$_3$; —CN; —OR$^{16}$; —SR$^{17}$; or denote a residue selected from the group consisting of methyl, —CF$_3$, —CHF$_2$, —CH$_2$F, ethyl, n-propyl, isopropyl, n-butyl, sec.-butyl, isobutyl and tert.-butyl;

R$^6$ denotes H or an alkyl residue selected from the group consisting of isopropyl, n-butyl, sec.-butyl, isobutyl, tert-butyl, methyl, ethyl and n-propyl;

R$^7$ denotes hydrogen or —OH; or

R$^6$ and R$^7$ together with the carbon atom to which they are attached form a residue selected from the group consisting of cyclopropyl, cyclobutyl, cyclopentyl, cyclohexyl and cycloheptyl;

R$^8$ denotes —SF$_5$; —O—CF$_3$; —CF$_3$; tert.-butyl, or —C(CH$_3$)$_2$(CH$_2$OH);

T denotes C—R$^{35}$; U denotes C—R$^{36}$ V denotes N, and W denotes C—R$^{38}$; or
T denotes C—R$^{35}$; U denotes C—R$^{36}$; V denotes C—R$^{37}$, and W denotes C—R$^{38}$;

R$^{16}$ and R$^{17}$ each independently denote a residue selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methyl-butyl, n-hexyl and (3,3)-dimethylbutyl;

R$^{35}$, R$^{36}$ and R$^{37}$ each independently denote H; F; Cl; Br; I; —SF$_5$; —NO$_2$; —CN; —NH$_2$; —OH; —SH; —OR$^{16}$; —SR$^{17}$; or a residue selected from the group consisting of —CH$_2$—OH, methyl, —CF$_3$, —CHF$_2$, —CH$_2$F, ethyl, n-propyl, isopropyl, n-butyl, sec.-butyl, isobutyl and tert.-butyl;

R$^{38}$ denotes H; —SF$_5$; —NO$_2$; —CN; —NH$_2$; —OH; —SH; —NHR$^{39}$; —NR$^{40}$R$^{41}$; —OR$^{42}$; —SR$^{43}$;

or a residue selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, wherein said residue is attached via a carbon atom of the ring thereof to the parent structure, and wherein said residue may be unsubstituted or optionally substituted with 1, 2, 3, 4 or 5 substituents independently selected from the group consisting of —CH$_2$—N(CH$_3$)$_2$, —CH$_2$—N(C$_2$H$_5$)$_2$, —CH$_2$—NH—CH$_3$, —CH$_2$—NH—C$_2$H$_5$, —NC(=O)—C$_2$H$_5$]-phenyl, —NC(=O)—CH$_3$]-phenyl, methyl, ethyl, n-propyl, isopropyl, n-butyl, sec.-butyl, isobutyl and tert.-butyl; or a residue selected from the group consisting of phenyl, thiophenyl, furanyl, pyrrolyl, pyrazolyl, pyrazinyl, pyranyl, triazolyl, pyridinyl, imidazolyl, thiazolyl, oxazolyl, isoxazolyl, pyridazinyl, pyrazinyl and pyrimidinyl, wherein said residue optionally may be substituted with 1, 2, 3, 4 or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CF$_3$, methyl, ethyl, n-propyl, isopropyl, n-butyl, sec.-butyl, isobutyl, tert.-butyl and n-pentyl;

R$^{39}$, R$^{40}$, R$^{41}$, R$^{42}$ and R$^{43}$ each independently denote a residue selected from the group consisting of methyl, —CH$_2$—O—CH$_3$, ethyl, n-propyl, isopropyl, n-butyl, sec.-butyl, isobutyl, tert.-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$ and —CH$_2$—CH$_2$—CH$_2$—O—CH$_3$; or a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, wherein said residue optionally may be substituted with 1, 2, 3, 4 or 5 substituents independently selected from the group consisting of methyl, ethyl, n-propyl, isopropyl, n-butyl, sec.-butyl, isobutyl, tert.-butyl, n-pentyl; or R$^{40}$ and R$^{41}$ together with the nitrogen atom to which they are attached form a residue selected from the group consisting of 3-aza-bicyclo[3.1.1]heptyl, 6-aza spiro[2.5]octyl, 3-aza-bicyclo[3.2.1]octyl, 6-aza-bicyclo[3.3.1]heptyl, 8-aza-bicyclo[3.2.1]octyl, 1-oxa-2,8- diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, wherein the heterocycloaliphatic moiety of said residue may be unsubstituted or optionally substituted with 1, 2, 3, 4 or 5 residues $R^{57}$;

$R^{57}$ denotes —$NHR^{58}$, —$NR^{59}R^{60}$; or an alkyl residue selected from the group consisting of —$CF_3$, —$CH_2$—$CF_3$, methyl, ethyl, n-propyl, isopropyl, tert.-butyl, n-butyl, sec.-butyl, and isobutyl;

$R^{58}$, $R^{59}$ and $R^{60}$ each independently denote —C(=O)—$R^{61}$; or an alkyl residue selected from the group consisting of —$CF_3$, —$CH_2$—$CF_3$, methyl, ethyl, n-propyl, isopropyl, tert.-butyl, n-butyl, sec.-butyl, and isobutyl; or a residue selected from the group consisting of phenyl and naphthyl, wherein said residue optionally may be attached via a —$(CH_2)$—, —$(CH_2)_2$— or —$(CH_2)_3$ group, and wherein said residue may be unsubstituted or optionally substituted with 1, 2, 3, 4 or 5 substituents independently selected from the group consisting of F, Cl, Br, I, —CN, —$CF_3$, —O—$CH_3$, —O—$C_2H_5$, —O—$CH(CH_3)_2$, —O—$C(CH_3)_3$, methyl, ethyl, n-propyl, isopropyl, n-butyl, sec.-butyl, isobutyl, tert.-butyl and n-pentyl;

$R^{61}$ denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl; and $R^{64}$ denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl;

or a salt thereof.

7. A compound according to claim 1, wherein:
n is 0, 1 or 2;
$R^2$ and $R^3$ together denote —N=CH—NH—; or —N=CH—$NR^{64}$, which is attached in any desired direction to the parent structure; or
$R^3$ and $R^4$ together denote —N=CH—NH—; or —N=CH—$NR^{64}$, which is attached in any desired direction to the parent structure;
and
the remaining residues of $R^1$, $R^2$, $R^3$, $R^4$ and $R^5$ each independently denote H; —$OR^{16}$; —$SR^{17}$; or a residue selected from the group consisting of methyl, —$CF_3$, —$CHF_2$, —$CH_2F$, ethyl, n-propyl, isopropyl, n-butyl, sec.-butyl, isobutyl and tert.-butyl;
$R^6$ denotes H or an alkyl residue selected from the group consisting of isopropyl, n-butyl, sec.-butyl, isobutyl, tert-butyl, methyl, ethyl and n-propyl;
$R^7$ denotes hydrogen or —OH;
$R^8$ denotes —$SF_5$; —O—$CF_3$; —$CF_3$; tert.-butyl, or —$C(CH_3)_2(CH_2OH)$;
T denotes C—$R^{35}$; U denotes C—$R^{36}$; V denotes N, and W denotes C—$R^{38}$; or
T denotes C—$R^{35}$; U denotes C—$R^{36}$; V denotes C—$R^{37}$, and W denotes C—$R^{38}$;
$R^{16}$ and $R^{17}$ each independently denote a residue selected from the group consisting of methyl, ethyl, n-propyl, isopropyl, n-butyl, sec.-butyl, isobutyl, tert.-butyl, and n-pentyl;
$R^{35}$, $R^{36}$ and $R^{37}$ each denote H;
$R^{38}$ denotes H; —$NHR^{39}$; —$NR^{40}R^{41}$; —$OR^{42}$; or —$SR^{43}$;
$R^{39}$, $R^{42}$ and $R^{43}$ each independently denote a residue selected from the group consisting of methyl, ethyl, n-propyl, isopropyl, n-butyl, sec.-butyl, isobutyl, tert.-butyl, n-pentyl, 3-pentyl, n-hexyl, and (3,3)-dimethyl-butyl; or a residue selected from the group consisting of cyclopropyl, cyclobutyl, cyclopentyl, cyclohexyl and cycloheptyl, which optionally may be substituted with 1, 2, 3, 4 or 5 substituents independently selected from the group consisting of methyl, ethyl, n-propyl, isopropyl, n-butyl, sec.-butyl, isobutyl, tert.-butyl, and n-pentyl; or $R^{40}$ and $R^{41}$ together with the nitrogen atom to which they are attached form a residue selected from the group consisting of pyrrolidinyl, piperidinyl, piperazinyl, morpholinyl and azepanyl, wherein the heterocycloaliphatic moiety may be unsubstituted or optionally substituted with 1, 2, 3, 4 or 5 residues $R^{57}$;

$R^{57}$ denotes an alkyl residue selected from the group consisting of methyl, ethyl, n-propyl, isopropyl, tert.-butyl, n-butyl, sec.-butyl, and isobutyl; and $R^{64}$ denotes an alkyl residue selected from the group consisting of methyl, ethyl, n-propyl, isopropyl, tert-butyl, n-butyl, sec.-butyl, and isobutyl;

or a salt thereof.

8. A compound according to claim 1, wherein:
n is 1;
$R^2$ and $R^3$ together denote —N=CH—NH—, which is attached in any desired direction to the parent structure; or
$R^3$ and $R^4$ together denote —N=CH—NH—, which is attached in any desired direction to the parent structure;
and
the remaining residues of $R^1$, $R^2$, $R^3$, $R^4$ and $R^5$ each independently denote H; —$OR^{16}$; —$SR^{17}$; or a residue selected from the group consisting of methyl, —$CF_3$, —$CHF_2$, —$CH_2F$, ethyl, n-propyl, isopropyl, n-butyl, sec.-butyl, isobutyl and tert.-butyl;
$R^6$ denotes H or an alkyl residue selected from the group consisting of isopropyl, n-butyl, sec.-butyl, isobutyl, tert-butyl, methyl, ethyl and n-propyl;
$R^7$ denotes hydrogen or —OH;
$R^8$ denotes —$SF_5$; —O—$CF_3$; —$CF_3$; tert.-butyl, or —$C(CH_3)_2(CH_2OH)$;
T denotes C—$R^{35}$; U denotes C—$R^{36}$; V denotes N, and W denotes C—$R^{38}$; or
T denotes C—$R^{35}$; U denotes C—$R^{36}$; V denotes C—$R^{37}$, and W denotes C—$R^{38}$;
$R^{16}$ and $R^{17}$ each independently denote a residue selected from the group consisting of methyl, ethyl, n-propyl, isopropyl, n-butyl, sec.-butyl, isobutyl, tert.-butyl, and n-pentyl;
$R^{35}$, $R^{36}$ and $R^{37}$ each denote H;
$R^{38}$ denotes H; —$NHR^{39}$; —$NR^{40}R^{41}$; —$OR^{42}$; or —$SR^{43}$;
$R^{39}$, $R^{42}$ and $R^{43}$ each independently denote a residue selected from the group consisting of methyl, ethyl, n-propyl, isopropyl, n-butyl, sec.-butyl, isobutyl, tert.-butyl, n-pentyl, 3-pentyl, n-hexyl, and (3,3)-dimethyl-butyl; or a cycloalkyl residue selected from the group consisting of cyclopropyl, cyclobutyl, cyclopentyl, cyclohexyl and cycloheptyl, which optionally may be substituted with 1, 2, 3, 4 or 5 substituents independently selected from the group consisting of methyl, ethyl, n-propyl, isopropyl, n-butyl, sec.-butyl, isobutyl, tert.-butyl, n-pentyl; or $R^{40}$ and $R^{41}$ together with the nitrogen atom to which they are attached form a residue selected from the group consisting of pyrrolidinyl, piperidinyl, piperazinyl, morpholinyl and azepanyl, wherein the heterocycloaliphatic moiety may be unsubstituted or optionally substituted with 1, 2, 3, 4 or 5 residues $R^{57}$; and $R^{57}$ denotes an alkyl residue selected from the group consisting of methyl, ethyl, n-propyl, isopropyl, tert.-butyl, n-butyl, sec.-butyl, and isobutyl; and or a salt thereof.

9. A compound according to claim 6, corresponding to formula Ia:

Ia wherein

D denotes N or CH; and $R^1$, $R^2$, $R^3$, $R^4$, $R^5$ and $R^8$ have the respective meanings given in claim 6;

or a salt thereof.

10. A compound according to claim 7, corresponding to formula Ia:

Ia wherein

D denotes N or CH; and $R^1$, $R^2$, $R^3$, $R^4$, $R^5$ and $R^8$ have the respective meanings given in claim 7;

or a salt thereof.

11. A compound according to claim 8, corresponding to formula Ia:

Ia wherein

D denotes N or CH; and $R^1$, $R^2$, $R^3$, $R^4$, $R^5$ and $R^8$ have the respective meanings given in claim 8;

or a salt thereof.

12. A compound according to claim 6, corresponding to formula Ib:

Ib wherein

D denotes N or CH; and $R^1$, $R^2$, $R^3$, $R^4$, $R^5$, $R^8$ and $R^{42}$ have the respective meanings given in claim 6;

or a salt thereof.

13. A compound according to claim 7, corresponding to formula Ib:

Ib wherein

D denotes N or CH; and $R^1$, $R^2$, $R^3$, $R^4$, $R^5$, $R^8$ and $R^{42}$ have the respective meanings given in claim 7;

or a salt thereof.

14. A compound according to claim 8, corresponding to formula Ib:

Ib wherein

D denotes N or CH; and $R^1$, $R^2$, $R^3$, $R^4$, $R^5$, $R^8$ and $R^{42}$ have the respective meanings given in claim 8;

or a salt thereof.

15. A compound according to claim 6, corresponding to formula Ic:

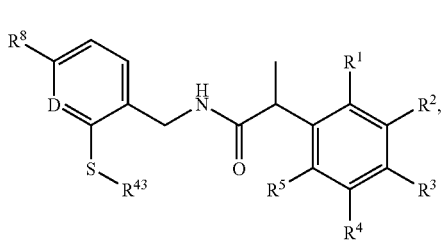

wherein
D denotes N or CH; and
$R^1, R^2, R^3, R^4, R^5, R^8$ and $R^{43}$ have the respective meanings given in claim 6;
or a salt thereof.

16. A compound according to claim 7, corresponding to formula Ic:

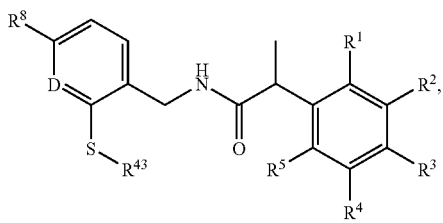

wherein
D denotes N or CH; and
$R^1, R^2, R^3, R^4, R^5, R^8$ and $R^{43}$ have the respective meanings given in claim 7;
or a salt thereof.

17. A compound according to claim 8, corresponding to formula Ic:

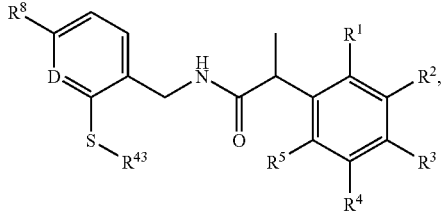

wherein
D denotes N or CH; and
$R^1, R^2, R^3, R^4, R^5, R^8$ and $R^{43}$ have the respective meanings given in claim 8;
or a salt thereof.

18. A compound according to claim 6, corresponding to formula Id:

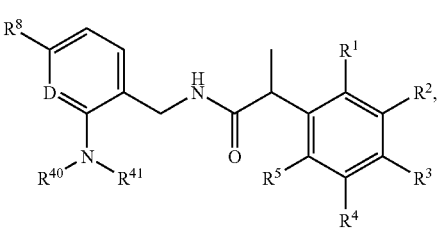

wherein
D denotes N or CH; and
$R^1$, $R^2$, $R^3$, $R^4$, $R^5$, $R^8$, $R^{42}$ and $R^{41}$ have the respective meanings given in claim 6;
or a salt thereof.

19. A compound according to claim 7, corresponding to formula Id:

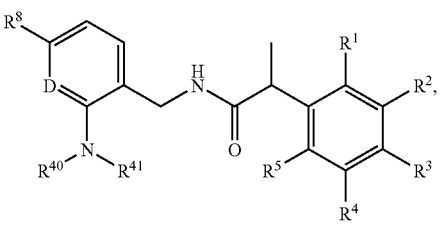

wherein
D denotes N or CH; and
$R^1$, $R^2$, $R^3$, $R^4$, $R^5$, $R^8$, $R^{42}$ and $R^{41}$ have the respective meanings given in claim 7;
or a salt thereof.

20. A compound according to claim 8, corresponding to the formula Id:

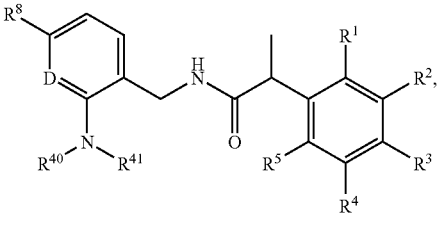

wherein
D denotes N or CH; and
$R^1$, $R^2$, $R^3$, $R^4$, $R^5$, $R^8$, $R^{42}$ and $R^{41}$ have the respective meanings given in claim 8;
or a salt thereof.

21. A compound according to claim 1, selected from the group consisting of:
N-(4-tert.-butylbenzyl)-2-(2-oxo-2,3-dihydro-1H-benzo[d]imidazol-5-yl)-propanamide,
N-(4-tert.-butylbenzyl)-2-(2-thioxo-2,3-dihydro-1H-benzo[d]imidazol-5-yl)-propanamide,
2-(1H-benzo[d]imidazol-5-yl)-N-((2-(4-methylpiperidin-1-yl)-6-(trifluoromethyl)-pyridine-3-yl)methyl)propanamide, 2-(1H-benzo[d]imidazol-5-yl)-N-(4-tert.-butylbenzyl) propanamide, 2-(1H-benzo[d]imidazol-5-yl)-N-((2-butoxy-6-tert.-butylpyridin-3-yl)methyl)-propanamide, 2-(1H-benzo[d]imidazol-5-yl)-N-((6-tert.-butyl-2-(4-methylpiperidin-1-yl)pyridin-3-yl)methyl)propanamide, and 2-(1H-benzo[d]imidazol-5-yl)-N-((6-tert.-butyl-2-(cyclohexylthio)pyridin-3-yl)-methyl)propanamide, or a salt thereof.

22. A compound according to claim 1, wherein, in a FLIPR assay with CHO K1 cells transfected with a human gene VR1, said compound in a concentration of less than 2000 nM, causes a 50% displacement of capsaicin which is present in a concentration of 100 nM.

23. A compound according to claim 22, wherein said compound in a concentration of less then 300 nM, causes a 50% displacement of capsaicin which is present in a concentration of 100 nM.

24. A compound according to claim 23, wherein said compound in a concentration of less then 75 nM, causes a 50% displacement of capsaicin which is present in a concentration of 100 nM.

25. A compound according to claim 24, wherein said compound in a concentration of less then 10 nM, causes a 50% displacement of capsaicin which is present in a concentration of 100 nM.

26. A pharmaceutical composition comprising a compound according to claim 1 and at least one pharmaceutically acceptable carrier or adjuvant.

27. A process for producing a compound according to claim 1, said process comprising:

reacting a compound corresponding to formula II:

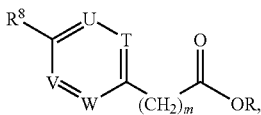

wherein $R^8$, U, T, V, and W have the respective meanings given in claim 1;

m is 0, 1, 2 or 3, and

R denotes hydrogen or a linear or branched $C_{1-6}$ alkyl residue, in a reaction medium, in the presence of a reducing agent, to yield a compound corresponding to formula III:

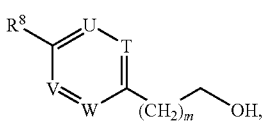

wherein $R^8$, U, T, V, W and m have the respective meanings given above, and optionally isolating or purifying said compound of formula III;

reacting the compound corresponding to formula III, in a reaction medium, in the presence of diphenylphosphoryl azide or of $HN_3$ to yield a compound corresponding to formula IV:

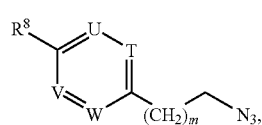

wherein $R^8$, U, T, V, W and m have the respective meanings given above, and optionally isolating or purifying said compound of formula IV;

reacting a compound corresponding to formula IV, in a reaction medium in the presence of a reducing agent, or in a reaction medium in the presence of a catalyst and of hydrogen or hydrazine, or in a reaction medium in the presence of triphenylphosphine, to yield a compound corresponding to formula V:

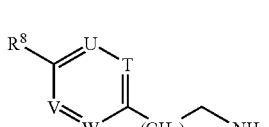

wherein $R^8$, U, T, V, W and m have the respective meanings given above;

and optionally isolating or purifying said compound of formula V;

or reacting a compound corresponding to formula VI:

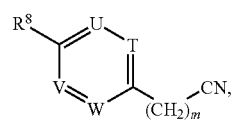

wherein $R^8$, U, T, V, W and m have the respective meanings given above, in a reaction medium and in the presence of at least one catalyst under a hydrogen atmosphere, optionally in the presence of an acid; or in the presence of a reducing agent selected from the group consisting of $BH_3.S(CH_3)_2$, lithium aluminium hydride and sodium borohydride, and optionally in the presence of $NiCl_2$, to yield a compound corresponding to formula V or a salt thereof, and optionally isolating or purifying said compound of formula V or salt thereof;

and
reacting the compound corresponding to formula V
with a compound corresponding to formula VII:

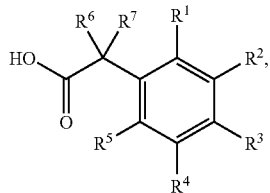

VII wherein $R^1$, $R^2$, $R^3$, $R^4$, $R^5$, $R^6$ and $R^7$ have the respective meanings given in claim 1,
in a reaction medium, optionally in the presence of a coupling agent and optionally in the presence of a base, or
with a compound corresponding to formula VIII:

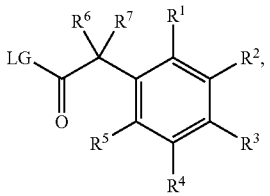

VIII wherein $R^1$, $R^2$, $R^3$, $R^4$, $R^5$, $R^6$ and $R^7$ have the respective meanings given above, and LG denotes a leaving group,
in a reaction medium, optionally in the presence of a base,
to yield a compound corresponding to formula I:

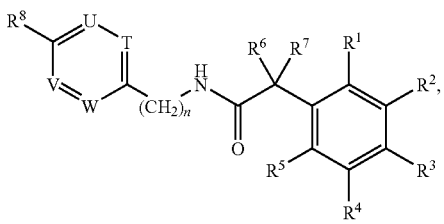

I wherein T, U, V, W, $R^1$, $R^2$, $R^3$, $R^4$, $R^5$, $R^6$ $R^7$ and $R^8$ have the respective meanings given above, and n is 1, 2, 3 or 4,
and optionally isolating or purifying the compound of formula I.

28. A process according to claim 27, wherein:
said compound of formula II is reacted in the presence of a reducing agent selected from the group consisting of sodium hydride, sodium, potassium hydride, lithium aluminium hydride, sodium borohydride and di(isobutyl)aluminium hydride; or
said compound of formula IV is reacted in the presence of a reducing agent selected from the group consisting of sodium hydride, potassium hydride, lithium aluminium hydride, sodium borohydride and di(isobutyl)aluminium hydride; or
said compound of formula IV is reacted in the presence of a platinum or palladium catalyst; or
said compound of formula VI is reacted in the presence of a palladium or platinum catalyst; or
said compound of formula VI is reacted in the presence of hydrochloric acid; or
LG denotes a chlorine or bromine atom.

29. A process for producing a compound according to claim 1, said process comprising:
reacting a compound corresponding to formula X:

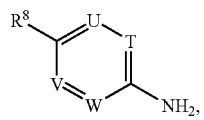

X wherein
$R^8$, U, T, V, and W have the respective meanings given in claim 1,
with a compound corresponding to formula VII:

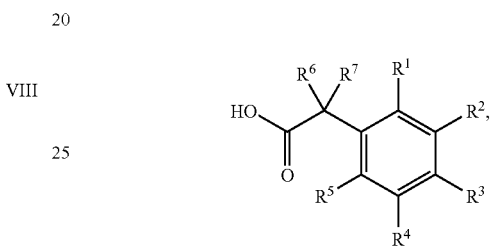

VII wherein $R^1$, $R^2$, $R^3$, $R^4$, $R^5$, $R^6$ and $R^7$ have the respective meanings given in claim 1,
in a reaction medium, and optionally in the presence of a coupling agent, and optionally in the presence of a base,
or
with a compound corresponding to formula VIII:

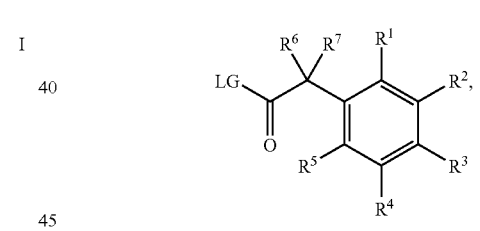

VIII wherein $R^1$, $R^2$, $R^3$, $R^4$, $R^5$, $R^6$ and $R^7$ have the respective meanings given above, and LG denotes a leaving group,
in a reaction medium, and optionally in the presence of a base,
to yield a compound corresponding to formula Im:

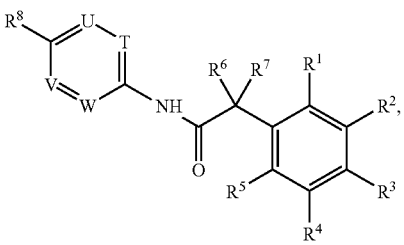

Im wherein T, U, V, W, $R^1$, $R^2$, $R^3$, $R^4$, $R^5$, $R^6$, $R^7$ and $R^8$ have the respective meanings given above,
and optionally isolating or purifying the compound of formula Im.

30. A method of treating pain in a subject, said method comprising administering to said subject a pharmacologically effective amount of a compound according to claim 1.

31. A method according to claim 30, wherein said pain is selected from the group consisting of acute pain, chronic pain, neuropathic pain, visceral pain, joint pain, hyperalgesia, allodynia, causalgia and migraine.

32. A method of treating a disorder or condition selected from the group consisting of depression; nerve injury; multiple sclerosis, Parkinson's disease, Huntington's chorea, and epilepsy in a subject, said method comprising administering to said subject a pharmacologically effective amount of a compound according to claim 1.

33. A method of treating a disorder or condition selected from the group consisting of asthma; bronchitis; pulmonary inflammation; coughing; urinary incontinence; overactive bladder; duodenal ulcers; gastric ulcers; irritable bowel syndrome; strokes; eye irritation; skin irritation; neurotic skin conditions; allergic skin diseases; psoriasis; vitiligo; herpes simplex; inflammation of the intestines, eyes, bladder, skin or nasal mucosa; diarrhoea; pruritus; osteoporosis; osteoarthritis; rheumatic diseases; bulimia; cachexia; anorexia; obesity; development of tolerance towards opioids; drug dependency; and alcohol dependency; or for diuresis; antinatriuresis; increasing vigilance; treating wounds or burns; treating severed nerves; increasing libido; anxiolysis; or local anaesthesia; or inhibiting hyperthermia, high blood pressure or constriction of bronchial tubes triggered by administration of vanilloid receptor 1 agonists in a subject; said method comprising administering to said subject a pharmacologically effective amount of a compound according to claim 1.

* * * * *